US010934304B2

(12) United States Patent
Huang et al.

(10) Patent No.: US 10,934,304 B2
(45) Date of Patent: Mar. 2, 2021

(54) SPIROCYCLIC COMPOUNDS

(71) Applicant: Recurium IP Holdings, LLC, San Diego, CA (US)

(72) Inventors: Peter Qinhua Huang, San Diego, CA (US); Mehmet Kahraman, San Diego, CA (US); Kevin Duane Bunker, Escondido, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 16 days.

(21) Appl. No.: 16/336,854

(22) PCT Filed: Oct. 3, 2017

(86) PCT No.: PCT/US2017/054865
§ 371 (c)(1),
(2) Date: Mar. 26, 2019

(87) PCT Pub. No.: WO2018/067512
PCT Pub. Date: Apr. 12, 2018

(65) Prior Publication Data
US 2020/0207776 A1 Jul. 2, 2020

Related U.S. Application Data

(60) Provisional application No. 62/404,668, filed on Oct. 5, 2016.

(51) Int. Cl.
*C07D 487/10* (2006.01)
*A61P 35/00* (2006.01)
*C07D 519/00* (2006.01)

(52) U.S. Cl.
CPC ............ *C07D 487/10* (2013.01); *A61P 35/00* (2018.01); *C07D 519/00* (2013.01)

(58) Field of Classification Search
CPC .................................................... C07D 487/10
USPC ...................................................... 546/270.4
See application file for complete search history.

(56) References Cited

U.S. PATENT DOCUMENTS

| | | | | |
|---|---|---|---|---|
| 10,493,060 | B2 * | 12/2019 | Huang ............... | A61K 31/4162 |
| 2014/0135335 | A1 | 5/2014 | Wang et al. | |
| 2014/0275245 | A1 | 9/2014 | Bunker et al. | |
| 2018/0207132 | A1 | 7/2018 | Huang et al. | |

FOREIGN PATENT DOCUMENTS

| | | |
|---|---|---|
| CN | 103130775 | 6/2013 |
| CN | 105732636 | 7/2016 |
| WO | WO 2005/113541 | 12/2005 |
| WO | WO 2007/070398 | 6/2007 |
| WO | WO 2008/063609 | 5/2008 |
| WO | WO 2010/027567 | 3/2010 |
| WO | WO 2011/071860 | 6/2011 |
| WO | WO 2013/033059 | 3/2013 |
| WO | WO 2016/106009 | 6/2016 |
| WO | WO 2016/161160 | 10/2016 |

OTHER PUBLICATIONS

Blake, James F., et al., "Discovery of {S)-1-(1-(4-Chloro-3-fluorophenyl)-2-hydroxyethyl)-4-{2-{{1-methyl-1 H-pyrazol-5-yl)amino)pyrimidin-4-yl)pyridin-2{1 H)-one {GDC-0994), an Extracellular Signal-Regulated Kinase ½ {ERK½) Inhibitor in Early Clinical Development", J. Med. Chem. (2016), 59, 5650-5660.

Extended Search Report for EP Application 17858989.1 dated Apr. 20, 2020.

Adjei, A.A., "The role of mitogen-activated ERK-kinase inhibitors in lung cancer therapy" Clin. Lung. Cancer (2005) 7(3):221-223.

Buonata et al., "ERK½ blockade prevents epithelial-mesenchymal transition in lung cancer cells and promotes their sensitivity to EGFR inhibition" Cancer Res (2014) 74(1):309-319.

Carlo-Stella et al., "Sorafenib inhibits lymphoma xenografts by targeting MAPK/ERK and AKT pathways in tumor and vascular cells" PLoS One (2013) 8(4):e61603.

Chambers et al., "Self-renewal of teratocarcinoma and embryonic stem cells" Oncogene (2004) 23(43):7150-7160.

Chen et al., "Glioma cell proliferation controlled by ERK activity-dependent surface expression of PDGFRA" PLoS One (2014) 9(1):e87281.

Chen et al., "Expression and prognostic role of MEKK3 and pERK in patients with renal clear cell carcinoma" Asian Pac J Cancer Prev (2015) 16(6):2495-2499.

Fang et al., "The MAPK signalling pathways and colorectal cancer" Lancet Oncol (2005) 6(5):322-327.

Hayes, et al., "Long-Term ERK Inhibition in KRAS-Mutant Pancreatic Cancer Is Associated with MYC Degradation and Senescence-like Growth Suppression" Cancer Cell (2016) 29(1):75-89 with Supplemental Information.

Huang et al., "Apelin-13 induces autophagy in hepatoma HepG2 cells through ERK½ signaling pathway-dependent upregulation of Beclin1" Oncol Lett (2016) 11(2):1051-1056.

Jimenez et al., "Mechanisms of Invasion in Head and Neck Cancer" Arch Pathol Lab Med (2015) 139(11):1334-1348.

Jin et al., "USO1 promotes tumor progression via activating Erk pathway in multiple myeloma cells" Biomed Pharmacother (2016) 78:264-271.

Khavari et al., "Ras/Erk MAPK signaling in epidermal homeostasis and neoplasia" Cell Cycle (2007) 6(23)2928-2931.

Maiello et al., "EGFR and MEK Blockade in Triple Negative Breast Cancer Cells" J Cell Biochem (2015) 116(12):2778-2785.

Milosevic et al., "Targeting RAS-MAPK-ERK and PI3K-AKT-mTOR signal transduction pathways to chemosensitize anaplastic thyroid carcinoma" Transl Res (2014) 164(5):411-423.

(Continued)

*Primary Examiner* — Nizal S Chandrakumar
(74) *Attorney, Agent, or Firm* — Knobbe, Martens, Olson & Bear LLP

(57) ABSTRACT

Disclosed herein are spirocyclic compounds, together with pharmaceutical compositions and methods of ameliorating and/or treating a cancer described herein with one or more of the compounds described herein.

23 Claims, No Drawings

(56) References Cited

OTHER PUBLICATIONS

Morris et al., "Discovery of a novel ERK inhibitor with activity in models of acquired resistance to BRAF and MEK inhibitors" Cancer Discov (2013) 3(7):742-750.
Noguchi et al., "Replacement treatment with microRNA-143 and -145 induces synergistic inhibition of the growth of human bladder cancer cells by regulating PI3K/Akt and MAPK signaling pathways" Cancer Lett (2013) 328(2):353-361.
Roberts et al., "Targeting the Raf-MEK-ERK mitogen-activated protein kinase cascade for the treatment of cancer" Oncogene (2007) 26(22):3291-3310.
Rodriguez-Berriguete et al., "Relationship between IL-6/ERK and NF-κB: a study in normal and pathological human prostate gland" Eur Cytokine Netw (2010) 21(4):241-250.
Serrano et al., "RAS/MAPK pathway hyperactivation determines poor prognosis in undifferentiated pleomorphic sarcomas" Cancer (2016) 122(1):99-107.
Sheppard et al., "Synergistic inhibition of ovarian cancer cell growth by combining selective PI3K/mTOR and RAS/ERK pathway inhibitors" Eur J Cancer (2013) 49(18):3936-3944.
Steelman et al., "Roles of the Ras/Raf/MEK/ERK pathway in leukemia therapy" Leukemia (2011) 25(7):1080-1094.
Vieira et al., "LGR5 regulates pro-survival MEK/ERK and proliferative Wnt/β-catenin signalling in neuroblastoma" Oncotarget (2015) 6(37):40053-40067.
Wang et al., "ERK inhibition rescues defects in fate specification of Nf1-deficient neural progenitors and brain abnormalities" Cell (2012) 150(4):816-830 with Supplemental Information.
International Preliminary Report on Patentability for International Application No. PCT/US2017/054865 dated Jan. 29, 2019.
Written Opinion for SG Application 11201902842T dated Apr. 15, 2020.
First Examination Report issued in New Zealand Patent Application No. 751398 dated Mar. 20, 2020.
Second Written Opinion for Singapore Application 11201902842T dated Sep. 28, 2020.
Patent Examination Report 2 issued in corresponding New Zealand Patent Application No. 751398 dated Sep. 18, 2020.

* cited by examiner

SPIROCYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

BACKGROUND

Field

The present application relates to the fields of chemistry, biochemistry and medicine. More particularly, disclosed herein are spirocyclic compounds, together with pharmaceutical compositions, and methods of synthesizing the same. Also disclosed herein are methods of ameliorating and/or treating a cancer described herein with one or more of the compounds described herein.

Description

The RAS/MAPK pathway is activated in response to growth factor binding and regulates cellular growth, differentiation and survival in a variety of cell types. Activation of this pathway occurs via a cascade of protein phosphorylation events, which culminates in the phosphorylation and activation of ERK (ERK1 and/or ERK2). ERK lies downstream from the small GTPase RAS and the protein kinases RAF and MEK in the RAS/MAPK pathway. Following its activation by RAS, RAF phosphorylates MEK, which in turn phosphorylates ERK. Activated ERK phosphorylates other substrates that govern the transcriptional output of cells.

SUMMARY

Some embodiments disclosed herein relate to a compound of Formulae (I), (II) or (III), or a pharmaceutically acceptable salt thereof.

Some embodiments described herein relate to a pharmaceutical composition, that can include an effective amount of a compound of Formulae (I), (II) or (III), or a pharmaceutically acceptable salt thereof.

Some embodiments described herein relate to a method for ameliorating and/or treating a cancer described herein that can include administering an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) to a subject having a cancer described herein. Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for ameliorating and/or treating a cancer described herein. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof), wherein the malignant growth or tumor is due to a cancer described herein. Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for inhibiting replication of a malignant growth or a tumor, wherein the malignant growth or tumor is due to a cancer described herein. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes an effective amount of a compound described herein (for example, a compound of Formulae (I), (II) or (III), or a pharmaceutically acceptable salt thereof) in a subject having a cancer described herein. Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for ameliorating or treating a cancer described herein that can include contacting with a malignant growth or a tumor, wherein the malignant growth or tumor is due to a cancer described herein. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for ameliorating or treating a cancer described herein that can include contacting with a malignant growth or a tumor, wherein the malignant growth or tumor is due to a cancer described herein.

Some embodiments described herein relate to a method for inhibiting the activity of ERK1 and/or ERK2 that can include providing an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) to a sample that includes a cancer cell from a cancer described herein. Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for inhibiting the activity of ERK1 and/or ERK2. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for inhibiting the activity of ERK1 and/or ERK2.

Some embodiments described herein relate to a method for ameliorating or treating a cancer described herein that can include inhibiting the activity of ERK1 and/or ERK2 using an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof). Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for ameliorating or treating a cancer described herein by inhibiting the activity of ERK1 and/or ERK2. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for ameliorating or treating a cancer described herein by inhibiting the activity of ERK1 and/or ERK2.

DETAILED DESCRIPTION

Inhibition of ERK can have therapeutic effects in the treatment of certain types of cancer. It has been shown that the RAS/MAPK/ERK pathway can be aberrantly activated in certain tumors via activating mutations in RAS and BRAF, and this activation has been implicated in the growth and pathologic behavior of certain cancer cells. Constitutive activation of this pathway has been observed in human cancers and has been associated with high rates of cancer cell proliferation. Tumor cells that harbor either BRAF or RAS mutations are generally dependent on the activity of the altered proteins for growth and survival, a phenomenon described as "oncogene addiction." Activating mutations of RAS have been reported in ~30% of all cancers, with some, such as pancreatic and colon cancer, harboring mutation rates of ~90% and ~50%, respectively. RAS mutations have been identified in ~15% of melanomas and ~30% of NSCLCs (non-small cell lung cancers). BRAF somatic mutations have been identified in 50-70% of malignant melanomas, where all mutations are within the kinase domain and a single substitution (V600E) accounts for 80% of mutations. Activating BRAF mutations have also been documented in a variety of human cancers, including colorectal cancer (~10%), NSCLC (2-3%), and thyroid cancer (~36%). The high frequency of mutations makes targeting this pathway a strategy for cancer therapy. Accordingly, there is a large unmet medical need for improved therapies in these diseases especially in the advanced, refractory setting.

Provided herein are compounds that can inhibit the kinase activity of ERK1 and/or the kinase activity of ERK2. The compounds described herein can also inhibit the phosphorylation of ERK1 and ERK2, and thus can be ERK inhibitors (for example, ERK1 inhibitors and/or ERK2 inhibitors). The compounds described herein may also effectively inhibit MAPK signaling through a dual mechanism, via inhibiting both the phosphorylation and activation of ERK by MEK, in addition to inhibiting ERK phosphorylation of RSK. As ERK inhibitors, the compounds described herein can be used to ameliorate and/or treat a variety of cancers, such as, lung cancer, pancreatic cancer, colon cancer, myeloid leukemia, thyroid cancer, myelodysplastic syndrome (MDS), bladder carcinoma, epidermal carcinoma, melanoma, breast cancer, prostate cancer, head and neck cancer, ovarian cancer, brain cancer, cancer of mesenchymal origin, sarcoma, tetracarcinoma, neuroblastoma, kidney carcinoma, hepatoma, non-Hodgkin's lymphoma, multiple myeloma and anaplastic thyroid carcinoma.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R", "Y" or "Z" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $Y^1$, $Y^2$, $Y^3$, $Y^4$, $Y^5$, $Y^6$, $Y^7$, $Y^8$, $Y^9$, $Y^{10}$ and $Z^1$ represent substituents that can be attached to the indicated atom. Such R, Y and/or Z groups may be referred to herein in a general way as "R" groups. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^a R^b$ group are indicated to be "taken together," it means that they are covalently bonded to one another to form a ring:

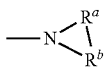

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, acylalkyl, hydroxy, alkoxy, alkoxyalkyl, aminoalkyl, amino acid, aryl, heteroaryl, heterocyclyl, aryl (alkyl), heteroaryl(alkyl), heterocyclyl(alkyl), hydroxyalkyl, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl, cycloalkenyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Typical mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, bicyclo[2.1.1]heptane, adamantanyl, and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one, two, three or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, those described herein and the following: furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion, as described herein with respect to "cycloalkyl." Additionally, any nitrogens in a heterocyclyl may be quaternized. Heterocyclyl or heteroalicyclic groups may be unsubstituted or substituted. Examples of such "heterocyclyl" or "heteroalicyclyl" groups include, but are not limited to, those described herein and the following: 1,3-dioxin, 1,3-dioxane, 1,4-dioxane, 1,2-dioxolane, 1,3-dioxolane, 1,4-dioxolane, 1,3-oxathiane, 1,4-oxathiin, 1,3,4-oxadiazol-2(3H)-one, 1,2,3-oxadiazol-5(2H)-one, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained $—CH_2—$ tethering groups, forming bonds to connect molecular fragments via their terminal carbon atoms. Examples include but are not limited to methylene ($—CH_2—$), ethylene ($—CH_2CH_2—$), propylene ($—CH_2CH_2CH_2—$), and butylene ($—CH_2CH_2CH_2CH_2—$). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) as defined herein. A non-limiting list of alkoxys are methoxy, ethoxy, n-propoxy, 1-methylethoxy (isopropoxy), cyclopropoxy, n-butoxy, iso-butoxy, sec-butoxy, tert-butoxy, cyclobutoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "acylalkyl" refers to an acyl connected, as a substituent, via a lower alkylene group. Examples include aryl-C(═O)—$(CH_2)_n$— and heteroaryl-C(═O)—$(CH_2)_n$—, where n is an integer in the range of 1 to 6.

As used herein, "alkoxyalkyl" refers to an alkoxy group connected, as a substituent, via a lower alkylene group. Examples include $C_{1-4}$ alkyl-O—$(CH_2)_n$—, wherein n is an integer in the range of 1 to 6.

As used herein, "aminoalkyl" refers to an optionally substituted amino group connected, as a substituent, via a lower alkylene group. Examples include $H_2N(CH_2)_n$—, wherein n is an integer in the range of 1 to 6.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, chloro-fluoroalkyl, chloro-difluoroalkyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, chloro-fluoroalkyl, chloro-difluoroalkoxy and 2-fluoroisobutoxy. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—$SO_2N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carbamyl" group refers to a "—OC(=O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "urea" group refers to "N(R)—C(=O)—$NR_AR_B$ group in which R can be hydrogen or an alkyl, and $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A urea may be substituted or unsubstituted.

An "oxime" group refers to "—C(=N—OH)$R_A$" in which $R_A$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An oxime may be substituted or unsubstituted.

An "acyl hydrozone" refers to "—C(=N—NH-acyl)-$R_A$." in which the acyl portion has the structure as provided herein for "acyl", and $R_A$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An acyl hydrozone may be substituted or unsubstituted.

A "hydrazine" refers to "—$NHNR_AR_B$" in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A hydrazine may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, "------" indicates a single or double bond, unless stated otherwise.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" (and the abbreviation "PG") as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "leaving group" (and the abbreviation "LG") as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates, mesylates, trifluoroacetates and halogens (e.g., I, Br, and Cl). Non-limiting characteristics and examples of leaving groups can be found, for example in *Organic Chemistry,* 2d ed., Francis Carey (1992), pages 328-331*; Introduction to Organic Chemistry,* 2d ed., Andrew Streitwieser and Clayton Heathcock (1981), pages 169-171; and *Organic Chemistry,* $5^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z, or a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Formula (I)

Some embodiments disclosed herein relate to a compound of Formula (I), or a pharmaceutically acceptable salt thereof, having the structure:

(I)

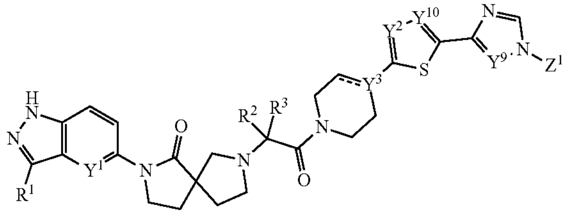

In various embodiments of Formula (I), $R^1$ can be selected from $C_{3-4}$ cycloalkyl, halophenyl, $C_{1-4}$ alkoxyphenyl, $C_{1-4}$ alkoxyhalophenyl, $C_{1-4}$ dialkoxyphenyl, halopyridinyl, $C_{1-4}$ alkoxypyridinyl (e.g., isopropoxypyridinyl), $C_{1-4}$ alkylpyridinyl, $C_{3-5}$ cycloalkoxypyridinyl, methylbenzoxazolyl and tetraydropyranyl. In some embodiments, $R^1$ can be halophenyl. For example, in some embodiments $R^1$ can be fluorophenyl. In other embodiments, $R^1$ can be halopyridinyl. For example, in some embodiments $R^1$ can be fluoropyridinyl. In some embodiments, $R^1$ can be isopropoxypyridinyl. In other embodiments, $R^1$ is not isopropoxypyridinyl. In some embodiments, $R^1$ can be $C_{1-4}$ alkoxypyridinyl. For example, in some embodiments $R^1$ can be methoxypyridinyl, ethoxypyridinyl, propoxypyridinyl, cycloproxypyridinyl, butoxypyridinyl or cyclobutoxypyridinyl. In some embodiments, $R^1$ can be $C_{1-4}$ alkylpyridinyl. For example, in some embodiments $R^1$ can be methylpyridinyl, ethylpyridinyl, propylpyridinyl or butylpyridinyl. In some embodiments, $R^1$ can be methylbenzoxazolyl. In some embodiments, $R^1$ can be tetraydropyranyl.

In some embodiments, $R^2$ and $R^3$ are each independently methyl, hydrogen or deuterium. For example, in an embodiment, $R^2$ and $R^3$ are both hydrogen. In another embodiment, $R^2$ is methyl and $R^3$ is hydrogen. In another embodiment, $R^2$ and $R^3$ are both deuterium.

In various embodiments of Formula (I), $Y^1$ and $Y^2$ are each independently CH or N. For example, in an embodiment, $Y^1$ is CH. In another embodiment, $Y^1$ is N. In another embodiment, $Y^2$ is CH. In another embodiment, $Y^2$ is N.

In various embodiments of Formula (I), $Y^3$ is C, CH or N. The ring structure that includes $Y^3$ can include a double or a single bond from an atom adjacent to $Y^3$ depending on whether $Y^3$ is C, CH or N. For example, in an embodiment, the ------ in the ring structure is a single bond when $Y^3$ is N. In another embodiment, the ------ in the ring structure is a single bond when $Y^3$ is CH. In another embodiment, the ------ in the ring structure is a double bond when $Y^3$ is C.

In various embodiments of Formula (I), $Y^9$ and $Y^{10}$ are each independently CH or N. For example, in an embodiment, $Y^9$ is CH. In another embodiment, $Y^9$ is N. In another embodiment, $Y^{10}$ is CH. In another embodiment, $Y^{10}$ is N. In an embodiment of Formula (I), $Y^9$ is N and $Y^{10}$ is CH, as illustrated by the following Formula (IA):

(IA)

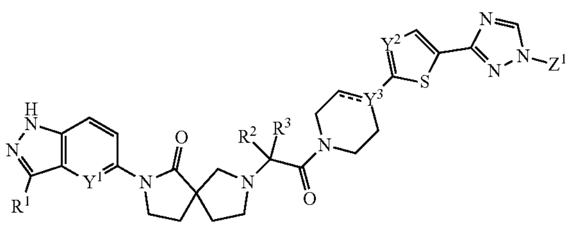

In various embodiments of Formula (IA), $R^1$ is selected from the group consisting of halophenyl, halopyridinyl, $C_{1-4}$ alkoxypyridinyl, $C_{1-4}$ alkylpyridinyl, methylbenzoxazolyl and tetraydropyranyl. In various embodiments of Formula (IA), $R^2$ and $R^3$ are each independently hydrogen or deuterium. In various embodiments of Formula (IA), $Y^1$ and $Y^2$ are each independently CH or N. In various embodiments of Formula (IA), $Y^3$ is C, CH or N. In Formula (IA), ------ is a single bond when Y is N or CH and ------ is a double bond when $Y^3$ is C. In various embodiments of Formula (IA), $Z^1$ is $C_{1-3}$ alkyl optionally substituted with hydroxyl.

In various embodiments of Formula (I), $Z^1$ is $C_{1-3}$ alkyl optionally substituted with hydroxyl. For example, in an embodiment $Z^1$ is methyl. In another embodiment, $Z^1$ is ethyl. In another embodiment, $Z^1$ is hydroxyethyl.

In various embodiments, Formula (I) and/or Formula (IA) does not represent a compound that is disclosed in International Application No. PCT/US2016/025345, which is hereby incorporated herein by reference in its entirety, including for the purpose of describing compounds that Formula (I) and/or Formula (IA) does not represent. For example, in an embodiment, Formula (I) and/or Formula (IA) does not represent the following compound

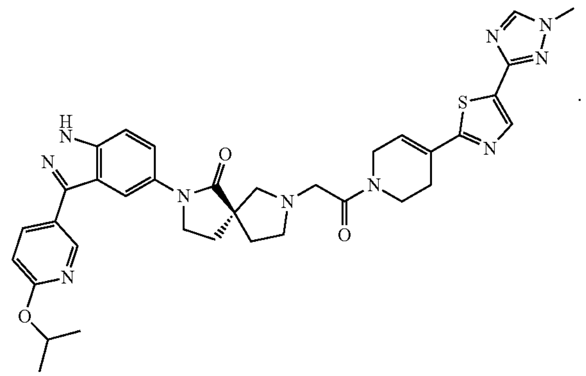

Examples of compounds of Formula (I), or pharmaceutically acceptable salts thereof, include the following:

(Ia)

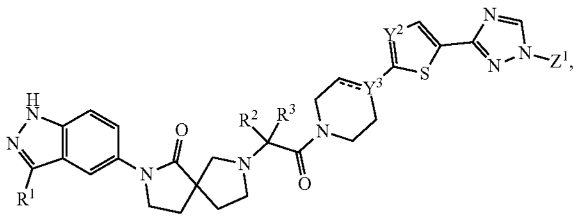

(Ib)

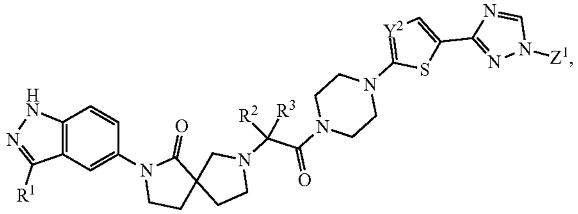

(Ic)

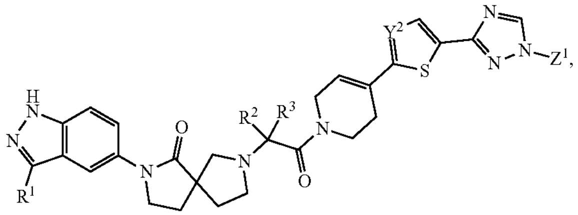

-continued (Id)

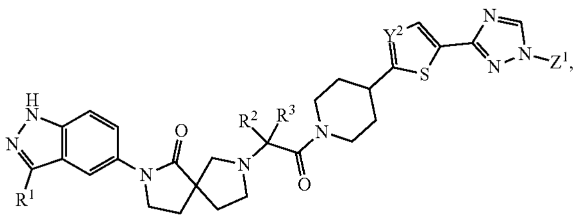

(Ie)

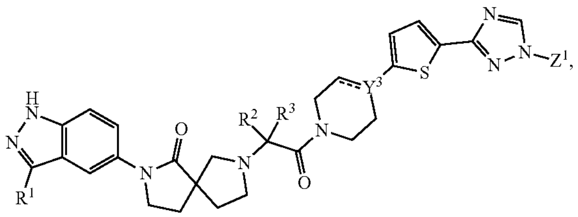

(If)

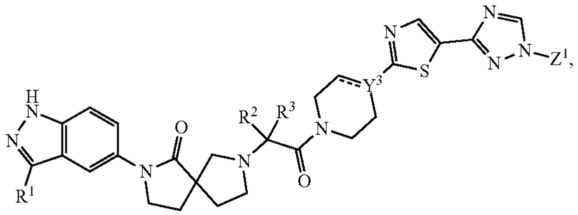

(Ig)

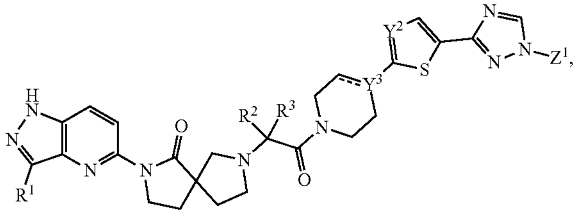

(Ih)

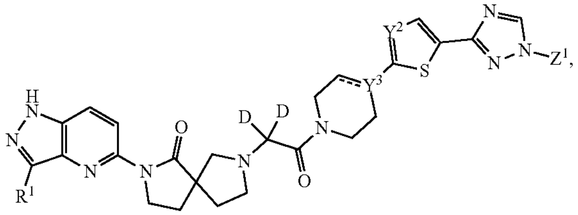

(Ii)

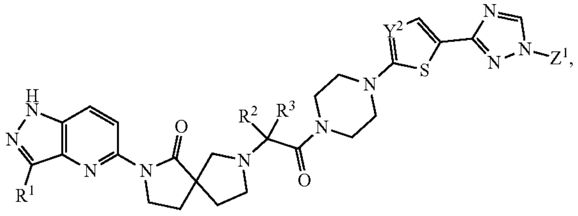

-continued (Ij)

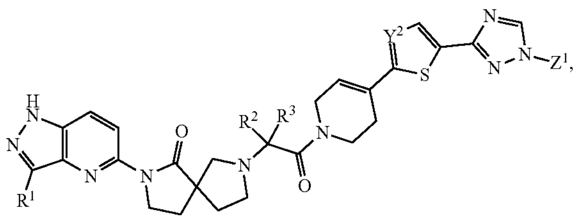

(Ik)

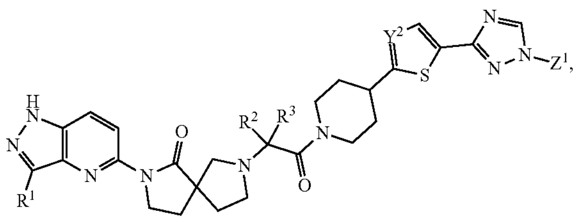

(Il)

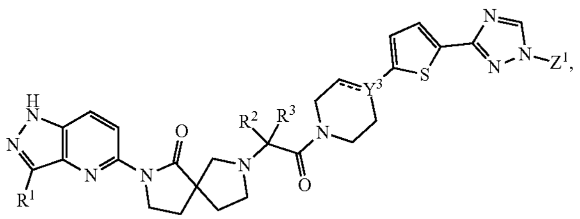

(Im)

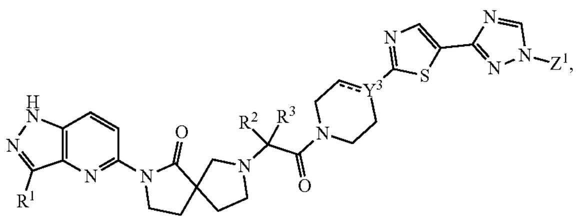

or a pharmaceutically acceptable salt of the foregoing.

Those skilled in the art will recognize that compounds of the Formulae (IA), (Ia), (Ib), (Ic), (Id), (Ie), (If), (Ig), (Ih), (Ii), (Ij), (Ik), (Il) and (Im) are compounds of the Formula (I). Therefore, reference herein to variables defined for Formula (I) (such as $R^1$, $R^2$, $R^3$, $Y^1$, $Y^2$, $Y^3$, $Y^9$, $Y^{10}$, and $Z^1$) will also be understood as definitions for the corresponding variables of the Formulae (IA), (Ia), (Ib), (Ic), (Id), (Ie), (If), (Ig), (Ih), (Ii), Ij), (Ik), (Il) and (Im), and vice versa.

Examples of compounds of Formula (I) include, but are not limited to, the following:

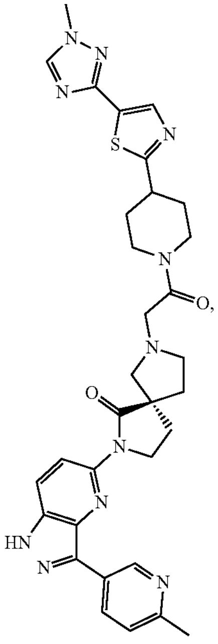

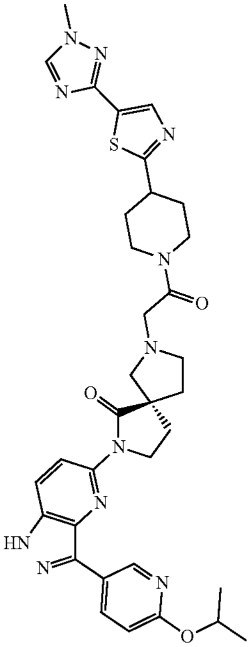

,

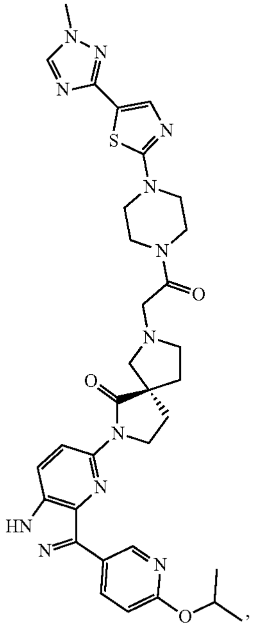

,

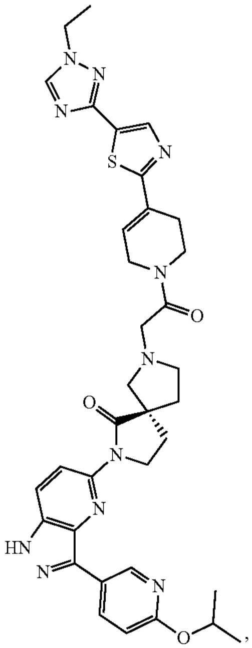

,

-continued
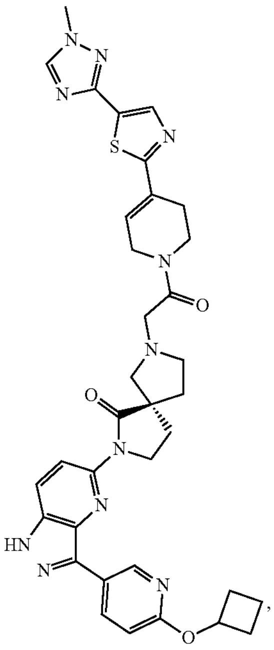
,
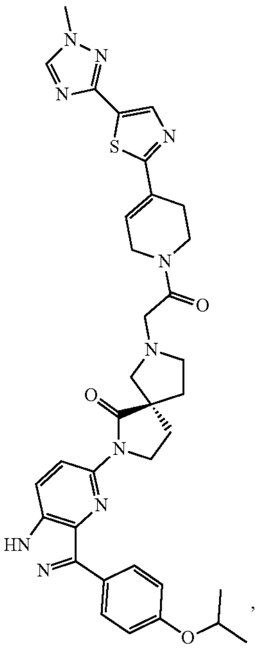
,
-continued
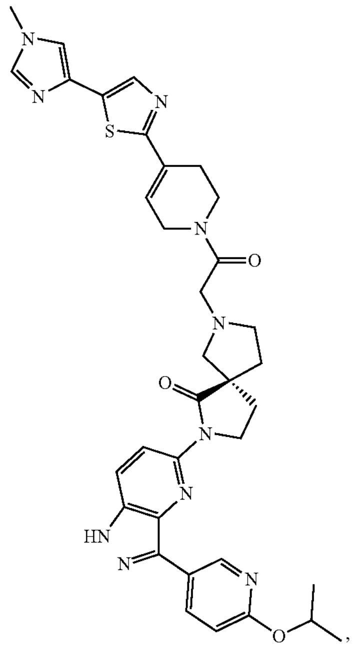
,
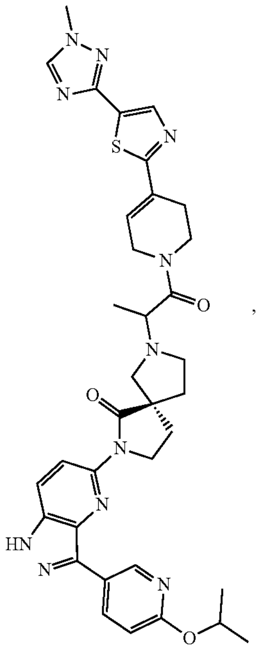
,
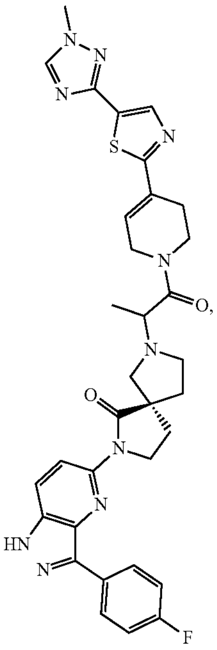
,
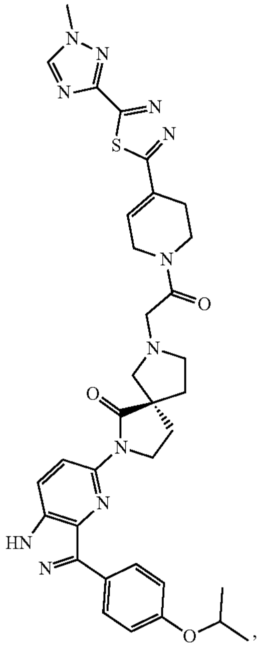
,
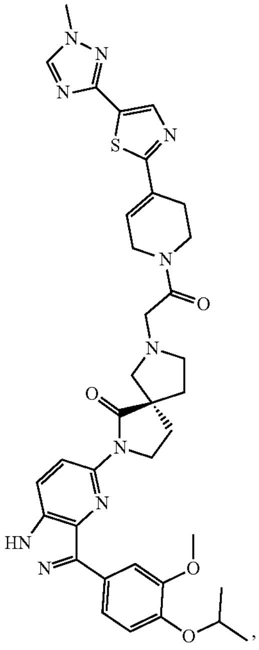
, -continued
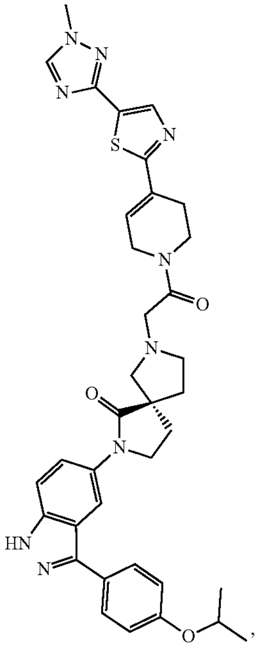,
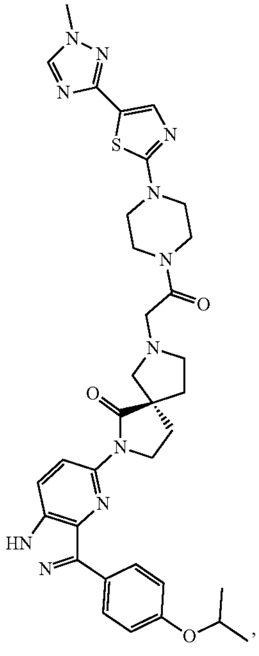,
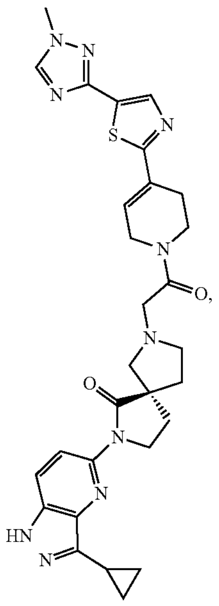, and
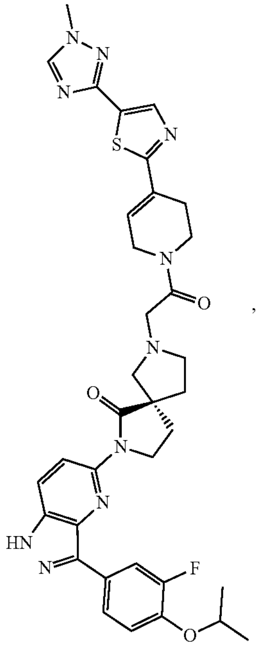,
or a pharmaceutically acceptable salt of the foregoing.
Examples of compounds of Formula (IA) (which are also compounds of the Formula (I)) include, but are not limited to, the following:
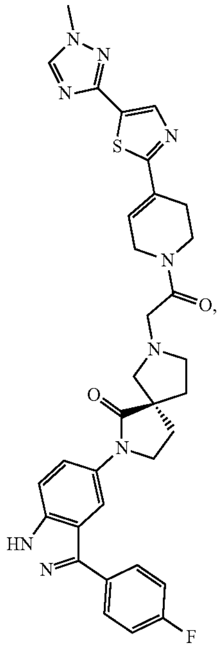,
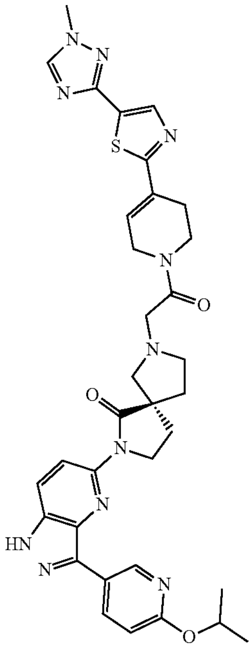,
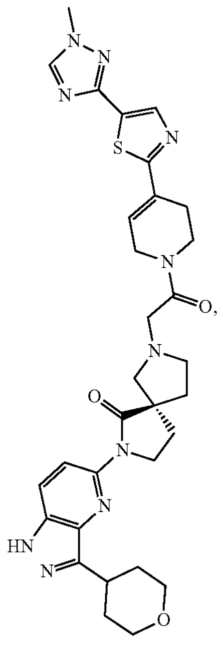,
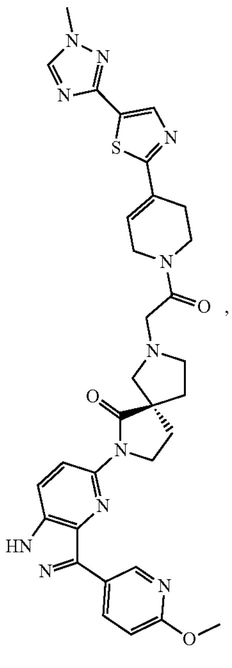, -continued
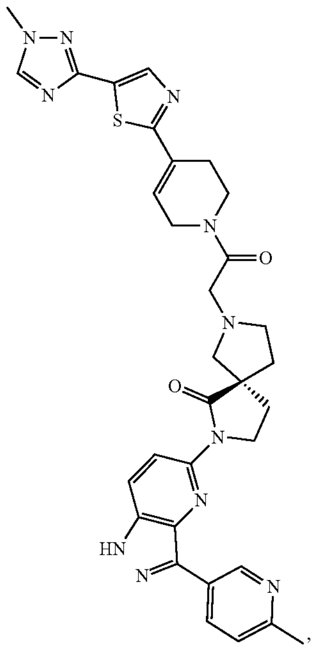
,
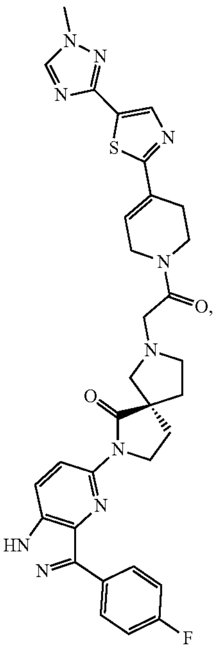
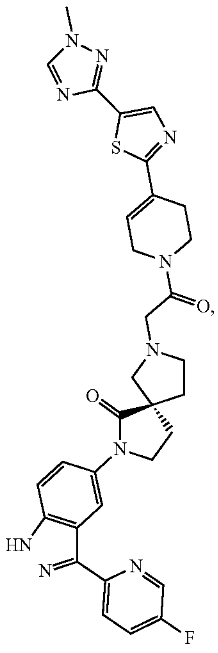
-continued
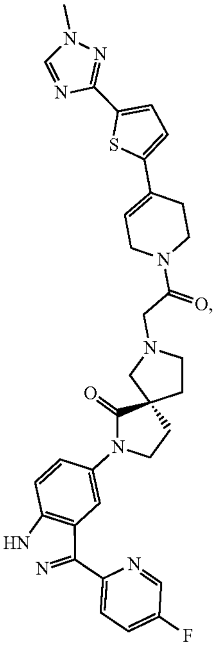
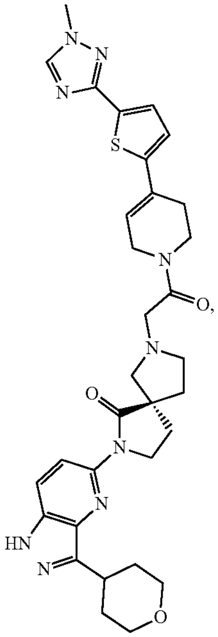
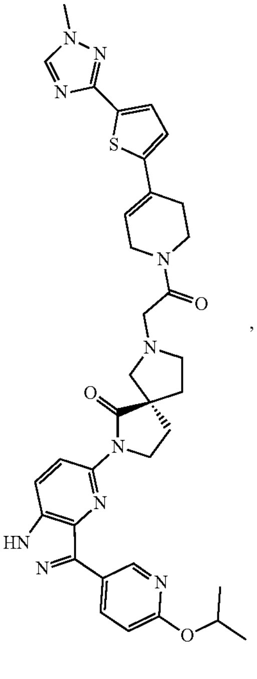
, and
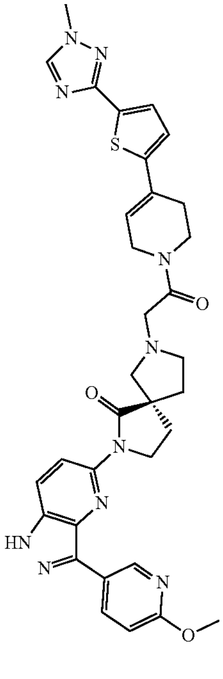
,
or a pharmaceutically acceptable salt of the foregoing.
Further examples of compounds of Formula (I) include, but are not limited to, the compounds described in Example 120 below.
Formula (II)
Some embodiments disclosed herein relate to a compound of Formula (II), or a pharmaceutically acceptable salt thereof, having the structure:

(II)

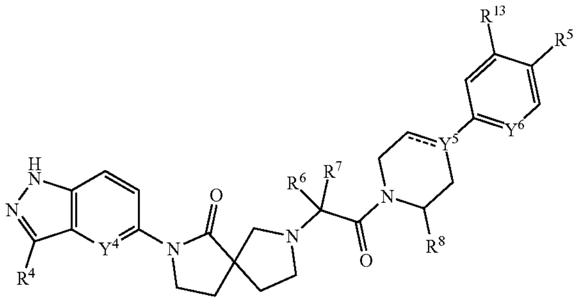

In various embodiments of Formula (II), $R^4$ is:

a methyloxazolopyridinyl;

a dimethylbenzodioxolyl;

a methylbenzoxazolyl, an isopropylbenzoxazolyl, a methylindazolyl or a methylbenzoisoxazolyl;

a pyridinyl substituted with one or two substituents independently selected from the group consisting of methyl, $C_{1-4}$ alkoxy, $C_{3-5}$ cycloalkoxy, isopropylthio, fluoro, chloro, cyano, trifluoromethyl, pyrrolidinyl and —C(═O)NHCH$_3$; or a phenyl substituted with one or two substituents independently selected from the group consisting of methoxy, fluoro, chloro, cyano, trifluoromethyl and —C(═O)NHCH$_3$.

In an embodiment of Formula (II), $R^4$ is a methyloxazolopyridinyl. In another embodiment, $R^4$ is a dimethylbenzodioxolyl. In another embodiment, $R^4$ is a methylbenzoxazolyl. In another embodiment, $R^4$ is a isopropylbenzoxazolyl. In another embodiment, $R^4$ is a methylindazolyl. In another embodiment, $R^4$ is a methylbenzoisoxazolyl.

In an embodiment of Formula (II), $R^4$ is a pyridinyl substituted with one or two substituents independently selected from the group consisting of methyl, $C_{1-4}$ alkoxy, isopropylthio, fluoro, chloro, cyano, trifluoromethyl, pyrrolidinyl and —C(═O)NHCH$_3$. For example, in an embodiment $R^4$ is a pyridinyl substituted with one or two methyl groups. In an embodiment $R^4$ is a pyridinyl substituted with one or two $C_{1-4}$ alkoxy groups. For example, in an embodiment $R^4$ is a pyridinyl substituted with one or two groups independently selected from methoxy, ethoxy, propoxy (e.g., isopropoxy), cyclopropoxy, butoxy and cyclobutoxy. In an embodiment $R^4$ is a pyridinyl substituted with one or two isopropylthio groups. In an embodiment $R^4$ is a pyridinyl substituted with one or two fluoro groups. In an embodiment $R^4$ is a pyridinyl substituted with one or two chloro groups. In an embodiment $R^4$ is a pyridinyl substituted with one or two cyano groups. In an embodiment $R^4$ is a pyridinyl substituted with one or two trifluoromethyl groups. In an embodiment $R^4$ is a pyridinyl substituted with one or two —C(═O)NHCH$_3$ groups.

In various embodiments of Formula (II), $R^4$ is a pyridinyl substituted with two substituents selected from the group consisting of methyl, $C_{1-4}$ alkoxy, isopropylthio, fluoro, chloro, cyano, trifluoromethyl, pyrrolidinyl and —C(═O)NHCH$_3$, wherein both of the substituents are the same. In other embodiments, $R^4$ is a pyridinyl substituted with two substituents selected from the group consisting of methyl, $C_{1-4}$ alkoxy, isopropylthio, fluoro, chloro, cyano, trifluoromethyl, pyrrolidinyl and —C(═O)NHCH$_3$, wherein both of the substituents are different.

In an embodiment of Formula (II), R is a phenyl substituted with one or two substituents independently selected from the group consisting of methoxy, fluoro, chloro, cyano, trifluoromethyl and —C(═O)NHCH$_3$. For example, in an embodiment $R^4$ is a phenyl substituted with one or two methoxy groups. In an embodiment $R^4$ is a phenyl substituted with one or two fluoro groups. In an embodiment $R^4$ is a phenyl substituted with one or two chloro groups. In an embodiment $R^4$ is a phenyl substituted with one or two cyano groups. In an embodiment $R^4$ is a phenyl substituted with one or two trifluoromethyl groups. In an embodiment $R^4$ is a phenyl substituted with one or two —C(═O)NHCH$_3$ groups.

In various embodiments of Formula (II), $R^4$ is a phenyl substituted with two substituents selected from the group consisting of methoxy, fluoro, chloro, cyano, trifluoromethyl and —C(═O)NHCH$_3$, wherein both of the substituents are the same. In other embodiments, $R^4$ is a phenyl substituted with two substituents selected from the group consisting of methoxy, fluoro, chloro, cyano, trifluoromethyl and —C(═O)NHCH$_3$, wherein both of the substituents are different.

In various embodiments of Formula (II), $R^5$ is

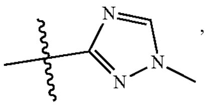 [SMILES: *c1ncn(C)n1]

,

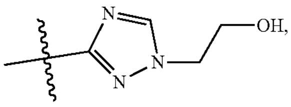

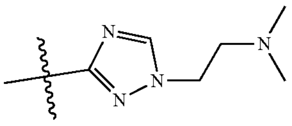

or

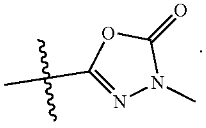 [SMILES: *c1nn(C)c(=O)o1]

For example, in an embodiment $R^5$ is

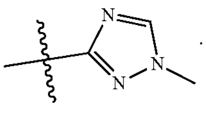 [SMILES: *c1ncn(C)n1]

In another embodiment, $R^5$ is

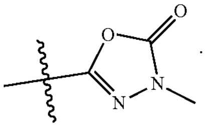

In various embodiments of Formula (II), $R^6$ and $R^7$ are each independently hydrogen or deuterium. For example, in an embodiment, $R^6$ and $R^7$ are both hydrogen. In another embodiment, $R^6$ and $R^7$ are both deuterium.

In various embodiments of Formula (II), $R^8$ is H or methyl. For example, in an embodiment $R^8$ is H. In another embodiment, $R^8$ is methyl.

In various embodiments, $R^{13}$ is hydrogen or fluoro. For example, in an embodiment of Formula (II), $R^{13}$ is hydrogen as illustrated by the following Formula (IIA):

(IIA)

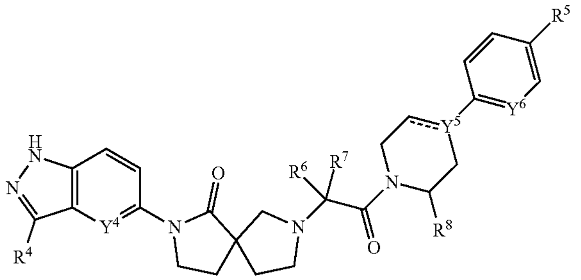

In various embodiments of the Formula (IIA), $R^4$ is a methyloxazolopyridinyl, or a pyridinyl substituted with one or two substituents independently selected from the group consisting of methyl, $C_{1-4}$ alkoxy, isopropylthio, fluoro, chloro, cyano, trifluoromethyl, and —C(=O)$NHCH_3$; or $R^4$ is a dimethylbenzodioxolyl, a methylbenzoxazolyl, or a phenyl substituted with one or two substituents independently selected from the group consisting of methoxy, fluoro, chloro, cyano, trifluoromethyl and —C(=O)$NHCH_3$; and $R^5$ is

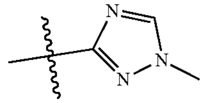

or

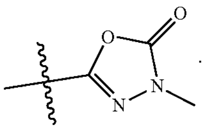

.

Those skilled in the art will recognize that compounds of the Formula (IIA) are compounds of the Formula (II). Therefore, reference herein to variables defined for Formula (II) (such as $R^4$, $R^5$, $R^6$, $R^7$, $R^8$, $R^{13}$, $Y^4$, $Y^5$, and $Y^6$) will also be understood as definitions for the corresponding variables of the Formulae (HA), and vice versa.

In various embodiments of Formula (II), $Y^4$ is N, CH or CF. In an embodiment, $Y^4$ is N. In another embodiment, $Y^4$ is CH. In another embodiment, $Y^4$ is CF.

In various embodiments of Formula (II), $Y^5$ is N, C, CH or CF. The ring structure that includes $Y^5$ can include a double or a single bond from an atom adjacent to $Y^5$, depending on whether $Y^5$ is N, C, CH or CF. For example, in an embodiment, the ------ in the ring structure is a single bond when $Y^5$ is N. In another embodiment, the ------ in the ring structure is a single bond when $Y^5$ is CH. In another embodiment, the ------ in the ring structure is a single bond when $Y^5$ is CF. In another embodiment, the ------ in the ring structure is a double bond when $Y^5$ is C.

In various embodiments of Formula (II), the ring structure that includes $Y^5$ is bonded to a pyridinyl ring or a phenyl ring, and that pyridinyl ring or phenyl ring is bonded to $R^5$. For example, in an embodiment $Y^6$ is N or CH. In an embodiment, $Y^6$ is N. In another embodiment, $Y^6$ is CH.

In various embodiments of Formula (II), when $Y^4$ is CH and $R^5$ is

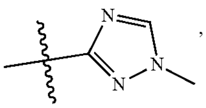 [SMILES: *c1ncn(C)n1]

, then $R^4$ cannot be pyridinyl substituted with a single substituent selected from the group consisting of methyl, methoxy, fluoro, trifluoromethyl and isopropoxy.

In various embodiments of Formula (II), when $Y^4$ is CH, $Y^5$ is C and $R^5$ is

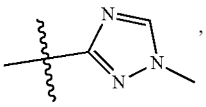 [SMILES: *c1ncn(C)n1]

, then $R^4$ cannot be phenyl substituted with a single substituent selected from the group consisting of fluoro, methoxy and cyano.

In various embodiments of Formula (II), when $Y^4$ is CH, $Y^5$ is C and $R^5$ is

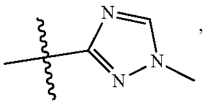

, then $R^4$ cannot be phenyl substituted with both a methoxy and a cyano and $R^4$ cannot be phenyl substituted with both a trifluoromethyl and a cyano In various embodiments of Formula (II), when $Y^4$ is CH, $Y^5$ is C and $R^5$ is

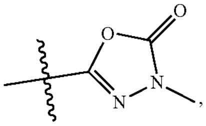

, then $R^4$ cannot be pyridinyl substituted with a single isopropoxy and $R^4$ cannot be phenyl substituted with a single cyano.

In various embodiments of Formula (II), when $Y^4$ is CH, $Y^5$ is C and $R^5$ is

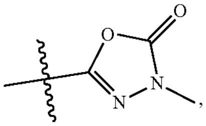 [SMILES: *c1nn(C)c(=O)o1]

, then $R^4$ cannot be phenyl substituted with both a methoxy and a cyano.

In various embodiments of Formula (II), when $Y^4$ is CH, $Y^5$ is C and $R^5$ is

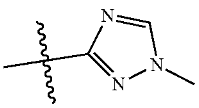

or

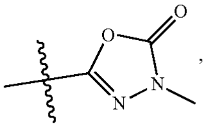 [SMILES: *c1nn(C)c(=O)o1]

, then $R^4$ cannot be a dimethylbenzodioxolyl and $R^4$ cannot be a methylbenzoxazolyl.

In various embodiments, Formula (II) does not represent a compound that is disclosed in International Application No. PCT/US2016/025345, which is hereby incorporated herein by reference in its entirety, including for the purpose of describing compounds that Formula (II) does not represent. For example, in various embodiments, Formula (II) does not represent one or more of the following compounds:
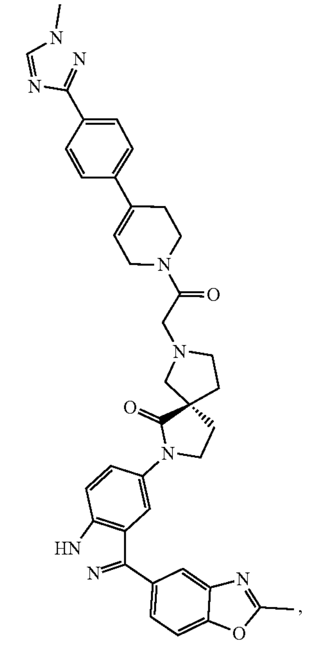
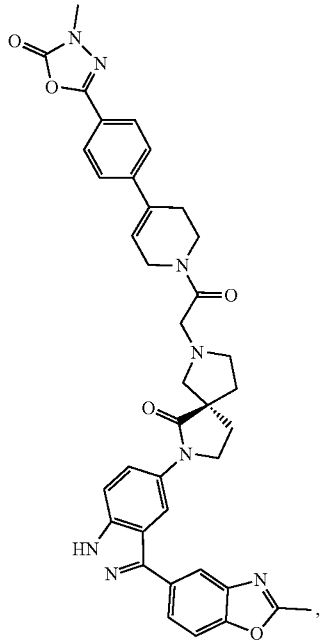
-continued
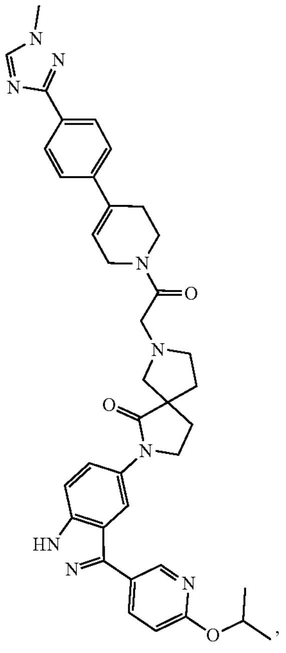
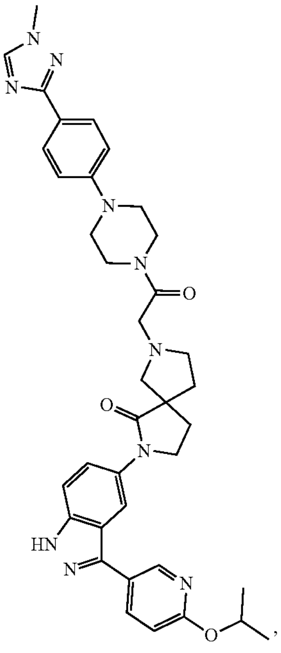
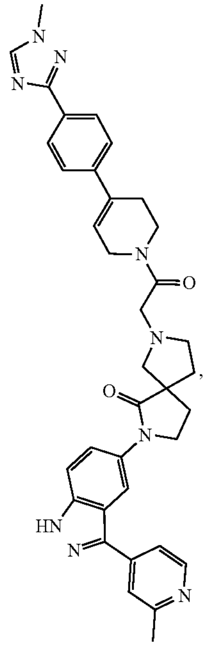
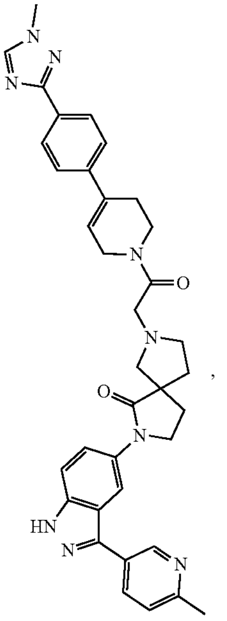

-continued
-continued
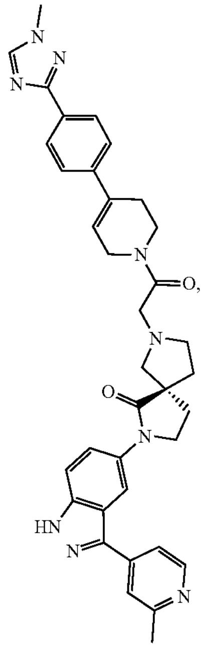
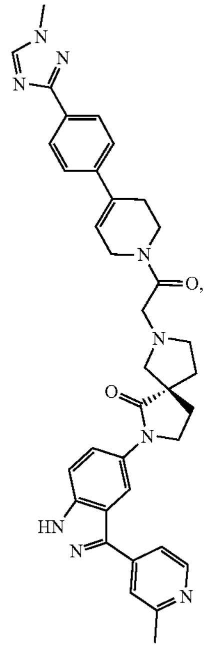
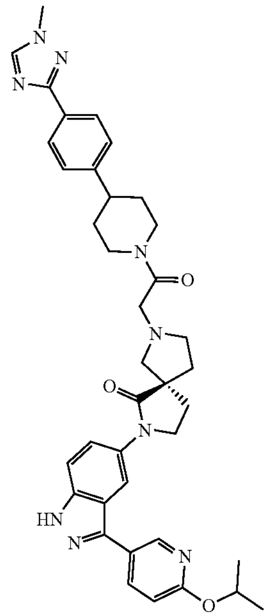
,
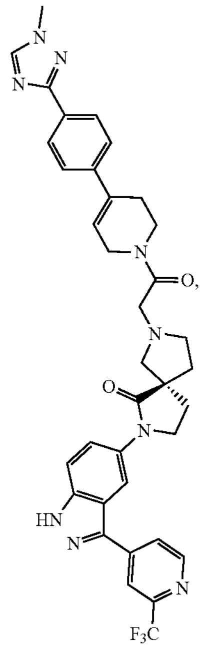
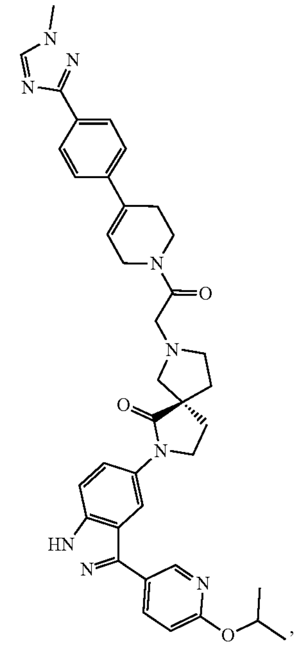
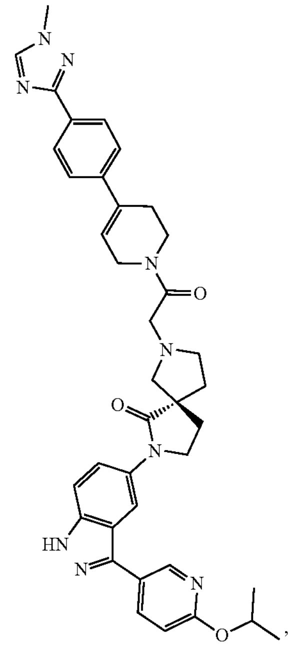
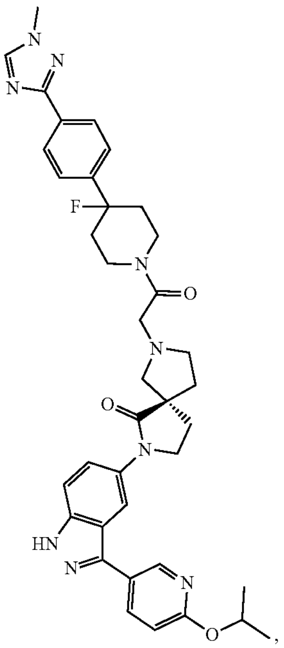
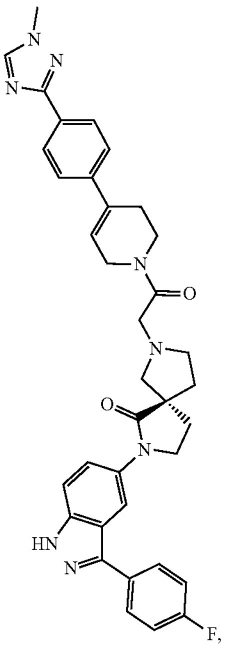

-continued
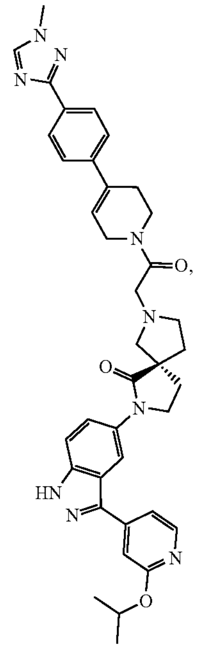
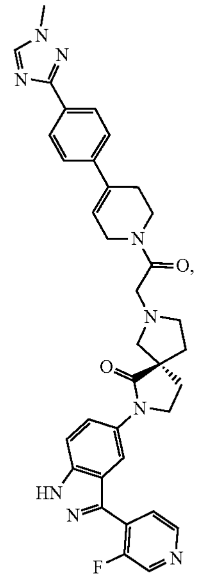
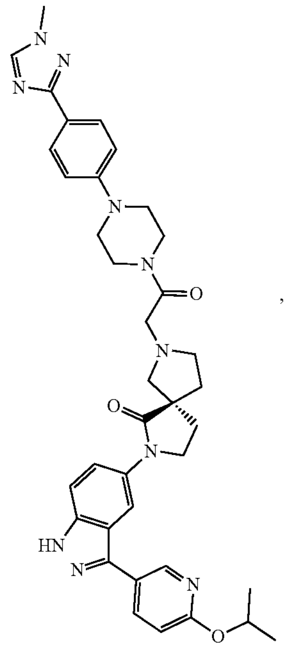
,
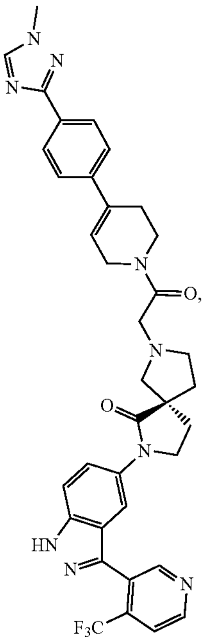
-continued
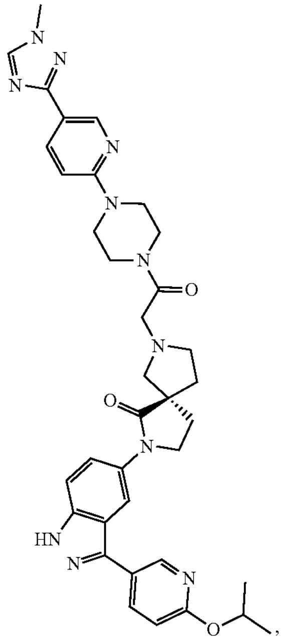
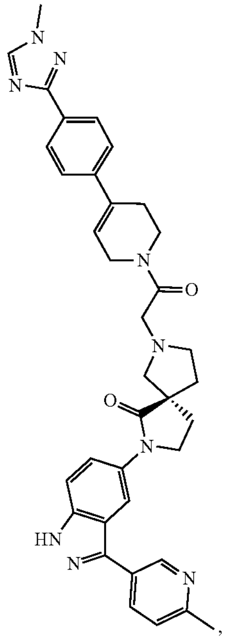
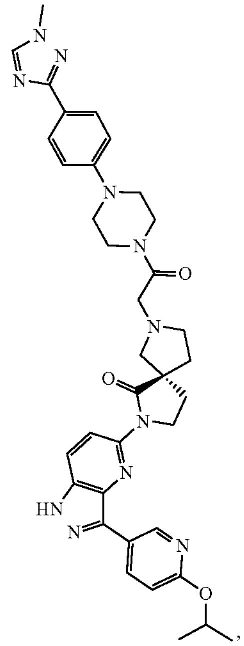
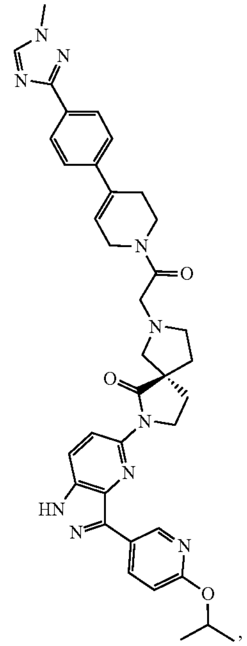

-continued
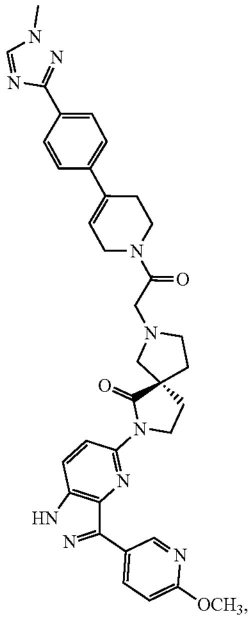
,
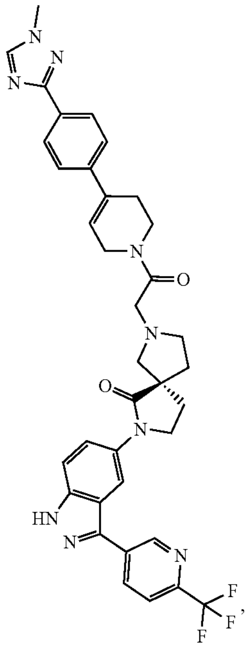
,
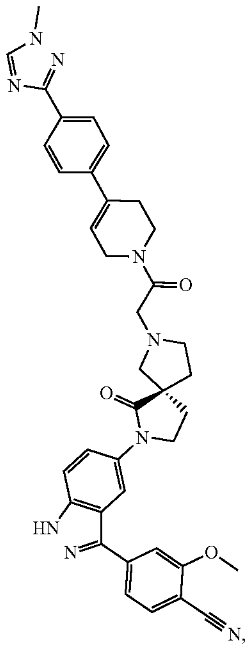
,
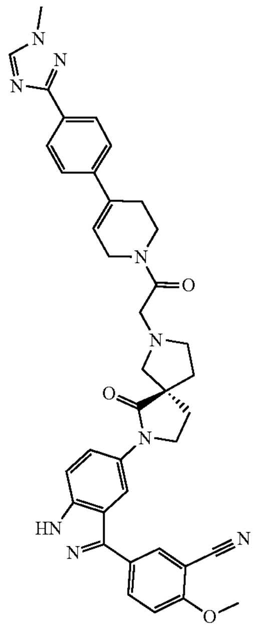
,
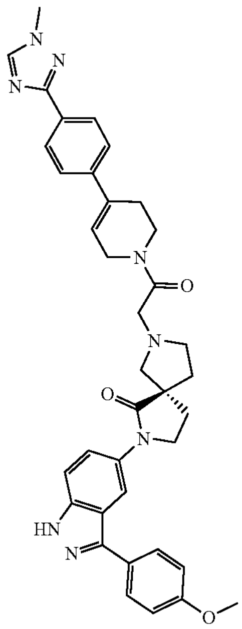
,
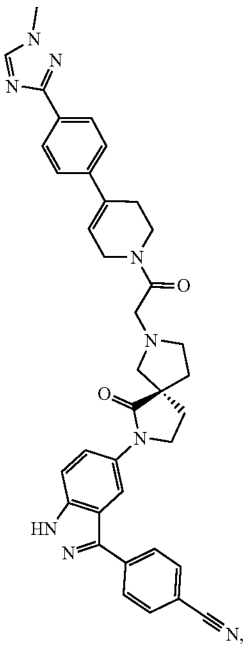
,
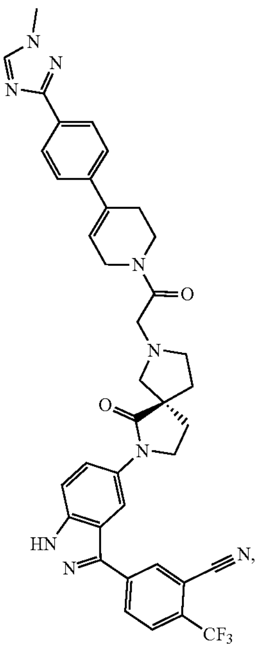
,
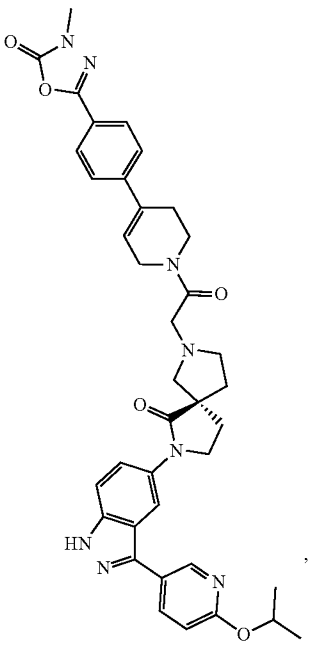
, -continued
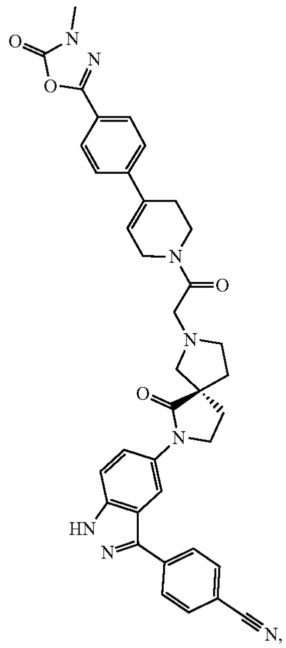
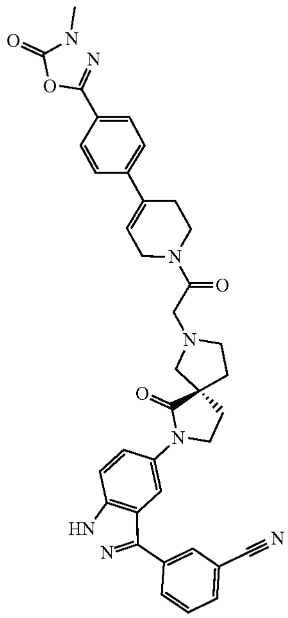
,
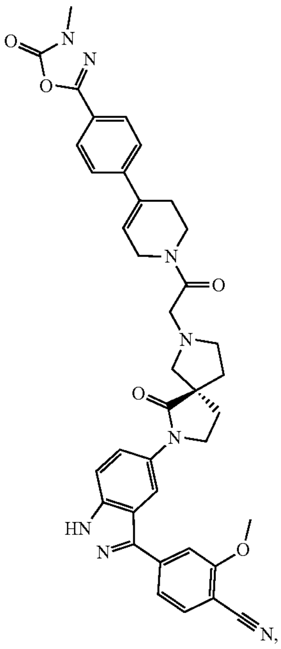
and
-continued
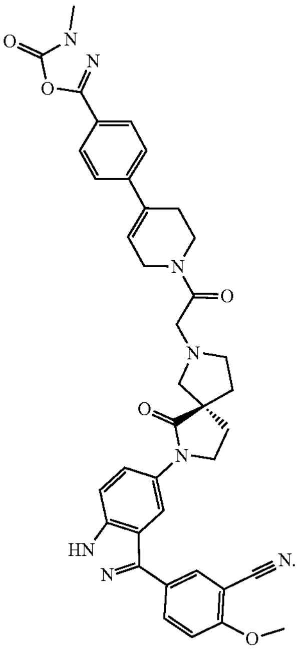 [SMILES: CNC(=O)OC(=N)c1ccc(C2=CCN(C(=O)CN3CC[C@]4(CCN(c5ccc(N)c(C(=N)c6ccc(OC)c(C#N)c6)c5)C4=O)C3)CC2)cc1]
Examples of compounds of Formula (II), or pharmaceutically acceptable salts thereof, include the following:
(IIa)
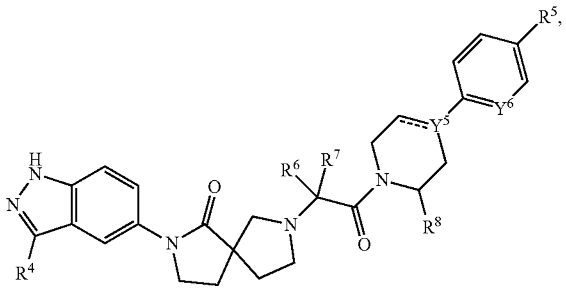
(IIb)
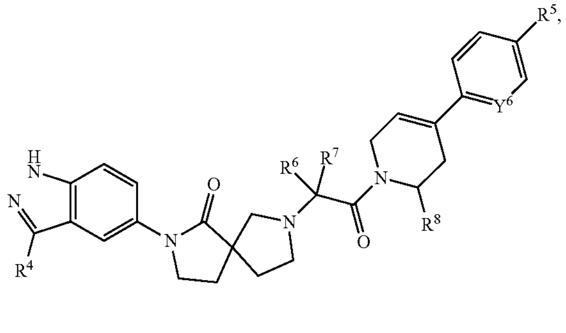

-continued
(IIc)
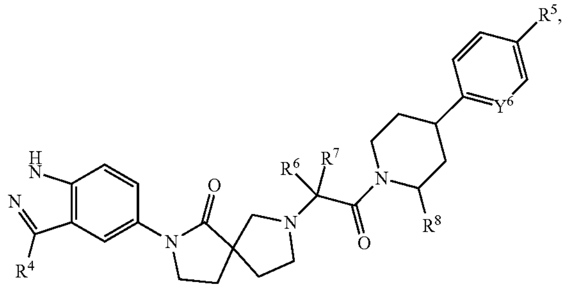
(IId)
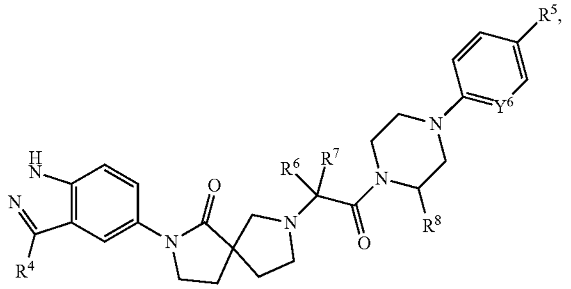
(IIe)
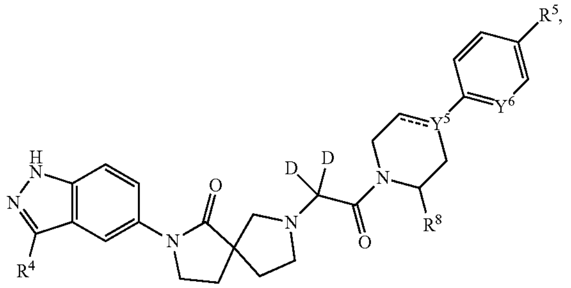
(IIf)
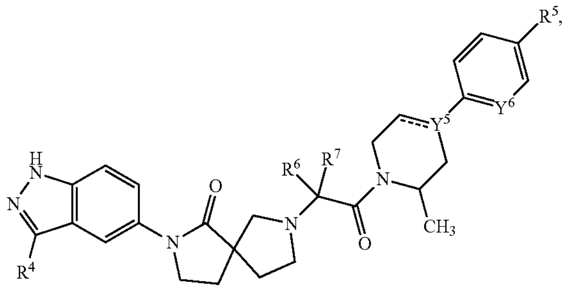
(IIg)
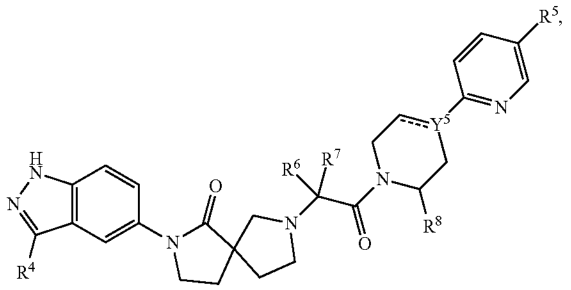
-continued
(IIh)
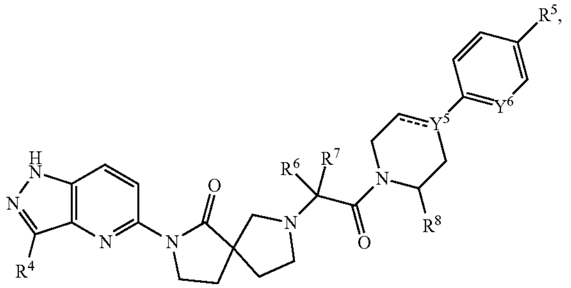
(IIi)
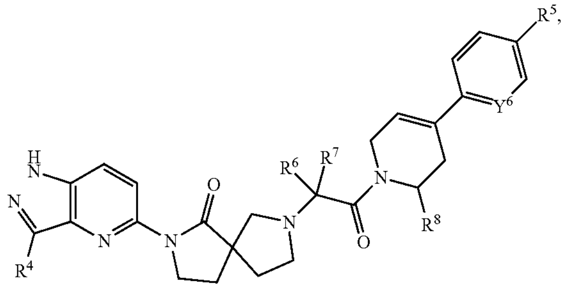
(IIj)
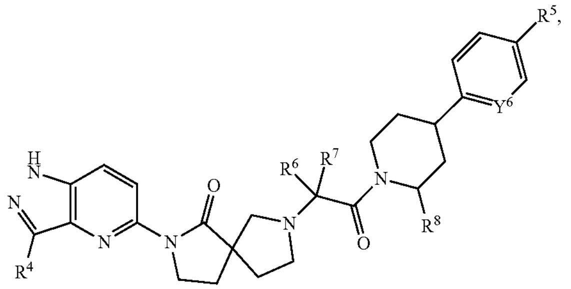
(IIk)
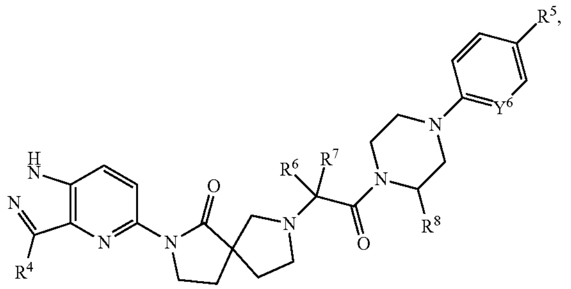
(IIl)
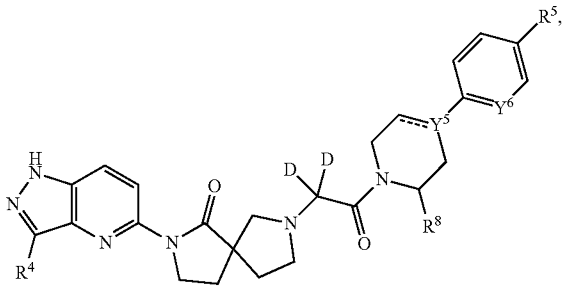

-continued
(IIm)
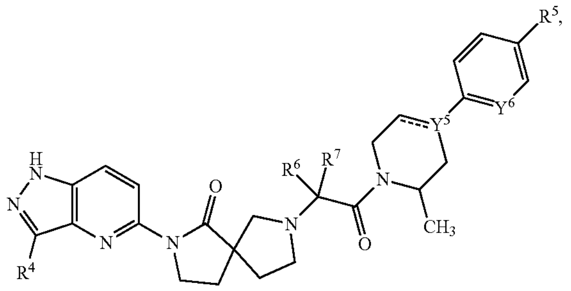
(IIn)
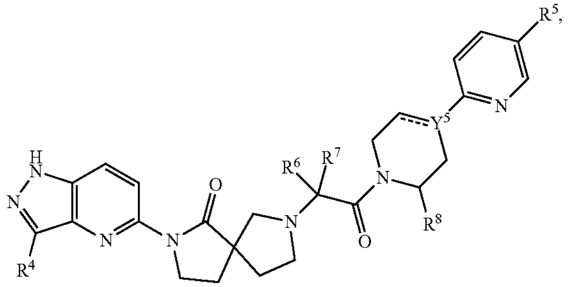
or a pharmaceutically acceptable salt of the foregoing.
Examples of compounds of Formula (II) include, but are not limited to, the following:
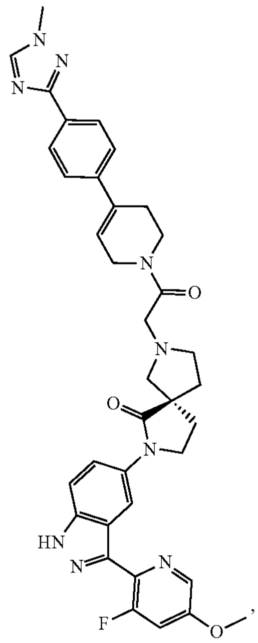
,
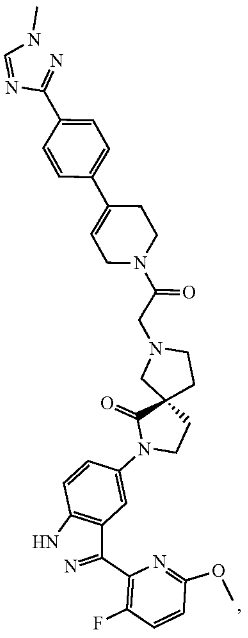
,
-continued
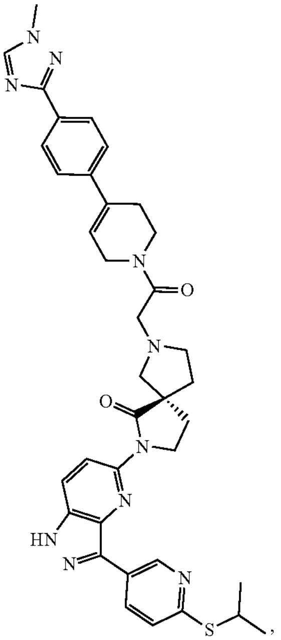
,
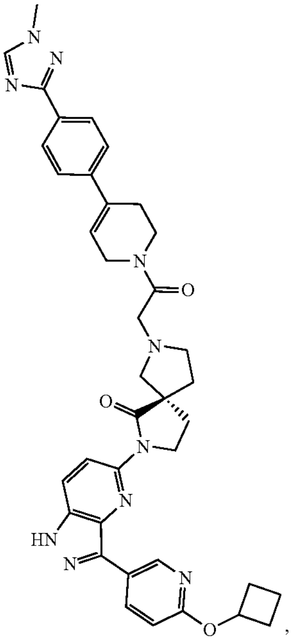
,
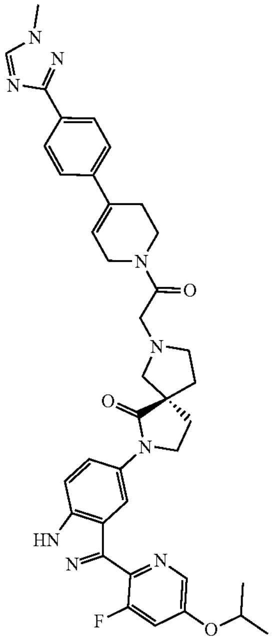
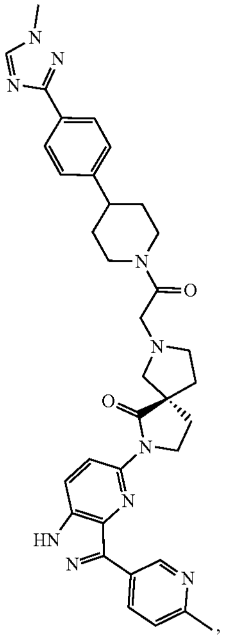
, -continued
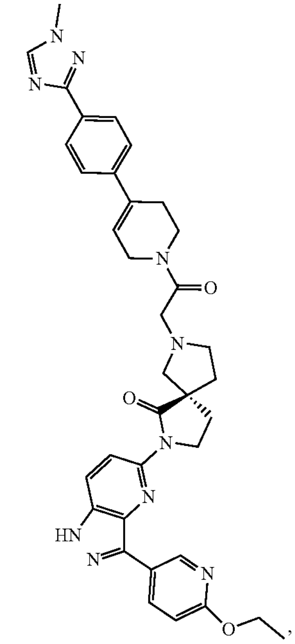
,
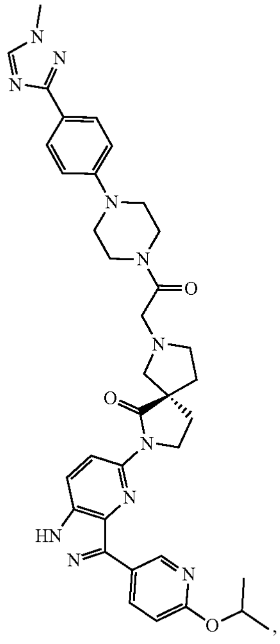
,
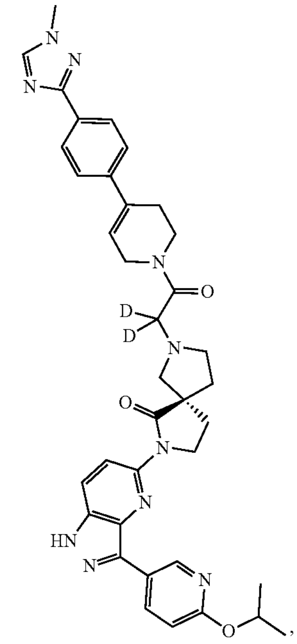
,
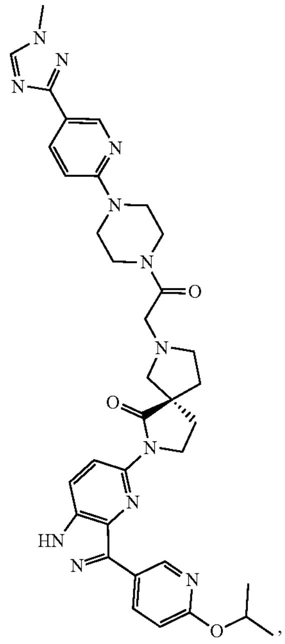
,
-continued
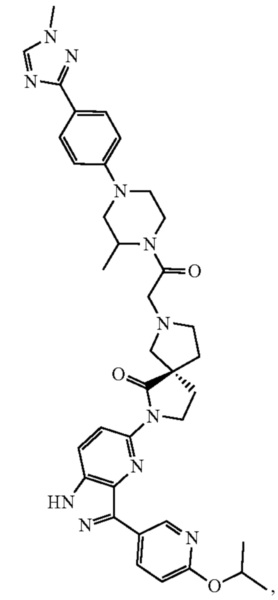
,
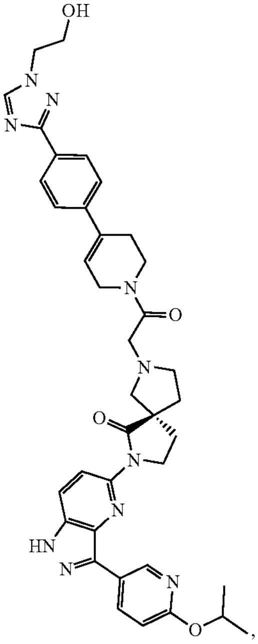
,
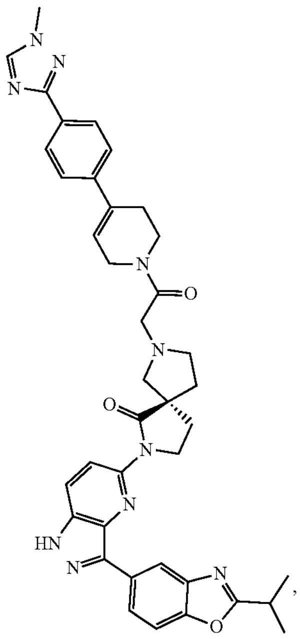
,
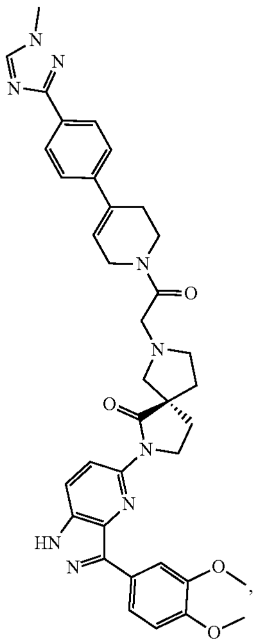
,

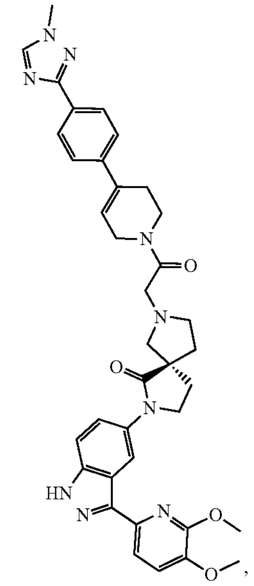
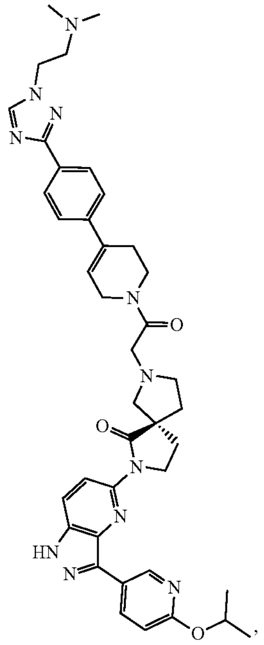
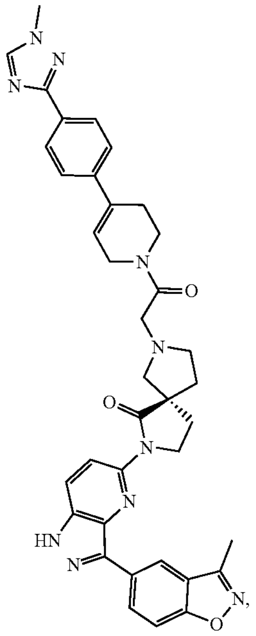
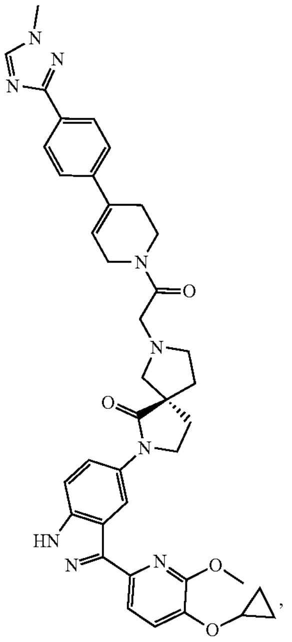
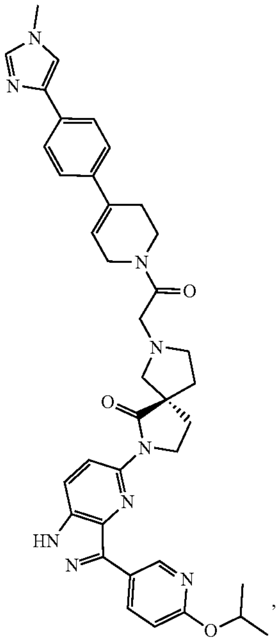
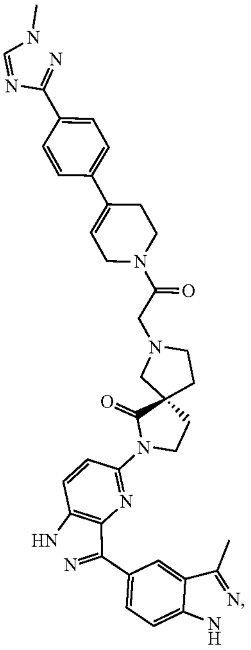
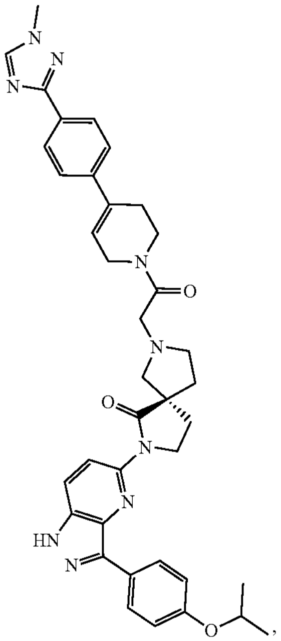
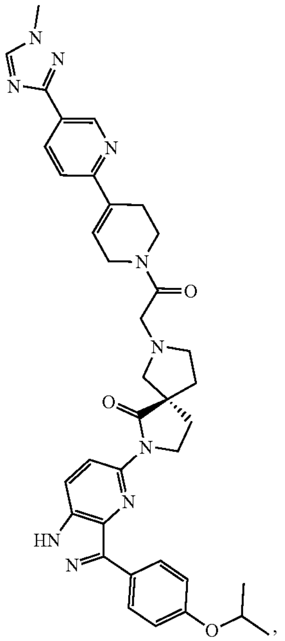

-continued
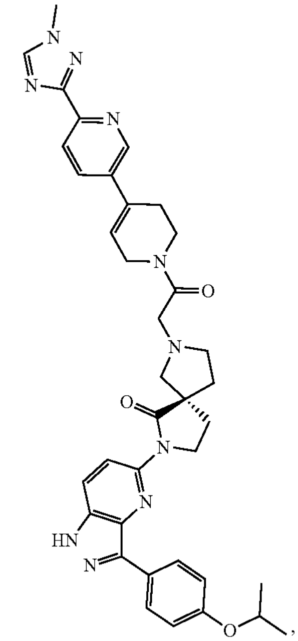
,
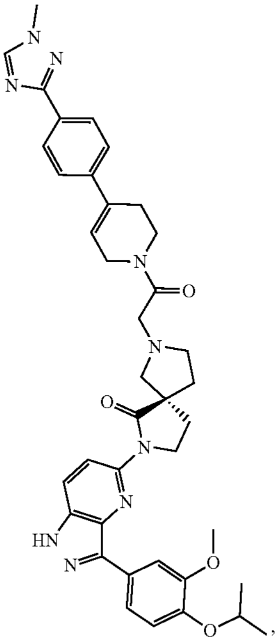
,
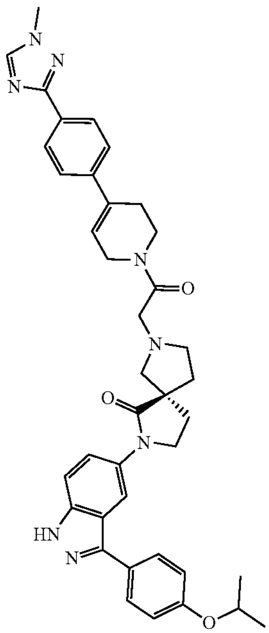
,
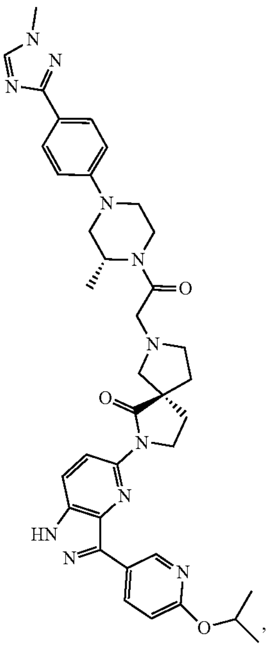
,
-continued
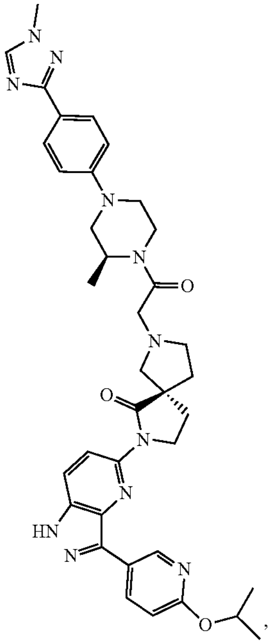
,
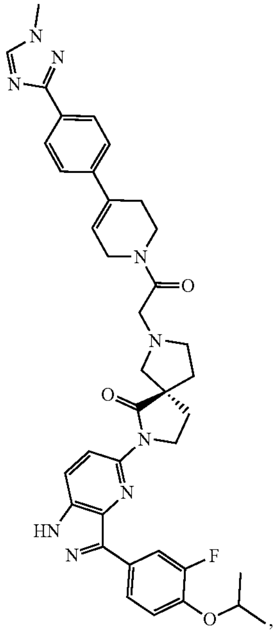
,
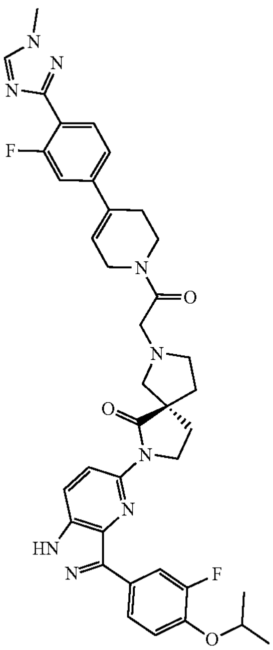
, and -continued
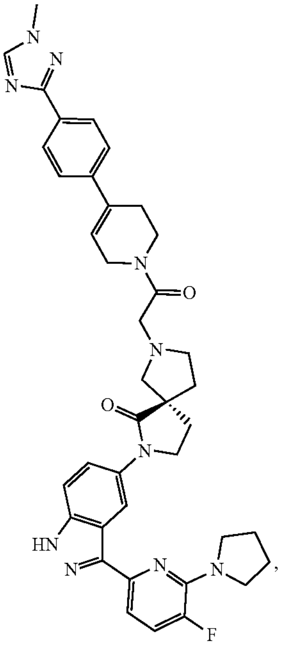
,
or a pharmaceutically acceptable salt of the foregoing.
Examples of compounds of Formula (IIA) (which are also compounds of the Formula (II)) include, but are not limited to, the following:
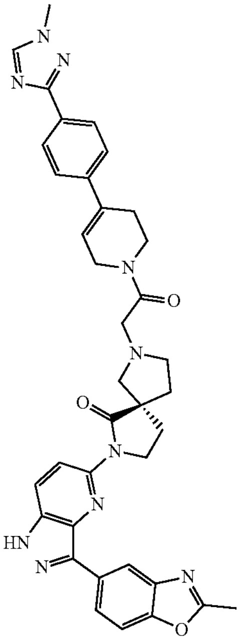
,
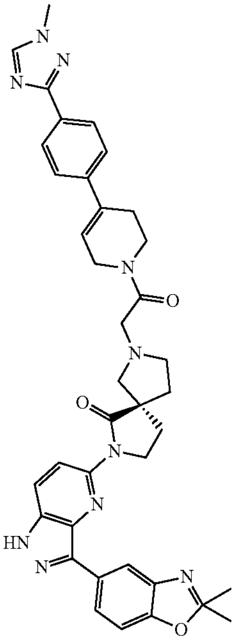
,
-continued
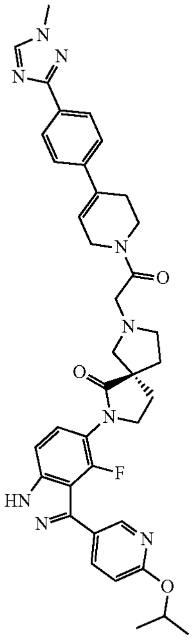
,
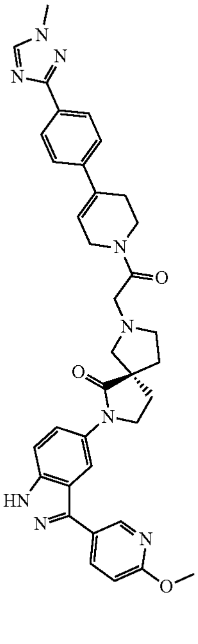
,
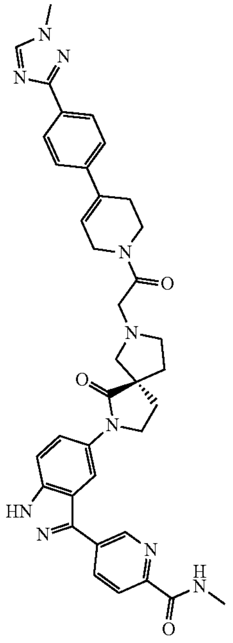
,
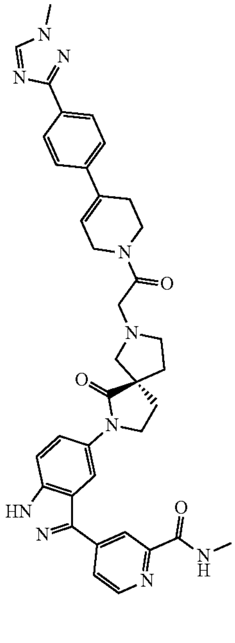
, -continued
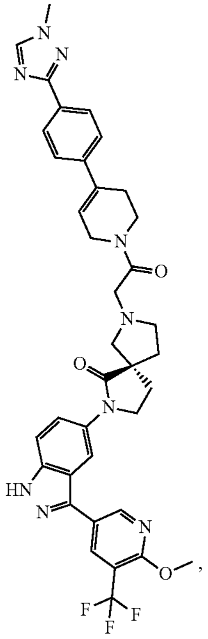
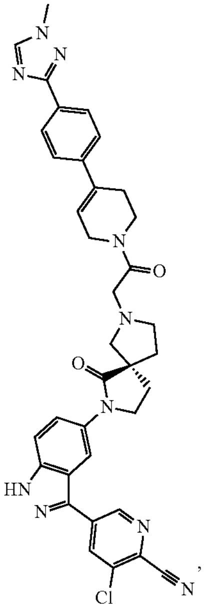
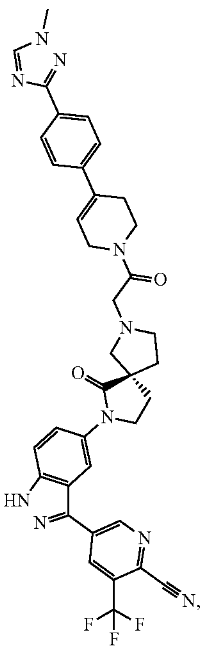
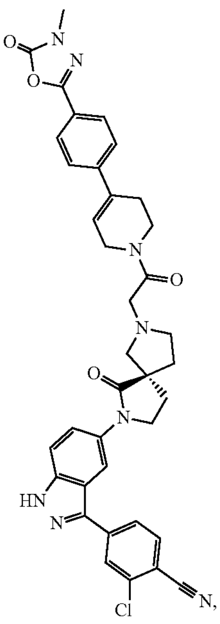
-continued
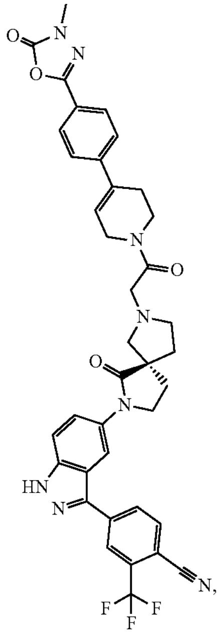
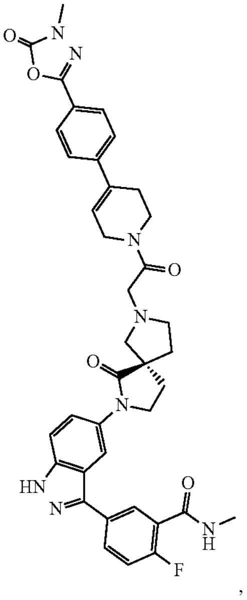
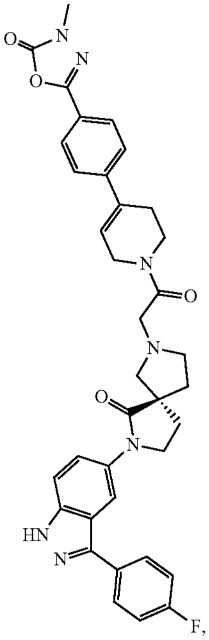
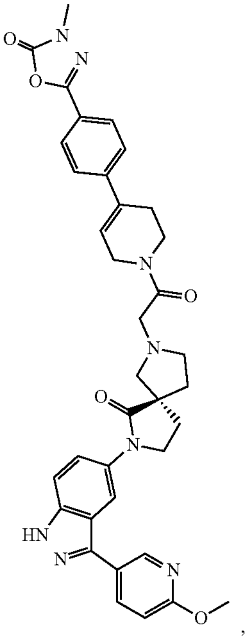

-continued
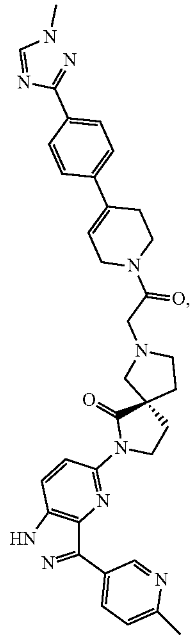
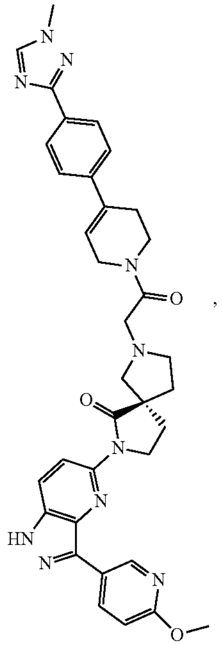
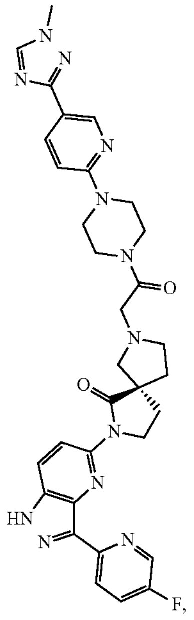
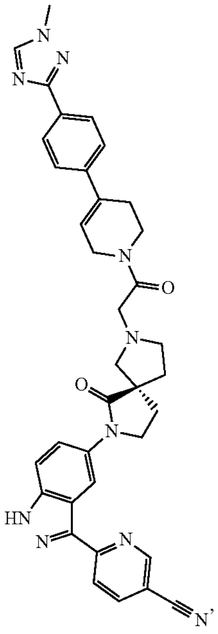
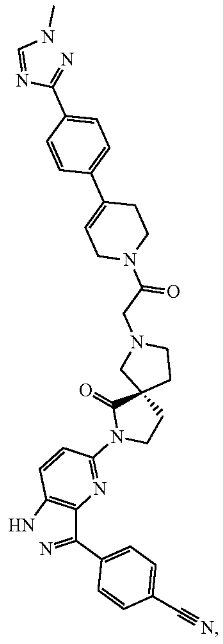
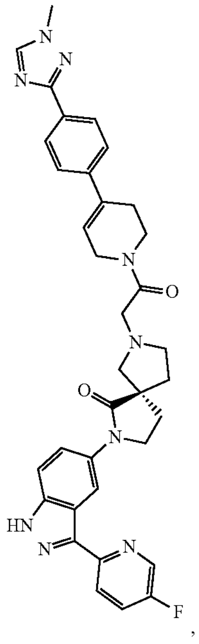
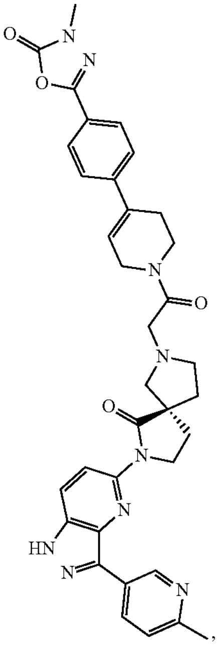
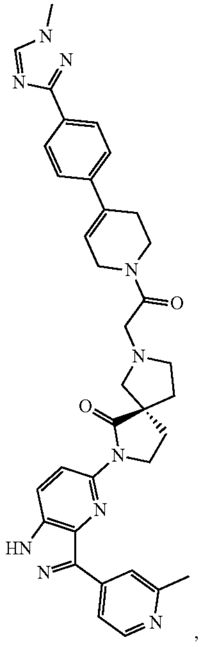

-continued
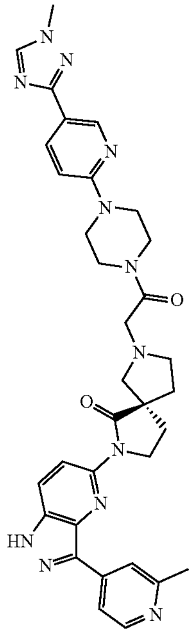,
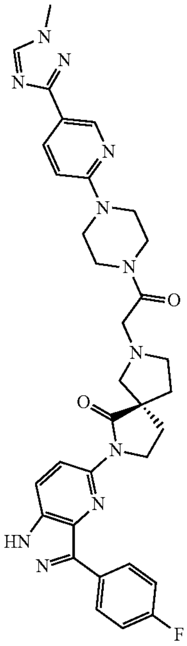,
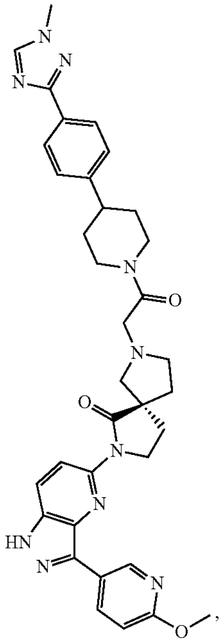,
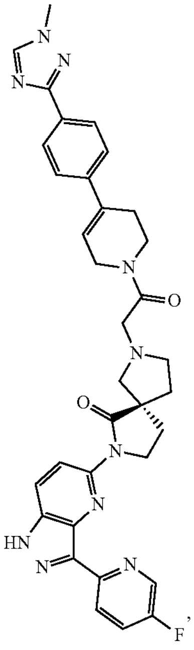,
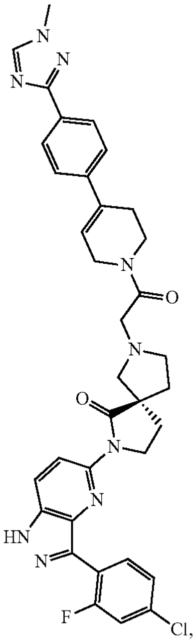
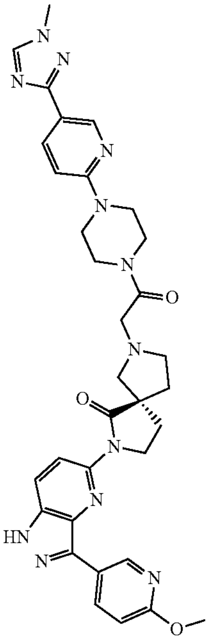,
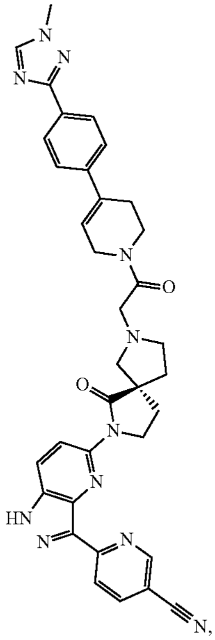
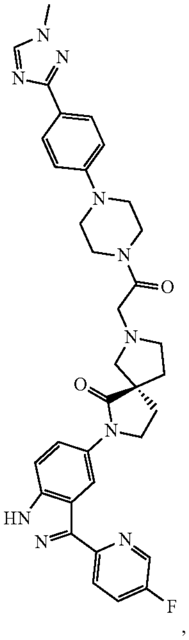,
-continued -continued

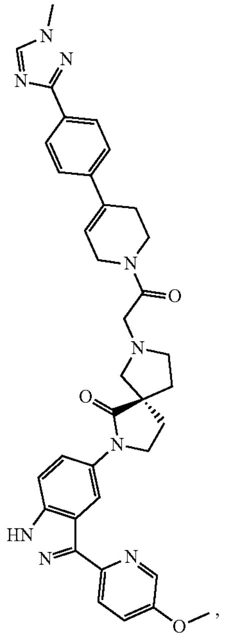
,

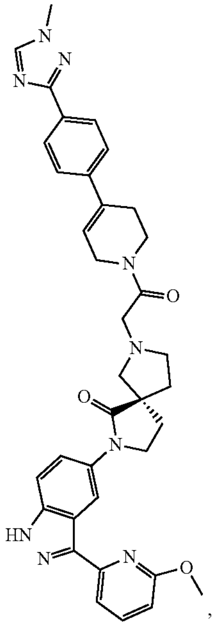
,

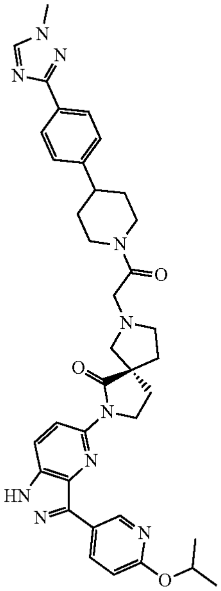
,

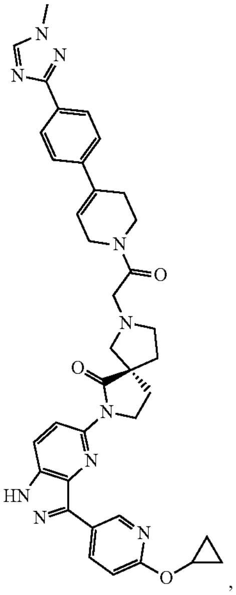
,

-continued

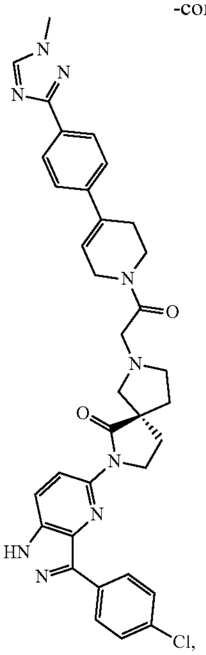
,

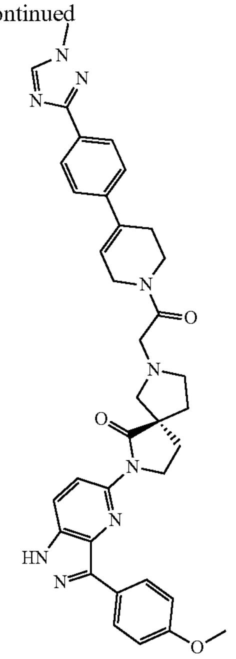
, or a pharmaceutically acceptable salt of the foregoing.

Further examples of compounds of Formula (II) include, but are not limited to, the compounds described in Example 121 below.

Formula (III)

Some embodiments disclosed herein relate to a compound of Formula (III), or a pharmaceutically acceptable salt thereof, having the structure:

(III)

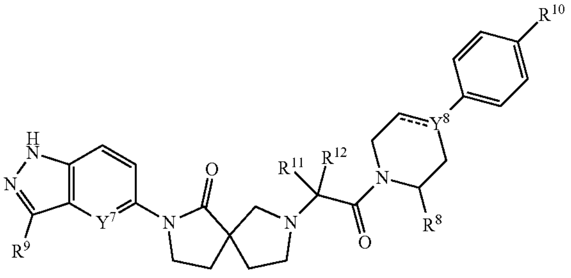

In various embodiments of Formula (III), $R^9$ can be a heterocyclyl selected from piperidinyl, 1,1-dioxidotetrahydrothiopyranyl, pyrrolidinyl, tetrahydrofuranyl, tetrahydropyranyl, dihydropyranyl, 2-oxaazaspiro[3.5]nonanyl, and morpholino. In some embodiments, the heterocyclyl can be optionally substituted with one or two substituents selected from methyl, fluoro and trifluoroethyl.

In an embodiment of Formula (III), $R^9$ is piperidinyl. In another embodiment, $R^9$ is piperidinyl substituted with a methyl. In another embodiment, $R^9$ is piperidinyl substituted with a fluoro. In another embodiment, $R^9$ is piperidinyl substituted with a trifluoroethyl. In an embodiment, $R^9$ is piperidinyl substituted with two substituents selected from methyl, fluoro and trifluoroethyl. In an embodiment, $R^9$ is piperidinyl substituted with two substituents that are the same. In an embodiment, $R^9$ is piperidinyl substituted with two substituents that are different.

In an embodiment of Formula (III), $R^9$ is 1,1-dioxidotetrahydrothiopyranyl. In another embodiment, $R^9$ is 1,1-dioxidotetrahydrothiopyranyl substituted with a methyl. In another embodiment, $R^9$ is 1,1-dioxidotetrahydrothiopyranyl substituted with a fluoro. In another embodiment, $R^9$ is 1,1-dioxidotetrahydrothiopyranyl substituted with a trifluoroethyl. In an embodiment, $R^9$ is 1,1-dioxidotetrahydrothiopyranyl substituted with two substituents selected from methyl, fluoro and trifluoroethyl. In an embodiment, $R^9$ is 1,1-dioxidotetrahydrothiopyranyl substituted with two substituents that are the same. In an embodiment, $R^9$ is 1,1-dioxidotetrahydrothiopyranyl substituted with two substituents that are different.

In an embodiment of Formula (III), $R^9$ is pyrrolidinyl. In another embodiment, $R^9$ is pyrrolidinyl substituted with a methyl. In another embodiment, $R^9$ is pyrrolidinyl substituted with a fluoro. In another embodiment, $R^9$ is pyrrolidinyl substituted with a trifluoroethyl. In an embodiment, $R^9$ is pyrrolidinyl substituted with two substituents selected from methyl, fluoro and trifluoroethyl. In an embodiment, $R^9$ is pyrrolidinyl substituted with two substituents that are the same. In an embodiment, $R^9$ is pyrrolidinyl substituted with two substituents that are different.

In an embodiment of Formula (III), $R^9$ is tetrahydrofuranyl. In another embodiment, $R^9$ is tetrahydrofuranyl substituted with a methyl. In another embodiment, $R^9$ is tetrahydrofuranyl substituted with a fluoro. In another embodiment, $R^9$ is tetrahydrofuranyl substituted with a trifluoroethyl. In an embodiment, $R^9$ is tetrahydrofuranyl substituted with two substituents selected from methyl, fluoro and trifluoroethyl. In an embodiment, $R^9$ is tetrahydrofuranyl substituted with two substituents that are the same. In an embodiment, $R^9$ is tetrahydrofuranyl substituted with two substituents that are different.

In an embodiment of Formula (III), $R^9$ is tetrahydropyranyl. In another embodiment, $R^9$ is tetrahydropyranyl substituted with a methyl. In another embodiment, $R^9$ is tetrahydropyranyl substituted with a fluoro. In another embodiment, $R^9$ is tetrahydropyranyl substituted with a trifluoroethyl. In an embodiment, $R^9$ is tetrahydropyranyl substituted with two substituents selected from methyl, fluoro and trifluoroethyl. In an embodiment, $R^9$ is tetrahydropyranyl substituted with two substituents that are the same. In an embodiment, $R^9$ is tetrahydropyranyl substituted with two substituents that are different.

In an embodiment of Formula (III), $R^9$ is dihydropyranyl. In another embodiment, $R^9$ is dihydropyranyl substituted with a methyl. In another embodiment, $R^9$ is dihydropyranyl substituted with a fluoro. In another embodiment, $R^9$ is dihydropyranyl substituted with a trifluoroethyl. In an embodiment, $R^9$ is dihydropyranyl substituted with two substituents selected from methyl, fluoro and trifluoroethyl. In an embodiment, $R^9$ is dihydropyranyl substituted with two substituents that are the same. In an embodiment, $R^9$ is dihydropyranyl substituted with two substituents that are different.

In an embodiment of Formula (III), $R^9$ is 2-oxaazaspiro[3.5]nonanyl. In another embodiment, $R^9$ is 2-oxaazaspiro[3.5]nonanyl substituted with a methyl. In another embodiment, $R^9$ is 2-oxaazaspiro[3.5]nonanyl substituted with a fluoro. In another embodiment, $R^9$ is 2-oxaazaspiro[3.5]nonanyl substituted with a trifluoroethyl. In an embodiment, $R^9$ is 2-oxaazaspiro[3.5]nonanyl substituted with two substituents selected from methyl, fluoro and trifluoroethyl. In an embodiment, $R^9$ is 2-oxaazaspiro[3.5]nonanyl substituted with two substituents that are the same. In an embodiment, $R^9$ is 2-oxaazaspiro[3.5]nonanyl substituted with two substituents that are different.

In an embodiment of Formula (III), $R^9$ is morpholino. In another embodiment, $R^9$ is morpholino substituted with a methyl. In another embodiment, $R^9$ is morpholino substituted with a fluoro. In another embodiment, $R^9$ is morpholino substituted with a trifluoroethyl. In an embodiment, $R^9$ is morpholino substituted with two substituents selected from methyl, fluoro and trifluoroethyl. In an embodiment, $R^9$ is morpholino substituted with two substituents that are the same. In an embodiment, $R^9$ is morpholino substituted with two substituents that are different.

In an embodiment of Formula (III), $R^9$ is a five-membered heteroaryl selected from the group consisting of thiazolyl, pyrazolyl, and triazolyl. In various embodiments the five-membered heteroaryl is substituted with methyl or isopropyl. In an embodiment, $R^9$ is a methylthiazolyl. In an embodiment, $R^9$ is a isopropylthiazolyl. In an embodiment, $R^9$ is a methyl pyrazolyl. In an embodiment, $R^9$ is a isopropylpyrazolyl. In an embodiment, $R^9$ is a methyltriazolyl. In an embodiment, $R^9$ is a isopropyltriazolyl.

In an embodiment of Formula (III), $R^9$ is a

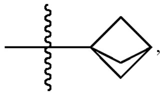, a 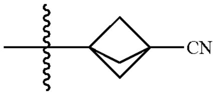

or a

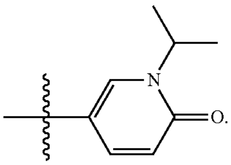 [SMILES: *c1ccc(=O)n(C(C)C)c1]

In various embodiments of Formula (III), $R^{10}$ is

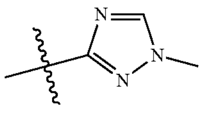 or 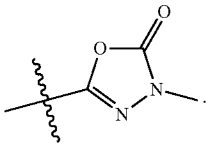 [SMILES: *c1nn(C)c(=O)o1]

For example, in an embodiment $R^{10}$ is

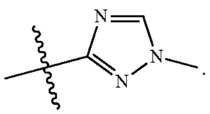 [SMILES: *c1ncn(C)n1]

In another embodiment, $R^{10}$ is

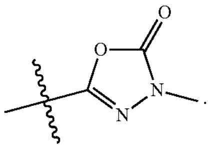

In various embodiments of Formula (III), $R^{11}$ and $R^{12}$ are each independently hydrogen or deuterium. For example, in an embodiment, $R^{11}$ and $R^{12}$ are both hydrogen. In another embodiment, $R^{11}$ and $R^{12}$ are both deuterium.

In various embodiments of Formula (III), $Y^7$ is N or CH. In an embodiment, $Y^7$ is N. In another embodiment, $Y^7$ is CH.

In various embodiments of Formula (III), $Y^8$ is N, C, or CH. The ring structure that includes $Y^8$ can include a double or a single bond from an atom adjacent to $Y^8$, depending on whether Y is N, C, or CH. For example, in an embodiment, the ------ in the ring structure is a single bond when $Y^8$ is N. In another embodiment, the ------ in the ring structure is a single bond when $Y^8$ is CH. In another embodiment, the ------ in the ring structure is a double bond when $Y^8$ is C.

In various embodiments of Formula (III), when $Y^7$ is CH, $Y^8$ is C and $R^{10}$

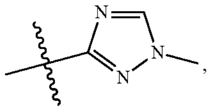

then $R^9$ cannot be tetrahydropyranyl, dihydropyranyl, methylpyrazolyl or morpholino.

In various embodiments of Formula (III), when $Y^7$ is CH, $Y^8$ is C and $R^{10}$ is

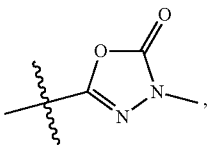 [SMILES: *c1nn(C)c(=O)o1]

then $R^9$ cannot be tetrahydropyranyl or morpholino.

In various embodiments, Formula (III) does not represent a compound that is disclosed in International Application No. PCT/US2016/025345, which is hereby incorporated herein by reference in its entirety, including for the purpose of describing compounds that Formula (III) does not represent. For example, in various embodiments, Formula (III) does not represent one or more of the following compounds:

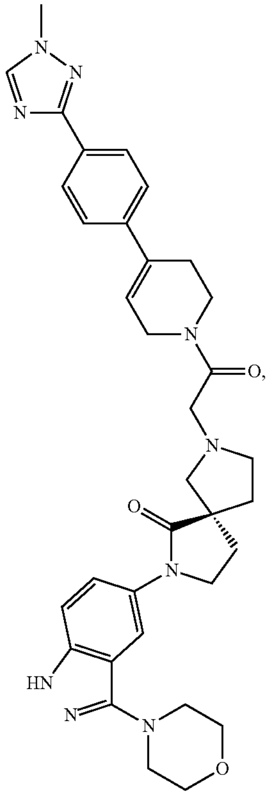

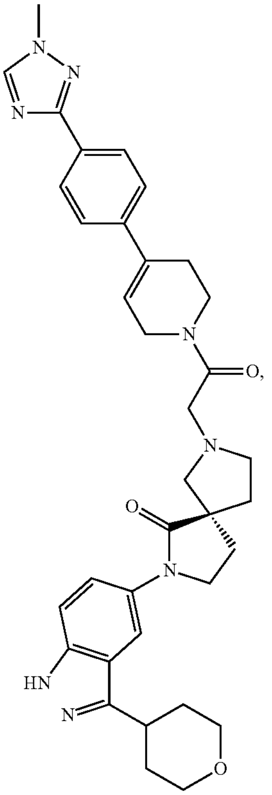

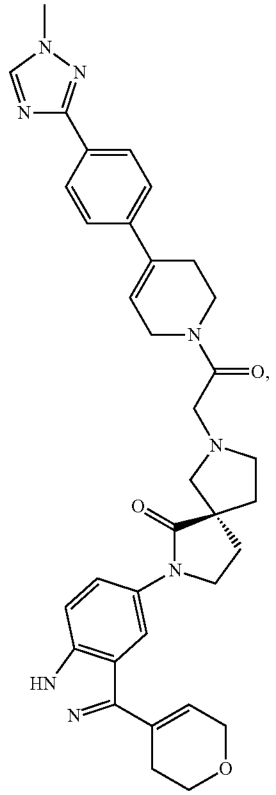

-continued
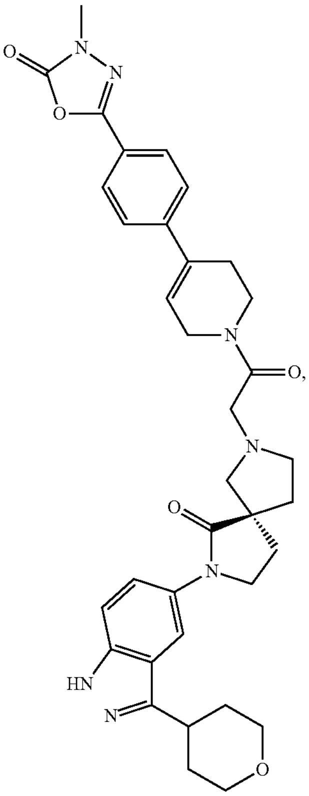
,
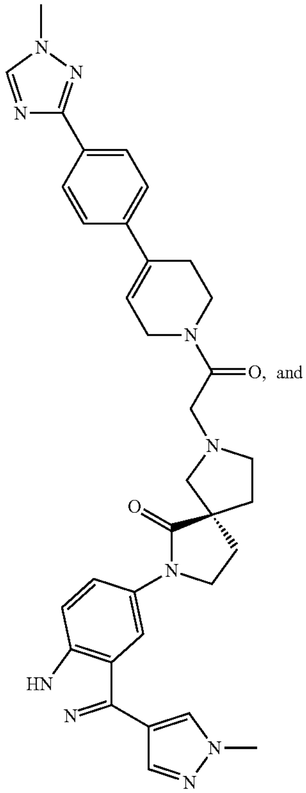
, and
-continued
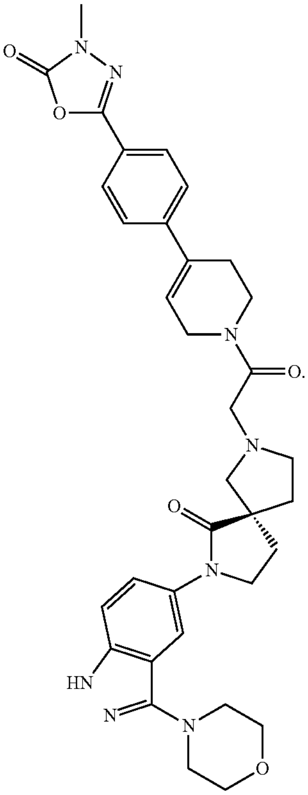 [SMILES: Cn1nc(-c2ccc(C3=CCN(C(=O)CN4CC[C@]5(CCN(c6ccc(N)c(C(=N)N7CCOCC7)c6)C5=O)C4)CC3)cc2)oc1=O]
.
Examples of compounds of Formula (II), or pharmaceutically acceptable salts thereof, include the following:
(IIIa)
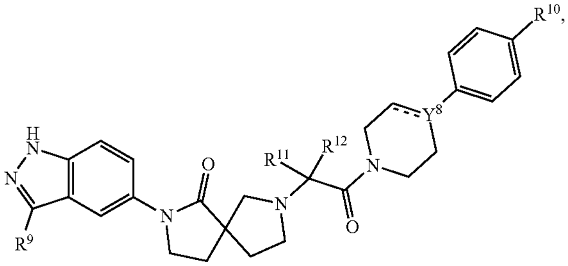
,
(IIIb)
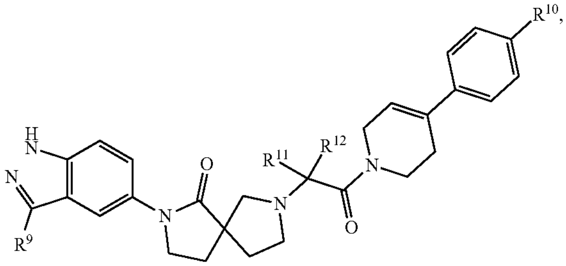
, -continued
(IIIc)
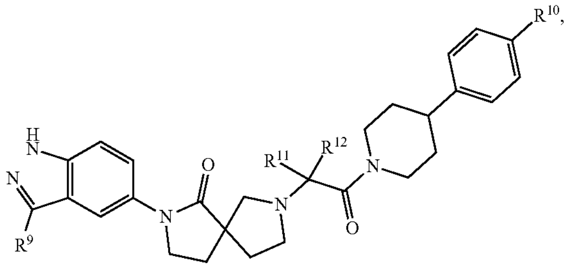
(IIId)
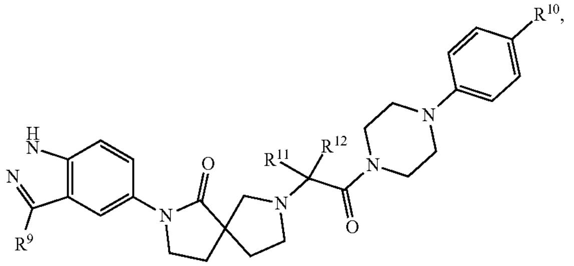
(IIIe)
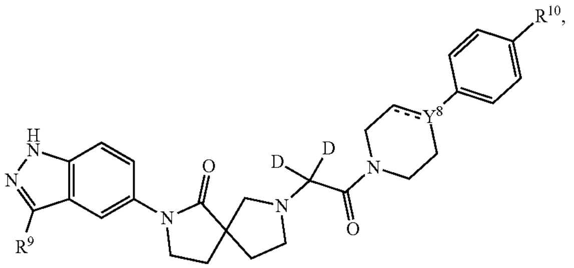
(IIIf)
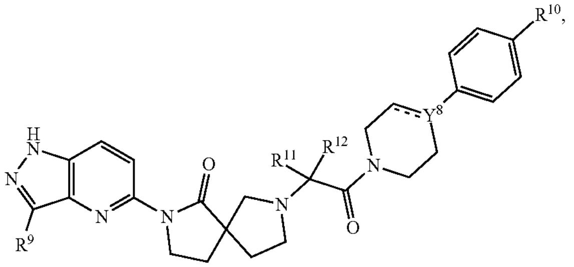
(IIIg)
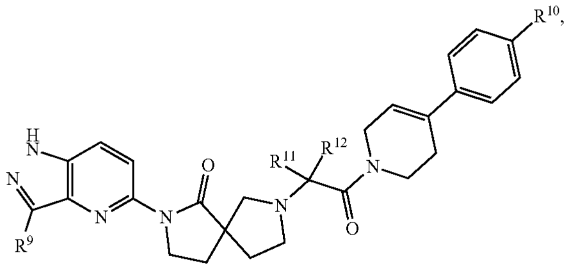
-continued
(IIIh)
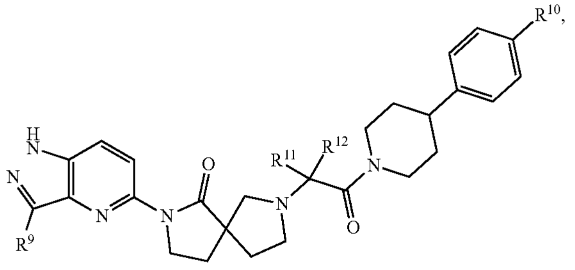
(IIIi)
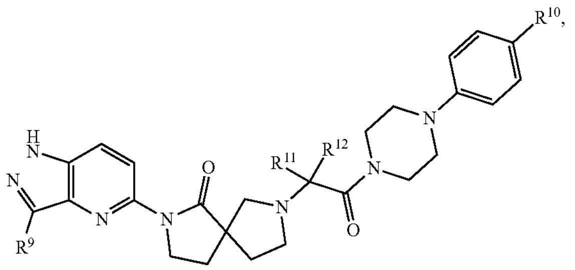
(IIIj)
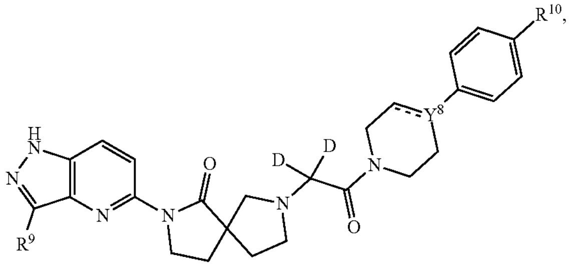
or a pharmaceutically acceptable salt of the foregoing.
Examples of compounds of Formula (III), or pharmaceutically acceptable salts thereof, include the following:
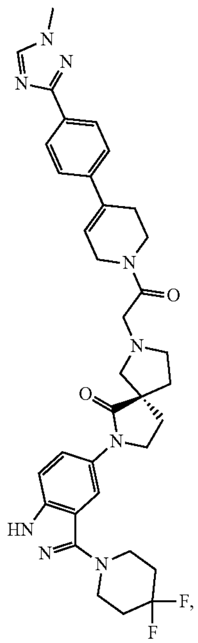
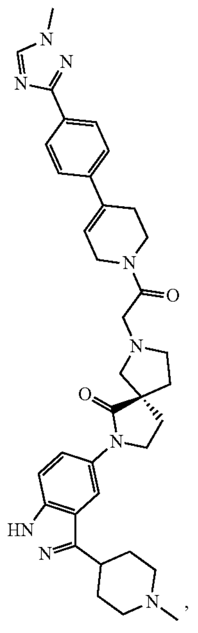

-continued
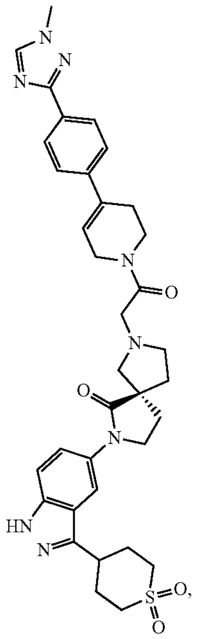
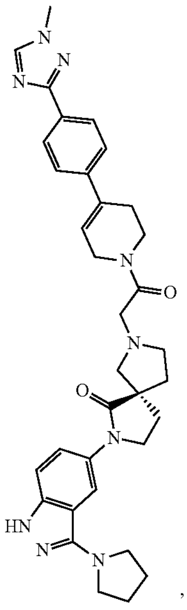
,
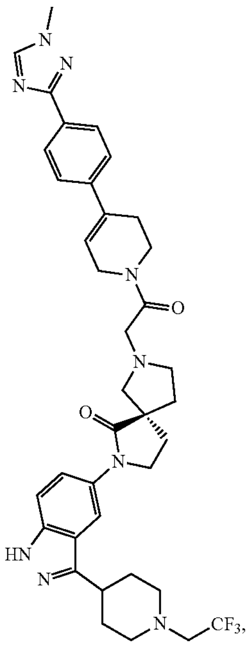
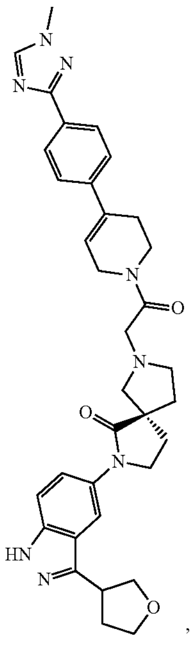
,
-continued
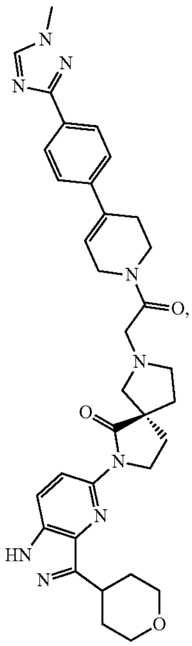
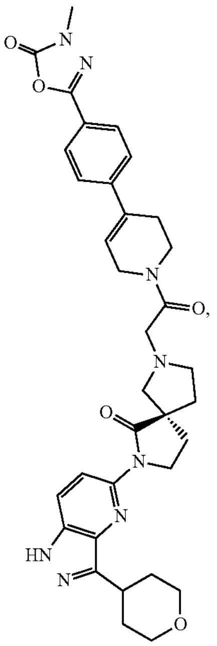
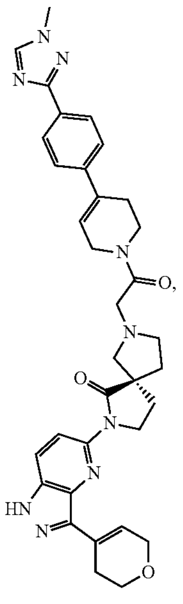
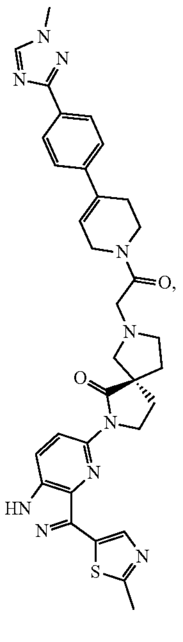

-continued
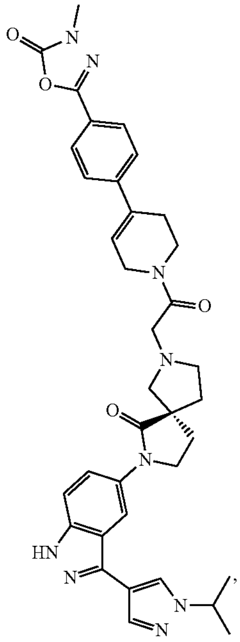,
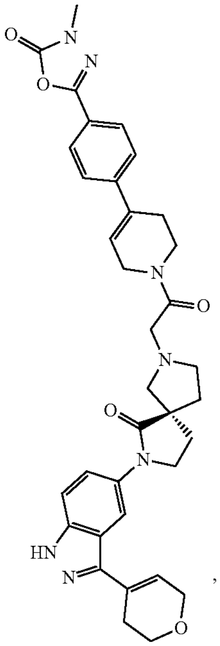,
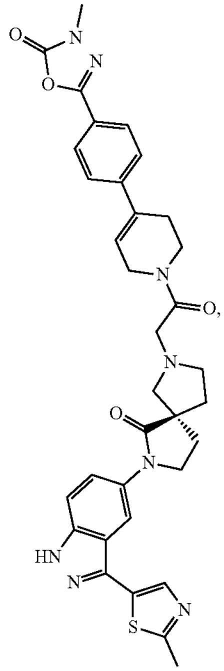
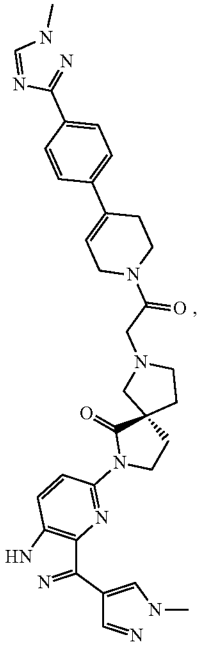
-continued
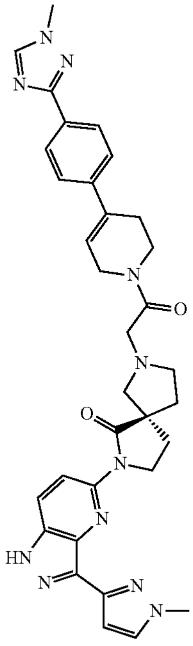,
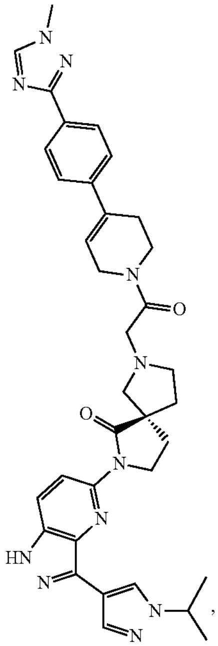,
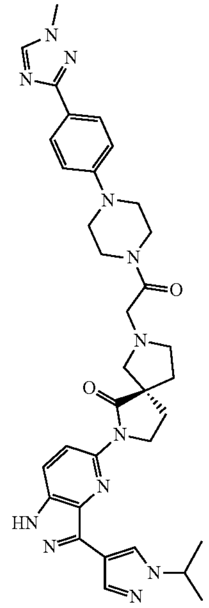,
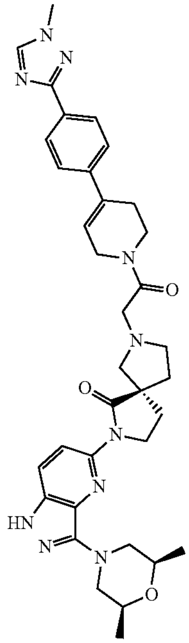, -continued
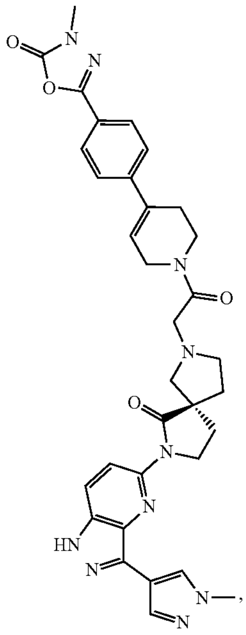
,
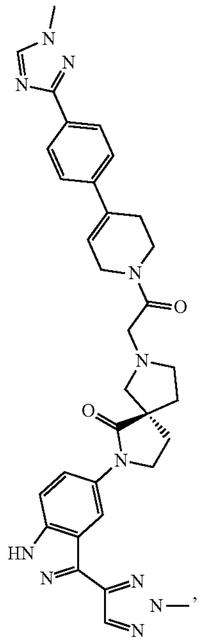
,
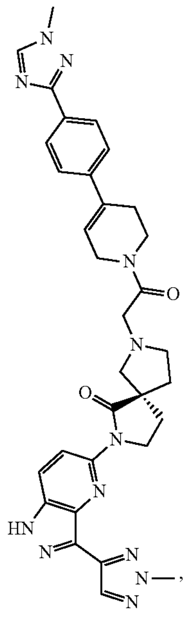
,
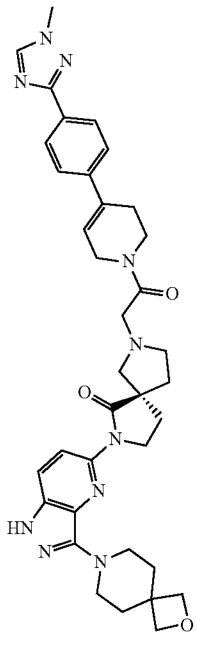
,
-continued
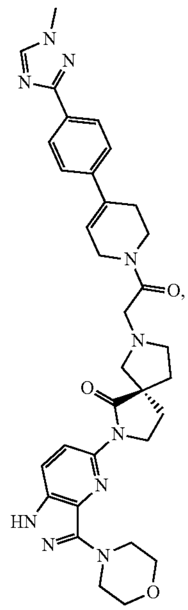
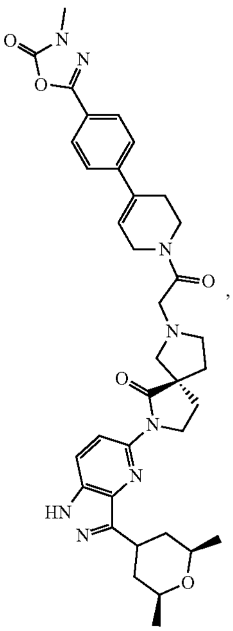
,
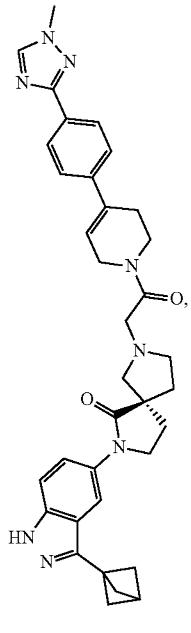
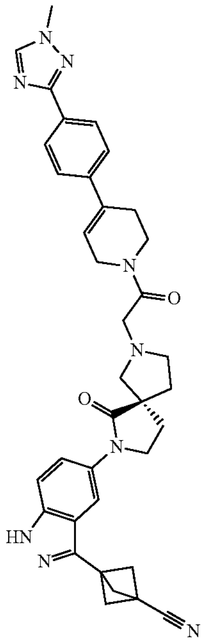
, and -continued

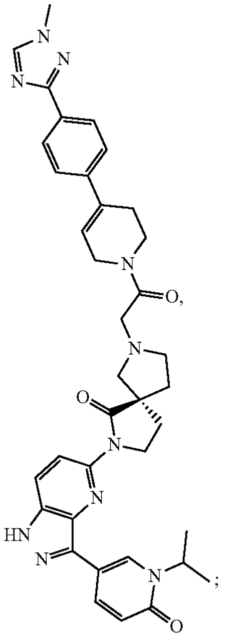

or a pharmaceutically acceptable salt of the foregoing.

Further examples of compounds of Formula (III) include, but are not limited to, the compound described in Example 122 below.

Synthesis

Compounds of Formulae (I), (II) or (III), and those described herein may be prepared in various ways. Some compounds of Formulae (I), (II) or (III) can be obtained commercially and/or prepared utilizing known synthetic procedures. General synthetic routes to the compounds of Formulae (I), (II) or (III), and some examples of starting materials used to synthesize the compounds of Formulae (I), (II) or (III) are shown and described herein in Schemes 1-12. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

-continued

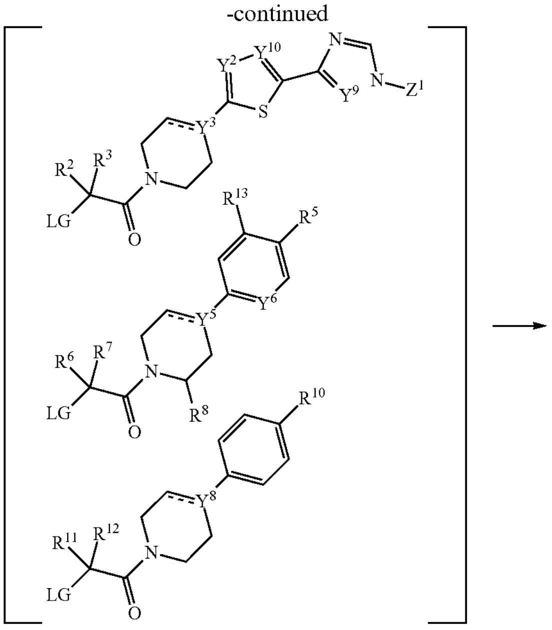

(2)

(I), (II), (III)

Compounds of Formulae (I), (II) or (III) can be prepared as shown in Scheme 1. In some embodiments, a suitable compound of Structure 1 ($R=R^1$, $R^4$ or $R^9$; $Y=Y^1$, $Y^4$ or $Y^7$) and suitable electrophile compounds of Structure 2, where LG is a suitable leaving group such as tosylates, mesylates, trifluoroacetates and halogens (e.g. LG=Cl, Br and I) are coupled to form compounds of Formulae (I), (II) or (III). In some embodiments, an amine base can be utilized in the reaction of compounds of Structure 1 and compounds of Structure 2. Examples of suitable amine bases, include, but are not limited to, alkylamine (including mono-, di- and tri-alkylamines (e.g., triethylamine), optionally substituted pyridines (e.g. collidine) and optionally substituted imidazoles (e.g., N-methylimidazole). In some embodiments, compounds of Structure 1 and compounds of Structure 2 can be coupled in the presence of a suitable amine base in a solvent with optional heating. In some embodiments, the solvent can be N,N-dimethylformamide.

In some embodiments, the triazoyl-$Z^1$, $R^5$ or $R^{10}$ group is attached the remainder of the molecule after the reaction between compounds of Structure 1 and compounds of Structure 2, wherein compounds of Structure 2 includes a leaving group. In some embodiments, the pyrazoyl-$Z^1$, $R^5$ or $R^{10}$ group can be attached to the remainder of the molecule by a Pd-mediated cross coupling reactions. Examples of suitable Pd-mediated cross coupling reactions are Suzuki, Buchwald and/or Ullmann cross coupling reactions.

Scheme 1

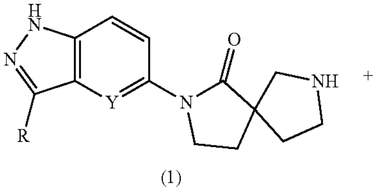

(1)

Scheme 2

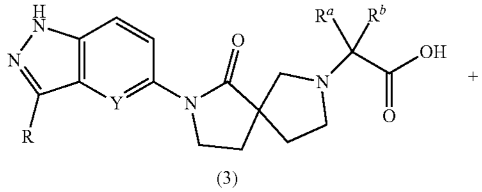

(3)

-continued

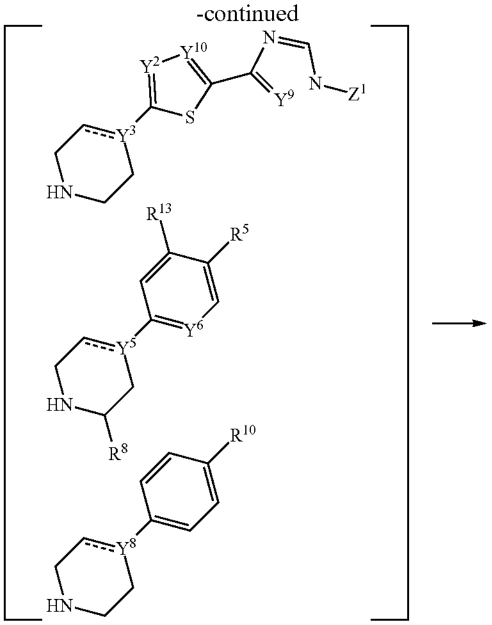

(4)

(I), (II), (III)

Another method for obtaining compounds of Formulae (I), (II) or (III) is provided in Scheme 2. Compounds of Structure 3 (R=$R^1$, $R^4$ or $R^9$; Y=$Y^1$, $Y^4$ or $Y^7$; $R^a$ and $R^b$=H and/or D) and compounds of Structure 4 can be coupled with a suitable coupling agent in a suitable solvent. A non-limiting list of suitable coupling agents include: 1-[bis(dimethylamino)methylene]-1H-1,2,3-triazolo[4,5-b]pyridinium 3-oxid hexafluorophosphate (HATU), N,N,N',N'-tetramethyl-O-(1H-benzotriazol-1-yl)uronium hexafluorophosphate, O-(Benzotriazol-1-yl)-N,N,N',N'-tetramethyluronium hexafluorophosphate (HBTU) and any such amide coupling agent known to those skilled in the art. In some embodiments, a suitable solvent can be N,N-dimethylformamide. If desired, the reaction can be carried out with heating.

Scheme 3

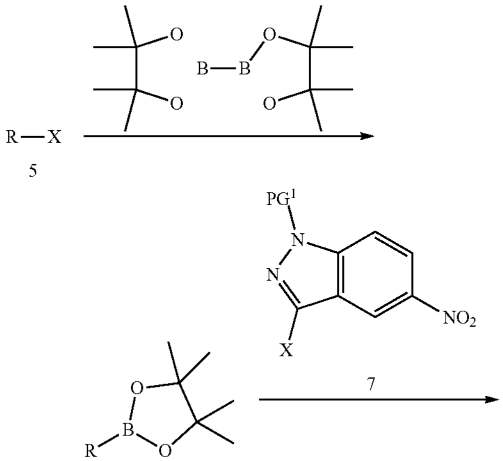

5

7

6

-continued

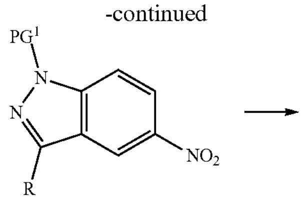

8

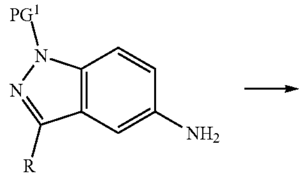

9

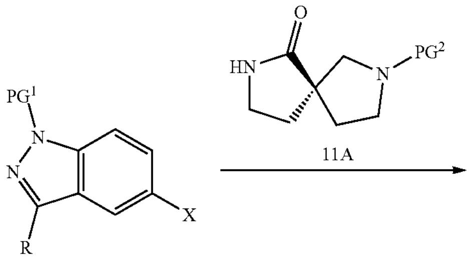

11A

10

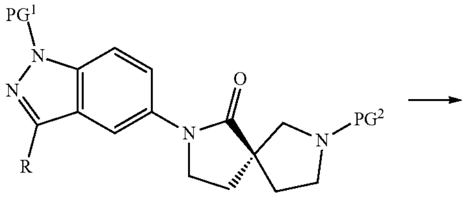

12

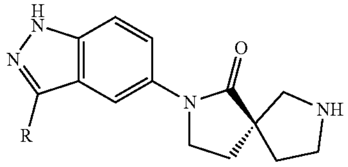

13

Compounds of Structure 13 can be prepared as outlined in Scheme 3. In some embodiments, halide compounds of Structure 5 (where X can be Br or I and R can be $R^1$, $R^4$ or $R^9$) are reacted with a boron reagent in the presence of a palladium catalyst and a base in a suitable solvent with optional heating. A suitable example of a boron reagent is bis(pinacolato)diboron, a suitable example of a palladium catalyst is [1,1'-bis(diphenylphosphino)ferrocene] dichloropalladium(II) complex, and an example of a suitable solvent is tetrahydrofuran. In some embodiments, a suitable base can be potassium acetate and a suitable solvent can be 1,4-dioxane. In some embodiments, halide compounds of Structure 5, bis(pinacolato)diboron, [1,1'-bis(diphenylphosphino) ferrocene]dichloropalladium(II) complex with dichloromethane, potassium acetate can be reacted in 1,4-dioxane with optional heating. In some embodiments, compounds of Structure 6 and compounds of Structure 7 (PG=protecting group such as trityl or THP) are reacted under Suzuki cross coupling condition using a suitable palladium catalyst and a base in a suitable solvent to prepare compounds of Structure 8. An example of a suitable palladium catalyst is [1,1'-bis(diphenylphosphino) ferrocene]dichloropalladium(II) complex, an example of a suitable solvent is tetrahydrofuran and an example of a suitable base is potassium carbonate. In some embodiments, the solvent can be a mixture of 1,2-dimethoxyethane and water. If desired, the reaction can be conducted with optional heating. In some embodiments, compounds of Structure 8 can be hydrogenated using a palladium catalyst in a suitable solvent such as methanol, ethanol or a mixture of methanol and toluene. In some embodiments, aryl amine compounds of Structure 9 can be converted to aryl halides of Structure 10 where X can be Br or I using a Sandmeyer reaction. In some embodiments, compounds of Structure 9 can be reacted with sodium nitrite, hydrobromic acid in the presence of copper (I) bromide catalyst to prepare compounds of Structure 10 where X is Br. In some embodiments, compounds of Structure 9 can be reacted with sodium nitrite, hydrochloric acid, sodium iodide in the presence of copper (I) iodide to prepare compounds of Structure 10 where X is I. In some embodiments, aryl halides of compounds of Structure 10 where X is I and amides of Structure 11A ($PG^2$=Boc or Cbz) can be coupled under Ullmann coupling conditions. In some embodiments, compounds of Structure 10 and amides of Structure 11A ($PG^2$=Boc or Cbz) can be reacted in the presence of copper (I) iodide in a suitable solvent (e.g. dimethylsulfoxide) in the presence of a suitable base (such as potassium phosphate) with optimal heating. In some embodiments, compounds of Structure 10 (X═Br or I) and amides of Structure 11A ($PG^2$=Boc or Cbz) can be reacted under Buchwald cross coupling conditions using a suitable palladium catalyst and a suitable solvent with optional heating to prepare compounds of Structure 12. In some embodiment, when $PG_1$ is trityl or THP and $PG^2$ is Boc or Cbz, both $PG^1$ and $PG^2$ protecting groups can be removed simultaneously with an acid (such as trifluoroacetic acid) in a suitable solvent (such as dichloromethane). In some embodiments, when $PG^2$ is Cbz, the Cbz group can be removed under hydrogenation conditions catalyzed by palladium on carbon in a suitable solvent (for example, methanol) followed by the removal of $PG^1$ under acidic conditions to prepare compounds of Structure 13.

Scheme 4

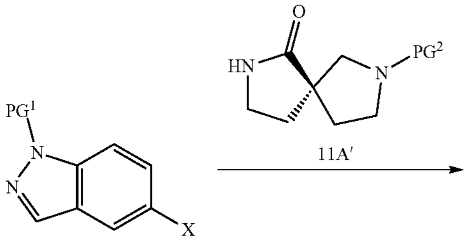

14

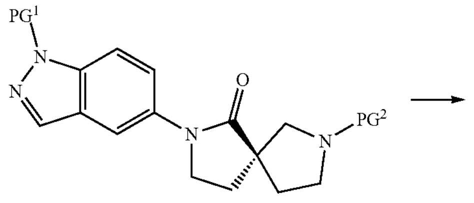

15

-continued

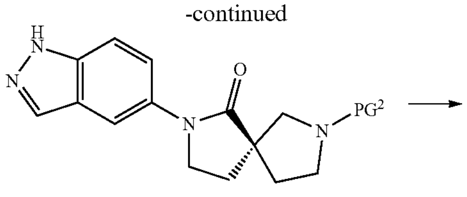

16

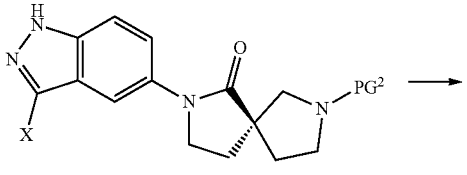

17

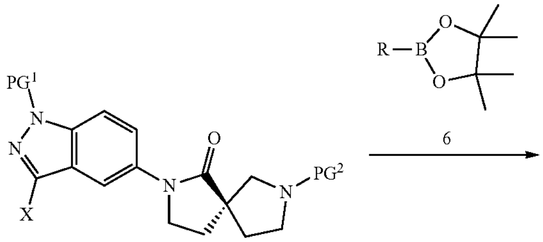

18

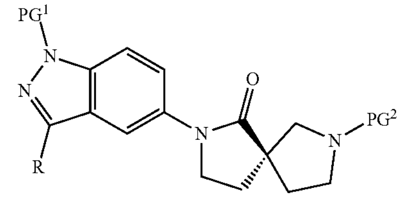

19

Compounds of Structure 19 can be prepared as outlined in Scheme 4. In some embodiments, aryl halides of compounds of Structure 14 ($PG_1$=trityl or THP and X=I) and amides of Structure 11A' ($PG^2$=Boc or Cbz) can be coupled under Ullmann coupling conditions. In some embodiments, compounds of Structure 14 and amides of Structure 11A' ($PG^2$=Boc or Cbz) can be reacted with catalytic copper (I) iodide in the presence of a suitable base (such as potassium phosphate) in a suitable solvent (for example, dimethyl sulfoxide) at elevated temperature (such as 100° C.). In some embodiments, compounds of Structure 14 where X is Br and amides of Structure 11A' can be coupled under Buchwald coupling conditions using a suitable palladium catalyst and a suitable base in a suitable solvent. In some embodiments, compounds of Structure 15 where $PG^1$=trityl or THP and $PG^2$=Cbz can be selectively deprotected under acidic conditions. In some embodiments, compounds of Structure 15 can be deprotected with trifluoroacetic acid in a suitable solvent (such as dichloromethane) at ambient temperature to prepare compounds of Structure 16.

In some embodiments, compounds of Structure 16 can be reacted with an electrophilic halide reagent to prepare compounds of Structure 17 where X is Br or I. In some embodiments, compounds of Structure 16 can be reacted with iodine in the presence of a base (such as potassium hydroxide) in a suitable solvent (such as N,N-dimethylformamide) with an optional heating. In some embodiments, compounds of Structure 16 can be reacted with NBS in the presence of a suitable base in a suitable solvent (such as dichloromethane) to prepare compounds of Structure 17. In some embodiments, compounds of Structure 17 can be reacted with trityl chloride in the presence of a base (such as potassium carbonate) in a suitable solvent(s) (such as acetonitrile) with optional heating to prepare compounds of Structure 18. In some embodiments, compounds of Structure 18 can be reacted with boronic esters of compounds of Structure 6 or boronic acids under Suzuki cross coupling conditions to prepare compounds of Structure 19. In some embodiments, the palladium catalyst can be [1,1'-bis(diphenylphosphino) ferrocene]dichloropalladium (II) complex with dichloromethane and cesium carbonate as the base. In some embodiments, the solvent can be a mixture of 1,2-dimethoxyethane and water, and the reaction can be conducted with optional heating.

Scheme 5

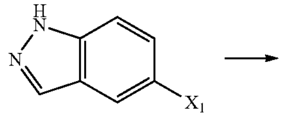

20

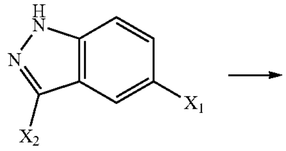

21

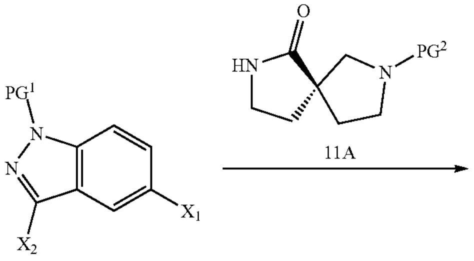

22

11A

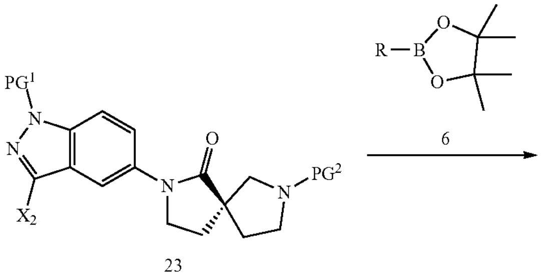

6

23

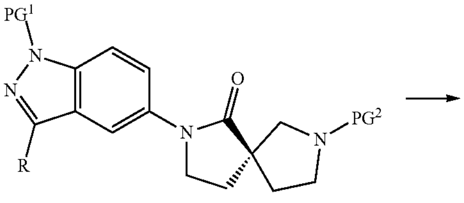

24

-continued

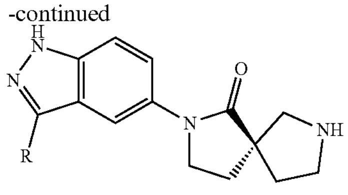

25

Alternatively, compounds of Structure 25 can be prepared as shown in Scheme 5. In some embodiments, compounds of Structure 20 can be reacted with an electrophilic halide reagent to prepare compounds of Structure 21 where $X_1$ is I or Br. In some embodiments, compounds of Structure 20 can be reacted with NBS in the presence of a suitable base in a suitable solvent (such as dichloromethane) to prepare compounds of Structure 21 where $X_2$ is Br or alternatively compounds of Structure 20 can be reacted with NCS in the presence of a suitable base in a suitable solvent to prepare compounds of Structure 21 where $X_2$ is Cl. In some embodiments, compounds of Structure 21 can be reacted with trityl chloride in the presence of a base (such as potassium carbonate) in a suitable solvent(s) (such as acetonitrile) with optional heating to prepare compounds of Structure 22.

In some embodiments, aryl halides of compounds of Structure 22 where $X_1$ is I and $X_2$=Br or Cl and amides of Structure 11A ($PG^2$=Boc or Cbz) can be coupled under Ullmann coupling conditions. In some embodiments, compounds of Structure 22 and amides of Structure 11A ($PG^2$=Boc or Cbz) can be reacted in the presence of copper (I) iodide in a suitable solvent (e.g. dimethylsulfoxide) in the presence of a suitable base (such as potassium phosphate) with optional heating. In some embodiments, compounds of Structure 22 ($X_1$=I and $X_2$=Br or Cl) and amides of Structure 11A ($PG^2$=Boc or Cbz) can be reacted under Buchwald cross coupling conditions using a suitable palladium catalyst and a suitable solvent with optional heating to prepare compounds of Structure 23. In some embodiments, compounds of Structure 23 can be reacted with boronic esters of compounds of Structure 6 or boronic acids under Suzuki cross coupling conditions to prepare compounds of Structure 24. In some embodiments, the palladium catalyst can be [1,1'-bis(diphenylphosphino) ferrocene]dichloropalladium (II) complex with dichloromethane and cesium carbonate as the base. In some embodiments, the solvent can be a mixture of 1,2-dimethoxyethane and water, and the reaction can be conducted with optional heating. In some embodiments, when $PG^1$ is trityl or THP and $PG^2$ is Boc or Cbz, both $PG^1$ and $PG^2$ protecting groups can be removed simultaneously with an acid (such as trifluoroacetic acid) in a suitable solvent (such as dichloromethane). In some embodiments, when $PG^2$ is Cbz, the Cbz group can be removed under hydrogenation conditions catalyzed by palladium on carbon in a suitable solvent (for example, methanol) followed by the removal of $PG^1$ under acidic conditions to prepare compounds of Structure 25.

Scheme 6

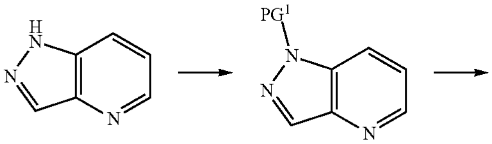

26 27

-continued

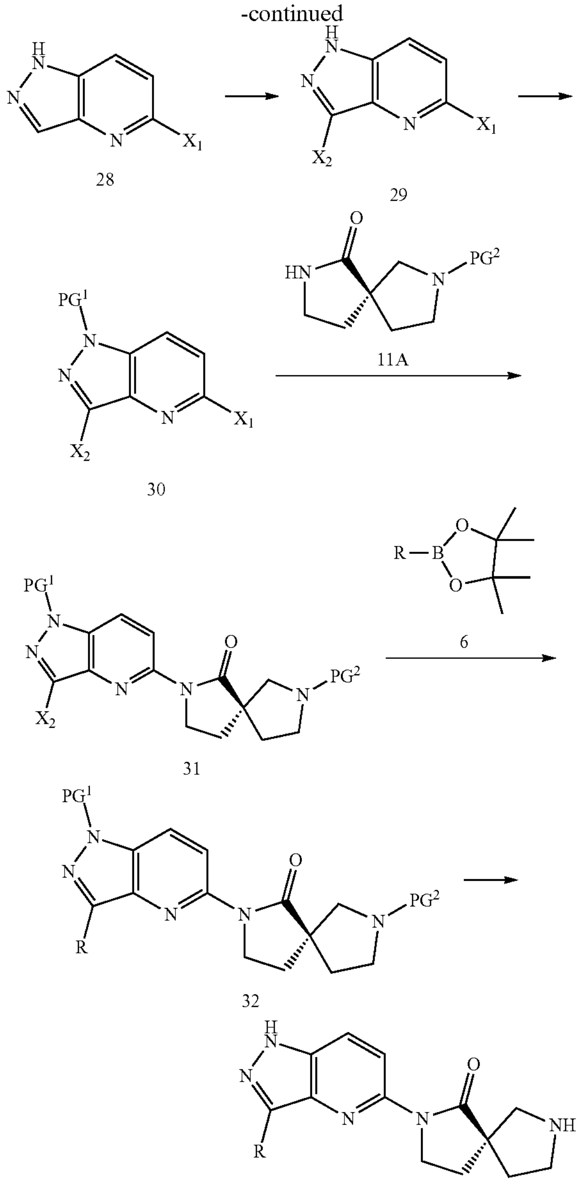

28 29 11A 30 6 31 32 33

Compounds of Structure 33 can be prepared as shown in Scheme 6. A compound of Structure 26 can be protected with a suitable protecting group ($PG^1$=Trityl, THP or acetyl). In some embodiments, a compound of Structure 26 can be reacted with trityl chloride in the presence of a suitable base (such as potassium carbonate) in a suitable solvent (such as acetonitrile) with optional heating. In some embodiments, compounds of Structure 27 can be reacted with mCPBA followed by $POCl_3$ and $PCl_5$ (or $POBr_3$) to prepare compounds of Structure 28 where $X_1$ is Cl or Br. In some embodiments, $PG^1$ (trity, THP or acetyl) can be removed using acidic conditions (e.g. methanol and hydrochloric acid) to afford compounds of Structure 28. In some embodiments, compounds of Structure 28 can be reacted with an electrophilic halogen reagent to prepare compounds of Structure 29 where $X_2$ is Br or Cl. In some embodiments, compounds of Structure 28 can be reacted with NBS in a suitable solvent to prepare compounds of Structure 29 where $X_2$ is Br, or compounds of Structure 28 can be reacted with NCS (or NaOCl) in a suitable solvent (such as dichloromethane) with optional heating to prepare compounds of Structure 29 where $X_2$ is Cl. In some embodiments, compounds of Structure 30 can be prepared using a suitable protecting group such as trityl, THP or acetyl as described in Scheme 3-5. In some embodiments, compounds of Structure 30 ($X_1$=Br and $X_2$=Br or Cl) and amides of Structure 11A ($PG^2$=Boc or Cbz) can be reacted under Buchwald cross coupling conditions using a suitable palladium catalyst and a suitable solvent with optional heating to prepare compounds of Structure 31. In some embodiments, compounds of Structure 30 and amides of Structure 11A ($PG^2$=Boc or Cbz) can be reacted in the presence of copper (I) iodide in a suitable solvent (e.g. dimethyl sulfoxide) in the presence of a suitable base (such as potassium phosphate) with optional heating to prepare compounds of Structure 31.

In some embodiments, compounds of Structure 6 and compounds of Structure 31 can be reacted under Suzuki cross coupling conditions using a suitable palladium catalyst and a base in a suitable solvent to prepare compounds of Structure 32. An example of a suitable palladium catalyst is [1,1'-bis(diphenylphosphino) ferrocene]dichloropalladium (II) complex, an example of a suitable solvent is dichloromethane and an example of a suitable base is potassium carbonate. In some embodiments, the solvent can be a mixture of 1,2-dimethoxyethane and water, and the reaction can be conducted with optional heating. In some embodiments, when $PG^2$ is Boc, the Boc group can be removed simultaneously with trifluoroacetic acid in a suitable solvent (such as dichloromethane). In some embodiments, when $PG^2$ is Cbz, Cbz group can be removed under hydrogenation conditions catalyzed by palladium on carbon in a suitable solvent (such as methanol) followed by removal of $PG^1$ under acidic condition to prepare compounds of Structure 33.

Scheme 7
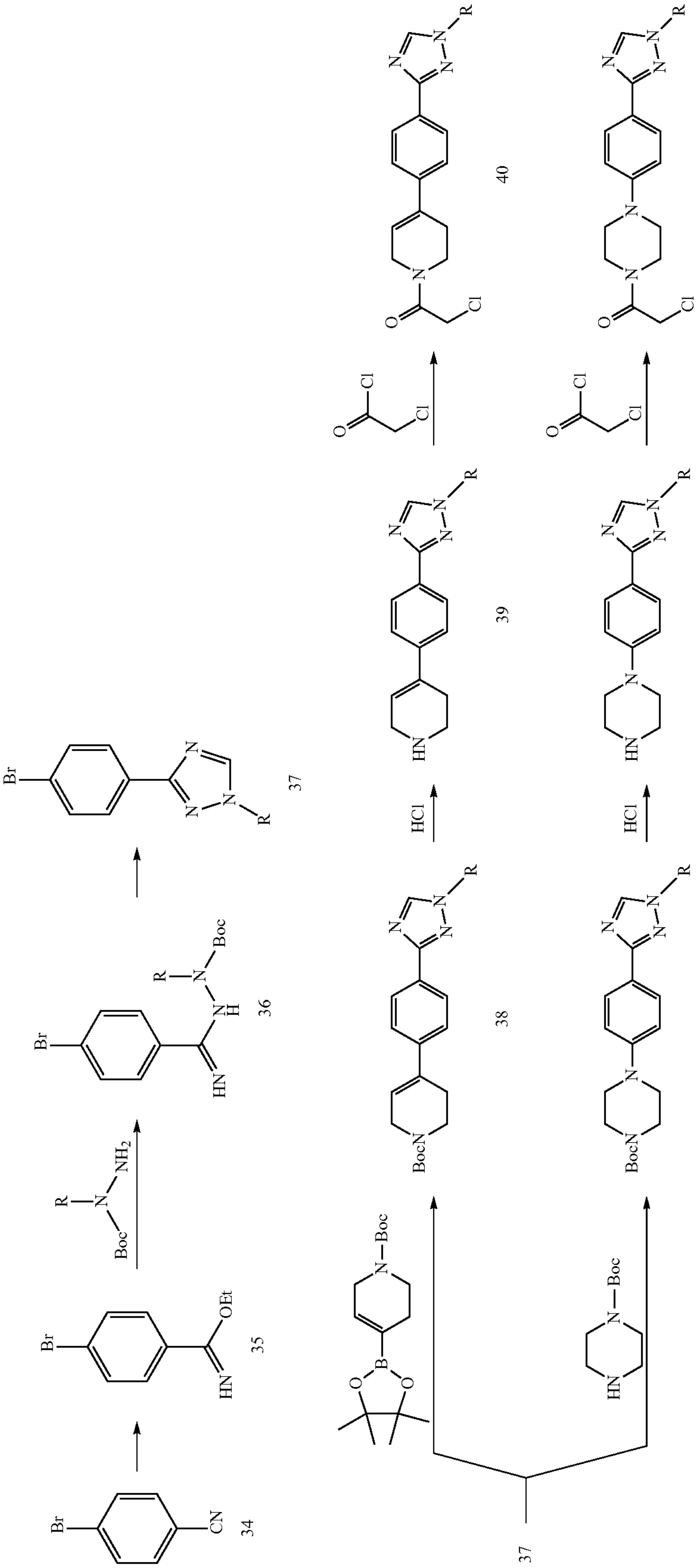
34 35 36 37 37 38 39 40 41 42 43

In some embodiments, compounds of Structures 40 and 43 can be prepared as outlined in Scheme 7. In some embodiments, a compound of Structure 34 can be reacted with hydrochloric acid gas in an alcohol (such as ethanol) to prepare a compound of Structure 35. In some embodiments, compound 35 can be reacted with a substituted hydrazine in an alcoholic solvent (such as methanol) in the presence of a base (such as sodium bicarbonate) to prepare compounds of Structure 36. In some embodiments, compounds of Structure 36 can be cyclized to form a triazole ring in the presence of formic acid to prepare compounds of Structure 37. In some embodiments, compounds of Structure 37 can be reacted under Suzuki cross coupling conditions using a suitable palladium catalyst (for example, palladium catalyst is [1,1'-bis(diphenylphosphino) ferrocene]dichloropalladium (II) complex) and a base (for example, potassium carbonate) in a suitable solvent (such as tetrahydrofuran) to prepare compounds of Structure 38. In some embodiments, the solvent can be a mixture of 1,2-dimethoxyethane and water, and the reaction can be conducted with optional heating. In some embodiments, compounds of Structure 37 can be reacted under Buchwald cross coupling conditions using a suitable palladium catalyst and a suitable solvent with optional heating to prepare compounds of Structure 41. In some embodiments, compounds of Structures 38 or 41 can be reacted with an acid (such as hydrochloric acid) in a suitable solvent (such as 1,4-dioxane) to prepare compounds of Structures 39 or 42. In some embodiments, compounds of Structures 39 or 42 can be reacted with chloroacetyl chloride or chloroacetic anhydride in the presence of a suitable base (such as triethylamine) in a suitable solvent (such as dichloromethane) to prepare compounds of Structures 40 and 43 where R is an alkyl or optionally substituted alkyl, e.g., an optionally substituted $C_{1-3}$ alkyl.

Scheme 8

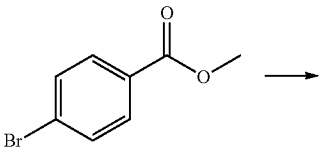

44

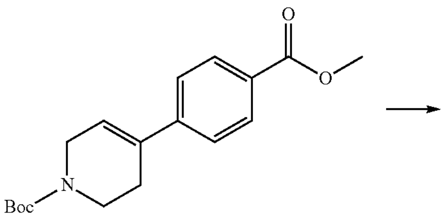

45

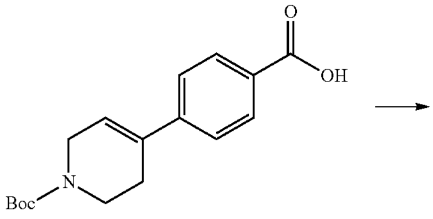

46

-continued

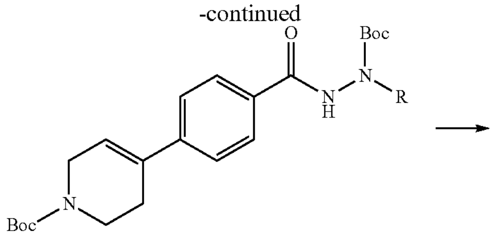

47

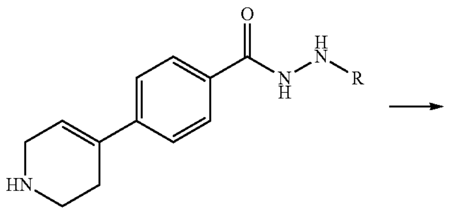

48

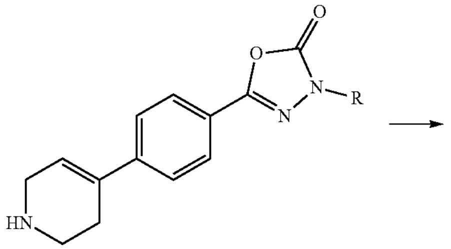

49

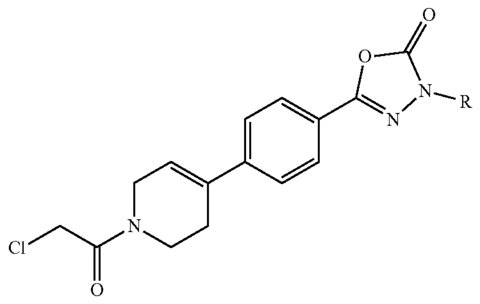

50

Compounds of Structure 50 can be prepared as outlined in Scheme 8. In some embodiments, a compound of Structure 45 can be prepared using Suzuki cross coupling conditions. In some embodiments, a compound of structure 44 can be coupled with tert-butyl 4-(4,4,5,5-tetramethyl-1,3,2-dioxaborolan-2-yl)-3,6-dihydropyridine-1(2H)-carboxylate in the presence of palladium catalyst (such as bistriphenylphosphinepalladium(II) dichloride) and a base (such as cesium carbonate) in a mixture of solvents (such as 1,2-dimethoxyethane and water) with optional heating to prepare a compound of Structure 45. In some embodiments, a compound of Structure 45 can be reacted with lithium hydroxide in a suitable solvent (such as tetrahydrofuran and water) to prepare a compound of Structure 46. In some embodiments, a compound of Structure 46 can be reacted with 1,1'-carbonyldiimidazole followed by tert-butyl 1-methylhydrazine-1-carboxylate (or other suitably R-substituted hydrazine-1-carboxylate) in a suitable solvent (such as N,N-dimethylformamide) with optional heating to prepare compounds of Structure 47. In some embodiments, compounds of Structure 47 can be reacted with hydrochloric acid in a suitable solvent (such as 1,4-dioxane). In some embodiments, compounds of Structure 48 can be treated with a suitable reagent (such as bis(trichloromethyl) carbonate) and a base (such as trimethylamine) in a suitable solvent (such as dichloromethane) to prepare compounds of Structure 49.

In some embodiments, compounds of Structure 49 can be converted to compounds of Structure 50 where R is an optionally substituted $C_{1-3}$ alkyl group using methods similar to those for preparing compounds of Structures 40 and 43 as outlined in Scheme 7.

Scheme 9

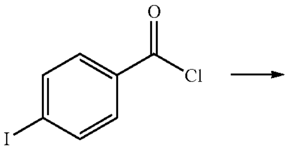

51

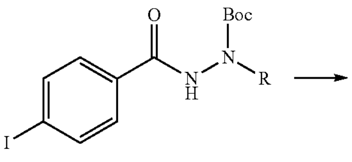

52

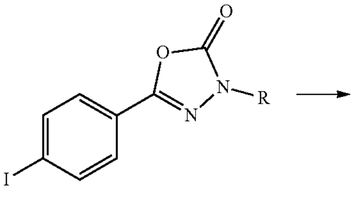

53

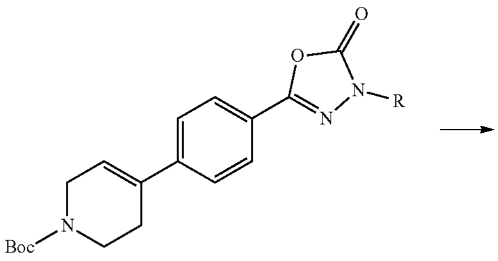

54

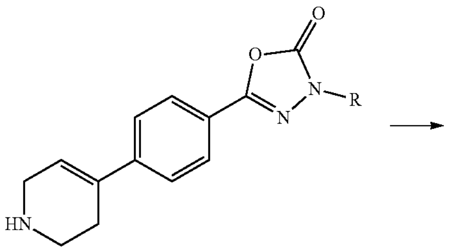

55

-continued

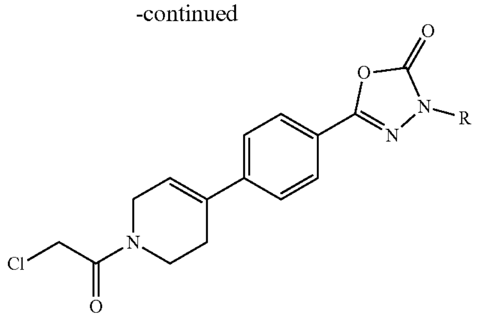

50

Alternatively, compounds of Structure 50 can be prepared as outlined in Scheme 9. In some embodiments, a compound of Structure 51 can be reacted with tert-butyl 1-methylhydrazine-1-carboxylate in a suitable solvent (such as tetrahydrofuran) and in the presence of a suitable base (such as triethylamine) to prepare compounds of Structure 52. In some embodiments, compounds of Structure 52 can be reacted with hydrochloric acid to remove Boc group and then can be reacted with a suitable reagent (such as 4-nitrophenylchloroformate) in a suitable solvent (such as dichloromethane) in the presence of a suitable base (such as triethylamine) to prepare compounds of Structure 53. In some embodiments, compounds of Structure 54 can be prepared using Suzuki cross coupling conditions. In some embodiments, compounds of Structure 53 can be coupled with tert-butyl 4-(4,4,5,5-tetramethyl-1,3,2-dioxaborolan-2-yl)-3,6-dihydropyridine-1(2H)-carboxylate in the presence of palladium catalyst (such as bistriphenylphosphinepalladium (II) dichloride) and a base (such as cesium carbonate) in a mixture of solvents (such as 1,2-dimethoxyethane and water) with optional heating to prepare compounds of Structure 54. In some embodiments, compounds of Structure 54 can be converted to compounds of Structure 50 as outlined in Scheme 9. Throughout the specification, groups and substituents thereof are chosen by one skilled in the field to provide stable moieties and/or compounds.

Scheme 10

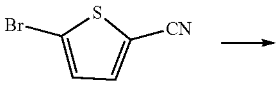

56

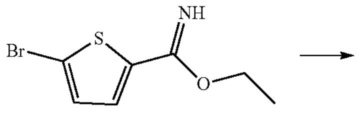

57

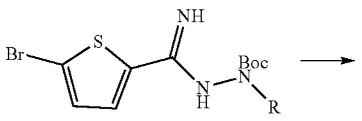

58

-continued

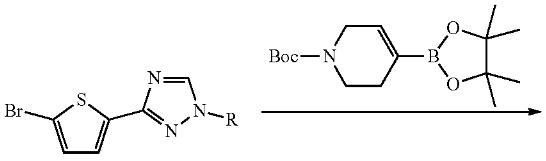

59

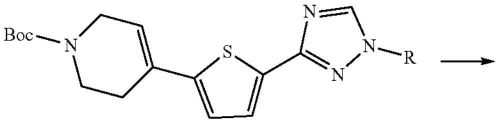

60

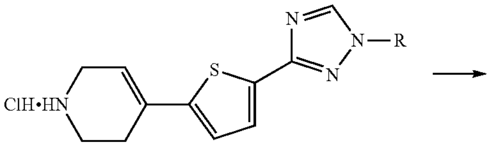

61

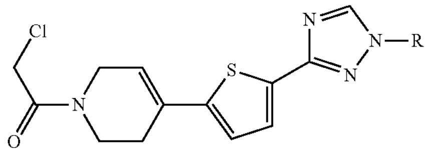

62

In some embodiments, compounds of Structure 62 can be prepared as outlined in Scheme 10. In some embodiments, a compound of Structure 56 can be reacted with hydrochloric acid gas in an alcohol (such as ethanol) to prepare a compound of Structure 57. In some embodiments, compound 57 can be reacted with a substituted hydrazine (e.g., R is optionally substituted $C_{1-3}$ alkyl) in a suitable solvent (such as pyridine) to prepare compounds of Structure 58. In some embodiments, compounds of Structure 58 can be cyclized to form a triazole ring in the presence of formic acid to prepare compounds of Structure 59. In some embodiments, compounds of Structure 59 can be reacted under Suzuki cross coupling conditions using a suitable palladium catalyst (for example, palladium catalyst is [1,1'-bis(diphenylphosphino) ferrocene]dichloropalladium (II) complex) and a base (for example, potassium carbonate) in a suitable solvent (such as tetrahydrofuran) to prepare compounds of Structure 60. In some embodiments, the solvent can be a mixture of 1,2-dimethoxyethane and water, and the reaction can be conducted with optional heating. In some embodiments, compounds of Structure 60 can be converted to compounds of Structure 62 as outlined in Scheme 7-9. Throughout the specification, groups and substituents thereof are chosen by one skilled in the field to provide stable moieties and/or compounds.

Scheme 11

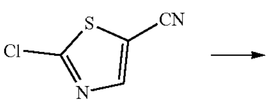

63

-continued

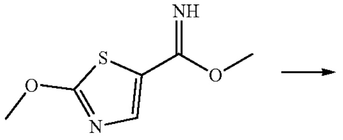

64

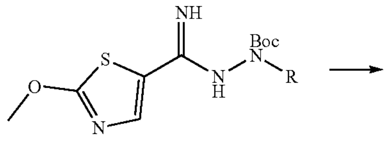

65

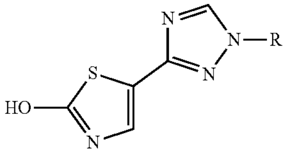

66

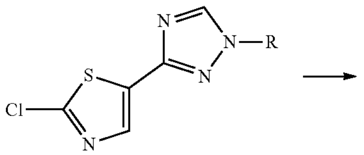

67

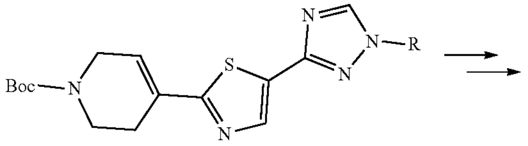

68

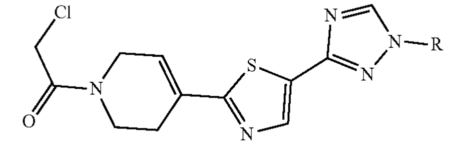

69

In some embodiments, compounds of Structure 69 can be prepared as outlined in Scheme 11. In some embodiments, a compound of Structure 63 can be reacted with sodium methoxide in methanol to prepare a compound of Structure 64. In some embodiments, compound 64 can be reacted with a substituted hydrazine (e.g., R is optionally substituted $C_{1-3}$ alkyl) in a suitable solvent (such as pyridine) to prepare compounds of Structure 65. In some embodiments, compounds of Structure 65 can be cyclized to form a triazole ring in the presence of formic acid to prepare compounds of Structure 66. In some embodiments, compounds of Structure 66 can be reacted with $POCl_3$ to form compounds of Structure 67. In some embodiments, compounds of Structure 67 can be reacted under Suzuki cross coupling conditions using a suitable palladium catalyst (for example, palladium catalyst is [1,1'-bis(diphenylphosphino) ferrocene]dichloropalladium (II) complex) and a base (for example, potassium carbonate) in a suitable solvent (such as tetrahydrofuran) to prepare compounds of Structure 68. In some embodiments, compounds of Structure 68 can be converted to compounds of Structure 69 as outlined in Scheme 7-9.

Throughout the specification, groups and substituents thereof are chosen by one skilled in the field to provide stable moieties and/or compounds.

Scheme 12

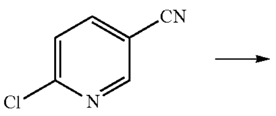

70

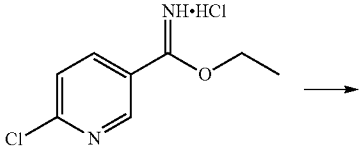

71

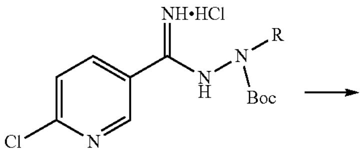

72

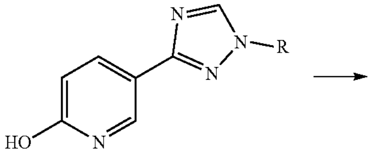

73

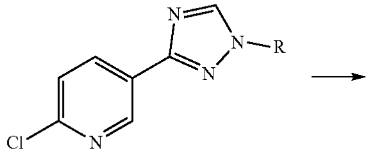

74

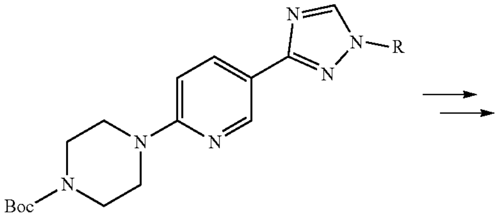

75

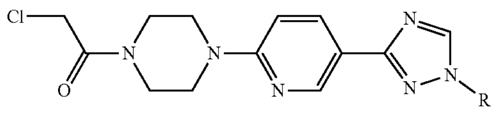

76

In some embodiments, compounds of Structure 76 can be prepared as outlined in Scheme 12. In some embodiments, a compound of Structure 70 can be reacted with hydrochloric acid gas in an alcohol (such as ethanol) to prepare a compound of Structure 71. In some embodiments, compound 71 can be reacted with a substituted hydrazine (e.g., R is optionally substituted $C_{1-3}$ alkyl) in a suitable solvent (such as pyridine) to prepare compounds of Structure 72. In some embodiments, compounds of Structure 72 can be cyclized to form a triazole ring in the presence of formic acid to prepare compounds of Structure 73. In some embodiments, compounds of Structure 73 can be treated with POCl3 to form compounds of Structure 74. In some embodiments, compounds of Structure 74 can be converted to compounds of Structure 76 as outlined in Scheme 7-9. Throughout the specification, groups and substituents thereof are chosen by one skilled in the field to provide stable moieties and/or compounds.

Pharmaceutical Compositions

Some embodiments described herein relate to a pharmaceutical composition, that can include an effective amount of one or more compounds described herein (e.g., a compound of Formulae (I), (II) or (III), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

As described herein, compounds of Formulae (I), (II) or (III), or a pharmaceutically acceptable salt thereof, can be administered by a variety of methods. In some of the methods described herein, administration can be by injection, infusion and/or intravenous administration over the course of 1 minute, 5 minutes, 10 minutes, 30 minutes, 1 hour, 2 hours, 6 hours, 12 hours, 24 hours or longer, or any intermediate time. Other methods described herein can include oral, intravenous and/or intraperitoneal administration to a subject in need thereof, for example, to a subject to treat a cancer described herein responsive to an ERK inhibitor.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments described herein relate to a method for ameliorating and/or treating a cancer described herein that can include administering an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) to a subject having a cancer described herein. Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for ameliorating and/or treating a cancer described herein. Still other embodiments described herein relate to the use of an effective amount of a compound described herein (for example, a compound of Formulae (I), (II) or (III), or a pharmaceutically acceptable salt thereof) or a pharmaceutical composition that includes of a compound described herein (for example, a compound of Formulae (I), (II) or (III), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof), wherein the malignant growth or tumor is due to a cancer described herein. Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for inhibiting replication of a malignant growth or a tumor, wherein the malignant growth or tumor is due to a cancer described herein. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in a subject having a cancer described herein. Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for ameliorating or treating a cancer that can include contacting with a malignant growth or a tumor, wherein the malignant growth or tumor is due to a cancer described herein. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for ameliorating or treating a cancer that can include contacting with a malignant growth or a tumor, wherein the malignant growth or tumor is due to a cancer described herein.

Some embodiments described herein relate to a method for inhibiting the activity of ERK1 and/or ERK2 that can include providing an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) to a sample that includes a cancer cell from a cancer described herein. Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for inhibiting the activity of ERK1 and/or ERK2. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for inhibiting the activity of ERK1 and/or ERK2.

Some embodiments described herein relate to a method for ameliorating or treating a cancer described herein that can include inhibiting the activity of ERK1 and/or ERK2 using an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof). Other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) in the manufacture of a medicament for ameliorating or treating a cancer described herein by inhibiting the activity of ERK1 and/or ERK2. Still other embodiments described herein relate to the use of an effective amount of a compound described herein (for example, a compound of Formulae (I), (II) or (III), or a pharmaceutically acceptable salt thereof) or a pharmaceutical composition that includes an effective amount of a compound described herein (for example, a compound of Formulae (I), (II) or (III), or a pharmaceutically acceptable salt thereof) for ameliorating or treating a cancer described herein by inhibiting the activity of ERK1 and/or ERK2.

Examples of suitable cancers include, but are not limited to: lung cancer (e.g., lung adenocarcinoma and non-small cell lung cancer, see Adjei, A. A., "The role of mitogen-activated ERK-kinase inhibitors in lung cancer therapy" Clin. Lung. Cancer (2005) 7(3):221-223 and Roberts et al., "Targeting the Raf-MEK-ERK mitogen-activated protein kinase cascade for the treatment of cancer" Oncogene (2007) 26(22):3291-3310), pancreatic cancers (e.g., pancreatic carcinoma such as, for example, exocrine pancreatic carcinoma, see Hayes, et al., "Long-Term ERK Inhibition in KRAS-Mutant Pancreatic Cancer Is Associated with MYC Degradation and Senescence-like Growth Suppression" Cancer Cell (2016) 29(1):75-89 and Morris et al., "Discovery of a novel ERK inhibitor with activity in models of acquired resistance to BRAF and MEK inhibitors" Cancer Discov (2013) 3(7):742-750), colon cancers (e.g., colorectal carcinomas, such as, for example, colon adenocarcinoma and colon adenoma, see Fang et al., "The MAPK signalling pathways and colorectal cancer" Lancet Oncol (2005) 6(5):322-327), myeloid leukemias (for example, acute myelogenous leukemia (AML), CML, and CMML, see Steelman et al., "Roles of the Ras/Raf/MEK/ERK pathway in leukemia therapy" Leukemia (2011) 25(7):1080-1094), thyroid cancer, myelodysplastic syndrome (MDS), bladder carcinoma (see Noguchi et al., "Replacement treatment with microRNA-143 and -145 induces synergistic inhibition of the growth of human bladder cancer cells by regulating PI3K/Akt and MAPK signaling pathways" Cancer Lett (2013) 328(2):353-361), epidermal carcinoma (see Khavari et al., "Ras/Erk MAPK signaling in epidermal homeostasis and neoplasia" Cell Cycle (2007) 6(23)2928-2931), melanoma (see Morris et al., "Discovery of a novel ERK inhibitor with activity in models of acquired resistance to BRAF and MEK inhibitors" Cancer Discov (2013) 3(7):742-750), breast cancer (see Maiello et al., "EGFR and MEK Blockade in Triple Negative Breast Cancer Cells" J Cell Biochem (2015) 116(12):2778-2785), prostate cancer (see Rodriguez-Berriguete et al., "Relationship between IL-6/ERK and NF-κB: a study in normal and pathological human prostate gland" Eur Cytokine Netw (2010) 21(4):251-250), head and neck cancers (e.g., squamous cell cancer of the head and neck, see Jimenez et al., "Mechanisms of Invasion in Head and Neck Cancer" Arch Pathol Lab Med (2015) 139(11):1334-1348), ovarian cancer (see Sheppard et al., "Synergistic inhibition of ovarian cancer cell growth by combining selective PI3K/mTOR and RAS/ERK pathway inhibitors" Eur J Cancer (2013) 49(18):3936-3944), brain cancers (e.g., gliomas, such as glioma blastoma multiforme, see Chen et al., "Glioma cell proliferation controlled by ERK activity-dependent surface expression of PDGFRA" PLoS One (2014) 9(1)e87281), cancers of mesenchymal origin (e.g., fibrosarcomas and rhabdomyosarcomas, see Buonata et al., "ERK1/2 blockade prevents epithelial-mesenchymal transition in lung cancer cells and promotes their sensitivity to EGFR inhibition" Cancer Res (2014) 74(1):309-319), sarcomas (see Serrano et al., "RAS/MAPK pathway hyperactivation determines poor prognosis in undifferentiated pleomorphic sarcomas" Cancer (2016) 122(1):99-107), tetracarcinomas (see Chambers et al., "Self-renewal of teratocarcinoma and embryonic stem cells" Oncogene (2004) 23(43):7150-7160), neuroblastomas (see Vieira et al., "LGR5 regulates pro-survival MEK/ERK and proliferative Wnt/β-catenin signalling in neuroblastoma" Oncotarget (2015) 6(37):40053-40067), kidney carcinomas (see Chen et al., "Expression and prognostic role of MEKK3 and pERK in patients with renal clear cell carcinoma" Asian Pac J Cancer Prev (2015) 16(6):2495-2499), hepatomas (see Huang et al., "Apelin-13 induces autophagy in hepatoma HepG2 cells through ERK1/2 signaling pathway-dependent upregulation of Beclinl" Oncol Lett (2016) 11(2):1051-1056), non-Hodgkin's lymphoma (see Carlo-Stella et al., "Sorafenib inhibits lymphoma xenografts by targeting MAPK/ERK and AKT pathways in tumor and vascular cells" PLoS One (2013) 8(4):e61603), multiple myeloma (see Jin et al., "USO1 promotes tumor progression via activating Erk pathway in multiple myeloma cells" Biomed Pharmacother (2016) 78:264-271), anaplastic thyroid carcinoma (see Milosevic et al., "Targeting RAS-MAPK-ERK and PI3K-AKT-mTOR signal transduction pathways to chemosensitize anaplastic thyroid carcinoma" Transl Res (2014) 164(5):411-423) and neurofibromatosis (NF-1) (see Wang et al., "ERK inhibition rescues defects in fate specification of Nf1-deficient neural progenitors and brain abnormalities" Cell (2012) 150(4):816-830).

The compound(s) of Formulae (I), (II) or (III) or a pharmaceutically acceptable salt thereof, that can be used can be any of the embodiments described in the "Compounds" section above.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance, and may positively affect one or more symptoms or aspects of the disease while having effects on other aspects of the disease or on unrelated systems that may be considered undesirable.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to treat, alleviate or ameliorate one or more symptoms or conditions of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein.

For example, an effective amount of a compound, or radiation, is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. In the treatment of lung cancer (such as non-small cell lung cancer) a therapeutically effective amount is that amount that alleviates or eliminates cough, shortness of breath and/or pain. As another example, an effective amount, or a therapeutically effective amount of an ERK inhibitor is the amount which results in the reduction in ERK (ERKI and/or ERK2) activity and/or phosphorylation. The reduction in ERK activity are known to those skilled in the art and can be determined by the analysis of pharmacodynamic markers such as phosphorylated RSKI,2 and phosphorylated ERKI,2 and/or or gene expression profile (mRNA).

The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a cancer, are known to those skilled in the art. Example of suitable indicators include, but are not limited to, the reduction, alleviation or disappearance of one or more symptoms caused by the cancer, the reduction of tumor size, the elimination of the tumor, and/or long-term disease stabilization (growth arrest) of the tumor.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively, dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Intermediate 1

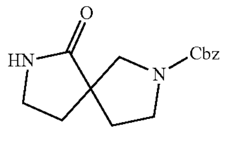

Intermediate 1 was prepared following a procedure described in a patent WO2016/161160A1. LCMS: 275.3 $[M+H]^+$.

Intermediate 1A

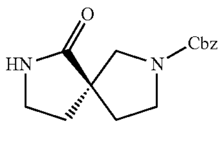

Intermediate 1A was prepared following a procedure described in a patent WO2016/161160A1. LCMS: 275.09 $[M+H]^+$.

Intermediate 1B

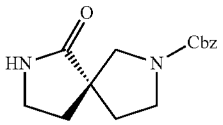

Intermediate 1B was prepared following a procedure described in a patent WO2016/161160A1. LCMS: 275.09 $[M+H]^+$.

Intermediate 2

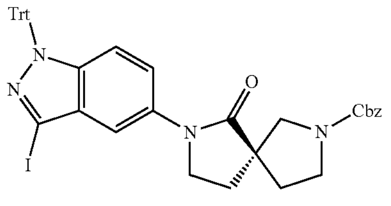

Intermediate 2 was prepared following a procedure described in a patent WO2016/161160A1. LCMS: 759.25 $[M+H]^+$.

Intermediate 3

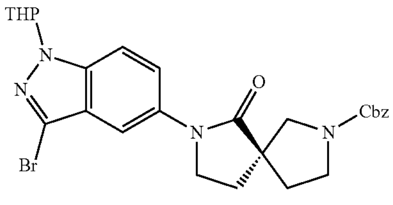

Intermediate 3 was prepared following a procedure described in a patent WO2016/161160A1 using 3-bromo-5-iodo-1-(tetrahydro-2H-pyran-2-yl)-1H-indazole and Intermediate 1A. LCMS: 554.95 $[M+H]^+$.

Intermediate 4

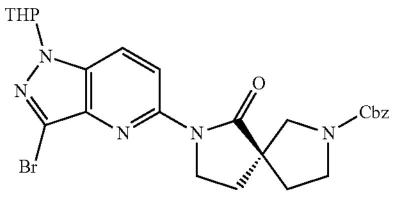

Intermediate 4 was prepared following a procedure described in a patent WO2016/161160A1 using 3,5-dibromo-1H-pyrazolo[4,3-b]pyridine and Intermediate 1A. LCMS: 555.92 $[M+H]^+$.

Intermediate 5

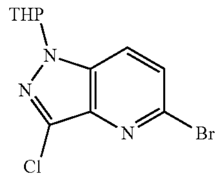

5-Bromo-3-chloro-1H-pyrazolo[4,3-b]pyridine (5-#1)

To a stirred solution of 5-bromo-1H-pyrazolo[4,3-b]pyridine (5.0 g, 25.3 mmol) in water (100 mL) was added NaOH (4.06 g, 101.5 mmol) at rt. The reaction was stirred at 70° C. and cooled to 0° C. followed by the addition of NaOCl (11.26 mL, 151.8 mmol) at 0° C. After being stirred at room temperature for 16 h, the reaction was quenched by cold water and extracted with EtOAc. The combined organic layers were washed with water and brine, dried over $Na_2SO_4$ and concentrated to afford 5-#1 (4.2 g, 18.2 mmol, 72%) as a yellow solid. LCMS: 233.75 $[M+H]^+$.

5-Bromo-3-chloro-1-(tetrahydro-2H-pyran-2-yl)-1H-pyrazolo[4,3-b]pyridine (Intermediate 5)

To a stirred solution of 5-#1 (3.0 g, 12.8 mmol) in DCM (20 mL) were added DHP (3.5 mL, 38.6 mmol) and PTSA (220 mg, 1.28 mmol) at 0° C. After being stirred at rt for 1 h, the reaction was quenched by cold water and extracted with DCM. The combined organic layers were washed with brine, dried over $Na_2SO_4$ and concentrated. The crude product was purified by column chromatography using 15% EtOAc in petroleum ether to afford Intermediate 5 (1.3 g, 32%) as an off white solid. mp: 80-82° C.; LCMS: 315.83 $[M+H]^+$.

Intermediate 6

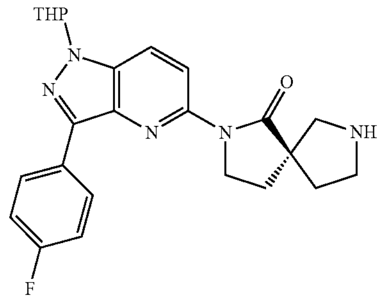

Benzyl (R)-7-(3-(4-fluorophenyl)-1-trityl-1H-indazol-5-yl)-6-oxo-2,7-diazaspiro[4.4]nonane-2-carboxylate (6-#1)

To a stirred solution of Intermediate 2 (1.8 g, 2.37 mmol) and 2-(4-fluorophenyl)-4,4,5,5-tetramethyl-1,3,2-dioxaborolane (0.398 g, 2.84 mmol) in ethanol/toluene/water (1:1:1 ratio, 60 mL) was added $K_2CO_3$ (1.63 g, 11.85 mmol). The mixture was degassed for 10 min, followed by the addition of $Pd(dppf)_2Cl_2$-DCM (0.273 g, 0.237 mmol), and degassed for another 10 mins. The resulting mixture was refluxing for 3 h. Upon completion, the mixture was cooled to rt and filtered through a Celite pad. The filtrate was diluted with cold water and extracted with EtOAc. The combined organic layers were washed with water and brine, dried over $Na_2SO_4$ and concentrated. The residue was purified by column chromatography using 50% EtOAc/hexanes to afford 6-#1 (1.5 g, 87%). LCMS: 727.29 $[M+H]^+$.

(S)-2-(3-(4-Fluorophenyl)-1-trityl-1H-indazol-5-yl)-2,7-diazaspiro[4.4]nonan-1-one (Intermediate 6)

To a solution of 6-#1 (0.5 g, 0.688 mmol) in toluene (3.44 mL) and methanol (3.44 mL) was added HCl (1.720 mL, 3.44 mmol). The solution was degassed, followed by addition of Pd/C (0.073 g, 0.069 mmol), and stirred at rt under hydrogen atmosphere overnight. The mixture was filtered through Celite and washed with methanol. The solvents were removed to afford Intermediate 6 as hydrochloride salt (0.46 g of crude material) as pale yellow foam. This material was used without further purification. LCMS: 593.30 $[M+H]^+$.

Intermediate 7

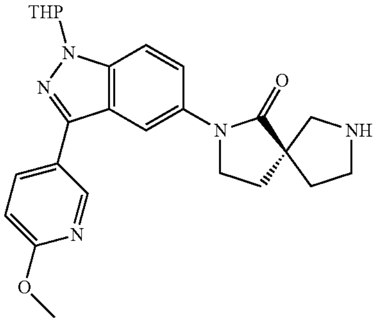

Intermediate 7 was prepared following a procedure described for Intermediate 6 using Intermediate 2 and 2-methoxy-5-(4,4,5,5-tetramethyl-1,3,2-dioxaborolan-2-yl)pyridine. LCMS: 606.52 $[M+H]^+$.

Intermediate 8

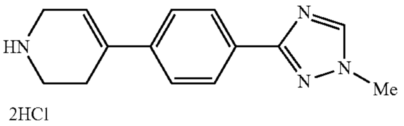

Intermediate 8 was prepared following a procedure described in a patent WO2016/161160A1 using 4-bromobenzonitrile, t-butyl 1-methylhydrazinecarboxylate and tert-butyl 4-(4,4,5,5-tetramethyl-1,3,2-dioxaborolan-2-yl)-5,6-dihydropyridine-1(2H)-carboxylate. LCMS: 241.34 $[M+H]^+$.

Intermediate 9

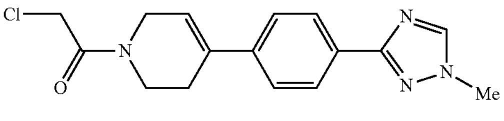

Intermediate 9 was prepared following a procedure described in a patent WO2016/161160A1 using 4-(4-(1- methyl-1H-1,2,4-triazol-3-yl)phenyl)-1,2,3,6-tetrahydropyridine hydrochloride and chloroacetyl chloride. LCMS: 317.12 $[M+H]^+$.

Intermediate 10

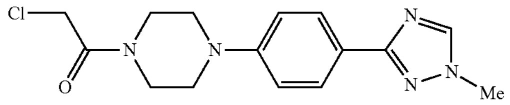

Intermediate 10 was prepared following a procedure described in a patent WO2016/161160A1 using 1-(4-(1-methyl-1H-1,2,4-triazol-3-yl)phenyl)piperazine and chloroacetic anhydride. LCMS: 320.19 $[M+H]^+$.

Intermediate 11

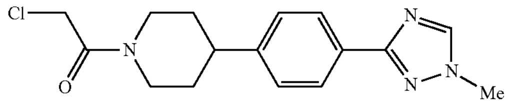

Intermediate 11 was prepared following a procedure described in a patent WO2016/161160A1 using 4-(4-(1-methyl-1H-1,2,4-triazol-3-yl)phenyl)piperidine hydrochloride and chloroacetyl chloride. LCMS: 319.08 $[M+H]^+$.

Intermediate 12

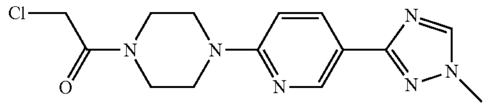

Intermediate 12 was prepared following a procedure described in a patent WO2016/161160A1 using 1-(5-(1-methyl-1H-1,2,4-triazol-3-yl)pyridin-2-yl)piperazine hydrochloride and chloroacetyl chloride. LCMS: 320.9 $[M+1]^+$.

Intermediate 13

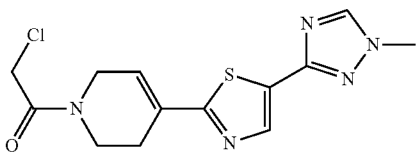

Intermediate 13 was prepared following a procedure described in a patent WO2011/041152A1 using 5-(1-methyl-1H-1,2,4-triazol-3-yl)-2-(1,2,3,6-tetrahydropyridin-4-yl)thiazole hydrochloride and chloroacetyl chloride. LCMS: 324.25 $[M+H]^+$.

Intermediate 14

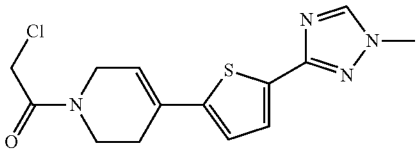

Intermediate 14 was prepared following a procedure described in a patent WO2011/041152A1 using 4-(5-(1-methyl-1H-1,2,4-triazol-3-yl)thiophen-2-yl)-1,2,3,6-tetrahydropyridine hydrochloride and chloroacetyl chloride. LCMS: 322.92 $[M+H]^+$.

Intermediate 15

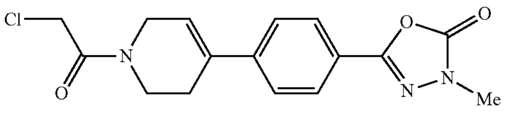

4-Iodobenzohydrazide (15-#1)

To a solution of 4-iodobenzoic acid (6 g, 24.19 mmol) in DCM (300 mL) was added 1,1-carbonyldiimidazole (4.315 g, 26.61 mmol) at 0° C. After being stirred at rt for 2 h, hydrazine monohydrate (7.26 g, 145.15 mmol) was added and the mixture was stirred at rt for 5 h. The mixture was then concentrated under reduced pressure followed by the addition of water to precipitate out the product. The product was collected by filtration and dried under reduced pressure to afford 15-#1 (5.2 g, 82%) as an off white solid. LCMS: 263.05 $[M+H]^+$.

5-(4-Iodophenyl)-1,3,4-oxadiazol-2(3H)-one (15-#2)

To a stirred solution of 15-#1 (5 g, 19.08 mmol) in THF (480 mL) at rt was added 1,1-carbonyldiimidazole (3.40 g, 20.99 mmol) at 0° C. After being stirred at rt for 2 h, the reaction mixture was concentrated and extracted with EtOAc. The combined organic layers were washed with 1 M hydrochloric acid and brine, dried over $Na_2SO_4$, and concentrated to afford 15-#2 (4.95 g, 90%) as an off white solid. LCMS: 288.86 $[M+H]^+$.

5-(4-Iodophenyl)-3-methyl-1,3,4-oxadiazol-2(3H)-one (15-#3)

To a solution of 15-#2 (4.95 g, 17.24 mmol) in dimethylformamide (350 mL) were added $K_2CO_3$ (4.75 g, 34.48 mmol) and methyl iodide (4.89 g, 34.48 mmol) at rt. After being stirred at rt for 2 h, the reaction was quenched by ice water. The solid was collected by filtration and dried under reduced pressure to afford 15-#3 (4.3 g, 82%) as an off white solid. LCMS: 303.13 $[M+H]^+$.

tert-butyl 4-(4-(4-Methyl-5-oxo-4,5-dihydro-1,3,4-oxadiazol-2-yl)phenyl)-5,6-dihydropyridine-1(2H)-carboxylate (15-#4)

To a stirred solution of 15-#3 (4.3 g, 14.23 mmol) and tert-butyl 4-(4,4,5,5-tetramethyl-1,3,2-dioxaborolan-2-yl)-5,6-dihydropyridine-1(2H)-carboxylate (5.71 g, 18.50 mmol) in 1,4-dioxane/water (3:1 ratio, 200 mL) was added $Na_2CO_3$ (3.01 g, 28.46 mmol). The mixture was degassed for 10 min, followed by the addition of $Pd(dppf)_2Cl_2$-DCM (1.161 g, 1.42 mmol), and degassed for another 10 min. After being refluxed for 16 h, the mixture was cooled to rt and filtered through a Celite pad. The filtrate was diluted with cold water and extracted with EtOAc. The combined organic layers were washed with water and brine, dried over $Na_2SO_4$ and concentrated. The residue was purified by column chromatography using 50% EtOAc/hexanes to afford 15-#4 (3.9 g, 76%). LCMS: 357.98 $[M+H]^+$.

3-Methyl-5-(4-(1,2,3,6-tetrahydropyridin-4-yl)phenyl)-1,3,4-oxadiazol-2(3H)-one hydrochloride (15-#5)

To a solution of 15-#4 (3.9 g, 10.08 mmol) in 1,4-dioxane (100 mL) was added 4 M HCl in 1,4-dioxane (50 mL) at 0° C. After being stirred at rt for 3 h, the mixture was concentrated and triturated with diethyl ether to afford 15-#5 (2.5 g, 78%) as an off white solid. LCMS: 258.5 $[M+H]^+$.

5-(4-(1-(2-Chloroacetyl)-1,2,3,6-tetrahydropyridin-4-yl)phenyl)-3-methyl-1,3,4-oxadiazol-2(3H)-one (Intermediate 15)

To a stirred solution of 15-#5 (2.5 g, 8.51 mmol) in DCM (100 mL) was added triethylamine (1.03 g, 10.21 mmol) followed by chloroacetyl chloride (1.24 g, 11.06 mmol) at 0° C. After being stirred at 0° C. for 1 h, the mixture was diluted with water and extracted with DCM. The combined organic layers were washed with brine, dried over $Na_2SO_4$ and concentrated under reduced pressure. The residue was purified by column chromatography using 70% EtOAc/hexanes to afford Intermediate 15 (2.2 g, 77%) as an off white solid. LCMS: 334.18 $[M+H]^+$.

Intermediate 16

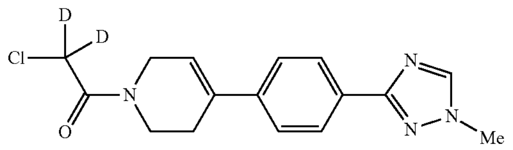

To a solution of chloroacetic acid-$d_3$ (250 mg, 2.57 mmol) in toluene (5 mL) was added a drop of DMF followed by addition of oxalyl chloride (0.4 mL, 3.86 mmol) at 0° C. and stirred at rt for 1 h. The resulting clear solution was added to DCM (15 mL) solution of Intermediate 8 (500 mg, 1.80 mmol) and N,N-diisopropylethylamine (0.4 mL, 2.57 mmol) at 0° C. drop wise and the reaction was stirred at rt for 1 h. The reaction mixture was quenched with $NaHCO_3$ (10 mL) and extracted with EtOAc. The combined organic layers were washed with water, brine, dried over $Na_2SO_4$ and concentrated. The resulting crude compound was purified by column chromatography using 5% of methanol/DCM to afford Intermediate 16 (200 mg, 20%) as an off-white solid. 1H NMR (300 MHz, DMSO-$d_6$) δ 8.51 (s, 1H), 7.96 (d, 2H), 7.56-7.52 (m, 2H), 6.28 (s, 1H), 4.20-4.14 (m, 2H), 3.91 (s, 3H), 3.72-3.66 (m, 2H), 2.73-2.61 (m, 2H); LCMS: 319.0 $[M+H]^+$.

Intermediate 17

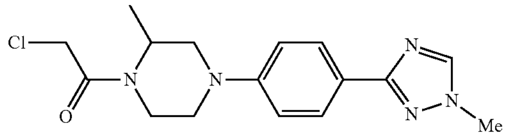

3-Methyl-1-(4-(1-methyl-1H-1,2,4-triazol-3-yl)phenyl)piperazine (17-#1)

A solution of 3-(4-bromophenyl)-1-methyl-1H-1,2,4-triazole (2.0 g, 8.43 mmol) and 2-methylpiperazine (1.68 g, 16.87 mmol) in dioxane:water (5:1, 60 mL) was degassed three times with nitrogen/vacuum cycles. To this mixture was added $Cs_2CO_3$ (4.11 g, 12.65 mmol) followed by 2-di-tert-(butylphosphino)-biphenyl (0.755 g, 2.531 mmol) and $Pd(OAc)_2$ (0.189 mg, 0.843 mmol). The mixture was further degassed for additional 10 min followed by heating at 100° C. for 48 h. After completion of the reaction, the mixture was cooled to room temperature, filtered through celite and washed with DCM. Filtrate was treated with 1N aqueous HCl solution and extracted with DCM. The aqueous solution was neutralized with 5N NaOH (10 mL) solution, then extracted with 5% methanol/DCM. The combined organic fractions were dried over $Na_2SO_4$ and concentrated to afford 17-#1 (900 mg, 42%) as a brown liquid. LCMS: 258.32 $[M+H]^+$.

2-Chloro-1-(2-methyl-4-(4-(1-methyl-1H-1,2,4-triazol-3-yl)phenyl)piperazin-1-yl)ethanone (Intermediate 17)

Intermediate 17 was prepared following the procedure described for Intermediate 10 using 17-#1 and chloroacetic anhydride to afford Intermediate 17. LCMS: 334.05 $[M+H]^+$.

Intermediate 18

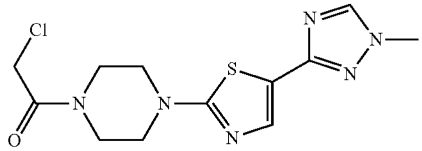

Tert-butyl 4-(5-(1-methyl-1H-1,2,4-triazol-3-yl)thiazol-2-yl)piperazine-1-carboxylate (18-#1)

A mixture of 2-chloro-5-(1-methyl-1H-1,2,4-triazol-3-yl)thiazole (600 mg, 3.0 mmol) and tert-butyl piperazine-1-carboxylate (1.78 g, 9.0 mmol) in NMP (5 mL) was refluxed for 24 h. The mixture was diluted with water and extracted with ethyl acetate. The combined organic layers were washed with brine, dried over $Na_2SO_4$ and concentrated under reduced pressure. The residue was purified by column chromatography eluted with 8% methanol/DCM to afford 18-#1. (0.4 g, 40%) as an off white solid. LCMS: 351.04 $[M+H]^+$.

5-(1-Methyl-1H-1,2,4-triazol-3-yl)-2-(piperazin-1-yl)thiazole hydrochloride (18-#2)

To a solution of 18-#1 (400 g, 1.14 mmol) in 1,4-dioxane (5 mL) was added 4 M HCl in 1,4-dioxane (5 mL) and stirred at rt for 3 h. The mixture was concentrated and triturated with diethyl ether to afford 18-#2 (200 mg, 75%) as an off white solid. LCMS: 250.95 [M+H]+.

2-Chloro-1-(4-(5-(1-methyl-1H-1,2,4-triazol-3-yl) thiazol-2-yl)piperazin-1-yl)ethanone (Intermediate 18)

Intermediate 18 was prepared following the procedure described for Intermediate 10 using 18-#2 and chloroacetyl chloride to afford Intermediate 18. LCMS: 327.30 [M+H]+.

Intermediate 19

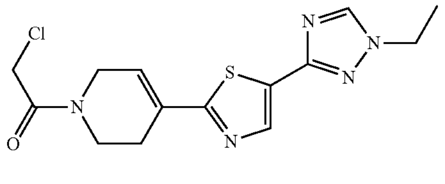

Intermediate 19 was prepared following the procedure described for Intermediate 13 using 2-methoxythiazole-5-carbimidate and ethyl hydrazine oxalate in Step 2 to afford Intermediate 19. LCMS: 338.23 [M+H]+.

Intermediate 20

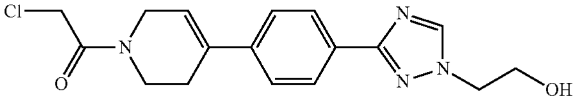

Intermediate 20 was prepared following the procedure described in WO2016161160A1. LCMS: 347.22 [M+H]+.

Intermediate 21

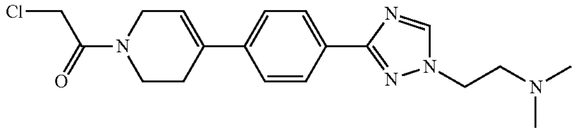

Tert-butyl 4-(4-(1-(2-hydroxyethyl)-1H-1,2,4-triazol-3-yl)phenyl)-5,6-dihydropyridine-1(2H)-carboxylate (21-#1)

To a stirred solution of 2-(3-(4-(1,2,3,6-tetrahydropyridin-4-yl)phenyl)-1H-1,2,4-triazol-1-yl)ethanol hydrochloride (2.5 g, 7.911 mmol) in DCM (50 mL) was added triethylamine (3.99 g, 39.555 mmol), Boc anhydride (1.89 g, 8.702 mmol) and stirred at rt for 3 h. The mixture was quenched with ice-cold water and extracted with DCM. The combined organic layer was washed with water and dried over $Na_2SO_4$ and concentrated under reduced pressure to afford a residue, which was purified by column chromatography eluted with 5-10% methanol/DCM to afford 21-#1. (2.6 g, 86%) as an off-white solid. LCMS: 371.17 [M+H]+.

Tert-butyl 4-(4-(1-(2-bromoethyl)-1H-1,2,4-triazol-3-yl)phenyl)-5,6-dihydropyridine-1(2H)-carboxylate (21-#2)

To a stirred solution of 21-#1 (2.4 g, 6.486 mmol) in DCM (50 mL) was added $Ph_3P$ (2.04 g, 7.783 mmol) and $CBr_4$ (4.301 g, 12.972 mmol) at 0° C. and stirred at rt for 3 h. The mixture was concentrated under reduced pressure to afford a residue, which was purified by column chromatography eluted with 5-10% methanol/DCM to afford 21-#2 (1.63 g, 58%) as an off-white solid. LCMS: 433.24 [M+H]+.

Tert-butyl 4-(4-(1-(2-(dimethylamino)ethyl)-1H-1,2,4-triazol-3-yl)phenyl)-5,6-dihydropyridine-1(2H)-carboxylate (21-#3)

To a stirred solution of 21-#2 (0.750 g, 1.739 mmol) in DMF (20 mL) was added $K_2CO_3$ (0.720 g, 5.219 mmol), dimethylamine in THF (2.0 M) (2.17 mL, 4.349 mmol) at rt and stirred at rt for 16 h. The mixture was quenched with ice-cold water and extracted with EtOAc. The combined organic layer was washed with water and dried over $Na_2SO_4$, concentrated under reduced pressure to afford a residue, which was purified by column chromatography eluted with 5-10% methanol/DCM to afford 21-#3 (0.5 g, 72%) as an off-white solid. LCMS: 398.36 M+H]+.

2-Chloro-1-(4-(4-(1-(2-(dimethylamino)ethyl)-1H-1,2,4-triazol-3-yl)phenyl)-5,6-dihydropyridin-1(2H)-yl)ethanone (Intermediate 21)

Intermediate 21 was prepared following the procedures described for Intermediate 9 using 21-#3 to afford 21. LCMS: 374.11 [M+H]+.

Intermediate 22

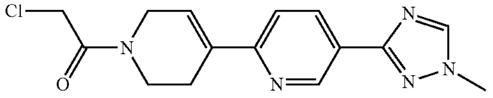

Intermediate 22 was prepared following the procedures described for Intermediate 9 using 6-chloronicotinonitrile to afford Intermediate 22. LCMS: 318.2 [M+H]+.

Intermediate 23

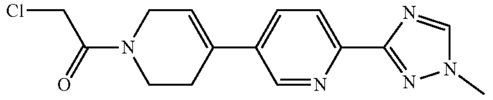

Intermediate 23 was prepared following the procedures described for Intermediate 9 using 5-bromonicotinonitrile to afford Intermediate 23. LCMS: 318.1 [M+H]+.

Intermediate 24

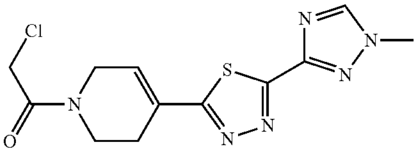

Intermediate 24 was prepared following the procedure described for Intermediate 13 using 5-bromo-1,3,4-thiadiazole-2-carbonitrile to afford Intermediate 24. LCMS: 325.28 [M+H]+.

Intermediate 25

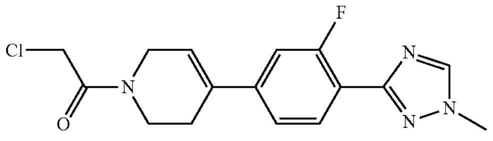

Intermediate 25 was prepared following the procedure described in WO2016161160A1. LCMS: 335.10 $[M+H]^+$.

Intermediate 26

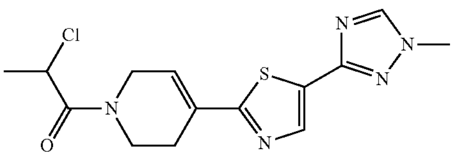

To a stirred solution of 5-(1-methyl-1H-1,2,4-triazol-3-yl)-2-(1,2,3,6-tetrahydropyridin-4-yl)thiazole hydrochloride (0.7 g, 2.472 mmol) in DCM (20 mL) was added triethylamine (1.24 g, 12.36 mmol), 2-chloropropanoyl chloride (0.467 g, 3.708 mmol) at 0° C. The mixture was stirred at 0° C. for 2 h. The mixture was quenched with ice-cold water and extracted with DCM. The combined organic layers were washed with water and dried over $Na_2SO_4$, concentrated under reduced pressure to afford a residue, which was purified by column chromatography eluted with 5-10% methanol/DCM to afford Intermediate 26. LCMS: 337.9$[M+H]^+$.

Intermediate 27

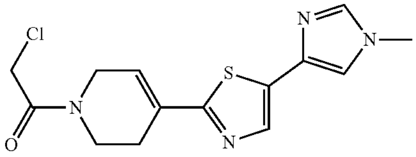

Tert-butyl 4-(5-Bromothiazol-2-yl)-5,6-dihydropyridine-1(2H)-carboxylate (27-#1)

A solution of 2,5-dibromothiazole (5 g, 20.57 mmol) and tert-butyl 4-(4,4,5,5-tetramethyl-1,3,2-dioxaborolan-2-yl)-5,6-dihydropyridine-1(2H)-carboxylate (3.17 g, 16.46 mmol) in mixture of benzene:methanol (4:1, 50 mL) was added $Na_2CO_3$ (6.5 g, 61.71 mmol) and degassed for 20 min. To this reaction mixture was then added $Pd(Ph_3P)_4$ (1.1 g, 1.02 mmol) and continued degassing for additional 10 min. Then, the mixture was heated at 80° C. for 12 h. The mixture was cooled to rt and filtered through the Celite pad. To the filtrate was added cold water and extracted with EtOAc. The combined organic layers were washed with water, brine, dried over $Na_2SO_4$ and concentrated. The residue was purified by column chromatography eluted with 20% EtOAc/hexanes to afford 27-#1 (3 g, 42%) as yellow solid. LCMS: 345.18 $[M+H]^+$.

Tert-butyl 4-(5-(4,4,5,5-Tetramethyl-1,3,2-dioxaborolan-2-yl)thiazol-2-yl)-5,6-dihydro pyridine-1(2H)-carboxylate (27-#2)

To a solution of 27-#1 (3 g, 8.72 mmol) in dioxane (30 mL) was added 4,4,4',4',5,5,5',5'-octamethyl-2,2'-bi(1,3,2-dioxaborolane) (4.4 g, 17.44 mmol), AcOK (1.7 g, 17.44 mmol) and degassed for 15 min. To this mixture was then added tricyclohexylphosphine (0.48 g, 1.74 mmol), $Pd_2(dba)_3$ (0.39 g, 0.43 mmol) and continued degassing for additional 10 min. This mixture was heated at 110° C. for 3 h. TLC indicated full consumption of starting material and formation of a polar spot. The reaction mixture was used in the next step without purification.

Tert-butyl 4-(5-(1-Methyl-1H-imidazol-4-yl)thiazol-2-yl)-5,6-dihydropyridine-1(2H)-carboxylate (27-#3)

To a crude mixture of 27-#2 in dioxane was added 4-iodo-1-methyl-1H-imidazole (1.2 g, 6.97 mmol), $K_2CO_3$ (2.8 g, 20.91 mmol) and degassed for 15 min. To this mixture was added $Pd(Ph_3P)_4$ (0.4 g, 0.34 mmol) and continued degassing for additional 10 min. This mixture was then heated at 100° C. for 16 h. The mixture was cooled to rt and filtered through the Celite pad. To the filtrate was added cold water and extracted with EtOAc. The combined organic layers were washed with water, brine, dried over $Na_2SO_4$ and concentrated. The residue was purified by column chromatography eluted with 6% methanol/DCM to afford 27-#3 (700 mg, 25% for 2 steps). LCMS: 347.34 $[M+H]^+$.

2-Chloro-1-(4-(5-(1-methyl-1H-imidazol-4-yl)thiazol-2-yl)-5,6-dihydropyridin-1(2H)-yl)ethanone (intermediate 27)

Intermediate 27 was prepared following a procedure described for Intermediate 13 using tert-butyl 4-(5-(1-Methyl-1H-imidazol-4-yl)thiazol-2-yl)-5,6-dihydropyridine-1(2H)-carboxylate. LCMS: 323.23 $[M+1]^+$.

General Procedure A: Suzuki Cross Coupling when $PG^1$=Trt or THP and $PG^2$=Cbz or Boc

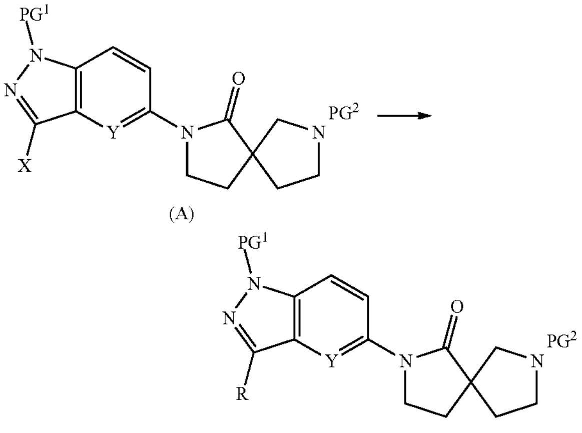

(A)

(B)

To a solution of corresponding halide A (X=Cl, Br or I; Y=$Y^1$, $Y^4$ or $Y^7$) (1.0 equiv) and appropriate boronic acid or boronic ester (1.0-1.2 equiv. Note #1) in ethanol/toluene/ water (0.2-0.5 M, 1:1:1 ratio, Note #2) was added $K_2CO_3$ (2-4 equiv). The mixture was degassed with vacuum/nitrogen purge three times, followed by the addition of $Pd(dppf)_2Cl_2$-DCM (0.05-0.2 equiv Note #3). The resulting mixture was heated to reflux for 2-16 h. Upon completion as determined by LCMS (or TLC), the mixture was cooled to rt and diluted with EtOAc. The combined organic layers were washed with water and brine, dried over $Na_2SO_4$ and concentrated. The crude product B ($R=R^1$, $R^4$ or $R^9$) was either 1) purified by column chromatography using silica gel, or 2) used directly in the next step without further purification.

Note #1: In some instances, additional quantities of boronic acid or boronic ester were added.

Note #2: In some instances, a mixture of DME/water, THF/water, dioxane/water or 2-methyl THF/water mixture were used as solvent mixtures.

Note #3: In some instances, $Pd(Ph_3P)_4$ or $Pd(Ph_3P)_2Cl_2$ was used as catalyst.

General Procedure B1: N-Deprotection when $PG^1$=Trt or THP and $PG^2$=CBz

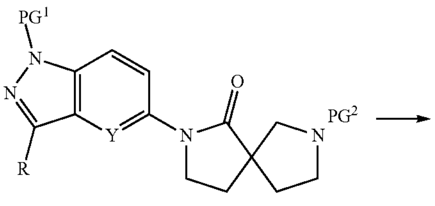

(B)

-continued

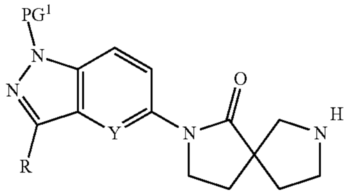

(C)

To a solution of corresponding protected amine B ($PG^1$=Trt or THP; $PG^2$=Cbz) (1.0 equiv) in MeOH (or ethanol, or acetic acid) was added 10% Pd/C (0.1 equiv) and stirred at rt for 6 h under hydrogen atmosphere. The mixture was filtered through Celite pad and washed with 10% MeOH/DCM. The filtrate was concentrated under reduced pressure to afford the crude product C. This product was either 1) purified on a silica gel column or RP HPLC; or 2) used directly in the next step without further purification.

General Procedure B2: Bis-Deprotection when $PG^1$=Trt or THP and $PG^2$=CBz or Boc A solution of corresponding protected amine B ($PG^1$=Trt or THP; $PG^2$=Cbz or Boc) (1.0 equiv) in TFA (0.1-0.5M solution) was stirred at rt for 24 h. The reaction mixture was concentrated under reduced pressure to afford crude product C (where $PG^1$=H; $PG^2$=H). This crude product was either 1) purified on a silica gel column or RP HPLC; or 2) used directly in the next step without further purification.

General Procedure C: Alkylation of Secondary Amine when $PG^1$=Trt, THP or H

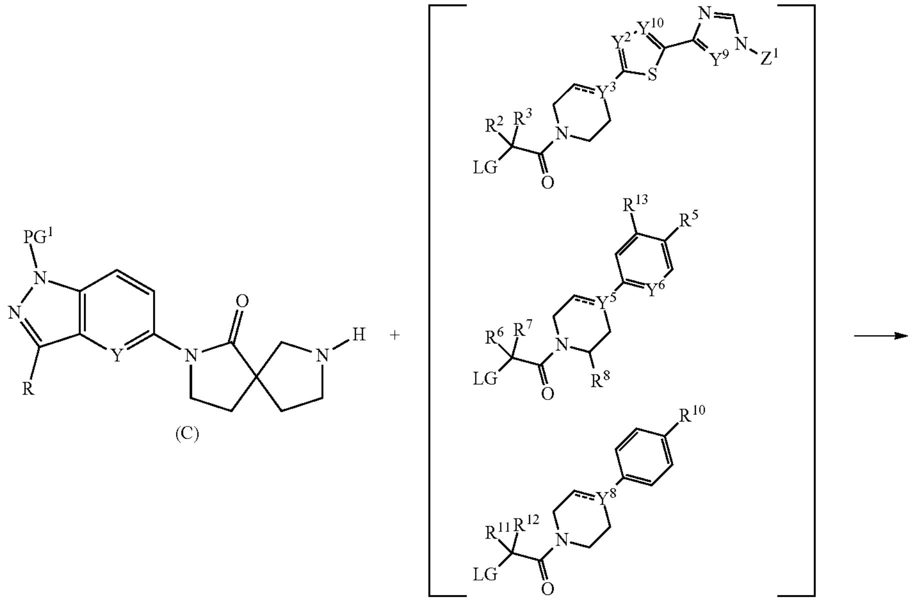

(C)

(ID), (IID), (IIID)

-continued

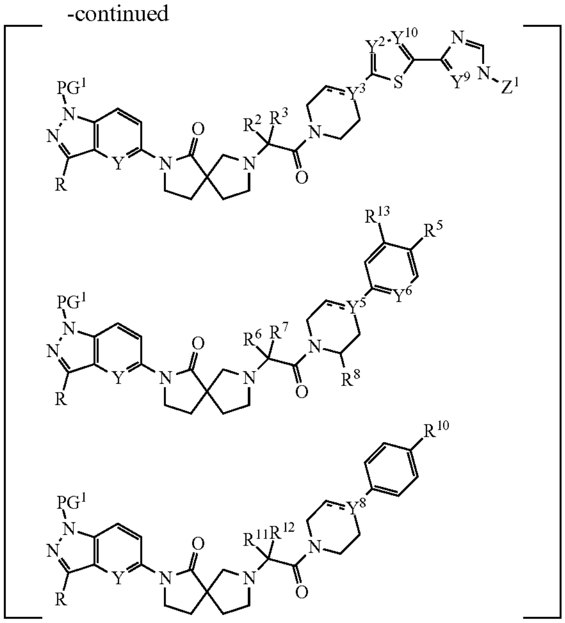

(IE), (IIE), (IIIE)

To a solution of corresponding secondary amine C (1 equiv) in N,N-dimethylformamide (0.1-0.5 M, initial concentration of secondary amine in DMF varied from 0.1 M to 0.5 M based on solubility) at rt were added neat N-ethyl-N-isopropylpropan-2-amine (3-6 equiv, excess N-ethyl-N-isopropylpropan-2-amine was used, or N-ethyl-N-isopropylpropan-2-amine was replaced for trimethylamine) and the corresponding alkylating agent ID, IID or IIID (1.0-1.1 equiv, preferably 1.0 equiv of alkylating agent was used in order to minimize over alkylation) in one portion. The mixture was stirred at rt for 6-24 h (if needed, the mixture was heated at 50° C.). Upon completion as determined by LCMS (or TLC), the mixture was either 1) concentrated directly on a rotary evaporator to give the crude mixture that was used in the next step without further purification, or 2) purified on a silica gel column eluted with methanol/DCM or purified on a RP-C18 column eluted with acetonitrile/water in the presence of 0.1% formic acid to afford the desired corresponding compound IE, IIE or IIIE.

General Procedure D: Deprotection of Indazole when $PG^1$=Trt or THP

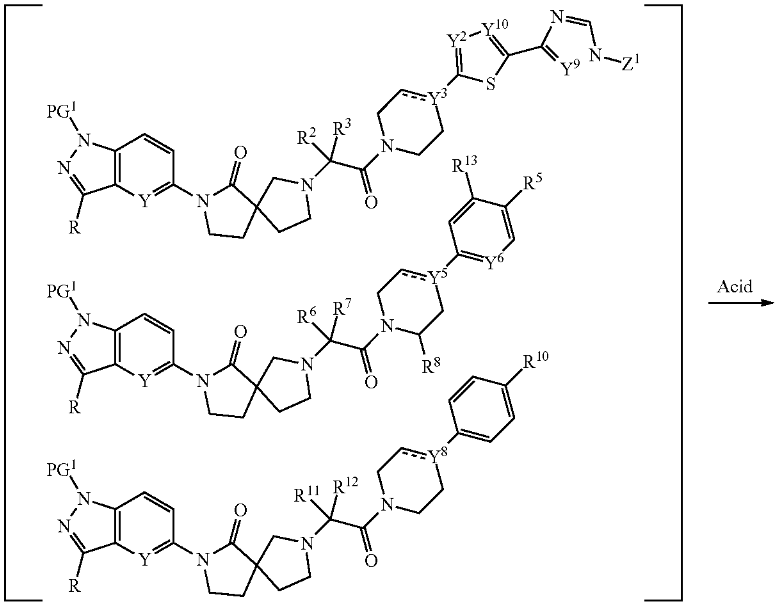

(IE), (IIE), (IIIE)

-continued

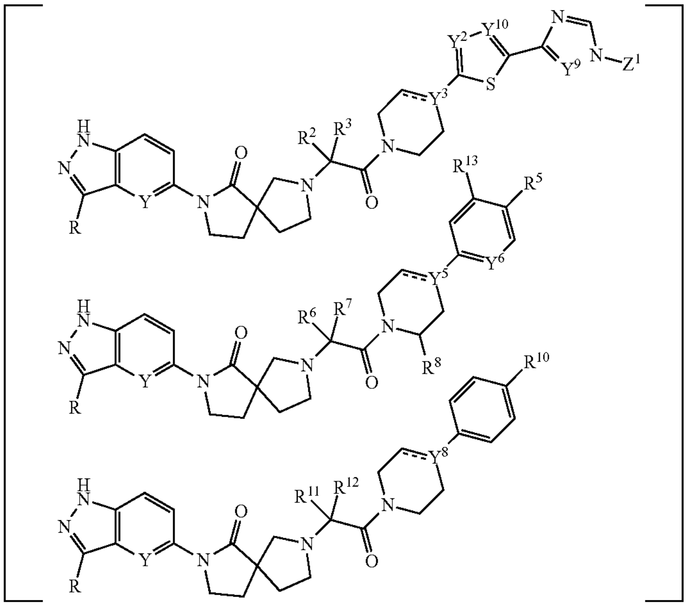

(I), (II), (III)

A solution of trityl or THP protected indazole IE, IIE or IIIE (1 equiv) in DCM/TFA/water (0.05 or 0.5 M, 3:1:0.5 ratio, conditions varied based on solubility of staring material, a mixed DCM/TFA solvent was used in some preparations, Note #1) was stirred at 25° C. 6-16 h. Upon completion as determined by LCMS, the reaction was quenched with sat'd aqueous $NaHCO_3$ and extracted with DCM (or extracted with EtOAc or EtOAc/THF). The combined organic layers were dried over $Na_2SO_4$, filtered and concentrated to afford the crude product I, II or III. Crude product I, II, or III was then either 1) purified on a silica gel column eluted with 0-100% (0-10% 7 M $NH_3$ in methanol)/DCM or 2) purified on a RP-C18 column eluted with 0-100% acetonitrile/water in the presence of 0.1% formic acid to afford the pure compound I, II, or III. When crude material was purified on RP-C18 HPLC column or C-18 cartridges, compounds were free-based using sat'd aqueous $NaHCO_3$ and extracted with either DCM, EtOAc or EtOAc/THF mixture.

Note #1: In some cases, $PG^1$ (Trt or THP) was deprotected using neat trifluoroacetic acid at room temperature.

General Procedure E: Preparation of Hydrochloride Salt

Compound I, II or III was dissolved in a suitable solvent (0.1-0.5 M, DCM, MeOH or i-PrOH). At 0° C., hydrochloric acid (1-3 equiv., 2.0 M in diethyl ether) was added via a syringe. In some cases, small amount of methanol was added prior to the addition of hydrochloric acid. The precipitate was stirred for 5-10 mins at 0° C. Excess solvent(s) and hydrochloric acid were removed using a rotary evaporator at 0° C. The product was dried to afford the corresponding compound I, II or III as a hydrochloric acid salt (equivalence of hydrochloride salt was determined by 1H NMR analysis).

Example 1

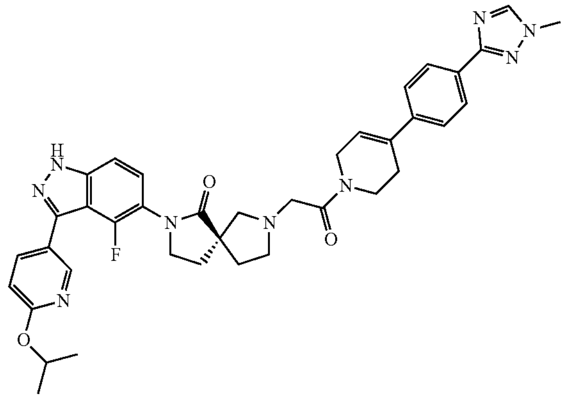 [SMILES: CC(C)Oc1ccc(-c2n[nH]c3ccc(N4CC[C@]5(CCN(CC(=O)N6CC=C(c7ccc(-c8ncn(C)n8)cc7)CC6)C5)C4=O)c(F)c23)cn1]

3-Fluoro-4-iodo-2-methylaniline (1-1)

To a stirred solution of 3-fluoro-2-methylaniline (10.0 g, 0.080 mmol) in acetic acid/water (1:1 ratio, 100 mL) was added $NaBO_3.4H_2O$ (12.3 g, 0.080 mmol). At 0° C., a solution of KI (13.3 g, 0.080 mmol) in 100 mL water was added dropwise over 30 min. After being stirred at rt for 1 h, the mixture was diluted with water, filtered, and air dried to afford 1-1 (15.0 g, 75%) as a brown solid. LCMS: 251.86 $[M+H]^+$.

4-Fluoro-5-iodo-1H-indazole (1-2)

To a stirred solution of 1-1 (10.0 g, 0.038 mmol) in acetic acid (400 mL) at 0° C. was added a solution of $NaNO_2$ (2.67 g, 0.038 mmol) in 10 mL water. After being stirred at rt for 6 h, the mixture was directly concentrated under reduced pressure. The residue was dissolved in EtOAc and washed with water. Organic layer was dried over $Na_2SO_4$ and concentrated under reduced pressure to afford 1-2 (9.0 g, 90%) as a brown solid. LCMS: 262.65 $[M+H]^+$.

3-Bromo-4-fluoro-5-iodo-1H-indazole (1-3)

To a stirred solution of 1-2 (9.0 g, 0.033 mmol) in DMF at 0° C. was added bromine (5.86 g, 0.036 mmol) dropwise. After being stirred at rt for 1 h, the mixture was then poured into water, filtered, and air dried to 1-3 (10.0 g, 85%) as a brown solid. LCMS: 340.78 $[M+H]^+$.

3-Bromo-4-fluoro-5-iodo-1-(tetrahydro-2H-pyran-2-yl)-1H-indazole (1-4)

To a stirred solution of 1-3 (2.0 g, 0.005 mmol) in DCM (20 mL) at 0° C. was added PTSA (0.1 g, 0.0005 mmol). After being stirred at rt for 1 h, the mixture was then poured into sat'd solution of $NaHCO_3$ and extracted with EtOAc. Combined organic layers were dried over $Na_2SO_4$ and concentrated under reduced pressure. The residue was purified by column chromatography to afford 1-4 (1.4 g, 56%) as an orange solid. LCMS: 424.66 $[M+H]^+$.

(5R)-Benzyl 7-(3-bromo-4-fluoro-1-(tetrahydro-2H-pyran-2-yl)-1H-indazol-5-yl)-6-oxo-2,7-diazaspiro[4.4]nonane-2-carboxylate (1-5)

To a stirred solution (15 min) of 1-5 (1.2 g, 4.370 mmol), Intermediate 1A (676 mg, 3.060 mmol) in dry DMSO (15 mL) was added CuI (83 mg, 0.437 mmol) followed by $K_3PO_4$ (1.1 g, 8.74 mmol). The mixture was degassed for 30 min and heated at 100° C. for 36 h. The mixture was cooled to rt, diluted with water, and extracted with EtOAc. The combined organic layers were washed with water and brine, dried over $Na_2SO_4$ and concentrated under reduced pressure. The residue was purified by column chromatographyto afford 1-5 (550 mg, 22%) as a pale yellow solid. LCMS: 572.88 $[M+1]^+$.

(5R)-Benzyl 7-(4-fluoro-3-(6-isopropoxypyridin-3-yl)-1-(tetrahydro-2H-pyran-2-yl)-1H-indazol-5-yl)-6-oxo-2,7-diazaspiro[4.4]nonane-2-carboxylate (1-6)

To a stirred solution of 1-5 (500 mg, 0.877 mmol) and 2-isopropoxy-5-(4,4,5,5-tetramethyl-1,3,2-dioxaborolan-2-yl)pyridine (253 mg, 0.964 mmol) in toluene/water/EtOH (1:1:1 ratio, 9 mL) was added $K_2CO_3$ (605 mg, 4.385 mmol). The mixture was degassed for 10 min, followed by addition of $Pd(PPh_3)_4$ (101 mg, 0.088 mmol), and degassed for another 10 min. After being heated at 100° C. for 3 h, the mixture was cooled to room temperature, diluted with water (30 mL), extracted with EtOAc. Combined organic layers were dried over $Na_2SO_4$ and concentrated under reduced pressure. The residue was purified by column chromatography to afford 1-6 (350 mg, 63%) as an off white solid. LCMS: 628.07 $[M+H]^+$.

(S)-2-(4-Fluoro-3-(6-isopropoxypyridin-3-yl)-1H-indazol-5-yl)-2,7-diazaspiro[4.4]nonan-1-on (1-7)

A solution of 1-6 (330 mg, 0.526 mmol) in TFA (5 mL) was stirred at rt for 16 h. The reaction mixture was directly concentrated under reduced pressure to afford crude 1-7 (120 mg, 22%) as a pale yellow sticky liquid. This crude compound was used in the next step without further purification. LCMS: 409.97 $[M+H]^+$.

(S)-2-(4-Fluoro-3-(6-isopropoxypyridin-3-yl)-1H-indazol-5-yl)-7-(2-(4-(4-(1-methyl-1H-1,2,4-triazol-3-yl)phenyl)-5,6-dihydropyridin-1(2H)-yl)-2-oxoethyl)-2,7-diazaspiro[4.4]nonan-1-one (1)

To a stirred solution of 1-7 (120 mg, 0.293 mmol) in DMF (5 mL) was added DIPEA (0.315 mL, 1.75 mmol) followed by Intermediate 9 (101 mg, 0.322 mmol). After being stirred at rt for 16 h, the mixture was diluted with cold water (10 mL) and extracted with EtOAc. The combined organic layers were washed with brine, dried over $Na_2SO_4$ and concentrated under reduced pressure. The residue was purified by column chromatography using 10% MeOH/DCM to afford Example 1. (60 mg, 29%) as an off white solid. mp: 138-140° C.; $^1H$ NMR (400 MHz, DMSO-$d_6$) δ 13.62 (s, 1H), 8.56 (s, 1H), 8.50 (s, 1H), 8.07 (d, 1H), 7.98-7.92 (m, 2H), 7.57-7.50 (m, 2H), 7.46-7.36 (m, 2H), 6.87 (d, 1H), 6.30-6.26 (m, 1H), 5.36-5.26 (m, 1H), 4.29-4.12 (m, 2H), 3.91 (s, 3H), 3.79-3.43 (m, 7H), 3.16-3.11 (m, 1H), 2.65-2.60 (m, 4H), 2.33-2.15 (m, 3H), 1.93-1.78 (m, 1H), 1.34-1.30 (m, 6H); LCMS: 690.06 $[M+H]^+$.

Example 2

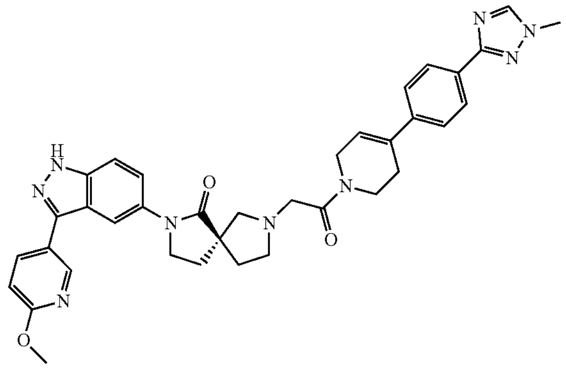 [SMILES: COc1ccc(-c2n[nH]c3ccc(N4CC[C@]5(CCN(CC(=O)N6CC=C(c7ccc(-c8ncn(C)n8)cc7)CC6)C5)C4=O)cc23)cn1]

Example 2 was prepared following General Procedures C and D using Intermediate 7 and Intermediate 9. $^1H$ NMR (400 MHz, DMSO-$d_6$) δ 13.23 (s, 1H), 8.76 (d, 1H), 8.5 (s, 1H), 8.26-8.23 (dd, 1H), 8.16 (s, 1H), 7.96 (d, 2H), 7.78-7.75 (m, 1H), 7.60-7.53 (m, 3H), 6.98 (d, 1H), 6.28 (s, 1H), 4.28 (br s, 1H), 4.19-4.09 (m, 3H), 3.92-3.91 (m, 8H), 3.76-3.67 (m, 2H), 3.50-3.36 (m, 2H), 2.97 (br s, 3H), 2.67-2.62 (m, 2H), 2.21-2.18 (m, 3H). LCMS: 644.45 $[M+H]^+$.

Example 3

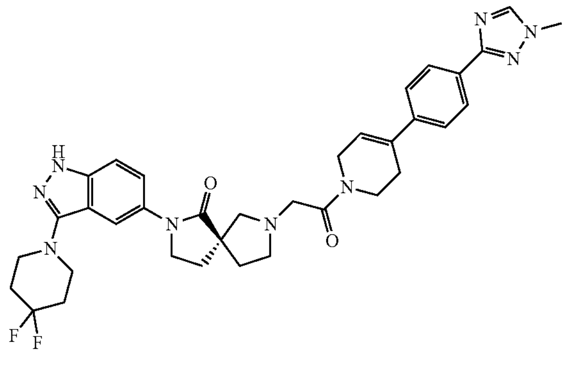 [SMILES: Cn1cnc(-c2ccc(C3=CCN(C(=O)CN4CC[C@]5(CCN(c6ccc7[nH]nc(N8CCC(F)(F)CC8)c7c6)C5=O)C4)CC3)cc2)n1]

(R)-Benzyl 7-(3-(4,4-difluoropiperidin-1-yl)-1-trityl-1H-indazol-5-yl)-6-oxo-2,7-diaza spiro[4.4]nonane-2-carboxylate (3-1)

To a stirred solution of Intermediate 2 (500 mg, 0.659 mmol) and 4,4-difluoropiperidine (95 mg, 0.791 mmol) in dioxane/water (9 mL, 2:1 ratio) was added $K_2CO_3$ (272.8 mg, 1.977 mmol). The mixture was degassed for 10 min, followed by addition of L-proline (22.7 mg, 0.197 mmol) and CuI (12.5 mg, 0.0659 mmol), and degassed again for another 10 min. After being stirred at 100° C. for 16 h, the mixture was diluted with water and extracted with EtOAc. The combined organic layers were dried over $Na_2SO_4$ and concentrated under reduced pressure. The residue was purified by column chromatography to afford 3-1. (250 mg, 50%) as an off white solid. LCMS: 752.55 $[M+H]^+$.

(S)-2-(3-(4,4-Difluoropiperidin-1-yl)-1-trityl-1H-indazol-5-yl)-2,7-diazaspiro[4.4]nonan-1-one (3-2)

To a stirred solution of 3-1 (250 mg, 0.332 mmol) in THF (10 mL) was added 10% Pd/C (500 mg). After being stirred at rt under hydrogen atmosphere for 16 h, the mixture was filtered through a Celite pad and washed with 10% MeOH/DCM. The combined organic layers were concentrated under reduced pressure to afford 3-2 (100 mg, 48%) which used in the next step without any purification. LCMS: 618.49 $[M+H]^+$.

(S)-2-(3-(4,4-Difluoropiperidin-1-yl)-1-trityl-1H-indazol-5-yl)-7-(2-(4-(4-(1-methyl-1H-1,2,4-triazol-3-yl)phenyl)-5,6-dihydropyridin-1(2H)-yl)-2-oxoethyl)-2,7-diazaspiro[4.4]nonan-1-one (3-3)

To a stirred solution 3-2 (100 mg, 0.162 mmol) in DMF (5 mL) was added DIPEA (125 mg, 0.972 mmol) followed by Intermediate 9 (51.2 mg, 0.162 mmol). After being stirred at rt for 16 h, the mixture was diluted with cold water and extracted with EtOAc. The combined organic layers were washed with brine, dried over $Na_2SO_4$ and concentrated under reduced pressure. The residue was purified by column chromatography using 5% methanol/DCM to afford 3-3 (70 mg, 48%) as an off white solid. LCMS: 898.74 $[M+H]^+$.

(S)-2-(3-(4,4-difluoropiperidin-1-yl)-1H-indazol-5-yl)-7-(2-(4-(4-(1-methyl-1H-1,2,4-triazol-3-yl)phenyl)-5,6-dihydropyridin-1 (2H)-yl)-2-oxoethyl)-2,7-diazaspiro[4.4]nonan-1-one (Example 3)

To a stirred solution of 3-3 (70 mg, 0.077 mmol) in DCM (4 mL) at 0° C. was added TFA (3 ml). After being stirred at rt for 3 h, the mixture was quenched with sat'd $NaHCO_3$ solution and extracted with EtOAc. The combined organic layers were dried over $Na_2SO_4$ and concentrated under reduced pressure. The residue was purified by column chromatography to afford Example 3 (25 mg, 45% yield) as an off white solid. $^1H$ NMR (400 MHz, DMSO-$d_6$) δ 12.08 (s, 1H), 8.50 (s, 1H), 7.96 (d, 2H), 7.83 (d, 1H), 7.63 (d, 1H), 7.54 (d, 2H), 7.36 (d, 1H), 6.28 (br s, 1H), 4.33-4.10 (m, 3H), 3.91 (s, 3H), 3.88-3.60 (m, 4H), 3.46-3.43 (m, 5H), 2.95-2.90 (m, 2H), 2.85-2.80 (m, 2H), 2.70-2.60 (m, 1H), 2.20-2.07 (m, 8H), 1.85-1.78 (m, 1H); LCMS: 656.45 $[M+H]^+$.

Example 4

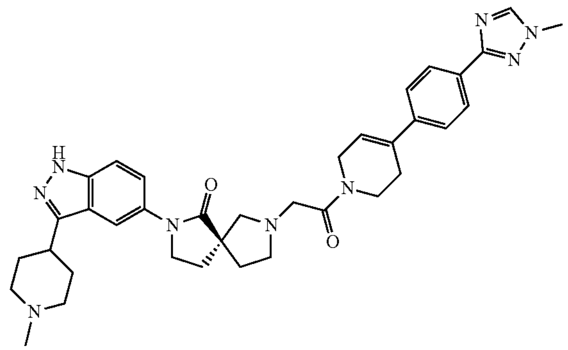 [SMILES: CN1CCC(c2n[nH]c3ccc(N4CC[C@]5(CCN(CC(=O)N6CC=C(c7ccc(-c8ncn(C)n8)cc7)CC6)C5)C4=O)cc23)CC1]

4-(4,4,5,5-Tetramethyl-1,3,2-dioxaborolan-2-yl)-1,2,3,6-tetrahydropyridine hydrochloride (4-1)

To a stirred solution of tert-butyl 4-(4,4,5,5-tetramethyl-1,3,2-dioxaborolan-2-yl)-5,6-dihydropyridine-1(2H)-carboxylate (2.0 g, 6.472 mmol) in MTBE (16 mL) was added 2 M HCl in $Et_2O$ (48 mL). After being stirred at rt for 16 h, the mixture was filtered. The obtained residue was washed with $Et_2O$ and air dried to afford 4-1 (1.2 g, 75%) as an off white solid.

1-Methyl-4-(4,4,5,5-tetramethyl-1,3,2-dioxaborolan-2-yl)-1,2,3,6-tetrahydropyridine (4-2)

To a stirred solution of 4-1 (500 mg, 2.040 mmol) in MeOH (8 mL) was added $Et_3N$ (0.58 mL, 4.08 mmol) followed by formaldehyde (3 mL) and 10% Pd/C (100 mg, wet). After being stirred at rt for 5 h under hydrogen atmosphere, the mixture was filtered through a Celite pad and washed with 10% MeOH/DCM. The organic layer was concentrated under reduced pressure to afford 4-2 (400 mg, crude) which was used in the next step without further purification.

(R)-Benzyl 7-(3-(1-methyl-1,2,3,6-tetrahydropyridin-4-yl)-1-trityl-1H-indazol-5-yl)-6-oxo-2,7-diazaspiro[4.4]nonane-2-carboxylate (4-3)

To a stirred solution of Intermediate 2 (300 mg, 0.395 mmol) in toluene/EtOH/water (9 mL, 1:1:1 ratio) were added $K_2CO_3$ (273 mg, 1.978 mmol) and N-methyl-4-(4,4,5,5-tetramethyl-1,3,2-dioxaborolan-2-yl)picolinamide (176 mg, 0.791 mmol). The mixture was degassed for 10 min, followed by addition of $Pd(PPh_3)_4$ (22 mg, 0.0197 mmol), and degassed again for another 10 min. After being stirred at 90° C. for 3 h, the mixture was diluted with water and extracted with EtOAc. The combined organic layers were dried over $Na_2SO_4$ and concentrated under reduced pressure to afford 4-3 (200 mg, 69%) as a brown thick liquid. LCMS: 728.57 $[M+H]^+$.

(S)-7-(2-(4-(4-(1-methyl-1H-1,2,4-triazol-3-yl)phenyl)-3,6-dihydropyridin-1(2H)-yl)-2-oxoethyl)-2-(3-(1-methylpiperidin-4-yl)-1H-indazol-5-yl)-2,7-diazaspiro[4.4]nonan-1-one (Example 4)

Example 4 was prepared following General Procedures B, C and D using (S)-2-(3-(1-methylpiperidin-4-yl)-1-trityl-1H-indazol-5-yl)-2,7-diazaspiro[4.4]nonan-1-one and Intermediate 9. $^1$H NMR (400 MHz, DMSO-$d_6$) δ 12.86 (br s, 1H), 10.70-10.22 (m, 2H), 8.52 (s, 1H), 8.00-7.95 (m, 2H), 7.82-7.72 (m, 1H), 7.59-7.48 (m, 2H), 6.31 (s, 1H), 4.6-4.50 (m, 2H), 4.22-4.10 (m, 2H), 4.09-3.90 (m, 6H), 3.65-3.25 (m, 8H), 3.12 (dd, 2H), 2.80-2.55 (m, 5H), 2.44-2.08 (m, 8H); LCMS: 634.08 $[M+H]^+$.

Example 5

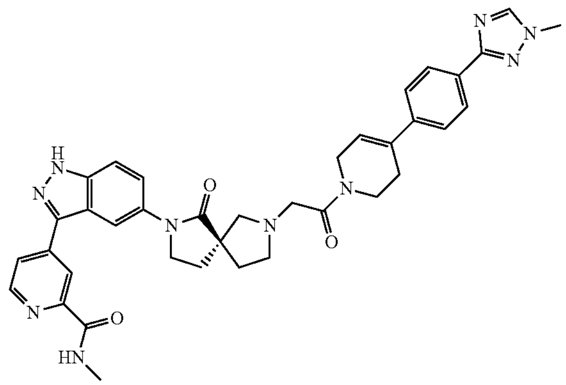 [SMILES: CNC(=O)c1cc(-c2n[nH]c3ccc(N4CC[C@]5(CCN(CC(=O)N6CC=C(c7ccc(-c8ncn(C)n8)cc7)CC6)C5)C4=O)cc23)ccn1]

4-Bromopicolinoyl chloride (5-1)

A mixture of 4-bromopicolinic acid (2.0 g, 9.90 mmol) and thionylchloride (15 mL) were stirred at 90° C. for 5 h. The reaction was then quenched with methanol and concentrated under reduced pressure to afford crude 5-1 (2 g) which was directly used in the next step without further purification.

4-Bromo-N-methylpicolinamide (5-2)

To a stirred solution of 5-1 (2.0 g, 9.09 mmol) in THF (20 mL) was added methylamine (2 M in THF) solution at 0° C. After being stirred at rt overnight, the mixture was concentrated under reduced pressure. The resulting residue was dissolved in EtOAc and washed with water. The organic layer was dried over $Na_2SO_4$ and concentrated under reduced pressure to afford 5-2 (1.5 g, 70% over 2 steps) which was used in the next step without further purification.

N-Methyl-4-(4,4,5,5-tetramethyl-1,3,2-dioxaborolan-2-yl)picolinamide (5-3)

To a stirred solution of 5-2 (600 mg, 1.0 eq.) in 1,4 dioxane (8 mL) were added bis(pinacalato)diboron (1.5 eq.) and KOAc (3.0 eq.). The mixture was degassed for 10 min, followed by the addition of $PdCl_2$(dppf)-DCM (0.1 eq.), and degassed again for 10 min. After being stirred at 80° C. for 3 h, TLC indicated formation of a new polar spot with complete consumption of starting material. The mixture was cooled to rt and the crude 5-3 was used in the next step without any workup and purification.

(S)—N-methyl-4-(5-(7-(2-(4-(4-(1-methyl-1H-1,2,4-triazol-3-yl)phenyl)-5,6-dihydropyridin-1(2H)-yl)-2-oxoethyl)-1-oxo-2,7-diazaspiro[4.4]nonan-2-yl)-1-trityl-1H-indazol-3-yl)picolinamide (Example 5)

Example 5 prepared following General Procedures A, B2, C and D using 5-3, (S)—N-Methyl-4-(5-(1-oxo-2,7-diazaspiro[4.4]nonan-2-yl)-1-trityl-1H-indazol-3-yl)picolinamide and Intermediate 9. $^1$H NMR (400 MHz, DMSO-$d_6$) δ 13.78 (s, 1H), 8.83 (d, 1H), 8.76-8.872 (m, 1H), 8.59 (s, 1H), 8.50 (s, 1H), 8.29 (s, 1H), 8.15 (dd, 1H), 7.95 (d, 2H), 7.82 (t, 1H), 7.67 (d, 1H), 7.58-7.52 (m, 2H), 6.28 (s, 1H), 4.35-4.28 (m, 1H), 4.16-4.00 (m, 1H), 3.98-3.75 (m, 5H), 3.80-3.65 (m, 2H), 3.48-3.30 (m, 2H), 3.00-2.82 (m, 5H), 2.75-2.50 (m, 4H), 2.30-2.10 (m, 3H), 1.86-1.79 (m, 1H); LCMS: 671.47 $[M+H]^+$.

Example 6

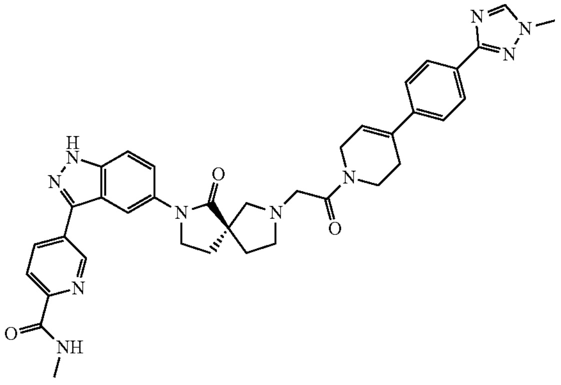 [SMILES: CNC(=O)c1ccc(-c2n[nH]c3ccc(N4CC[C@]5(CCN(CC(=O)N6CC=C(c7ccc(-c8ncn(C)n8)cc7)CC6)C5)C4=O)cc23)cn1]

Example 6 was prepared following the procedure described for Example 5 using N-methyl-5-(4,4,5,5-tetramethyl-1,3,2-dioxaborolan-2-yl)picolinamide, Intermediate 2, and Intermediate 9. $^1$H NMR (400 MHz, DMSO-$d_6$) δ 13.60 (s, 1H), 9.21 (d, 1H), 8.84 (br d, 1H), 8.54-8.50 (m, 2H), 8.27 (s, 1H), 8.16 (d, 1H), 7.95 (d, 2H), 7.81 (t, 1H), 7.66 (d, 1H), 7.55 (t, 2H), 6.28 (s, 1H), 4.28-4.13 (m, 2H), 3.91 (s, 5H), 3.77-3.73 (m, 3H), 3.51-3.41 (m, 2H), 2.95-2.85 (m, 6H), 2.67-2.61 (m, 2H), 2.35-2.17 (m, 3H), 1.84-1.83 (m, 1H).); LCMS: 671.47 $[M+H]^+$.

Example 7

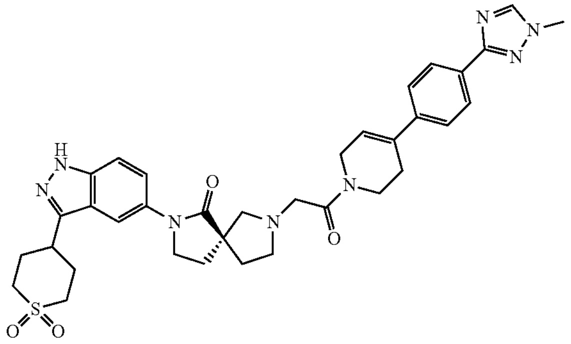 [SMILES: Cn1cnc(-c2ccc(C3=CCN(C(=O)CN4CC[C@]5(CCN(c6ccc7[nH]nc(C8CCS(=O)(=O)CC8)c7c6)C5=O)C4)CC3)cc2)n1]

(R)-Benzyl 7-(3-(3,6-dihydro-2H-thiopyran-4-yl)-1-trityl-1H-indazol-5-yl)-6-oxo-2,7-diazaspiro[4.4]nonane-2-carboxylate (7-1)

The title compound was prepared following a General Procedure A using Intermediate 2 and 4-(4,4,5,5-tetramethyl-1,3,2-dioxaborolan-2-yl)-1-(2,2,2-trifluoroethyl)-1,2,3,6-tetrahydropyridine to afford 7-1. (300 mg, 78%) as an off white solid. LC-MS (ESI) m/z 731.08 $[M+H]^+$.

(R)-Benzyl 7-(3-(1,1-dioxido-3,6-dihydro-2H-thiopyran-4-yl)-1-trityl-1H-indazol-5-yl)-6-oxo-2,7-diazaspiro[4.4]nonane-2-carboxylate (7-2)

To a stirred solution of 7-1 (300 mg, 0.410 mmol) in acetone/water (15 mL, 2:1 ratio) was added oxone (252.0 mg, 0.821 mmol) at 0° C. After being stirred at rt for 3 h, the mixture was diluted with water and extracted with EtOAc. The combined organic layers were dried over $Na_2SO_4$ and concentrated under reduced pressure to 7-2 (220 mg, 70%) which was used in the next step without further purification. LCMS: 763.06 $[M+H]^+$.

(S)-2-(3-(1,1-Dioxidotetrahydro-2H-thiopyran-4-yl)-1-trityl-1H-indazol-5-yl)-2,7-diazaspiro[4.4]nonan-1-one (7-3)

The title compound was prepared following General Procedure B using 7-2. LCMS: 631.65 $[M+H]^+$.

(S)-7-(2-(4-(4-(1-Methyl-1H-1,2,4-triazol-3-yl)phenyl)-5,6-dihydropyridin-1(2H)-yl)-2-oxoethyl)-2-(3-(tetrahydro-2H-thiopyran 1,1-dioxide-4-yl)-1H-indazol-5-yl)-2,7-diazaspiro[4.4]nonan-1-one (Example 7)

Example 7 was prepared following General Procedures C and D using 7-3 and Intermediate 9. $^1H$ NMR (400 MHz, DMSO-$d_6$) δ 12.79 (s, 1H), 8.50 (s, 1H), 7.96 (d, 2H), 7.89 (s, 1H), 7.68-7.65 (m, 1H), 7.56-7.49 (m, 2H), 7.48 (d, 1H), 6.28 (s, 1H), 4.32-4.10 (m, 3H), 3.91 (s, 3H), 3.88-3.60 (m, 4H), 3.50-3.30 (m, 3H), 3.22-3.15 (m, 2H), 3.10-2.75 (m, 5H), 2.70-2.55 (m, 2H), 2.40-2.10 (m, 7H), 1.90-1.75 (m, 1H); LCMS: 669.04 $[M+H]^+$.

Example 8

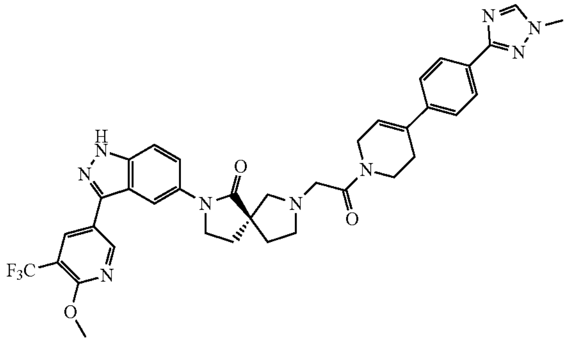 [SMILES: COc1ncc(-c2n[nH]c3ccc(N4CC[C@]5(CCN(CC(=O)N6CC=C(c7ccc(-c8ncn(C)n8)cc7)CC6)C5)C4=O)cc23)cc1C(F)(F)F]

Example 8 was prepared following General Procedures A, B2, and C using Intermediate 2, 2-methoxy-5-(4,4,5,5-tetramethyl-1,3,2-dioxaborolan-2-yl)-3-(trifluoromethyl)pyridine and Intermediate 9. $^1H$ NMR (400 MHz, DMSO-$d_6$) δ 13.41 (s, 1H), 9.04 (d, 1H), 8.51 (s, 1H), 8.50 (s, 1H), 8.19 (s, 1H), 7.97-7.94 (m, 2H), 7.84-7.80 (m, 1H), 7.62 (d, 1H), 7.57-7.52 (m, 2H), 6.28 (s, 1H), 4.33-4.28 (m, 1H), 4.18-4.09 (m, 1H), 4.07 (s, 3H), 3.91 (s, 3H), 3.90-3.85 (m, 1H), 3.80-3.60 (m, 3H), 3.50-3.35 (m, 2H), 2.95-2.80 (m, 3H), 2.70-2.58 (m, 3H), 2.25-2.10 (m, 3H), 1.85-1.75 (m, 1H); LCMS: 712.4 $[M+H]^+$.

Example 9

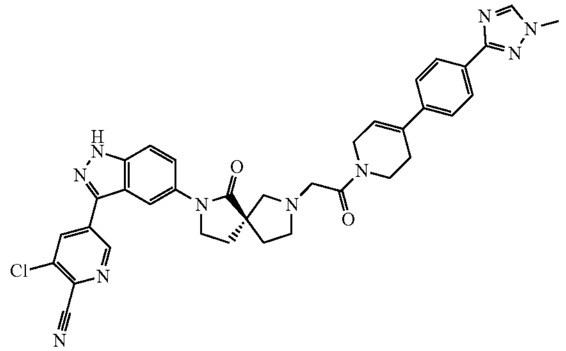 [SMILES: Cn1cnc(-c2ccc(C3=CCN(C(=O)CN4CC[C@]5(CCN(c6ccc7[nH]nc(-c8cnc(C#N)c(Cl)c8)c7c6)C5=O)C4)CC3)cc2)n1]

Example 9 was prepared following General Procedures A, B2, and C using Intermediate 2 and 3-chloro-5-(4,4,5,5-tetramethyl-1,3,2-dioxaborolan-2-yl)picolinonitrile and Intermediate 9. $^1H$ NMR (400 MHz, DMSO-$d_6$) δ 13.90 (s, 1H), 9.32 (d, 1H), 8.68 (s, 1H), 8.50 (s, 1H), 8.21 (d, 1H), 7.95-7.90 (m, 3H), 7.68 (d, 1H), 7.54-7.52 (m, 2H), 6.28 (s, 1H), 4.36-4.30 (m, 1H), 4.14-4.10 (m, 2H), 3.91 (s, 5H), 3.79-3.72 (m, 2H), 3.44-3.36 (m, 2H), 3.01-2.80 (m, 3H), 2.70-2.63 (m, 2H), 2.28-2.12 (m, 3H), 1.86-1.77 (m, 1H); LCMS: 673.30 $[M+H]^+$.

Example 10

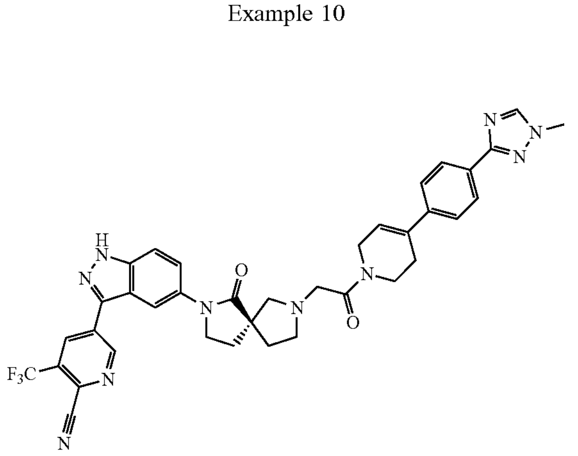

Example 10 was prepared following General Procedures A, B2, and C using Intermediate 2 5-(4,4,5,5-tetramethyl-1,3,2-dioxaborolan-2-yl)-3-(trifluoromethyl)picolinonitrile and Intermediate 9. $^{1}H$ NMR (400 MHz, DMSO-$d_6$) δ 12.98 (s, 1H), 9.63 (s, 1H), 8.80 (s, 1H), 8.50 (s, 1H), 8.27 (s, 1H), 7.97-7.90 (m, 3H), 7.70 (d, 1H), 7.57-7.52 (m, 2H), 6.27 (s, 1H), 4.32-4.10 (m, 2H), 3.98-3.90 (m, 2H), 3.91 (s, 3H), 3.85-3.60 (m, 2H), 3.50-3.31 (m, 2H), 3.00-2.80 (m, 3H), 2.75-2.51 (m, 3H), 2.78-2.60 (m, 3H), 1.80-1.75 (m, 1H); LCMS: 707.3 $[M+H]^+$.

Example 11

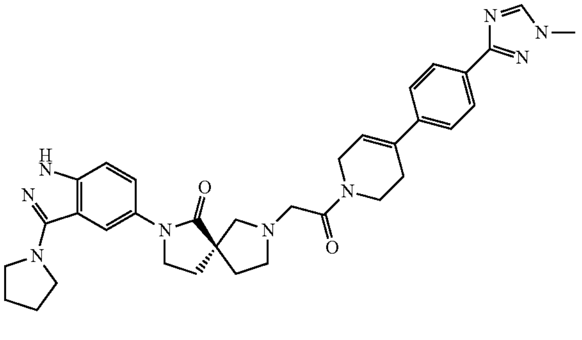

(R)-Benzyl 6-oxo-7-(3-(pyrrolidin-1-yl)-1-trityl-1H-indazol-5-yl)-2,7-diazaspiro[4.4]nonane-2-carboxylate (11-1)

To a stirred solution of Intermediate 2 (400 mg, 0.527 mmol) in DMSO (6 mL) were added $K_2CO_3$ (218 mg, 1.581 mmol), pyrrolidine (44 mg, 0.633 mmol), and L-proline (18 mg, 0.158 mmol). The mixture was degassed for 10 min, followed by the addition of CuI (10 mg, 0.052 mmol), and degassed again for another 10 min. The mixture was warmed up and stirred at 90 C for 36 h. The mixture was diluted with water (20 mL) and extracted with EtOAc. The combined organic layers were dried over $Na_2SO_4$ and concentrated under reduced pressure to afford 11-1 (400 mg, crude) as a brown thick liquid. LCMS: 702.16 $[M+H]^+$.

(S)-2-(3-(Pyrrolidin-1-yl)-1H-indazol-5-yl)-2,7-diazaspiro[4.4]nonan-1-one (11-2)

A mixture of 11-1 in TFA (5 mL) was stirred at rt for 16 h. The mixture was concentrated under reduced pressure to afford 11-2 (200 mg, crude TFA salt) which was used in the next step without further purification. LCMS: 326.10 $[M+H]^+$.

(S)-7-(2-(4-(4-(1-Methyl-1H-1,2,4-triazol-3-yl)phenyl)-5,6-dihydropyridin-1(2H)-yl)-2-oxoethyl)-2-(3-(pyrrolidin-1-yl)-1H-indazol-5-yl)-2,7-diazaspiro[4.4]nonan-1-one (Example 11)

Example 11 was prepared following General Procedure C and D using 11-2 and Intermediate 9. $^{1}H$ NMR (400 MHz, DMSO-$d_6$) δ 11.65 (s, 1H), 8.50 (s, 1H), 7.99-7.91 (m, 3H), 7.58-7.49 (m, 3H), 7.26 (d, 1H), 6.28 (s, 1H), 4.36-4.25 (m, 1H), 4.20-4.05 (m, 1H), 3.91 (s, 3H), 3.85-3.60 (m, 4H), 3.55-3.30 (m, 7H), 2.96-2.85 (m, 1H), 2.84-2.77 (m, 1H), 2.68-2.55 (m, 2H), 2.20-2.05 (m, 4H), 1.98-1.90 (m, 4H), 1.84-1.72 (m, 1H); LCMS: 606.16 $[M+H]^+$.

Example 12

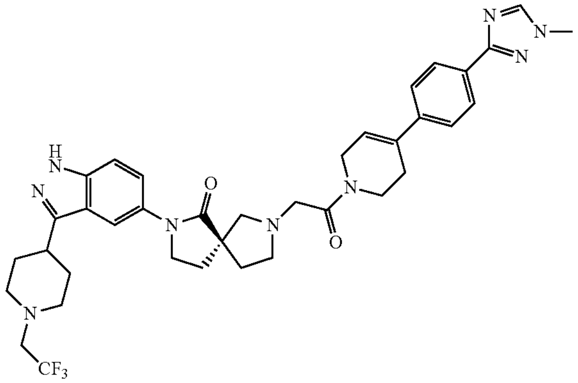

4-(4,4,5,5-Tetramethyl-1,3,2-dioxaborolan-2-yl)-1,2,3,6-tetrahydropyridine hydrochloride (12-1)

To a stirred solution of tert-butyl 4-(4,4,5,5-tetramethyl-1,3,2-dioxaborolan-2-yl)-5,6-dihydropyridine-1(2H)-carboxylate (2.0 g, 6.472 mmol) in MTBE (16 mL) was added 2 M HCl in $Et_2O$ (48 mL). After being stirred at rt for 16 h, the mixture was filtered. The residue was washed with $Et_2O$ and air dried to afford 12-1 (1.2 g, 75%) as an off white solid.

Step 2: 4-(4,4,5,5-Tetramethyl-1,3,2-dioxaborolan-2-yl)-1-(2,2,2-trifluoroethyl)-1,2,3,6-tetrahydropyridine (12-2)

To a stirred solution of 12-1 (500 mg, 2.040 mmol) in THF (5 mL) was added TEA (1.4 mL, 10.2 mmol). After being stirred at rt for 10 min, 2,2,2-trifluoroethyl trifluoromethane sulfonate (473 mg, 2.040 mmol) was added and stirred at rt for 16 h. The mixture was poured into a sat'd $NaHCO_3$ solution and extracted with EtOAc. The combined organic layers were dried over $Na_2SO_4$ and concentrated under reduced pressure to afford 12-2 (300 mg, 51%) which was used in the next step without further purification. GCMS: 291.1 $[M]^+$ (S)-7-(2-(4-(4-(1-Methyl-1H-1,2,4-triazol-3-yl)phenyl)-5,6-dihydropyridin-1(2H)-yl)-2-oxoethyl)-2-(3-(1-(2,2,2-trifluoroethyl)piperidin-4-yl)-1H-indazol-5-yl)-2,7-diazaspiro[4.4]nonan-1-one (Example 12)

Example 12 was prepared as described in Example 11 using 12-2 and (R)-benzyl 7-(3-iodo-1-trityl-1H-indazol-5- yl)-6-oxo-2,7-diazaspiro[4.4]nonane-2-carboxylate followed by General Procedures C and D using Intermediate 9. $^1$H NMR (400 MHz, DMSO-$d_6$) δ 12.62 (s, 1H), 8.50 (s, 1H), 7.96 (d, 2H), 7.90-7.88 (m, 1H), 7.64-7.61 (m, 1H), 7.59-7.53 (m, 2H), 7.44 (d, 1H), 6.28 (s, 1H), 4.32-4.20 (m, 3H), 3.91 (s, 3H), 3.88-3.60 (m, 4H), 3.50-3.30 (m, 3H), 3.25-3.15 (m, 2H), 3.05-2.98 (m, 5H), 2.70-2.60 (m, 4H), 2.23-2.05 (m, 3H), 1.95-1.75 (m, 5H); LCMS: 702.5 $[M+H]^+$.

Example 13

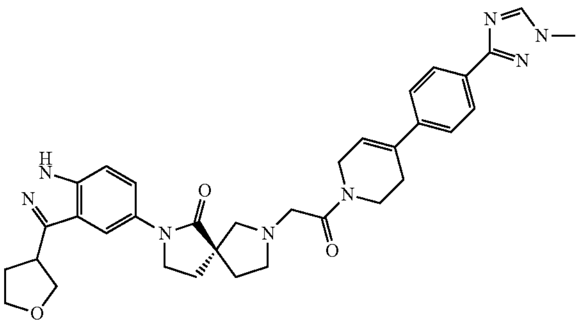

(R)-Benzyl 7-(3-(furan-3-yl)-1-trityl-1H-indazol-5-yl)-6-oxo-2,7-diazaspiro[4.4]nonane-2-carboxylate (13-1)

To a stirred solution Intermediate 2 (1.5 g, 1.981 mmol) and 2-(furan-3-yl)-4,4,5,5-tetramethyl-1,3,2-dioxaborolane (0.38 g, 1.981 mmol) in toluene/water/ethanol (30 mL, 1:1:1 ratio) were added $K_2CO_3$ (1.36 g, 9.840 mmol) and $Pd(Ph_3P)_4$ (0.22 g, 0.198 mmol). The mixture was degassed for 10 min followed by heating at 80° C. for 2 h. The mixture was cooled to room temperature, diluted with cold water, and extracted with EtOAc. The combined organic layers were washed with water, brine, dried over $Na_2SO_4$ and concentrated. The residue was purified by column chromatography using 50% EtOAc/hexanes to afford 13-1 (1.02 g, 73%) as an off white solid. LCMS: 699.10 $[M+H]^+$.

(5S)-2-(3-(Tetrahydrofuran-3-yl)-1-trityl-1H-indazol-5-yl)-2,7-diazaspiro[4.4]nonan-1-one (13-2)

To a solution of 13-1 (1.02 g, 1.461 mmol) in THF (60 mL) was added wet Pd/C (2.04 g). After being stirred at rt under $H_2$ atmosphere for 3 h, the mixture was filtered through a Celite pad and concentrated to afford 13-2 (0.57 g, 68%) as an off white solid. LCMS: 569.68 $[M+H]^+$.

(5S)-7-(2-(4-(4-(1-Methyl-1H-1,2,4-triazol-3-yl)phenyl)-5,6-dihydropyridin-1(2H)-yl)-2-oxoethyl)-2-(3-(tetrahydrofuran-3-yl)-1H-indazol-5-yl)-2,7-diazaspiro[4.4]nonan-1-one (Example 13)

Example 13 was prepared following General Procedures C and D using 13-2 and Intermediate 9 $^1$H NMR (DMSO-$d_6$, 400 MHz) δ 12.75 (s, 1H), 8.50 (s, 1H), 7.96 (d, 2H), 7.88-7.84 (m, 1H), 7.72-7.66 (m, 1H), 7.54 (d, 2H), 7.48-7.44 (m, 1H), 6.31-6.25 (m, 1H), 4.38-4.23 (m, 1H), 4.20-4.05 (m, 2H), 3.99-3.92 (m, 1H), 3.91 (s, 3H), 3.86-3.61 (m, 7H), 3.48-3.34 (m, 3H), 2.98-2.86 (m, 1H), 2.85-2.78 (m, 1H), 2.70-2.52 (m, 3H), 2.45-2.30 (m, 1H), 2.27-2.05 (m, 4H), 1.84-1.73 (m, 1H); LCMS: 607.17 $[M+H]^+$.

Example 14

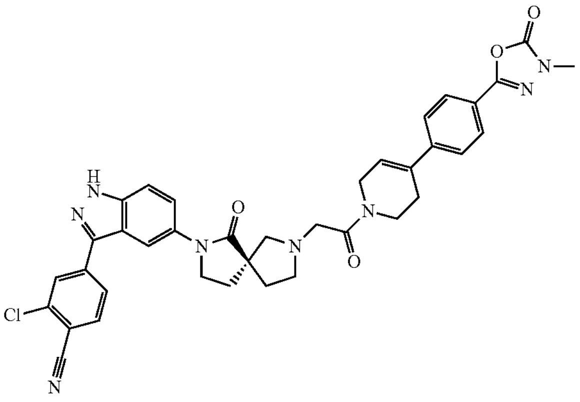

Example 14 was prepared following General Procedures A, B2, and C using Intermediate 3, 2-chloro-4-(4,4,5,5-tetramethyl-1,3,2-dioxaborolan-2-yl)benzonitrile, and Intermediate 15. Data for 1.0 HCl salt: 1H NMR (DMSO-$d_6$, 400 MHz) δ 13.80 (s, 1H), 10.40 (d, 1H), 8.26 (d, 2H), 8.16-8.11 (m, 2H), 7.85-7.78 (m, 3H), 7.73-7.63 (m, 3H), 6.41 (s, 1H), 4.64-4.53 (m, 2H), 4.22-4.15 (m, 2H), 4.10-3.95 (m, 2H), 3.81-3.75 (m, 2H), 3.61 (br, 1H), 3.50-3.43 (br, 2H), 3.42 (s, 2H), 3.40-3.30 (m, 3H), 2.67 (br, 1H), 2.56 (br, 1H), 2.44-2.27 (m, 3H), 2.20-2.15 (m, 1H); LCMS: 689.20 $[M+H]^+$.

Example 15

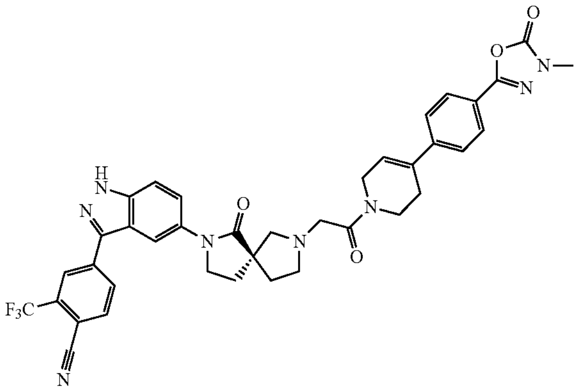

Example 15 was prepared following General Procedures A, B2, C, and E using Intermediate 3, (4-cyano-3-(trifluoromethyl)phenyl)boronic acid, and Intermediate 15. Data for 1.0 HCl salt: $^1$H NMR (DMSO-$d_6$, 400 MHz) δ 13.88 (s, 1H), 10.39 (d, 1H), 8.50 (d, 2H), 8.34 (br, 2H), 7.88-7.64 (m, 6H), 6.41 (s, 1H), 4.65-4.52 (m, 2H), 4.22-4.15 (m, 2H), 4.11-3.97 (m, 2H), 3.81-3.75 (m, 2H), 3.61 (br, 1H), 3.50-3.43 (br, 2H), 3.42 (s, 3H), 3.40-3.30 (m, 2H), 2.67 (br, 1H), 2.57 (br, 1H), 2.44-2.28 (m, 3H), 2.22-2.16 (m, 1H); LCMS: 723.20 $[M+H]^+$.

Example 16

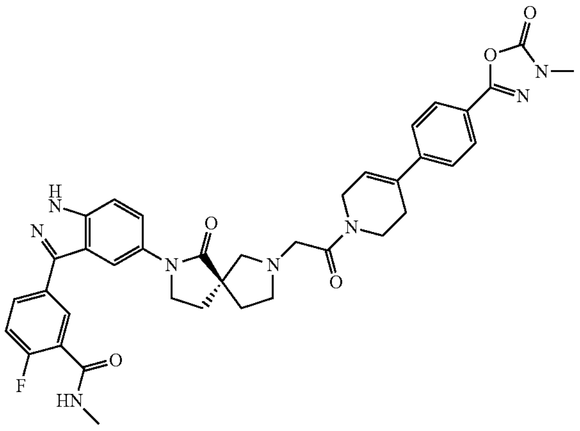

Example 16 was prepared following General Procedures A, B1, C, D and E using Intermediate 3, 2-fluoro-N-methyl-5-(4,4,5,5-tetramethyl-1,3,2-dioxaborolan-2-yl)benzamide, and Intermediate 15. Data for 1.0 HCl salt: 1H NMR ($DMSO-d_6$, 400 MHz) δ 13.45 (s, 1H), 10.40 (d, 1H), 8.20-8.14 (m, 2H), 8.08-8.06 (br, 1H), 7.81-7.77 (m, 3H), 7.67-7.63 (m, 3H), 7.49-7.43 (m, 1H), 6.40 (s, 1H), 4.65-4.52 (m, 2H), 4.22-4.15 (m, 2H), 4.11-3.97 (m, 2H), 3.81-3.75 (m, 2H), 3.61 (br, 1H), 3.50-3.43 (br, 2H), 3.42 (s, 3H), 3.40-3.30 (m, 2H), 2.83 (d, 3H), 2.67 (br, 1H), 2.57 (br, 1H), 2.44-2.28 (m, 3H), 2.22-2.16 (m, 1H); LCMS: 705.30 $[M+H]^+$.

Example 17

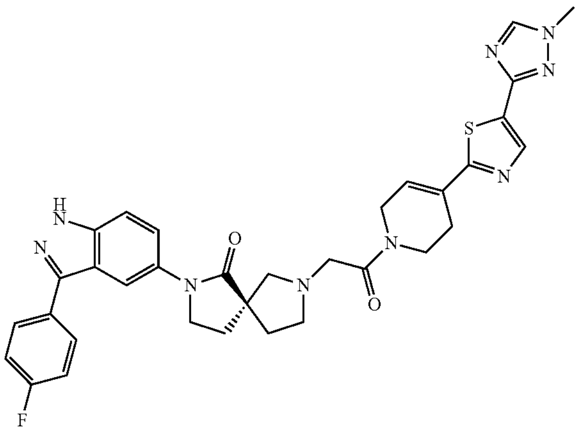

Example 17 was prepared following General Procedures A, B2, and C using Intermediate 3, 2-(4-fluorophenyl)-4,4,5,5-tetramethyl-1,3,2-dioxaborolane, and Intermediate 13. $^1H$ NMR (400 MHz, $DMSO-d_6$) δ 13.25 (s, 1H), 8.56 (s, 1H), 8.18 (s, 1H), 8.15 (s, 1H), 8.01-7.97 (m, 2H), 7.75 (d, 1H), 7.59 (d, 1H), 7.35 (t, 2H), 6.71 (s, 1H), 4.38-4.17 (m, 2H), 3.90-3.64 (m, 7H), 3.45-3.36 (m, 3H), 2.94-2.82 (m, 2H), 2.72 (s, 1H), 2.67-2.49 (m, 2H), 2.23-2.11 (m, 3H), 1.82-1.77 (m, 1H); LCMS: 638.01 $[M+H]^+$.

Example 18

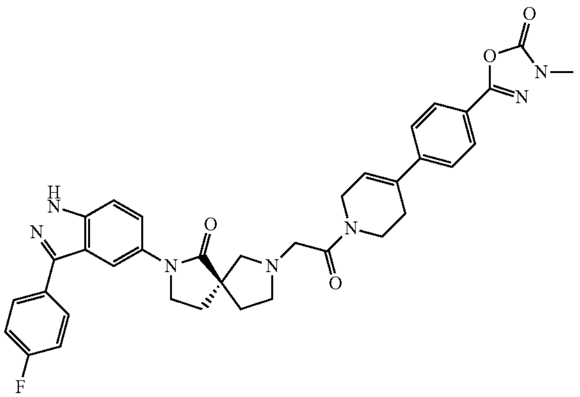

Example 18 was prepared following General Procedures A, B2, and C using Intermediate 3, 2-(4-fluorophenyl)-4,4,5,5-tetramethyl-1,3,2-dioxaborolane, and Intermediate 15. $^1H$ NMR ($DMSO-d_6$, 300 MHz) δ 13.65 (br s, 1H), 8.16 (s, 1H), 8.02-7.96 (m, 2H), 7.77-7.72 (m, 3H), 7.68-7.54 (m, 3H), 7.38-7.31 (m, 2H), 6.39-6.35 (m, 1H), 4.32-3.62 (m, 6H), 3.50-3.35 (m, 6H), 2.98-2.78 (m, 2H), 2.73-2.56 (m, 3H), 2.30-2.06 (m, 3H), 1.84-1.75 (m, 1H); LCMS: 648.41 $[M+H]^+$.

Example 19

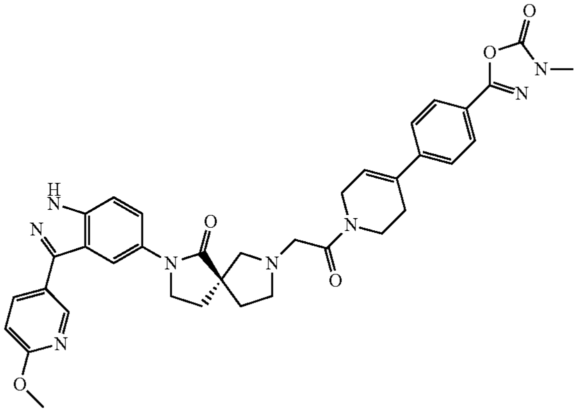

Example 19 was prepared following General Procedures A, B2, and C using Intermediate 3, 2-methoxy-5-(4,4,5,5-tetramethyl-1,3,2-dioxaborolan-2-yl)pyridine, and Intermediate 15. $^1H$ NMR ($DMSO-d_6$, 400 MHz) δ 13.26 (s, 1H), 8.75 (d, 1H), 8.24 (dd, 1H), 8.15 (br d, 1H), 7.78-7.71 (m, 3H), 7.66-7.55 (m, 3H), 6.98 (dd, 1H), 6.38-6.34 (m, 1H), 4.39-4.28 (m, 1H), 4.25-4.05 (m, 1H), 3.93 (s, 3H), 3.92-3.62 (m, 5H), 3.50-3.42 (m, 2H), 3.40 (s, 3H), 2.98-2.75 (m, 3H), 2.73-2.55 (m, 2H), 2.25-2.05 (m, 3H), 1.85-1.76 (m, 1H); LCMS 661.41 $[M+H]^+$.

Example 20

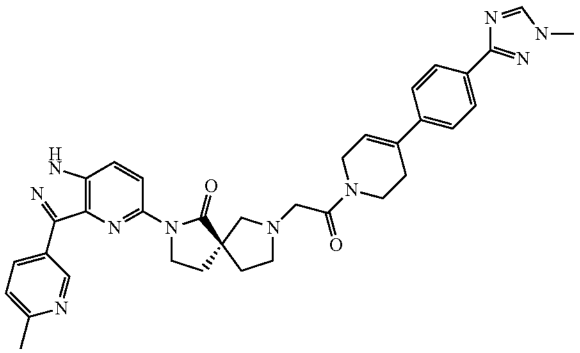

Example 20 was prepared following General Procedures A, B2, and C using Intermediate 4, 2-methyl-5-(4,4,5,5-tetramethyl-1,3,2-dioxaborolan-2-yl)pyridine, and Intermediate 9. $^1$H NMR (DMSO-d$_6$, 400 MHz) δ 13.50 (s, 1H), 9.50 (s, 1H), 8.60 (dd, 1H), 8.49 (d, 2H), 8.11 (d, 1H), 7.97 (d, 2H), 7.55 (d, 2H), 7.38 (d, 1H), 6.28 (s, 1H), 4.31 (s, 1H), 4.14-4.11 (m, 3H), 3.92 (s, 3H), 3.80-3.67 (m, 2H), 3.50-3.47 (m, 1H), 3.40-3.28 (m, 2H), 293-2.69 (m, 3H), 2.62-2.49 (m, 5H), 2.32-2.15 (m, 3H), 1.87-1.85 (m, 1H); LCMS: 629.1 [M+H]$^+$ Example 21

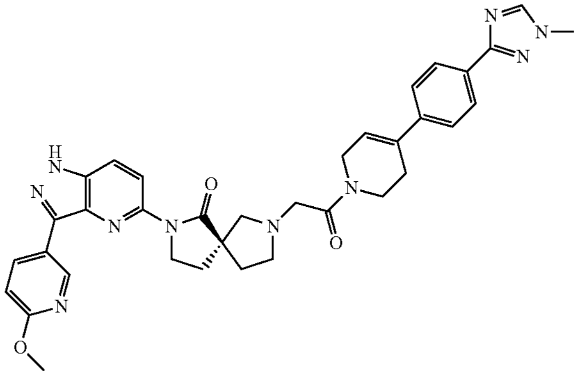

Example 21 was prepared following General Procedures A, B2, and C using Intermediate 4, 2-methoxy-5-(4,4,5,5-tetramethyl-1,3,2-dioxaborolan-2-yl)pyridine, and Intermediate 9. $^1$H NMR (DMSO-d$_6$, 400 MHz) δ 13.51 (s, 1H), 9.29 (s, 1H), 8.62 (dd, 1H), 8.53-8.46 (m, 2H), 8.10 (d, 1H), 7.97 (d, 2H), 7.55 (d, 2H), 6.97 (d, 1H), 6.30-6.26 (m, 1H), 4.33-4.29 (m, 1H), 4.21-4.05 (m, 3H), 3.92 (s, 5H), 3.86-3.78 (m, 1H), 3.74-3.65 (m, 2H), 3.52-3.45 (m, 1H), 3.41-3.36 (m, 1H), 2.97-2.81 (m, 2H), 2.78-2.55 (m, 4H), 2.30-2.10 (m, 3H), 1.91-1.80 (m, 1H); LCMS: 645.46 [M+H]$^+$.

Example 22

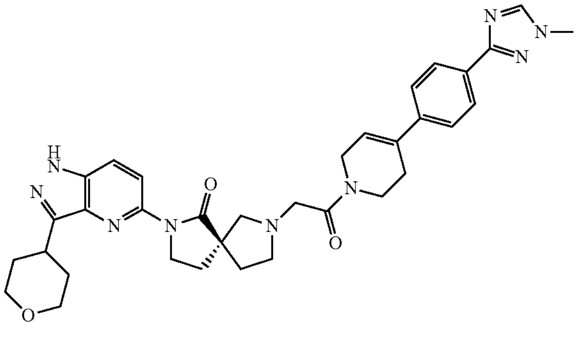

(5R)-Benzyl 7-(3-(3,6-dihydro-2H-pyran-4-yl)-1-(tetrahydro-2H-pyran-2-yl)-1H-pyrazolo[4,3-b]pyridin-5-yl)-6-oxo-2,7-diazaspiro[4.4]nonane-2-carboxylate (22-1)

To a stirred solution of Intermediate 4 (2.3 g, 4.151 mmol) and 2-(3,6-dihydro-2H-pyran-4-yl)-4,4,5,5-tetramethyl-1,3,2-dioxaborolane (0.87 g, 4.147 mmol) in toluene/ethanol/water (60 mL, 1:1:1 ratio) were added $K_2CO_3$ (2.86 g, 20.694 mmol) and $Pd(Ph_3P)_4$ (0.23 g, 0.206 mmol). The mixture was degassed for 10 min, followed by heating at 100° C. for 16 h. The mixture was cooled to rt, diluted with cold water, and extracted with EtOAc. The combined organic layers were washed with water and brine, dried over $Na_2SO_4$ and concentrated. The crude compound was purified by column chromatography using 50% EtOAc/hexanes to afford 22-1. LCMS: 558.05 [M+H]$^+$.

(5S)-2-(1-(Tetrahydro-2H-pyran-2-yl)-3-(tetrahydro-2H-pyran-4-yl)-1H-pyrazolo[4,3-b]pyridin-5-yl)-2,7-diazaspiro[4.4]nonan-1-one (22-2)

To a stirred solution of 22-1 (1.2 g, 2.154 mmol) in THF was added $Pd(OH)_2$ (3.6 g). After being stirred at rt for 3 h under hydrogen atmosphere, the mixture was filtered through a Celite pad and washed with 30% MeOH/DCM. The organic layers were combined and concentrated under reduced pressure to afford 22-2 (765 mg, 84%) as a colorless gummy liquid. LCMS: 425.99 [M+H]$^+$.

(S)-2-(3-(Tetrahydro-2H-pyran-4-yl)-1H-pyrazolo[4,3-b]pyridin-5-yl)-2,7-diazaspiro[4.4]nonan-1-one (22-3)

A solution of 22-2 (760 mg, 1.788 mmol) in TFA (3 mL) was stirred at rt for 1 h. The TFA solvent was evaporated under reduced pressure. The residue was triturated with diethyl ether to afford 22-3 (480 mg, 78%). LCMS: 342.09 [M+H]$^+$.

(S)-7-(2-(4-(4-(1-Methyl-1H-1,2,4-triazol-3-yl)phenyl)-5,6-dihydropyridin-1(2H)-yl)-2-oxoethyl)-2-(3-(tetrahydro-2H-pyran-4-yl)-1H-pyrazolo[4,3-b]pyridin-5-yl)-2,7-diazaspiro[4.4]nonan-1-one (Example 22)

Example 22 was prepared following General Procedure C using 22-3 and Intermediate 9. $^1$H NMR (DMSO-d$_6$, 400

MHz) δ 12.89 (s, 1H), 8.51 (s, 1H), 8.36 (d, 1H), 8.02-7.93 (m, 3H), 7.55 (d, 2H), 6.32-6.25 (m, 1H), 4.34-4.28 (m, 1H), 4.22-4.09 (m, 1H), 4.08-3.88 (m, 7H), 3.87-3.60 (m, 3H), 3.58-3.42 (m, 3H), 3.41-3.31 (m, 2H), 2.98-2.85 (m, 1H), 2.84-2.76 (m, 1H), 2.75-2.59 (m, 3H), 2.24-1.92 (m, 7H), 1.88-1.78 (m, 1H). LCMS: 622.49 $[M+H]^+$.

Example 23

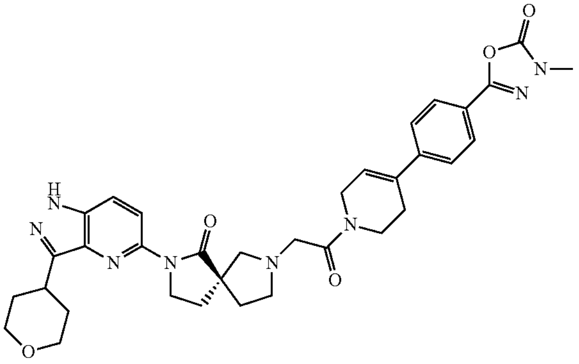

Example 23 was prepared following General Procedures A, B2, and C using (S)-2-(3-(tetrahydro-2H-pyran-4-yl)-1H-pyrazolo[4,3-b]pyridin-5-yl)-2,7-diazaspiro[4.4]nonan-1-one (Step 2, Example 22) and Intermediate 15. $^1$H NMR ($DMSO-d_6$, 400 MHz) δ 12.93 (s, 1H), 8.35 (d, 1H), 7.96 (d, 1H), 7.77 (d, 2H), 7.64 (d, 2H), 6.40-6.35 (m, 1H), 4.35-4.31 (m, 1H), 4.26-3.91 (m, 6H), 3.89-3.61 (m, 2H), 3.54-3.43 (m, 3H), 3.41 (s, 3H), 3.39-3.34 (m, 2H), 2.94-2.78 (m, 2H), 2.75-2.55 (m, 3H), 2.22-1.90 (m, 7H), 1.89-1.78 (m, 1H); LCMS: 639.45 $[M+H]^+$.

Example 24

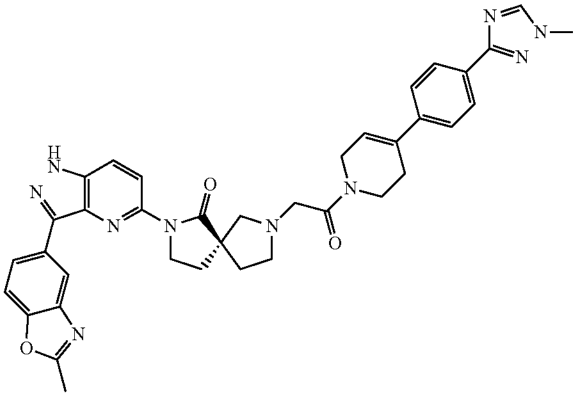

Example 24 was prepared following General Procedures A, B1, C and D using Intermediate 4, 2-methyl-5-(4,4,5,5-tetramethyl-1,3,2-dioxaborolan-2-yl)benzo[d]oxazole, and Intermediate 9. $^1$H NMR (400 MHz, $DMSO-d_6$) δ 8.77 (br, 1H), 8.52-8.45 (m, 3H), 8.13-8.10 (m, 1H), 7.99-7.97 (m, 2H), 7.78-7.75 (m, 1H), 7.57-7.55 (m, 2H), 6.29 (br, 1H), 4.32 (br, 1H), 4.20-411 (m, 3H), 3.93 (s, 3H), 3.87-3.80 (m, 1H), 3.75-3.63 (m, 2H), 3.52-3.34 (m, 3H), 2.96-2.84 (m, 3H), 2.78-2.69 (m, 1H), 2.65 (s, 3H), 2.60-2.55 (m, 1H), 2.32-2.15 (m, 3H), 1.92-1.82 (m, 1H); LCMS: 669.20 $[M+H]^+$.

Example 25

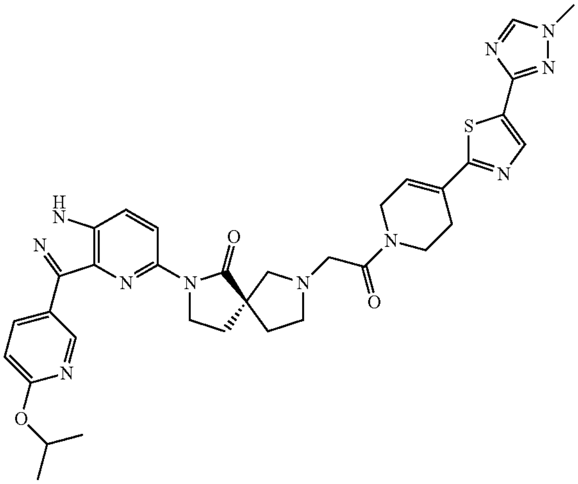

Example 25 was prepared following General Procedures A, B2, and C using Intermediate 4, 2-isopropoxy-5-(4,4,5,5-tetramethyl-1,3,2-dioxaborolan-2-yl)pyridine, and Intermediate 13. $^1$H NMR (400 MHz, $DMSO-d_6$) δ 13.4 (s, 1H), 9.25 (d, 1H), 8.58 (s, 1H), 8.56 (s, 1H), 8.47 (d, 1H), 8.19 (s, 1H), 8.09 (d, 1H), 6.88 (d, 1H), 6.71 (s, 1H), 5.32 (t, 1H), 4.37-4.11 (m, 4H), 3.91 (s, 3H), 3.81-3.68 (m, 2H), 3.49-3.31 (m, 2H), 2.90-2.82 (m, 2H), 2.74-2.69 (m, 2H), 2.59-2.49 (m, 2H), 2.25-2.17 (m, 3H), 1.90-1.82 (m, 1H), 1.33 (d, 6H); LCMS: 680.13 $[M+H]^+$.

Example 26

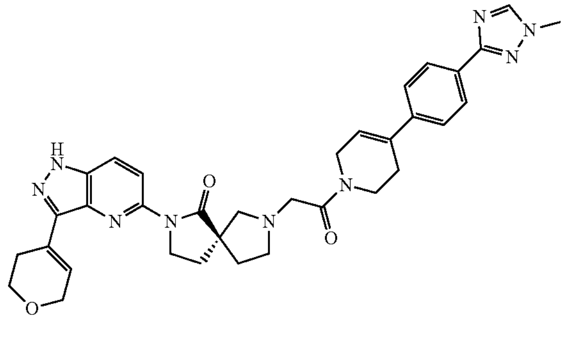 [SMILES: Cn1cnc(-c2ccc(C3=CCN(C(=O)CN4CC[C@]5(CCN(c6ccc7[nH]nc(C8=CCOCC8)c7n6)C5=O)C4)CC3)cc2)n1]

Example 26 was prepared following General Procedures A, B2, and C using Intermediate 4, 2-(3,6-dihydro-2H-pyran-4-yl)-4,4,5,5-tetramethyl-1,3,2-dioxaborolane, and Intermediate 9. $^1$H NMR ($DMSO-d_6$, 400 MHz) δ 13.15 (s, 1H), 8.51 (s, 1H), 8.41 (d, 1H), 8.02 (d, 1H), 7.96 (d, 2H), 7.55 (d, 2H), 7.36-7.31 (m, 1H), 6.30-6.25 (m, 1H), 4.58-4.69 (m, 3H), 4.42-3.97 (m, 4H), 3.92 (s, 3H), 3.86 (t, 2H), 3.82-3.60 (m, 2H), 3.55-3.36 (m, 2H), 2.98-2.76 (m, 2H), 2.75-2.55 (m, 5H), 2.25-2.03 (m, 3H), 1.89-1.67 (m, 1H); LCMS: 620.44 $[M+H]^+$.

Example 27

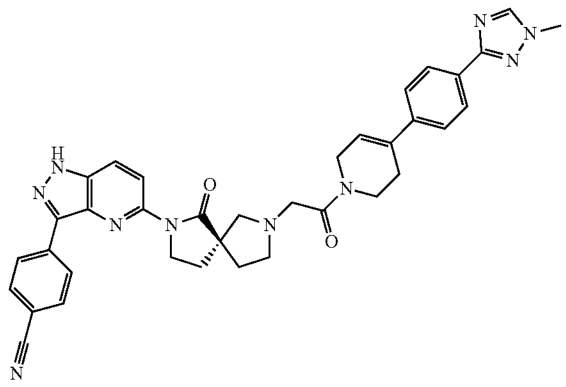 [SMILES: Cn1cnc(-c2ccc(C3=CCN(C(=O)CN4CC[C@]5(CCN(c6ccc7[nH]nc(-c8ccc(C#N)cc8)c7n6)C5=O)C4)CC3)cc2)n1]

Example 27 was prepared following General Procedures A, B2, and C using Intermediate 4, 4-(4,4,5,5-tetramethyl-1,3,2-dioxaborolan-2-yl)benzonitrile, and Intermediate 9. $^1$H NMR (400 MHz, DMSO-$d_6$) δ 13.75 (s, 1H), 8.65 (d, 2H), 8.52 (d, 2H), 8.15 (d, 1H), 7.98-7.95 (m, 4H), 7.55 (d, 2H), 6.29 (s, 1H), 4.31-4.11 (m, 4H), 3.92 (s, 3H), 3.80-3.73 (m, 2H), 3.50-3.35 (m, 2H), 2.95-2.83 (m, 3H), 2.74-2.49 (m, 3H), 2.26-2.18 (m, 3H), 1.89-1.84 (m, 1H); LCMS: 639.41 [M+H]$^+$.

Example 28

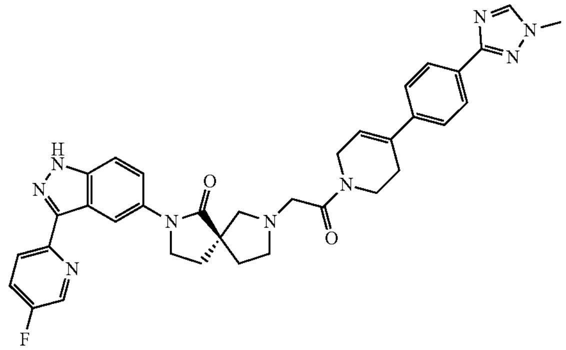 [SMILES: Cn1cnc(-c2ccc(C3=CCN(C(=O)CN4CC[C@]5(CCN(c6ccc7[nH]nc(-c8ccc(F)cn8)c7c6)C5=O)C4)CC3)cc2)n1]

(R)-Benzyl 7-(3-(5-fluoropyridin-2-yl)-1-trityl-1H-indazol-5-yl)-6-oxo-2,7-diazaspiro [4.4]nonane-2-carboxylate (28-1)

To a stirred solution of 2-bromo-5-fluoropyridine (0.5 g, 2.840 mmol) in DME (10 mL) was added hexamethylditin (0.9, 2.839 mmol). The mixture was degassed for 10 min, followed by the addition of $Pd(Ph_3P)_4$ (0.16 g, 0.138 mmol), and degassed again for another 10 min. The reaction mixture was sealed, heated to 80° C. for 16 h, and cooled to rt. To the mixture were added Intermediate 2 (0.53 g, 0.709 mmol), CuI (0.05 g, 0.284 mmol) and CsF (0.86 g, 5.661 mmol). The was degassed for 10 min, followed by the addition of $Pd(Ph_3P)_4$ (0.16 g, 0.138 mmol), and degassed again for another 10 min. The mixture was then sealed and heated at 80° C. for 5 h. Upon completion, the mixture was cooled to room temperature, diluted with cold water, and extracted with EtOAc. The combined organic layers were washed with water and brine, dried over $Na_2SO_4$ and concentrated. The crude compound was purified by column chromatography using 50% EtOAc/Hexanes to afford 28-1 (0.26 g, 52%) as an off white solid. LCMS: 728.08 [M+H]$^+$.

(S)-2-(3-(5-Fluoropyridin-2-yl)-1H-indazol-5-yl)-2,7-diazaspiro [4.4]nonan-1-one (28-2)

A solution of 28-1 (0.26 g, 0.357 mmol) in TFA (8.6 mL) was stirred at rt for 16 h. Upon completion, the mixture was concentrated followed by trituration with diethyl ether to afford 28-1 (0.075 g, 60%) as an off white solid. LCMS: 352.00 [M+H]$^+$.

Step 3: (S)-2-(3-(5-Fluoropyridin-2-yl)-1H-indazol-5-yl)-7-(2-(4-(4-(1-methyl-1H-1,2,4-triazol-3-yl)phenyl)-5,6-dihydropyridin-1(2H)-yl)-2-oxoethyl)-2,7-diazaspiro[4.4]nonan-1-one (Example 28)

Example 28 was prepared following General Procedure C using 28-2 and Intermediate 9. $^1$H NMR (DMSO-$d_6$, 400 MHz) δ 13.41 (s, 1H), 8.72-8.67 (m, 1H), 8.58-8.54 (m, 1H), 8.50 (s, 1H), 8.21 (q, 1H), 7.95 (d, 2H), 7.87-7.78 (m, 2H), 7.62-7.51 (m, 3H), 6.31-6.25 (m, 1H), 4.35-4.27 (m, 1H), 4.18-4.08 (m, 1H), 3.91 (s, 3H), 3.89-3.64 (m, 4H), 3.50-3.30 (m, 3H), 2.99-2.80 (m, 2H), 2.72-2.53 (m, 3H), 2.27-2.08 (m, 3H), 1.87-1.77 (m, 1H); LCMS: 632.16 [M+H]$^+$.

Example 29

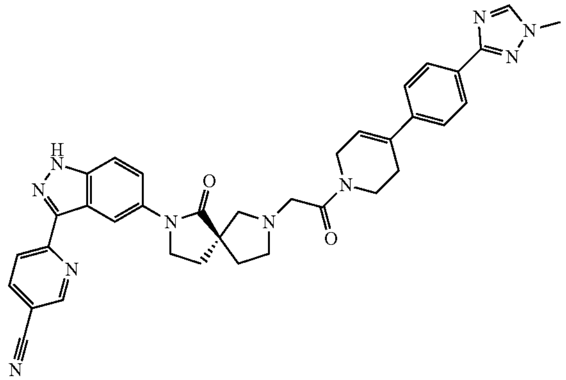 [SMILES: Cn1cnc(-c2ccc(C3=CCN(C(=O)CN4CC[C@]5(CCN(c6ccc7[nH]nc(-c8ccc(C#N)cn8)c7c6)C5=O)C4)CC3)cc2)n1]

Example 29 was prepared following procedures described for Example 28 using Intermediate 2, 6-bromonicotinonitrile, and Intermediate 9. $^1$H NMR (400 MHz, DMSO-$d_6$) δ 13.78 (s, 1H), 9.12 (s, 1H), 8.61 (s, 1H), 8.50 (s, 1H), 8.36-8.30 (m, 2H), 8.00-7.94 (m, 2H), 7.87-7.84 (m, 1H), 7.65 (d, 1H), 7.57-7.52 (m, 2H), 6.28 (s, 1H), 4.35-4.05 (m, 2H), 3.91 (s, 3H), 3.89-3.60 (m, 4H), 3.50-3.35 (m, 2H), 3.00-2.80 (m, 3H), 2.72-2.60 (m, 3H), 2.80-2.60 (m, 3H), 1.89-1.80 (m, 1H); LCMS: 639.14 [M+H]$^+$.

Example 30

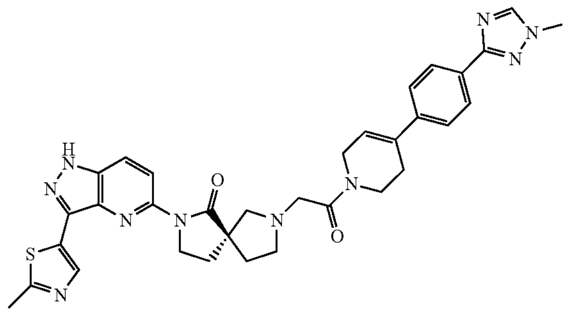

Example 30 was prepared following procedures described for Example 28 using Intermediate 4, 5-bromo-2-methylthiazole, and Intermediate 9. $^1$H NMR (400 MHz, DMSO-$d_6$) δ 13.49 (s, 1H), 8.53-8.48 (m, 3H), 8.11 (d, 1H), 7.97 (d, 2H), 7.55 (d, 2H), 6.28 (s, 1H), 4.35-4.09 (m, 4H), 3.92 (s, 3H), 3.85-3.65 (m, 2H), 3.10-2.80 (m, 4H), 2.72 (s, 3H), 2.70-2.60 (m, 1H), 2.50-2.40 (m, 2H), 2.30-2.10 (m, 4H), 1.95-1.85 (m, 1H); LCMS: 633.13 $[M+H]^+$.

Example 31

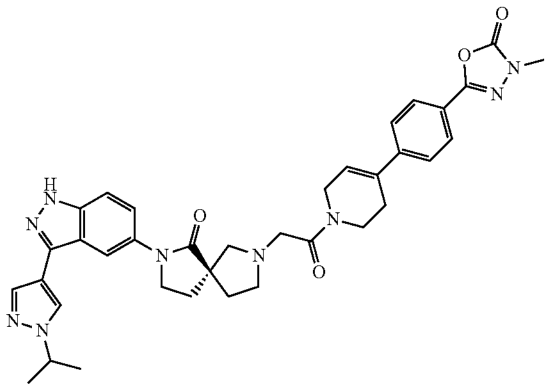 [SMILES: CC(C)n1cc(-c2n[nH]c3ccc(N4CC[C@]5(CCN(CC(=O)N6CC=C(c7ccc(-c8nn(C)c(=O)o8)cc7)CC6)C5)C4=O)cc23)cn1]

Example 31 was prepared following General Procedures A, B2, and C using Intermediate 3, 1-isopropyl-4-(4,4,5,5-tetramethyl-1,3,2-dioxaborolan-2-yl)-1H-pyrazole, and Intermediate 15. Data for 1.0 HCl salt: $^1$H NMR (DMSO-$d_6$, 400 MHz) δ 13.00 (br, 1H), 10.40 (d, 1H), 8.31 (s, 1H), 8.02-7.95 (m, 2H), 7.81-7.78 (m, 3H), 7.68-7.63 (m, 2H), 7.58-7.55 (m, 1H), 6.40 (br, 1H), 4.64-4.58 (m, 3H), 4.22 (br, 1H), 4.15 (br, 1H), 4.01-3.93 (m, 3H), 3.77 (br, 2H), 3.61-3.60 (m, 1H), 3.45-3.38 (m, 2H), 3.40 (s, 3H), 2.73 (br, 1H), 2.56-2.54 (m, 1H), 2.42-2.38 (m, 3H), 2.20-2.18 (m, 1H), 1.50 (d, 6H); LCMS: 662.30 $[M+H]^+$.

Example 32

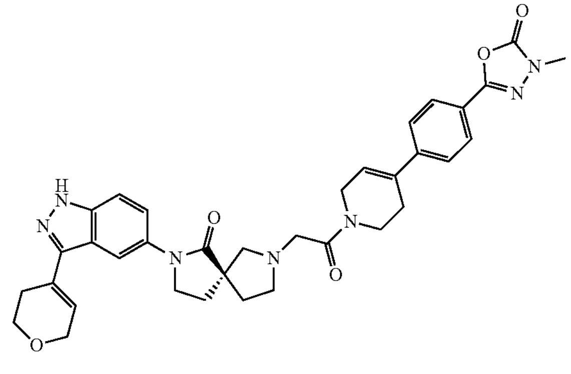 [SMILES: Cn1nc(-c2ccc(C3=CCN(C(=O)CN4CC[C@]5(CCN(c6ccc7[nH]nc(C8=CCOCC8)c7c6)C5=O)C4)CC3)cc2)oc1=O]

Example 32 was prepared following General Procedures A, B2, and C Intermediate 3, 2-(3,6-dihydro-2H-pyran-4-yl)-4,4,5,5-tetramethyl-1,3,2-dioxaborolane, and Intermediate 15. Data for 1.0 HCl salt: 1H NMR (DMSO-$d_6$, 400 MHz) δ 13.08 (s, 1H), 10.40 (d, 2H), 8.12 (s, 1H), 7.80-7.78 (m, 2H), 7.74-7.63 (m, 3H), 7.58-7.55 (m, 1H), 6.54 (br, 1H), 6.41 (br, 1H), 4.63-4.51 (m, 3H), 4.33 (m, 2H), 4.22 (br, 2H), 4.14 (m, 2H), 4.00-3.86 (m, 4H), 3.76 (br, 2H), 3.59 (br, 1H), 3.42 (s, 3H), 2.66 (m, 2H), 2.56 (br, 1H), 2.42-2.26 (m, 3H), 2.17 (br, 1H); LCMS: 636.30 $[M+H]^+$.

Example 33

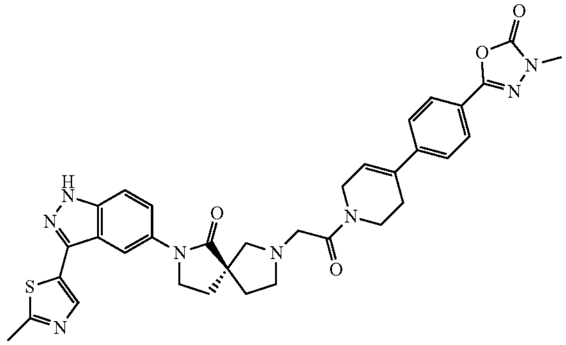

Example 33 was prepared following General Procedures A, B2, and C using Intermediate 3, (2-methylthiazol-5-yl) boronic acid, and (Intermediate 15. LCMS: 651.30 $[M+H]^+$.

Example 34

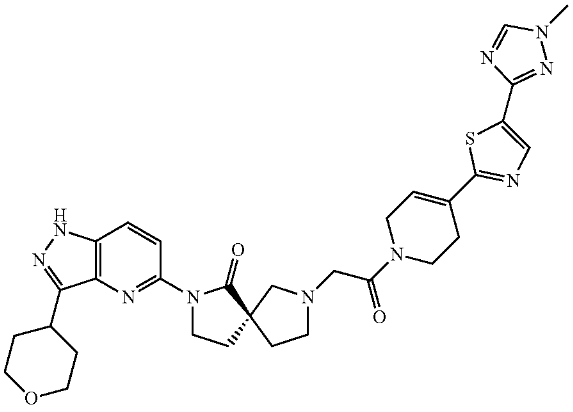 [SMILES: Cn1cnc(-c2cnc(C3=CCN(C(=O)CN4CC[C@]5(CCN(c6ccc7[nH]nc(C8CCOCC8)c7n6)C5=O)C4)CC3)s2)n1]

Example 34 was prepared following General Procedures A, B2, and C using Intermediate 4, 2-(3,6-dihydro-2H-pyran-4-yl)-4,4,5,5-tetramethyl-1,3,2-dioxaborolane, and Intermediate 13. $^{1}$H NMR (DMSO-$d_6$, 400 MHz) δ 12.91 (s, 1H), 8.56 (s, 1H), 8.35 (d, 1H), 8.19 (s, 1H), 7.96 (d, 1H), 6.74-6.68 (m, 1H), 4.40-4.36 (m, 1H), 4.24-4.09 (m, 2H), 4.05-3.89 (m, 7H), 3.87-3.60 (m, 3H), 3.55-3.46 (m, 2H), 3.43-3.38 (m, 1H), 3.29-3.24 (m, 1H), 2.93-2.86 (m, 1H), 2.84-2.78 (m, 1H), 2.75-2.65 (m, 2H), 2.63-2.54 (m, 1H), 2.22-1.92 (m, 7H), 1.87-1.80 (m, 1H).); LCMS: 629.04 $[M+H]^+$;

Example 35

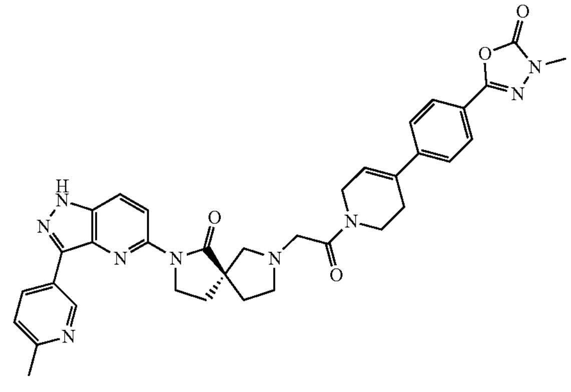 [SMILES: Cc1ccc(-c2n[nH]c3ccc(N4CC[C@]5(CCN(CC(=O)N6CC=C(c7ccc(-c8nn(C)c(=O)o8)cc7)CC6)C5)C4=O)nc23)cn1]

Example 35 was prepared following General Procedures A, B2, and C using Intermediate 4, 2-methyl-5-(4,4,5,5-tetramethyl-1,3,2-dioxaborolan-2-yl)pyridine, and Intermediate 15. $^{1}$H NMR (DMSO-$d_6$, 400 MHz) δ 13.50 (s, 1H), 9.50 (s, 1H), 8.59 (d, 1H), 8.49 (d, 1H), 8.11 (d, 1H), 7.77 (d, 2H), 7.64 (d, 2H), 7.39 (d, 1H), 6.40 (s, 1H), 4.33-4.06 (m, 4H), 3.82-3.67 (m, 2H), 3.51-3.35 (m, 5H), 2.93-2.70 (m, 4H), 267-2.49 (m, 5H), 2.32-2.13 (m, 3H), 1.88-1.83 (m, 1H). LCMS: 646.4$[M+H]^+$.

Example 36

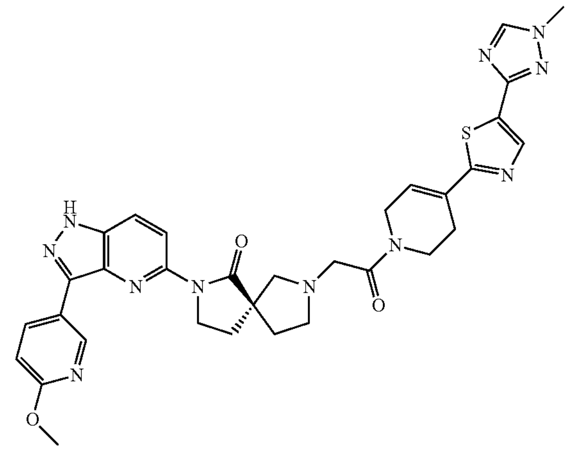 [SMILES: COc1ccc(-c2n[nH]c3ccc(N4CC[C@]5(CCN(CC(=O)N6CC=C(c7ncc(-c8ncn(C)n8)s7)CC6)C5)C4=O)nc23)cn1]

Example 36 was prepared following General Procedures A, B2, and C using Intermediate 4, 2-methoxy-5-(4,4,5,5-tetramethyl-1,3,2-dioxaborolan-2-yl)pyridine, and Intermediate 13. $^{1}$H NMR (DMSO-$d_6$, 400 MHz) δ 13.42 (s, 1H), 9.29 (s, 1H), 8.61-8.56 (m, 2H), 8.47 (d, 1H), 8.19 (s, 1H), 8.09 (d, 1H), 6.97 (d, 1H), 6.73-6.69 (m, 1H), 4.41-4.36 (m, 1H), 4.25-4.06 (m, 3H), 3.92 (s, 3H), 3.91 (s, 3H), 3.86-3.62 (m, 2H), 3.53-3.37 (m, 2H), 2.98-2.81 (m, 2H), 2.78-2.68 (m, 2H), 2.62-2.57 (m, 2H), 2.28-2.12 (m, 3H), 1.89-1.81 (m, 1H); LCMS: 652.11 $[M+H]^+$.

Example 37

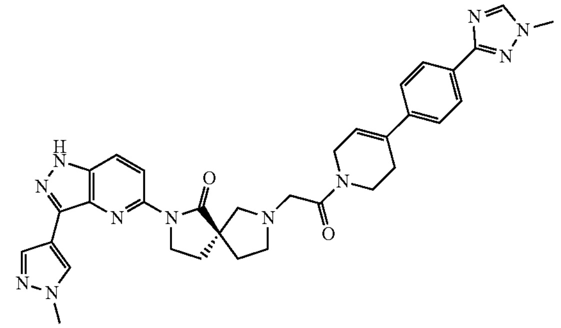 [SMILES: Cn1cc(-c2n[nH]c3ccc(N4CC[C@]5(CCN(CC(=O)N6CC=C(c7ccc(-c8ncn(C)n8)cc7)CC6)C5)C4=O)nc23)cn1]

Example 37 was prepared following General Procedures A, B1, C and D using Intermediate 4, 1-methyl-4-(4,4,5,5-tetramethyl-1,3,2-dioxaborolan-2-yl)-1H-pyrazole, Intermediate 9. $^{1}$H NMR (DMSO-$d_6$, 300 MHz) δ 13.11 (s, 1H), 8.51 (s, 1H), 8.43 (d, 1H), 8.38 (s, 1H), 8.10 (s, 1H), 8.03-7.95 (m, 3H), 7.55 (d, 2H), 6.28 (s, 1H), 4.30 (s, 1H), 4.14 (s, 3H), 3.93 (d, 6H), 3.89-3.64 (m, 2H), 3.50-3.39 (m, 2H), 2.99-2.80 (m, 3H), 2.78-2.53 (m, 3H), 2.27-2.17 (m, 3H), 1.87-1.79 (m, 1H). LCMS: 618.1 $[M+H]^+$.

Example 38

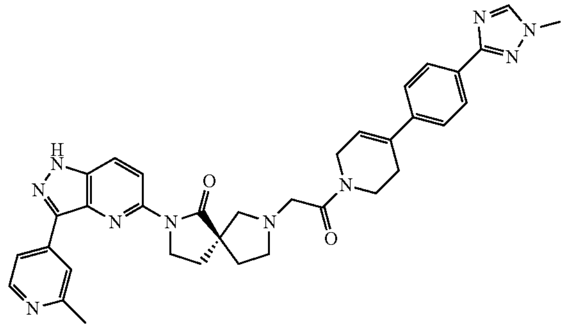 [SMILES: Cc1cc(-c2n[nH]c3ccc(N4CC[C@]5(CCN(CC(=O)N6CC=C(c7ccc(-c8ncn(C)n8)cc7)CC6)C5)C4=O)nc23)ccn1]

Example 38 was prepared following General Procedures A, B2, and C using Intermediate 4, 2-methyl-4-(4,4,5,5-tetramethyl-1,3,2-dioxaborolan-2-yl)pyridine and Intermediate 9. $^{1}$H NMR (DMSO-$d_6$, 400 MHz) δ 13.80 (s, 1H), 8.57-8.49 (m, 3H), 8.26-8.20 (m, 2H), 8.14 (d, 1H), 7.97 (d, 2H), 7.55 (d, 2H), 6.28 (br s, 1H), 4.31 (s, 1H), 4.20-4.09 (m, 3H), 3.92 (s, 3H), 3.81-3.64 (m, 2H), 3.51-3.37 (m, 2H), 2.94-2.83 (m, 2H), 2.75-2.60 (m, 3H), 2.57-2.54 (m, 4H), 2.29-2.10 (m, 3H), 1.90-1.83 (m, 1H); LCMS: 629.21 $[M+H]^+$.

Example 39

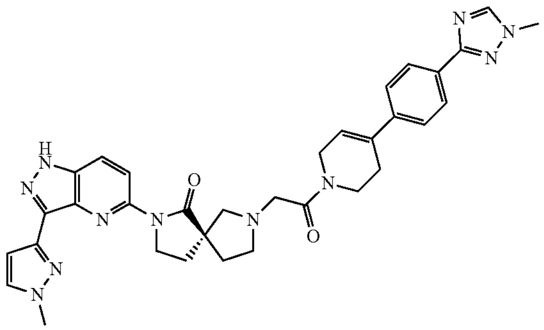 [SMILES: Cn1ccc(-c2n[nH]c3ccc(N4CC[C@]5(CCN(CC(=O)N6CC=C(c7ccc(-c8ncn(C)n8)cc7)CC6)C5)C4=O)nc23)n1]

Example 39 was prepared following General Procedures A, B2, and C using Intermediate 4, 1-methyl-3-(4,4,5,5-tetramethyl-1,3,2-dioxaborolan-2-yl)-1H-pyrazole, and Intermediate 9. $^1$H NMR (400 MHz, DMSO-$d_6$) δ 13.25 (s, 1H), 8.51 (s, 1H), 8.43 (d, 1H), 8.04 (d, 1H), 7.97 (d, 2H), 7.79 (s, 1H), 7.55 (d, 2H), 7.11 (s, 1H), 6.28 (s, 1H), 4.32-4.06 (m, 4H), 3.92 (d, 6H), 3.83-3.64 (m, 2H), 3.50-3.36 (m, 2H), 2.94-2.58 (m, 6H), 2.24-2.11 (m, 3H), 1.90-1.83 (m, 1H): LCMS: 618.15 $[M+H]^+$.

Example 40

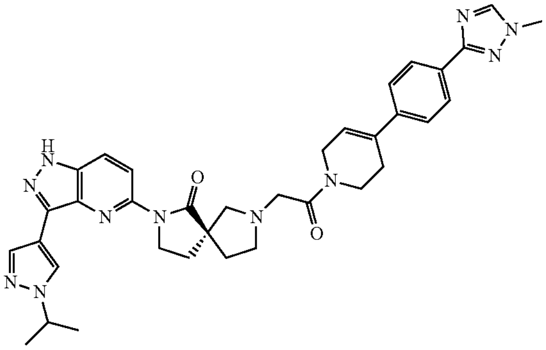 [SMILES: CC(C)n1cc(-c2n[nH]c3ccc(N4CC[C@]5(CCN(CC(=O)N6CC=C(c7ccc(-c8ncn(C)n8)cc7)CC6)C5)C4=O)nc23)cn1]

Example 40 was prepared following General Procedures A, B1, C, D and E using Intermediate 4, 1-isopropyl-4-(4,4,5,5-tetramethyl-1,3,2-dioxaborolan-2-yl)-1H-pyrazole, and Intermediate 9. Data for 1.0 HCl salt: 1H NMR (DMSO-$d_6$, 400 MHz) δ N—H proton not observed, 10.50 (d, 1H), 8.57 (s, 1H), 8.45-8.42 (m, 2H), 8.19-8.18 (m, 1H), 8.10-8.08 (m, 1H), 8.00-7.98 (m, 2H), 7.58-7.55 (m, 2H), 6.32 (br, 1H), 4.65-4.57 (m, 3H), 4.31-4.14 (m, 4H), 3.93 (m, 3H), 3.83-3.77 (br, 2H), 3.62-3.61 (m, 1H), 3.41-3.36 (m, 3H), 2.67 (br, 1H), 2.56-2.54 (m, 1H), 2.43-2.33 (m, 3H), 2.23-2.21 (m, 1H), 1.50 (d, 6H); LCMS: 646.30 $[M+H]^+$.

Example 41

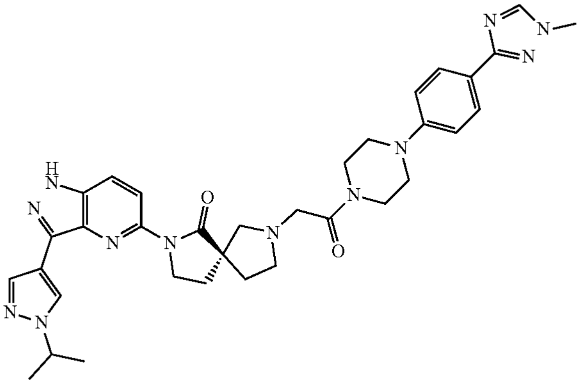

Example 41 was prepared following General Procedures A, B1, C and D using Intermediate 4, 1-isopropyl-4-(4,4,5,5-tetramethyl-1,3,2-dioxaborolan-2-yl)-1H-pyrazole, and Intermediate 10. $^1$H NMR (DMSO-$d_6$, 400 MHz) δ 13.08 (s, 1H), 8.45-8.41 (m, 3H), 8.15 (s, 1H), 8.02 (d, 1H), 7.85 (s, 2H), 7.04 (d, 2H), 4.64-4.59 (m, 1H), 4.16-4.11 (m, 2H), 3.89 (s, 3H), 3.74-3.58 (m, 4H), 3.44-3.33 (m, 3H), 3.22-3.17 (m, 3H), 2.92-2.90 (m, 1H), 2.78 (dd, 2H), 2.56-2.55 (m, 1H), 2.26-2.13 (m, 3H), 1.87-1.84 (m, 1H), 1.49 (d, 6H); LCMS: 649.30 $[M+H]^+$.

Example 42

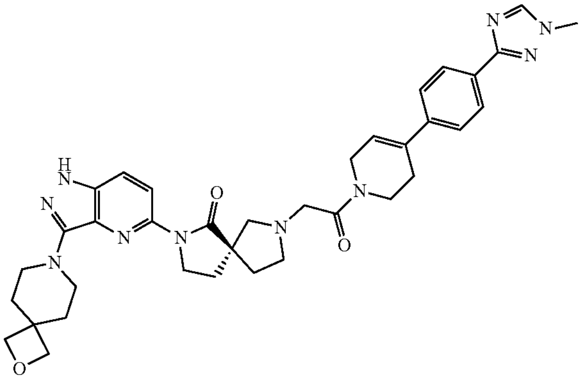

Step 1: (5R)-Benzyl 7-(3-(2-oxa-7-azaspiro[3.5]nonan-7-yl)-1-(tetrahydro-2H-pyran-2-yl)-1H-pyrazolo[4,3-b]pyridin-5-yl)-6-oxo-2,7-diazaspiro[4.4]nonane-2-carboxylate (42-1)

To a stirred solution of Intermediate 4 (400 mg, 0.722 mmol) in DMSO (8 mL) were added $K_2CO_3$ (299 mg, 2.166 mmol), 2-oxa-7-azaspiro[3.5]nonane (110 mg, 0.866 mmol) and L-proline (25 mg, 0.216 mmol). The mixture was degassed for 10 min, followed by the addition of CuI (13 mg, 0.072 mmol), and degassed again for another 10 min. The mixture was warmed up and stirred at 80° C. for 36 h. Upon completion, the mixture was cooled to 0° C., diluted with water, and extracted with EtOAc. The combined organic layers were dried over $Na_2SO_4$ and concentrated under reduced pressure to afford 42-1 (140 mg, 89%) as a colorless thick liquid. MS (ESI) m/z 601.07 [M+H]+.

Step 2: (S)-2-(3-(2-oxa-7-azaspiro[3.5]nonan-7-yl)-1H-pyrazolo[4,3-b]pyridin-5-yl)-7-(2-(4-(4-(1-methyl-1H-1,2,4-triazol-3-yl)phenyl)-3,6-dihydro-pyridin-1(2H)-yl)-2-oxoethyl)-2,7-diazaspiro[4.4]nonan-1-one (Example 42)

Example 42 was prepared following General Procedures B2, and C using 42-1 and Intermediate 9. $^1$H NMR (300 MHz, DMSO-$d_6$) δ 14.10 (s, 1H), 8.60-8.53 (m, 1H), 8.49 (s, 1H), 8.27 (d, 1H), 7.14 (s, 2H), 6.97 (s, 2H), 6.29 (s, 1H), 4.65-4.50 (m, 2H), 4.51-4.38 (m, 2H), 4.30-4.15 (m, 4H), 4.15-4.00 (m, 4H), 3.89 (s, 3H), 3.80-3.60 (m, 4H), 3.62-3.50 (m, 5H), 2.70-2.60 (m, 1H), 2.58-2.50 (m, 2H), 2.39-2.23 (m, 3H), 2.20-2.10 (m, 1H), 2.00-1.88 (m, 2H); LCMS: 663.16 [M+H]+.

Example 43

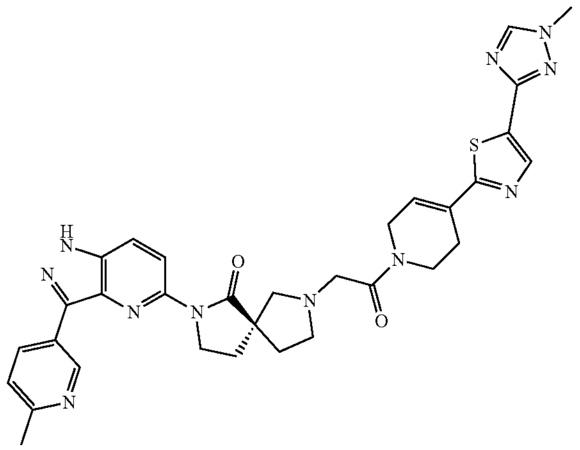

Example 43 was prepared following General Procedures A, B2, and C using Intermediate 4, 2-methyl-5-(4,4,5,5-tetramethyl-1,3,2-dioxaborolan-2-yl)pyridine, and Intermediate 13. $^1$H NMR (DMSO-$d_6$, 400 MHz) δ 13.50 (s, 1H), 9.51 (s, 1H), 8.59 (d, 1H), 8.57 (s, 1H), 8.49 (d, 1H), 8.20 (s, 1H), 8.12 (d, 1H), 7.39 (d, 1H), 6.71 (s, 1H), 4.35-4.12 (m, 5H), 3.9 (s, 3H), 3.77-3.71 (m, 3H), 2.93-2.70 (m, 3H), 2.73-2.60 (m, 3H), 2.53 (s, 3H), 2.32-2.18 (m, 3H), 1.90-1.80 (m, 1H); LCMS: 636.4 [M+H]+.

Example 44

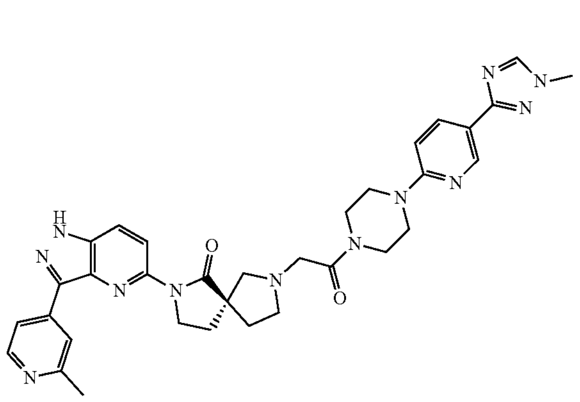

Example 44 was prepared following General Procedures A, B2, and C using Intermediate 4, 2-methyl-4-(4,4,5,5-tetramethyl-1,3,2-dioxaborolan-2-yl)pyridine Intermediate 12. $^1$H NMR (DMSO-$d_6$, 400 MHz) δ 13.70 (s, 1H), 8.72 (d, 1H), 8.67-8.45 (m, 3H), 8.25-8.20 (m, 2H), 8.15 (d, 1H), 8.07 (dd, 1H), 6.95 (d, 1H), 4.16-4.13 (m, 2H), 3.89 (s, 3H), 3.77-3.51 (m, 8H), 3.47-3.35 (m, 2H), 2.97-2.84 (m, 2H), 2.74-2.66 (m, 1H), 2.54-2.58 (m, 4H), 2.38-2.24 (m, 1H), 2.19-2.15 (m, 2H), 2.0-1.80 (m, 1H); LCMS: 633.3 [M+H]+.

Example 45

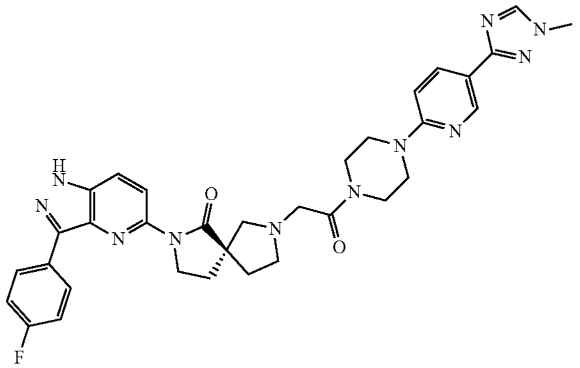

Example 45 was prepared following General Procedures A, B2, and C using Intermediate 4, 2-(4-fluorophenyl)-4,4,5,5-tetramethyl-1,3,2-dioxaborolane, and Intermediate 12. $^1$H NMR (400 MHz, DMSO-$d_6$) δ 13.61 (s, 1H), 8.72 (d, 1H), 8.52-8.46 (m, 4H), 8.11-8.05 (m, 2H), 7.34 (t, 2H), 6.95 (d, 1H), 4.14-4.11 (m, 2H), 3.89 (s, 3H), 3.69-3.53 (m, 8H), 3.43-3.37 (m, 2H), 2.94-2.92 (m, 1H), 2.85 (d, 1H), 2.71 (d, 1H), 2.56-2.54 (m, 1H), 2.27-2.13 (m, 3H), 1.87-1.84 (m, 1H); LCMS: 636.16 [M+H]+.

Example 46

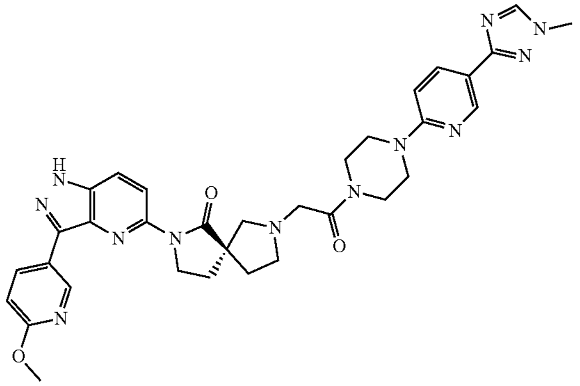

Example 46 was prepared following General Procedures A, B2, and C using Intermediate 4, 2-methoxy-5-(4,4,5,5-tetramethyl-1,3,2-dioxaborolan-2-yl)pyridine, and Intermediate 12. $^1$H NMR (DMSO-$d_6$, 400 MHz) δ 13.50 (s, 1H), 9.29 (d, 1H), 8.72 (d, 1H), 8.61 (dd, 1H), 8.49 (s, 1H), 8.46 (d, 1H), 8.13-8.04 (m, 2H), 6.96 (t, 2H), 4.13-4.10 (m, 2H), 3.91 (s, 3H), 3.89 (s, 3H), 3.68-3.52 (m, 8H), 3.42-3.36 (m, 2H), 2.92-2.82 (m, 2H), 2.71-2.60 (m, 1H), 2.55-2.54 (m, 1H), 2.31-2.10 (m, 3H), 1.90-1.84 (m, 1H); LCMS: 649.16 $[M+H]^+$.

Example 47

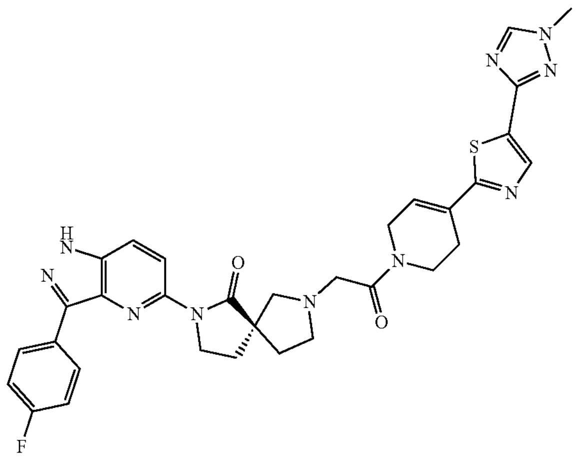

Example 47 was prepared following General Procedures A, B2, and C using Intermediate 4, 2-(4-fluorophenyl)-4,4,5,5-tetramethyl-1,3,2-dioxaborolane, and Intermediate 13. $^1$H NMR (400 MHz, DMSO-$d_6$) δ 13.4 (s, 1H), 8.57 (s, 1H), 8.52-8.46 (m, 3H), 8.20 (s, 1H), 8.09 (d, 1H), 7.36-7.31 (m, 2H), 6.71 (s, 1H), 4.38-4.08 (m, 4H), 3.91 (s, 3H), 3.83-3.64 (m, 2H), 3.49-3.36 (m, 2H), 2.92-2.83 (m, 2H), 2.74-2.59 (m, 2H), 2.57-2.54 (m, 2H), 2.26-2.15 (m, 3H), 1.87-1.82 (m, 1H); LCMS: 639.10 $[M+H]^+$.

Example 48

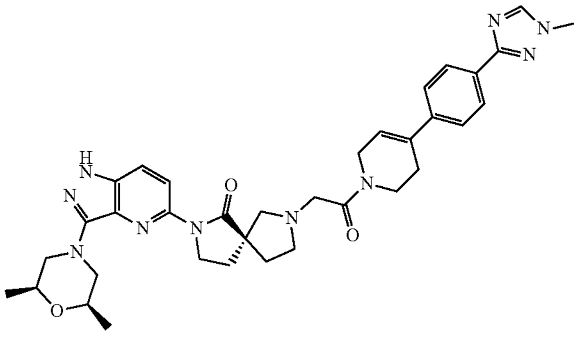

Example 48 was prepared as described in Example 42 using Intermediate 4, (2S,6R)-2,6-dimethylmorpholine, and Intermediate 9. $^1$H NMR (400 MHz, DMSO-$d_6$) δ 12.19 (s, 1H), 8.51 (s, 1H), 8.35-8.29 (m, 1H), 7.98 (d, 2H), 7.90 (d, 1H), 7.56 (t, 2H), 6.31 (s, 1H), 4.65-4.50 (m, 2H), 4.35-4.18 (m, 4H), 4.10-3.94 (m, 4H), 3.91 (s, 3H), 3.82-3.74 (m, 4H), 3.65-3.55 (m, 2H), 3.52-3.45 (m, 1H), 3.40-3.30 (m, 2H), 2.57-2.46 (m, 2H), 2.32-2.15 (m, 3H), 1.16 (d, 6H); LCMS: 651.4 $[M+H]^+$.

Example 49

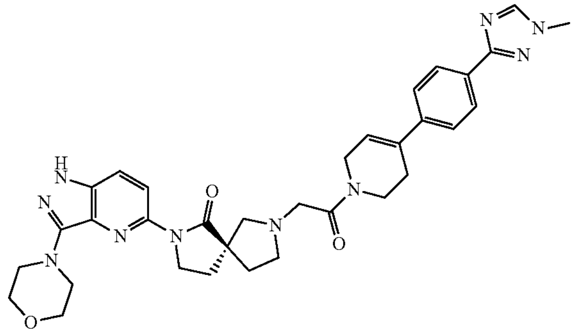

Example 49 was prepared as described in Example 42 using Intermediate 4, morpholine, and Intermediate 9. $^1$H NMR (400 MHz, DMSO-$d_6$) δ 12.13 (s, 1H), 8.51 (s, 1H), 8.32 (d, 1H), 7.96 (d, 2H), 7.84 (d, 1H), 7.55 (d, 2H), 5.92 (d, 1H), 4.35-4.05 (m, 2H), 4.00-3.90 (m, 5H), 3.85-3.65 (m, 7H), 3.60-3.52 (m, 4H), 3.50-3.35 (m, 2H), 3.00-2.85 (m, 1H), 2.85-2.70 (m, 2H), 2.65-2.50 (m, 2H), 2.20-2.05 (m, 3H), 1.86-1.78 (m, 1H); LCMS: 623.16 $[M+H]^+$.

Example 50

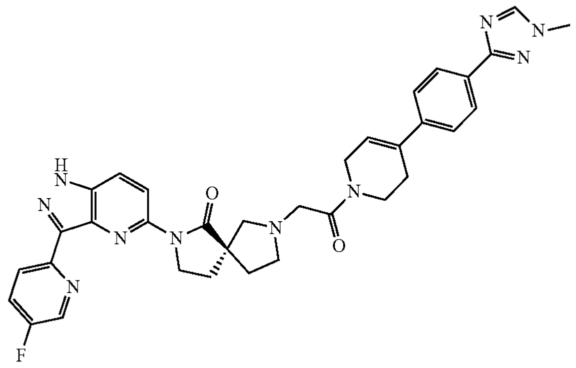

Example 50 was prepared as described in Example 28 using Intermediate 4, 2-bromo-5-fluoropyridine and Intermediate 9. $^1$H NMR (400 MHz, DMSO-$d_6$) δ 13.69 (s, 1H), 8.73-8.69 (m, 2H), 8.51-8.47 (m, 2H), 8.15 (br s, 1H), 7.97 (d, 2H), 7.89 (br s, 1H), 7.55 (d, 2H), 6.28 (s, 1H), 4.30-4.11 (m, 4H), 3.92 (s, 3H), 3.81-3.66 (m, 2H), 3.50-3.38 (m, 3H), 2.95-2.82 (m, 2H), 2.70-2.56 (m, 3H), 2.24-2.13 (m, 3H), 1.88-1.83 (m, 1H); LCMS: 633.15 $[M+H]^+$.

Example 51

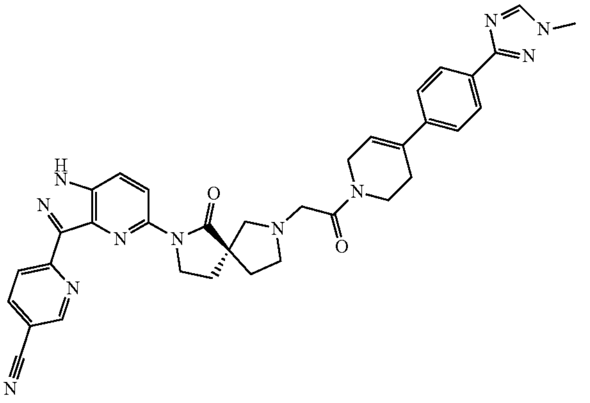

Example 51 was prepared as described in Example 50 using Intermediate 4, 6-bromonicotinonitrile, and Intermediate 9. $^{1}H$ NMR (400 MHz, DMSO-$d_6$) δ 14.00 (s, 1H), 9.11 (d, 1H), 8.83-8.80 (m, 1H), 8.54-8.50 (m, 2H), 8.43 (d, 1H), 8.19 (br s, 1H), 7.97 (d, 2H), 7.55 (d, 2H), 6.28 (s, 1H), 4.31 (s, 1H), 4.20-4.05 (m, 3H), 3.92 (s, 3H), 3.85-3.60 (m, 2H), 3.50-3.30 (m, 3H), 3.00-2.50 (s, 5H), 2.30-2.10 (m, 3H), 1.90-1.80 (m, 1H); LCMS: 640.15 $[M+H]^+$.

Example 52

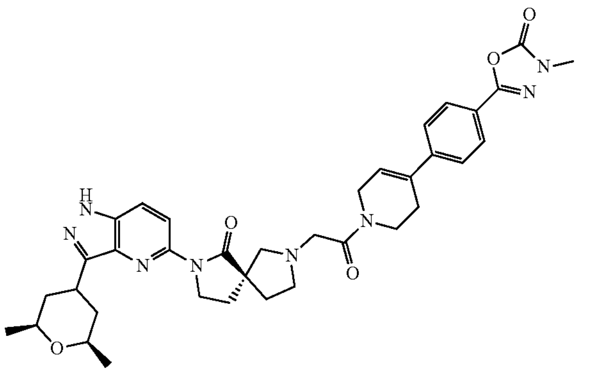

Example 52 was prepared following General Procedures A, B2, and C using Intermediate 4, 2-((2S,6R)-2,6-dimethyl-3,6-dihydro-2H-pyran-4-yl)-4,4,5,5-tetramethyl-1,3,2-dioxaborolane, and Intermediate 15. LCMS: 667.30 $[M+H]^+$.

Example 53

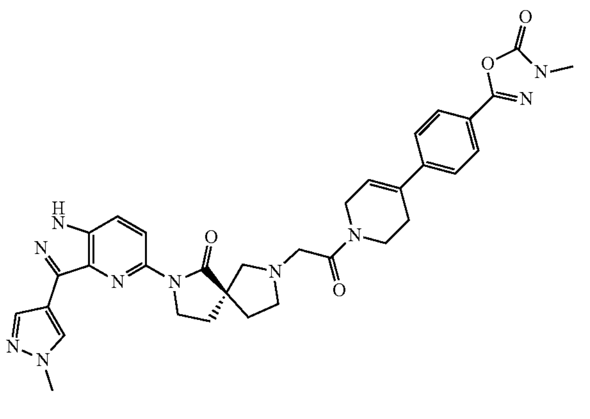

Example 53 was prepared following General Procedures A, B2, and C using Intermediate 4, 1-methyl-4-(4,4,5,5-tetramethyl-1,3,2-dioxaborolan-2-yl)-1H-pyrazole, and Intermediate 15. LCMS: 635.30 $[M+H]^+$.

Example 54

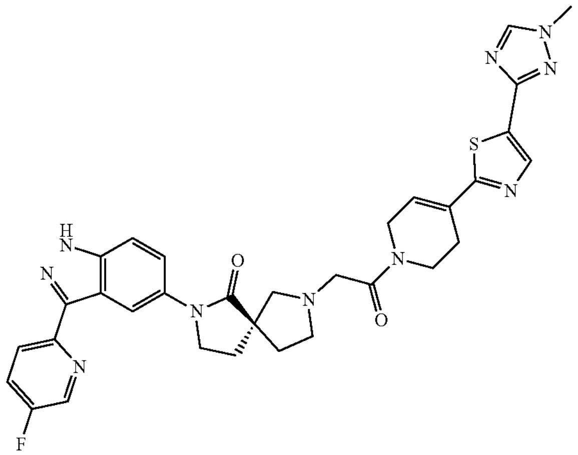

Example 54 was prepared following procedures described for Example 28 using Intermediate 3 and Intermediate 13. $^{1}H$ NMR (400 MHz, DMSO-$d_6$) δ 13.51 (s, 1H), 8.70 (d, 1H), 8.57-8.52 (m, 2H), 8.25-8.18 (m, 2H), 8.87-7.78 (m, 2H), 7.59 (d, 1H), 6.74-6.70 (m, 1H), 4.45-4.35 (m, 1H), 4.21-4.16 (m, 1H), 3.92-3.61 (m, 7H), 3.49-3.35 (m, 3H), 2.95-2.88 (m, 1H), 2.86-2.82 (m, 1H), 2.74-2.69 (m, 1H), 2.68-2.57 (m, 2H), 2.27-2.08 (m, 3H), 1.87-1.77 (m, 1H); LCMS: 639.11 $[M+H]^+$.

Example 55

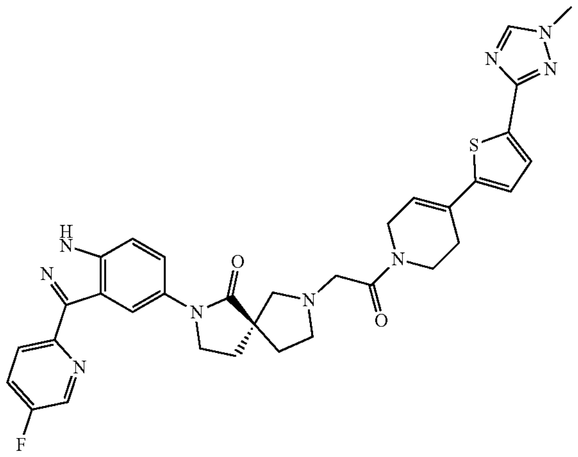

Example 55 was prepared following procedures described for Example 54 using Intermediate 3, 2-bromo-5-fluoropyridine, Intermediate 14. $^{1}H$ NMR (DMSO-$d_6$, 400 MHz) δ 13.51 (s, 1H), 8.70 (d, 1H), 8.57-8.54 (m, 1H), 8.48 (s, 1H), 8.24-8.18 (m, 1H), 7.87-7.77 (m, 2H), 7.59 (d, 1H), 7.47-7.41 (m, 1H), 7.13-7.08 (m, 1H), 6.23-6.18 (m, 1H), 4.35-4.27 (m, 1H), 4.14-4.09 (m, 1H), 3.90-3.64 (m, 7H), 3.48-

3.35 (m, 3H), 2.95-2.80 (m, 3H), 2.66-2.58 (m, 2H), 2.25-2.11 (m, 3H), 1.87-1.79 (m, 1H); LCMS: 638.10 $[M+H]^+$.

Example 56

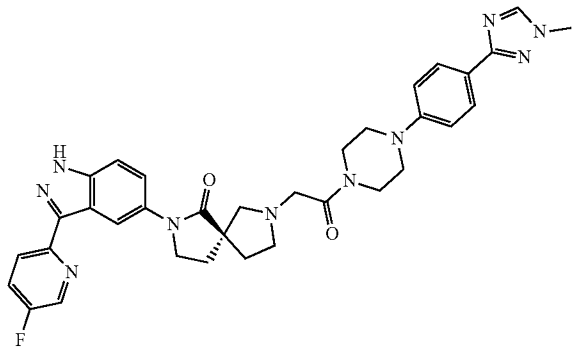

Example 56 was prepared following procedures described for Example 28 using Intermediate 3, 2-bromo-5-fluoropyridine and Intermediate 10. $^1H$ NMR (400 MHz, DMSO-$d_6$) δ 13.51 (s, 1H), 8.70 (d, 1H), 8.57-8.54 (m, 1H), 8.42 (s, 1H), 8.25-8.18 (m, 1H), 7.88-7.77 (m, 4H), 7.60 (d, 1H), 7.03 (d, 2H), 3.91-3.85 (m, 5H), 3.73-3.68 (m, 2H), 3.65-3.59 (m, 2H), 3.44-3.35 (m, 2H), 3.29-3.26 (m, 3H), 3.25-3.19 (m, 2H), 3.03-2.84 (m, 3H), 2.28-2.12 (m, 3H), 1.78-1.92 (m, 1H); LCMS: 635.15 $[M+H]^+$.

Example 57

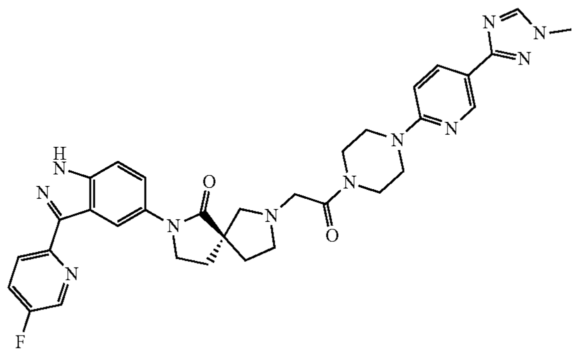

Example 57 was prepared as described in Example 28 using Intermediate 3, 2-bromo-5-fluoropyridine and Intermediate 12. $^1H$ NMR (400 MHz, DMSO-$d_6$) δ 13.51 (s, 1H), 8.71 (m, 2H), 8.55 (d, 1H), 8.46 (s, 1H), 8.21 (q, 1H), 8.05 (dd, 1H), 7.87-7.77 (m, 2H), 7.59 (d, 1H), 6.94 (d, 1H), 3.90-3.81 (m, 5H), 3.71-3.54 (m, 8H), 3.37 (s, 2H), 2.98-2.90 (m, 1H), 2.88-2.83 (m, 1H), 2.68-2.61 (m, 1H), 2.53-2.51 (m, 1H), 2.28-2.07 (m, 3H), 1.87-1.78 (m, 1H); LCMS: 636.16 $[M+H]^+$.

Example 58

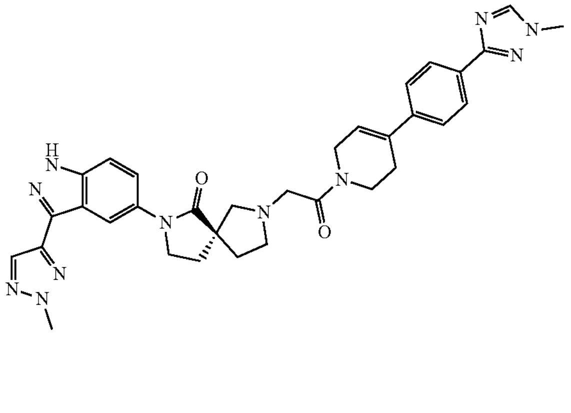

(5R)-Benzyl 7-(3-(2-methyl-2H-1,2,3-triazol-4-yl)-1-(tetrahydro-2H-pyran-2-yl)-1H-indazol-5-yl)-6-oxo-2,7-diazaspiro[4.4]nonane-2-carboxylate (58-1)

To a solution of 4-bromo-2-methyl-2H-1,2,3-triazole (250 mg, 1.543 mmol) in 1,4-dioxane (20 mL) were added 4,4,4',4',5,5,5',5'-octamethyl-2,2'-bi(1,3,2-dioxaborolane) (780.9 mg, 3.086 mmol) and KOAc (454.8 mg, 4.630 mmol). The mixture was degassed for 10 min, followed by addition of $Pd(Ph_3P)_4$ (126.0 mg, 0.154 mmol), and degassed for another 10 min. The reaction mixture was sealed, stirred at 80° C. for 3 h, and cooled to rt. To the mixture was added a mixture of Intermediate 3 (426.7 mg, 0.771 mmol) and $K_2CO_3$ (1.064 g, 7.717 mmol) in toluene/$H_2O$/ethanol (30 mL). The mixture was degassed for 10 min, followed by addition of $Pd(Ph_3P)_4$ (178.2 mg, 0.154 mmol), and degassed for another 10 min. After being stirred at 80° C. for 16 h, the mixture was cooled to rt, diluted with cold water, and extracted with EtOAc. The combined organic layers were washed with water and brine, dried over $Na_2SO_4$ and concentrated. The crude compound was purified by column chromatography using 60% EtOAc/hexanes to afford 58-1 (300 mg, 35%). LCMS: 556.1 $[M+H]^+$.

(S)-7-(2-(4-(4-(1-methyl-1H-1,2,4-triazol-3-yl)phenyl)-3,6-dihydropyridin-1(2H)-yl)-2-oxoethyl)-2-(3-(2-methyl-2H-1,2,3-triazol-4-yl)-1H-indazol-5-yl)-2,7-diazaspiro[4.4]nonan-1-one (Example 58)

Example 58 was prepared following General Procedures B2, and C using 58-1 and Intermediate 9. $^1H$ NMR (DMSO-$d_6$, 400 MHz) δ 13.40 (s, 1H), 8.50 (s, 1H), 8.24 (br s, 1H), 8.18 (s, 1H), 7.96 (d, 2H), 7.96 (t, 1H), 7.70-7.40 (m, 3H), 6.28 (br s, 1H), 4.40-4.09 (m, 5H), 3.91 (s, 3H), 3.90-3.70 (m, 5H), 3.48-3.30 (m, 2H), 2.96-2.89 (m, 1H), 2.87-2.80 (m, 1H), 2.70-2.60 (m, 2H), 2.57-2.50 (m, 1H), 2.30-2.10 (m, 3H), 1.87-1.80 (m, 1H); LCMS: 618.15 $[M+H]^+$.

Example 59

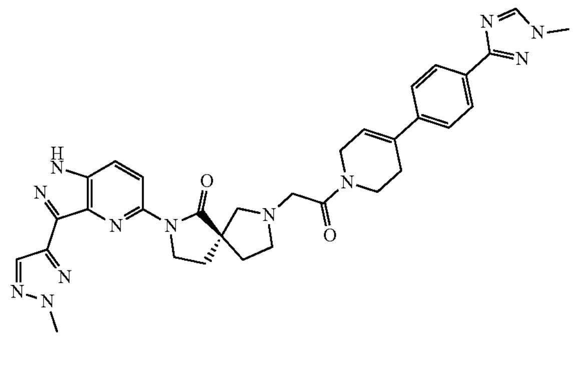

Example 59 was prepared following General Procedures A, B2, C and D using 2-methyl-4-(4,4,5,5-tetramethyl-1,3,2-dioxaborolan-2-yl)-2H-1,2,3-triazole, Intermediate 4 and Intermediate 9. $^1$H NMR (400 MHz, DMSO-$d_6$) δ 13.55 (s, 1H), 8.55-8.42 (m, 3H), 8.12 (d, 1H), 7.97 (d, 2H), 7.60-7.53 (m, 2H), 6.29 (br s, 1H), 4.30-4.10 (m, 7H), 3.92 (s, 3H), 3.80-3.70 (m, 3H), 3.20-2.7 (m, 4H), 2.60-2.64 (m, 1H), 2.55-2.40 (m, 2H), 2.32-2.22 (m, 3H), 2.10-1.19 (m, 1H); LCMS: 619.16 $[M+H]^+$.

Example 60

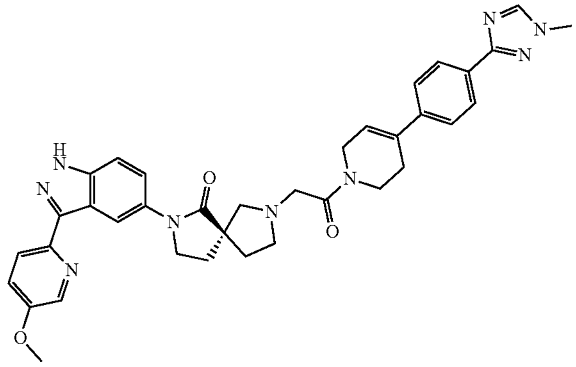

Example 60 was prepared following procedures described for Example 56 using Intermediate 3, 2-bromo-5-methoxy pyridine and Intermediate 9. $^1$H NMR (400 MHz, DMSO-$d_6$) δ 13.21 (s, 1H), 8.57 (s, 1H), 8.50 (s, 1H), 8.43 (s, 1H), 8.10 (d, 1H), 7.96 (d, 2H), 7.77 (t, 1H), 7.60-7.45 (m, 4H), 6.28 (br s, 1H), 4.40-4.10 (m, 2H), 3.95-3.64 (m, 10H), 3.50-3.30 (m, 2H), 2.95-2.82 (m, 2H), 2.70-2.61 (m, 2H), 2.56-2.40 (m, 2H), 2.25-2.10 (m, 3H), 1.90-1.80 (m, 1H); LCMS: 644.15 $[M+H]^+$.

Example 61

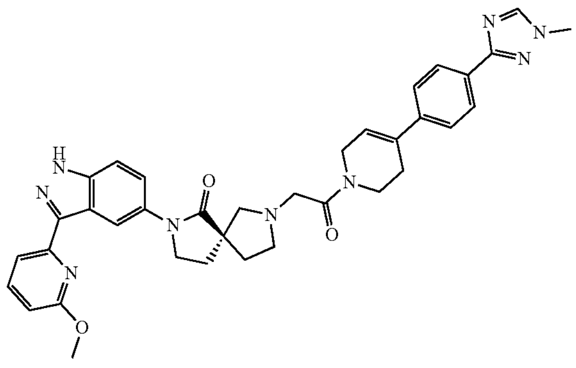

Example 61 was prepared following General Procedures A, B2, and C using Intermediate 3, 6-methoxypyridin-2-ylboronic acid, and Intermediate 9. $^1$H NMR (400 MHz, DMSO-$d_6$) δ 13.38 (s, 1H), 8.82 (s, 1H), 8.51 (s, 1H), 7.96 (d, 2H), 7.94-7.85 (m, 1H), 7.82-7.75 (m, 2H), 7.62-7.52 (m, 3H), 6.78 (d, 1H), 6.29 (s, 1H), 4.30-4.12 (m, 2H), 4.08 (s, 3H), 3.94-3.83 (m, 5H), 3.80-3.60 (m, 4H), 3.15-2.80 (m, 4H), 2.70-2.60 (m, 2H), 2.30-2.10 (m, 3H), 2.00-1.80 (m, 1H); LCMS: 644.49 $[M+H]^+$.

Example 62

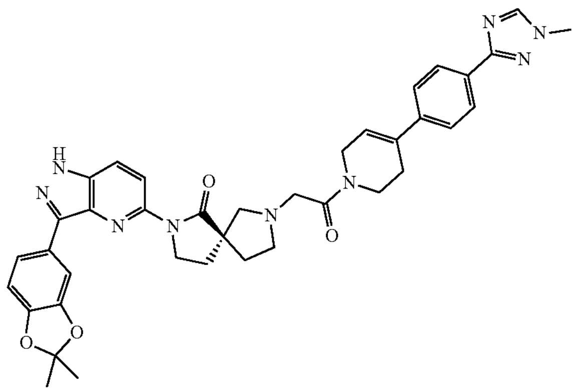

Example 62 was prepared following General Procedures A, B1, C and D using Intermediate 4, 2-(2,2-dimethylbenzo[d][1,3]dioxol-5-yl)-4,4,5,5-tetramethyl-1,3,2-dioxaborolane, and Intermediate 9. $^1$H NMR (400 MHz, DMSO-$d_6$) δ 13.23 (s, 1H), 8.50 (s, 1H), 8.45 (d, 1H), 8.05 (d, 1H), 8.00-7.96 (m, 3H), 7.90 (s, 1H), 7.55 (d, 2H), 6.95 (d, 1H), 6.28 (s, 1H), 4.31-4.10 (m, 4H), 3.92 (s, 3H), 3.85-3.69 (m, 2H), 3.50-3.37 (m, 3H), 2.91-2.82 (m, 2H), 2.76-2.57 (m, 3H), 2.24-1.85 (m, 4H), 1.60 (s, 6H); LCMS: 686.50 $[M+H]^+$.

Example 63

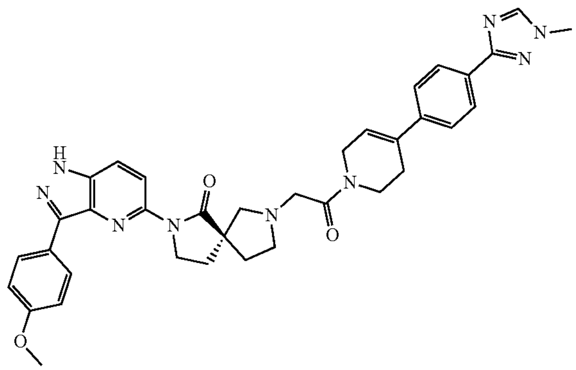

Example 63 was prepared following General Procedures A, B2, and C using Intermediate 4, 2-(4-methoxyphenyl)-4,4,5,5-tetramethyl-1,3,2-dioxaborolane, and Intermediate 9. $^1$H NMR (DMSO-$d_6$, 300 MHz) δ 13.31 (s, 1H), 8.52-8.38 (m, 4H), 8.06 (d, 1H), 7.97 (d, 2H), 7.55 (d, 2H), 7.07 (d, 2H), 6.28 (br s, 1H), 4.31 (br s, 1H), 4.15-4.12 (m, 3H), 3.92 (s, 3H), 3.81 (s, 3H), 3.73-3.71 (m, 2H), 3.50-3.37 (m, 2H), 2.90-2.70 (m, 4H), 2.63-2.50 (m, 2H), 2.30-2.12 (m, 3H), 1.89-1.80 (m, 1H); LCMS: 644.15 $[M+H]^+$.

Example 64

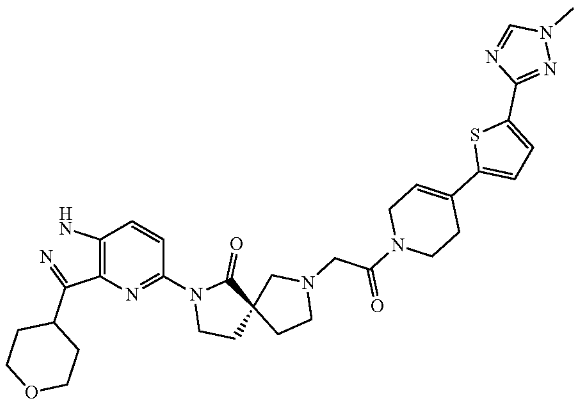

Example 64 was prepared following General Procedures A, B2, and C using Intermediate 4, 2-(3,6-dihydro-2H-pyran-4-yl)-4,4,5,5-tetramethyl-1,3,2-dioxaborolane, and Intermediate 14. $^1$H NMR (DMSO-$d_6$, 400 MHz) δ 12.89 (s, 1H), 8.49 (s, 1H), 8.35 (d, 1H), 7.96 (d, 1H), 7.45 (d, 1H), 7.11 (d, 1H), 6.19 (br s, 1H), 4.30-4.28 (m, 1H), 4.15-3.87 (m, 9H), 3.80-3.63 (m, 2H), 3.55-3.44 (m, 3H), 3.38-3.30 (m, 1H), 2.89-2.85 (m, 1H), 2.81-2.77 (m, 1H), 2.73-2.66 (m, 1H), 2.61-2.54 (m, 2H), 2.20-1.94 (m, 8H), 1.85-1.81 (m, 1H); LCMS: 628.46 $[M+H]^+$.

Example 65

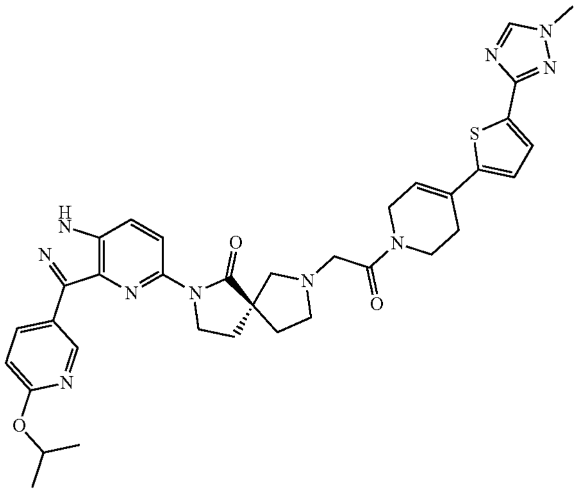

Example 65 was prepared following General Procedures A, B2, and C using Intermediate 4, 2-isopropoxy-5-(4,4,5,5-tetramethyl-1,3,2-dioxaborolan-2-yl)pyridine, and Intermediate 14. $^1$H NMR (DMSO-$d_6$, 400 MHz) δ 13.42 (s, 1H), 9.26 (d, 1H), 8.57 (dd, 1H), 8.50-8.44 (m, 2H), 8.09 (d, 1H), 7.46 (d, 1H), 7.11 (d, 1H), 6.88 (d, 1H), 6.22-6.18 (m, 1H), 5.36-5.29 (m, 1H), 4.31-4.28 (m, 1H), 4.19-4.04 (m, 3H), 3.86 (s, 3H), 3.85-3.62 (m, 2H), 3.52-3.43 (m, 1H), 3.39-3.34 (m, 1H), 2.94-2.79 (m, 2H), 2.76-2.65 (m, 1H), 2.64-2.55 (m, 3H), 2.27-2.09 (m, 3H), 1.91-1.80 (m, 1H), 132 (d, 6H); LCMS: 679.12 $[M+H]^+$.

Example 66

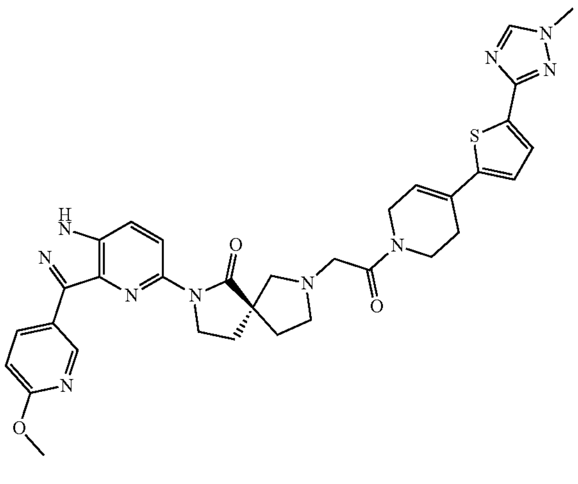

Example 66 was prepared following General Procedures A, B2, and C using Intermediate 4, 2-methoxy-5-(4,4,5,5-tetramethyl-1,3,2-dioxaborolan-2-yl)pyridine, and Intermediate 14. $^1$H NMR (DMSO-$d_6$, 400 MHz) δ 13.43 (s, 1H), 9.29 (s, 1H), 8.60 (dd, 1H), 8.51-8.44 (m, 2H), 8.10 (d, 1H), 7.46 (d, 1H), 7.11 (d, 1H), 6.97 (d, 1H), 6.23-6.18 (m, 1H), 4.31-4.27 (m, 1H), 4.19-4.02 (m, 3H), 3.92 (s, 3H), 3.88 (s, 3H), 3.84-3.62 (m, 2H), 3.51-3.44 (m, 1H), 3.41-3.35 (m, 1H), 2.96-2.79 (m, 2H), 2.77-2.54 (m, 4H), 2.28-2.10 (m, 3H), 1.91-1.80 (m, 1H); LCMS: 651.45 $[M+H]^+$.

Example 67

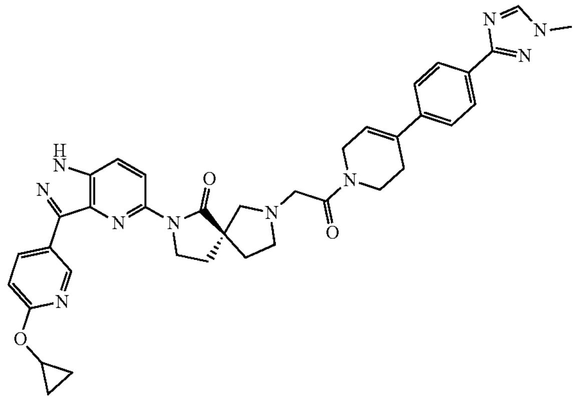

Example 67 was prepared following General Procedures A, B2, and C using Intermediate 4), 2-cyclopropoxy-5-(4,4,5,5-tetramethyl-1,3,2-dioxaborolan-2-yl) pyridine, and Intermediate 9. $^1$H NMR (400 MHz, DMSO-$d_6$) δ 13.38 (s, 1H), 9.29 (d, 1H), 8.65-8.60 (m, 1H), 8.50 (s, 1H), 8.47 (s, 1H), 8.10 (d, 1H), 7.97 (d, 2H), 7.55 (d, 2H), 7.00 (d, 1H), 6.28 (s, 1H), 4.32-4.25 (m, 2H), 4.20-4.05 (m, 3H), 3.91 (s, 3H), 3.82-3.65 (m, 2H), 3.52-3.35 (m, 2H), 2.95-2.55 (m, 6H), 2.30-2.10 (m, 3H), 1.90-1.80 (m, 1H), 0.83-0.76 (m, 2H), 0.75-0.68 (m, 2H); LCMS: 671.51 $[M+H]^+$.

Example 68

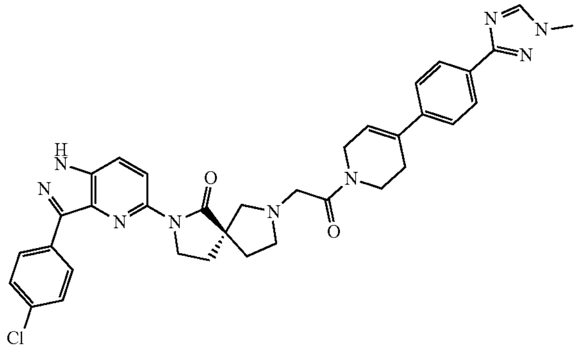

Example 68 was prepared following General Procedures A, B1, C and D using Intermediate 4, 2-(4-chlorophenyl)-4,4,5,5-tetramethyl-1,3,2-dioxaborolane, and Intermediate 9. $^1$H NMR (DMSO-$d_6$, 400 MHz) δ 13.51 (s, 1H), 8.52-8.48 (m, 4H), 8.12 (d, 1H), 7.78 (d, 2H), 7.58-7.55 (m, 4H), 6.29 (br, 1H), 4.31 (m, 1H), 4.15-4.07 (m, 3H), 3.92 (m, 3H), 3.83-3.65 (m, 2H), 3.49-3.37 (m, 2H), 3.32-3.27 (m, 1H), 2.92-2.84 (m, 2H), 2.78 (m, 1H), 2.66-2.62 (m, 2H), 2.33-2.12 (m, 3H), 1.91-1.85 (br, 1H); LCMS: 648.10 $[M+H]^+$.

Example 69

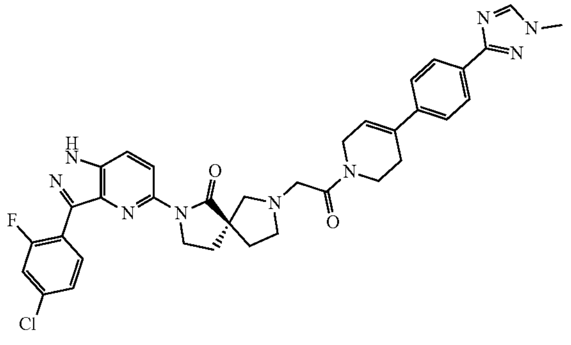

Example 69 was prepared following General Procedures A, B1, C and D using Intermediate 4, 2-(4-chloro-2-fluorophenyl)-4,4,5,5-tetramethyl-1,3,2-dioxaborolane, and Intermediate 9. $^1$H NMR (DMSO-$d_6$, 400 MHz) δ 13.64 (s, 1H), 8.52-8.39 (m, 4H), 8.15 (d, 1H), 7.97 (d, 2H), 7.61-7.55 (m, 3H), 6.29 (br, 1H), 4.30 (m, 1H), 4.15-4.07 (m, 3H), 3.92 (m, 3H), 3.83-3.65 (m, 2H), 3.49-3.37 (m, 2H), 3.32-3.27 (m, 1H), 2.92-2.84 (m, 2H), 2.78 (m, 1H), 2.66-2.62 (m, 2H), 2.23-2.09 (m, 3H), 1.88-1.83 (br, 1H); LCMS: 666.10 $[M+H]^+$.

Example 70

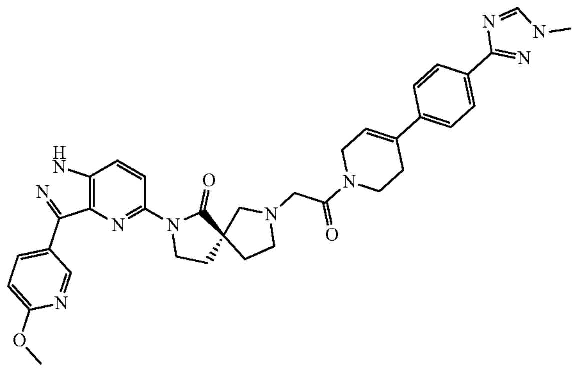

Example 70 was prepared following General Procedure B1 and E using Example 21. Data for 1.0 acetate salt: 1H NMR (DMSO-$d_6$, 400 MHz) δ 9.30 (br, 1H), 8.50 (br, 1H), 8.52-8.42 (m, 2H), 8.14 (d, 1H), 7.94 (d, 2H), 7.36 (d, 2H), 6.91-6.88 (m, 1H), 4.54-4.51 (m, 2H), 4.22-4.13 (m, 3H), 3.92 (m, 6H), 3.54-3.43 (m, 2H), 3.29-3.08 (m, 4H), 2.93-2.64 (m, 6H), 2.28-2.21 (m, 3H), 1.86 (s, 3H), 1.23 (br, 2H); LCMS: 647.20 $[M+H]^+$.

Example 71

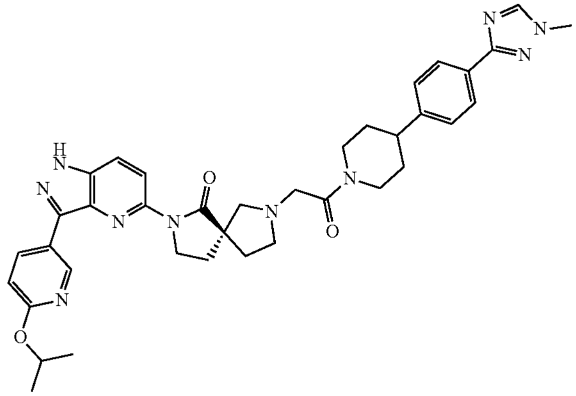

Example 71 was prepared following General Procedure B1 using (S)-2-(3-(6-isopropoxypyridin-3-yl)-1H-pyrazolo [4,3-b]pyridin-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one. Data for 1.0 acetate salt: 1H NMR (DMSO-$d_6$, 400 MHz) δ 9.27 (br, 1H), 8.59 (br, 1H), 8.52-8.42 (m, 2H), 8.12 (d, 1H), 7.93 (d, 2H), 7.35 (d, 2H), 6.91-6.88 (m, 1H), 5.34-5.30 (m, 1H), 4.54-4.51 (m, 1H), 4.22-4.13 (m, 3H), 3.92 (m, 4H), 3.54-3.43 (m, 2H), 3.29-3.08 (m, 4H), 2.93-2.64 (m, 6H), 2.28-2.21 (m, 3H), 1.86 (s, 3H), 1.33 (d, 6H), 1.23 (br, 2H); LCMS: 675.20 $[M+H]^+$ Example 72

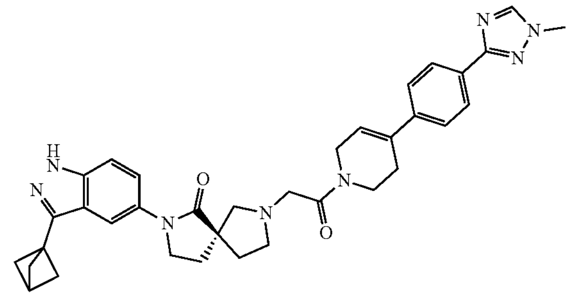

Methyl 3-(chlorocarbonyl)bicyclo[1.1.1]pentane-1-carboxylate (72-1)

To a stirred solution of 3-(methoxycarbonyl)bicyclo [1.1.1]pentane-1-carboxylic acid (1.5 g, 8.823 mmol) in DCM (20 mL) was added oxalyl chloride (1.19 mL, 13.235 mmol) and a drop of DMF at 0 C and continued stirring at rt for 3 h. The mixture was evaporated to dryness to afford 72-1 (1.6 g crude, 100%) as a gummy liquid which was used for the next step directly.

Methyl 3-(2-fluorobenzoyl)bicyclo[1.1.1]pentane-1-carboxylate (72-2)

To a stirred solution of fluorobenzene (200 mg, 2.220 mmol) in THF (10 mL) was added sec-Buli (1.6 mL, 2.260 mmol, 1.4 M in cyclohexane) drop wise at −78 C and the mixture was further stirred at same temperature for 30 min. To this mixture was then $ZnCl_2$ (2.2 mL, 2.220 mmol, IM in THF) was added and continued stirring at same temperature for 15 min. To the resulting mixture, CuCl (21 mg, 0.220 mmol) was added followed by 72-1 (200 mg, 1.063 mmol) in THF (10 mL) at −60 C slowly. The mixture was allowed to warm to rt and stirred at rt for 16 h. The reaction was quenched with 1N HCl, extracted with EtOAc (3×100 mL). The combined organic layers were washed with brine, dried $Na_2SO_4$ and concentrated. The crude compound was purified by column chromatography using 20% EtOAc/hexane to afford 72-2 (65 mg, 25%) as an oil. LCMS: 248.98 $[M+H]^+$.

3-(2-Fluorobenzoyl)bicyclo[1.1.1]pentane-1-carboxylic acid (72-3)

To a solution of 72-2 (50 mg, 0.201 mmol) in THF:MeOH (1:1, 6 mL) was added LiOH (42 mg, 1.008 mmol) at 0° C. and stirred at rt for 5 h. After completion of the reaction, the mixture was quenched with $KHSO_4$ and extracted with EtOAc. The combined organic layers were washed with water, brine, dried $Na_2SO_4$ and concentrated to afford 72-3 (33 mg, 70%) as an off white solid. LCMS: 234.86 $[M+H]^+$.

3-(2-Fluorobenzoyl)bicyclo[1.1.1]pentane-1-carbonyl chloride (72-4)

To a stirred solution of 72-3 (200 mg, 0.858 mmol) in DCM (10 mL) was added oxalyl chloride (0.1 mL, 1.287 mmol) and a drop of DMF at 0 C. Resulting mixture was stirred at rt for 3 h. After completion of the reaction, the mixture was concentrated under nitrogen atmosphere to afford 72-4 (200 mg, 100%) as a gummy solid. This material was used for the next step directly.

Bicyclo[1.1.1]pentan-1-yl(2-fluorophenyl)methanone (72-5)

To a stirred solution of sodium 2-thioxopyridin-1(2H)-olate (50 mg, 0.33 mmol) in $CHCl_3$ (5 mL) was added DMAP (4 mg, 0.033 mmol) at rt and then heated at 60 C for 30 min. To this mixture was then added 72-4 (77 mg, 0.305 mmol) in THF (5 mL) drop wise at 60° C. The mixture was then irradiated under U.V light at 60 C for 16 h. 1N HCl (50 mL) was added to the mixture and extracted with DCM. The combined organic layers were washed with brine, dried over $Na_2SO_4$ and concentrated. The crude was purified by column chromatography eluted with 10% EtOAc/petroleum ether to afford 72-5 (9 mg, 25%) as an off white solid. LCMS: 190.87 $[M+H]^+$.

3-(Bicyclo[1.1.1]pentan-1-yl)-1H-indazole (72-6)

To a solution of 72-5 (200 mg, 1.05 mmol) in DMSO (5 mL) was added hydrazine solution (10 mL, 1.0 M in THF) at rt and stirred at 120 C for 6 h. The mixture was then cooled to room temperature and dissolved in water and extracted with EtOAc. The combined organic layers were washed with water, dried over $Na_2SO_4$ and concentrated. The residue was purified by column chromatography using 4-6% MeOH/DCM to afford 72-6 (44 mg, 0.228 mmol, 22%) as a brown solid. LCMS: 184.86 $[M+H]^+$.

3-(Bicyclo[1.1.1]pentan-1-yl)-5-bromo-1H-indazole (72-7)

To a solution of 72-6 (300 mg, 1.630 mmol) in acetic acid (5 mL) was added bromine (0.1 mL in acetic acid (1.0 mL), 1.956 mmol) at 0 C and stirred at rt for 5 h. After completion of the reaction, cold sat'd $NaHSO_3$ was added to the mixture and extracted with EtOAc. The combined organic layers were washed with water, brine, dried over $Na_2SO_4$ and concentrated to afford 72-7 (200 mg, 46%) as an off white solid. LCMS: 264.85 $[M+H]^+$.

3-(Bicyclo[1.1.1]pentan-1-yl)-5-bromo-1-(tetrahydro-2H-pyran-2-yl)-1H-indazole (72-8)

To a stirred solution of 72-7 (200 mg, 0.763 mmol) in DCM (10 mL) was added DHP (0.348 mL, 3.816 mmol) followed by p-TSA (13.12 g, 0.076 mmol) at 0° C. Resulting mixture was stirred at rt for 3 h. After completion of the reaction, cold water was added to the reaction mixture and extracted with DCM. The combined organic layers were washed with brine, dried over $Na_2SO_4$ and concentrated. The residue was purified by silica gel column chromatography eluted with 20% EtOAc/petroleum ether to afford 72-8 (150 mg, 0.433 mmol, 56%) as an off white solid. LCMS: 348.95 $[M+H]^+$.

(5R)-Benzyl 7-(3-(bicyclo[1.1.1]pentan-1-yl)-1-(tetrahydro-2H-pyran-2-yl)-1H-indazol-5-yl)-6-oxo-2,7-diazaspiro[4.4]nonane-2-carboxylate (72-9)

A mixture of 72-8 (80 mg, 0.231 mmol), benzyl (R)-6-oxo-2,7-diazaspiro[4.4]nonane-2-carboxylate (189 mg, 0.693 mmol), $K_2CO_3$ (63.7 mg, 0.462 mmol), CuI (8.77 mg, 0.0462 mmol) and N,N''-dimethyl ethylenediamine (0.008 mL, 0.0924 mmol) in dioxane (8 mL) was degassed with nitrogen/vacuum cycles. The reaction mixture was heated at 110 C for 4 days. The reaction mixture was cooled to rt followed by addition of cold water and then extracted with EtOAc. The combined organic layers were washed with water, brine, dried over $Na_2SO_4$, and concentrated. The residue was purified by column chromatography using 5% MeOH/DCM to afford 72-9 (65 mg, 52%) as an off-white solid. LCMS: 541.45 $[M+H]^+$.

(S)-2-(3-(Bicyclo[1.1.1]pentan-1-yl)-1H-indazol-5-yl)-7-(2-(4-(4-(1-methyl-1H-1,2,4-triazol-3-yl)phenyl)-5,6-dihydropyridin-1(2H)-yl)-2-oxoethyl)-2,7-diazaspiro[4.4]nonan-1-one (Example 72)

Example 72 was prepared following General Procedures B2 and C using 72-9 and Intermediate 9. $^1H$ NMR (DMSO-$d_6$, 400 MHz) δ 12.67 (s, 1H), 8.49 (s, 1H), 7.96 (d, 2H), 7.88 (d, 1H), 7.63 (d, 1H), 7.54 (d, 2H), 7.45 (d, 1H), 6.30-6.26 (m, 1H), 4.10-4.38 (m, 2H), 3.91 (s, 3H), 3.88-3.63 (m, 4H), 3.55-3.30 (m, 3H), 2.98-2.88 (m, 1H), 2.85-2.80 (m, 1H), 2.72-2.55 (m, 4H), 2.25 (s, 6H), 2.22-2.05 (m, 3H), 1.88-1.75 (m, 1H). LCMS: 603.19 $[M+H]^+$;

Example 73

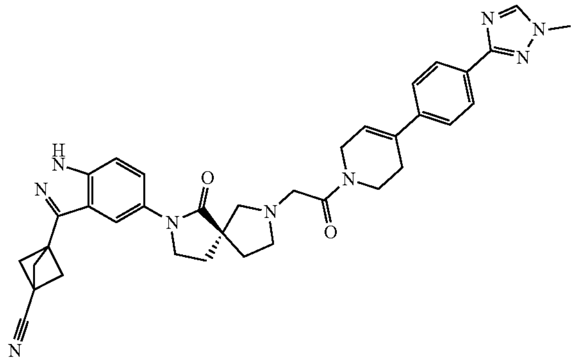

3-(2-Fluorobenzoyl)bicyclo[1.1.1]pentane-1-carboxamide (73-1)

To a stirred solution of methyl 3-(2-fluorobenzoyl)bicyclo[1.1.1]pentane-1-carboxylate (50 mg, 0.201 mmol) in MeOH (3 mL) was added methanolic ammonia (5 mL, 7N) at 0° C. and the mixture was heated at 100° C. in a sealed tube for 16 h. After completion of the reaction, the mixture cooled to rt and concentrated to afford 73-1 which was further washed with diethyl ether to afford 73-1 (33 mg, 70%) as an off white solid. LCMS: 234.86 $[M+H]^+$.

3-(2-Fluorobenzoyl)bicyclo[1.1.1]pentane-1-carbonitrile (73-2)

To a stirred solution of 73-1 (50 mg, 2.145 mmol) in DMF (3 mL) was added thionylchloride (0.04 mL, 6.437 mmol) at 0 C and continued stirring at rt for 3 h. After completion of the reaction, the mixture was diluted with ice water and extracted with EtOAc. The combined organic layers were washed with water, brine, dried over $Na_2SO_4$ and concentrated to obtain residue. Residue was purified by column chromatography using 10-20% EtOAc/petroleum ether to afford 73-2 (18 mg, 40%). LCMS: 216.02 $[M+H]^+$.

3-(1H-Indazol-3-yl)bicyclo[1.1.1]pentane-1-carbonitrile (73-3)

To a solution of 73-2 (200 mg, 0.853 mmol) in dimethyl sulfoxide (5 mL) was added hydrazine solution (10 mL, 1.0 M in THF) at rt and stirred at 120 C for 6 h. The mixture was then cooled to rt and dissolved in water and extracted with EtOAc. The combined organic layers were washed with water, brine, dried over $Na_2SO_4$ and concentrated. The residue was purified by column chromatography using 4-6% MeOH/DCM to afford 73-3 (0.1 g, 22%) as an oil. LCMS: 209.91 $[M+H]^+$.

3-(5-Iodo-1H-indazol-3-yl)bicyclo[1.1.1]pentane-1-carbonitrile (73-4)

To a stirred solution of 73-3 (50 mg, 0.239 mmol) in acetic acid (5 mL) was added ICl (0.1 mL in acetic acid (1.0 mL) 1.916 mmol) at 0° C. and continued stirring at rt for 3 h. After completion of the reaction, cold sat'd $NaHS_2O_3$ was added followed by extraction with EtOAc. The combined organic layers were washed with water, brine, dried over $Na_2SO_4$ and concentrated to afford 73-4 (60 mg, 31%) as a brown color liquid. LCMS: 336.13 $[M+H]^+$.

(S)-3-(5-(7-(2-(4-(4-(1-Methyl-1H-1,2,4-triazol-3-yl) phenyl)-5,6-dihydropyridin-1(2H)-yl)-2-oxoethyl)-1-oxo-2,7-diazaspiro[4.4]nonan-2-yl)-1H-indazol-3-yl) bicyclo[1.1.1]pentane-1-carbonitrile (Example 73)

Example 73 was prepared following procedures described for Example 72 using 73-4 and Intermediate 9. $^1H$ NMR ($DMSO-d_6$, 400 MHz) δ 12.98 (s, 1H), 8.50 (s, 1H), 7.96 (d, 2H), 7.82-7.80 (m, 1H), 7.76-7.69 (m, 1H), 7.57-7.51 (m, 2H), 7.50-7.47 (m, 1H), 6.30-6.27 (m, 1H), 4.34-4.29 (m, 1H), 4.15-4.10 (m, 2H), 3.91 (s, 3H), 3.88-3.65 (m, 4H), 3.50-3.40 (m, 2H), 2.95-2.90 (m, 1H), 2.85-2.78 (m, 1H), 2.72 (s, 6H), 2.65-2.55 (m, 3H), 2.23-2.09 (m, 3H), 1.87-1.72 (m, 1H). LCMS: 628.12 $[M+H]^+$.

Example 74

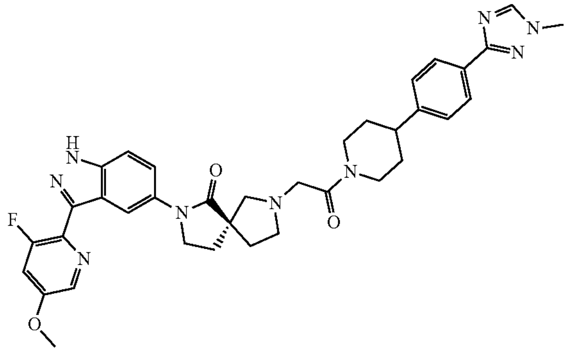

Example 74 was prepared following General Procedures A, B2, and C using Intermediate 4, 2-bromo-3-fluoro-5-methoxypyridine, and Intermediate 9. $^1H$ NMR (400 MHz, $DMSO-d_6$) δ 13.38 (s, 1H), 8.50 (s, 1H), 8.40-8.36 (m, 2H), 7.98-7.93 (m, 2H), 7.81-7.75 (m, 1H), 7.61-7.52 (m, 4H), 6.30-6.26 (m, 1H), 4.35-4.10 (m, 3H), 3.95-3.90 (m, 6H), 3.87-3.63 (m, 4H), 3.48-3.35 (m, 2H), 2.96-2.80 (m, 2H), 2.70-2.56 (m, 3H), 2.25-2.05 (m, 3H), 1.85-1.76 (m, 1H). LCMS: 662.47 $[M+H]^+$.

Example 75

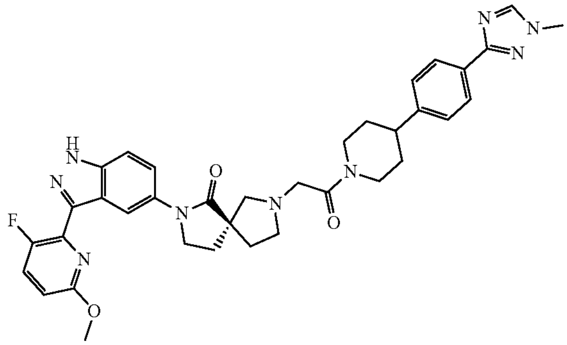

Example 75 was prepared following General Procedures A, B2, and C using Intermediate 4, 2-bromo-3-fluoro-6-methoxypyridine, and Intermediate 9. $^1H$ NMR ($DMSO-d_6$, 400 MHz) δ 13.52 (s, 1H), 8.72-8.68 (m, 1H), 8.50 (s, 1H), 7.95 (d, 2H), 7.89 (d, 1H), 7.78 (t, 1H), 7.62 (d, 1H), 7.54 (d, 2H), 6.85 (d, 1H), 6.30-6.26 (m, 1H), 4.36-4.22 (m, 1H), 4.20-4.03 (m, 4H), 3.93-3.60 (m, 8H), 3.49-3.35 (m, 2H), 2.97-2.79 (m, 2H), 2.70-2.58 (m, 3H), 2.26-2.03 (m, 3H), 1.88-1.75 (m, 1H). LCMS: 662.47 $[M+H]^+$.

Example 76

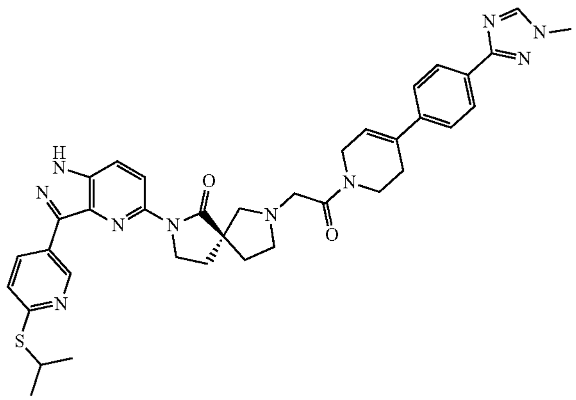

Example 76 was prepared following General Procedures A, B2, and C using Intermediate 4, 2-(isopropylthio)-5-(4,4,5,5-tetramethyl-1,3,2-dioxaborolan-2-yl)pyridine, and Intermediate 9. $^1H$ NMR ($DMSO-d_6$, 400 MHz) δ 13.51 (s, 1H), 9.50 (s, 1H), 8.53 (dd, 1H), 8.49 (d, 2H), 8.11 (d, 1H), 7.97 (d, 2H), 7.55 (d, 2H), 7.39 (d, 1H), 6.30-6.26 (m, 1H), 4.33-4.29 (m, 1H), 4.16-4.06 (m, 3H), 4.04-3.95 (m, 1H), 3.92 (s, 3H), 3.88-3.78 (m, 1H), 3.75-3.67 (m, 1H), 3.52-3.03 (m, 2H), 2.97-2.53 (m, 6H), 2.29-2.03 (m, 3H), 1.91-1.80 (m, 1H), 1.38 (d, 6H). LCMS: 689.16 $[M+H]^+$.

Example 77

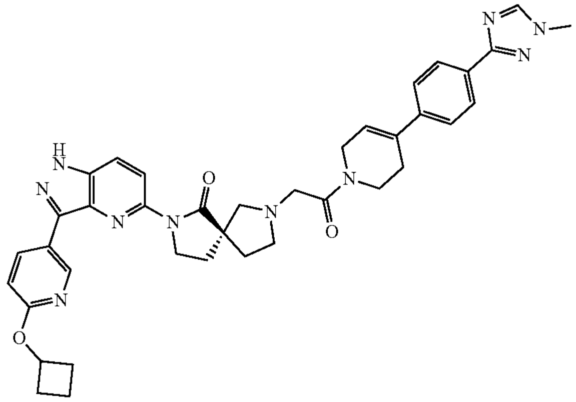

Example 77 was prepared following General Procedures A, B2, and C using Intermediate 4, 2-cyclobutoxy-5-(4,4,5,5-tetramethyl-1,3,2-dioxaborolan-2-yl)pyridine, and Intermediate 9. $^1H$ NMR (400 MHz, $DMSO-d_6$) δ 13.41 (s, 1H), 9.23 (d, 1H), 8.59 (dd, 1H), 8.51-8.47 (m, 2H), 8.09 (d, 1H), 7.97 (d, 2H), 7.55 (d, 2H), 6.92 (d, 1H), 6.30-6.26 (m, 1H), 5.21 (qt, 1H), 4.31 (s, 1H), 4.14-4.11 (m, 3H), 3.92 (s, 3H), 3.80-3.70 (m, 2H), 3.47-3.37 (m, 3H), 3.32-2.84 (m, 2H), 2.76-2.74 (m, 1H), 2.67-2.58 (m, 2H), 2.50-2.39 (m, 2H), 2.32-2.06 (m, 5H), 1.88-1.78 (m, 2H), 1.69-1.64 (m, 1H). LCMS: 685.49 $[M+H]^+$.

Example 78

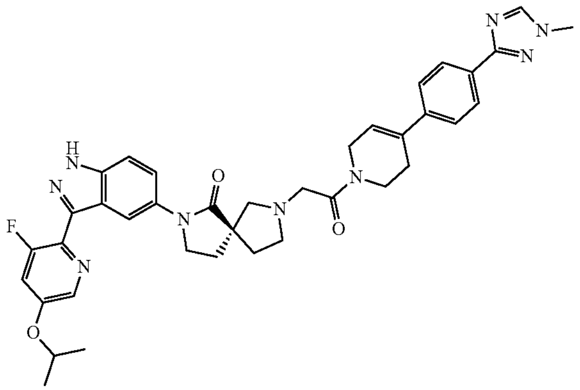

Example 78 was prepared following General Procedures A, B2, and C using Intermediate 4, 2-bromo-3-fluoro-5-methoxypyridine, and Intermediate 9. $^1H$ NMR (400 MHz, DMSO-$d_6$) δ 13.38 (s, 1H), 8.50 (s, 1H), 8.34 (d, 2H), 7.95 (d, 2H), 7.80-7.74 (m, 1H), 7.62-7.52 (m, 4H), 6.28 (s, 1H), 4.85-4.78 (m, 1H), 4.33-4.28 (m, 1H), 4.15-4.10 (m, 2H), 3.91 (s, 3H), 3.85-3.63 (m, 4H), 3.00-2.80 (m, 3H), 2.70-2.50 (m, 4H), 2.35-2.05 (m, 3H), 1.85-1.65 (m, 1H), 1.33 (d, 6H). LCMS: 690.46 $[M+H]^+$.

Example 79

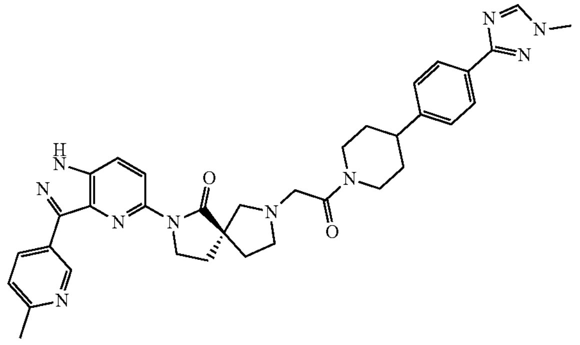

Example 79 was prepared following General Procedures A, B2, and C using Intermediate 4, 2-chloro-1-(4-(4-(1-methyl-1H-1,2,4-triazol-3-yl)phenyl)piperidin-1-yl)ethanone (prepared via $Pd(OH)_2$-mediated hydrogenation of Intermediate 9 in THF at rt). $^1H$ NMR (DMSO-$d_6$, 400 MHz) δ 13.50 (s, 1H), 9.51 (s, 1H), 8.63-8.58 (m, 1H), 8.52-8.50 (m, 2H), 8.13 (d, 1H), 7.92 (d, 2H), 7.40-7.38 (m, 3H), 4.52 (d, 1H), 4.17-4.11 (m, 3H), 3.91 (d, 3H), 3.61-3.38 (m, 2H) 3.15-3.09 (m, 1H), 2.98-2.81 (m, 4H), 2.68-2.61 (m, 2H), 2.53-2.51 (m, 3H), 2.34-2.12 (m, 3H), 1.93-1.79 (m, 3H), 1.74-1.63 (m, 1H), 1.52-1.42 (m, 1H). LCMS: 631.17 $[M+H]^+$.

Example 80

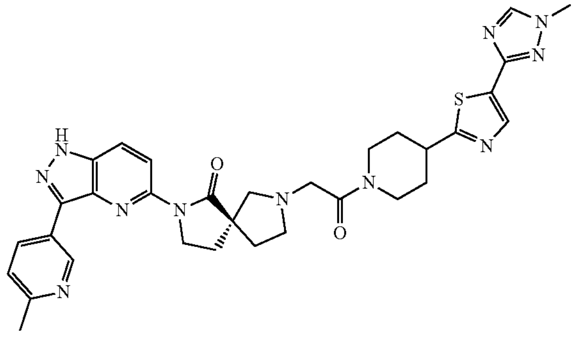 [SMILES: Cc1ccc(-c2n[nH]c3ccc(N4CC[C@]5(CCN(CC(=O)N6CCC(c7ncc(-c8ncn(C)n8)s7)CC6)C5)C4=O)nc23)cn1]

Example 80 was prepared following General Procedures A, B2, and C using Intermediate 4, 2-chloro-1-(4-(5-(1-methyl-1H-1,2,4-triazol-3-yl)thiazol-2-yl)piperidin-1-yl) ethanone (prepared via $Pd(OH)_2$-mediated hydrogenation of Intermediate 13 in THF at rt). 1H NMR (DMSO-$d_6$, 400 MHz) δ 13.50 (s, 1H), 9.51 (s, 1H), 8.60 (dd, 1H), 8.54 (s, 1H), 8.49 (d, 1H), 8.15-8.08 (m, 2H), 7.3 (d, 1H), 4.43-4.38 (m, 1H), 4.17-4.09 (m, 3H), 3.89 (d, 3H), 3.52-3.41 (m, 1H), 3.23-3.17 (m, 3H), 2.92-2.88 (m, 1H), 2.83-2.65 (m, 3H), 2.53-2.51 (m, 4H), 2.33-2.06 (m, 5H), 1.88-1.74 (m, 2H), 1.59-1.53 (m, 1H). LCMS: 638.44 $[M+H]^+$.

Example 81

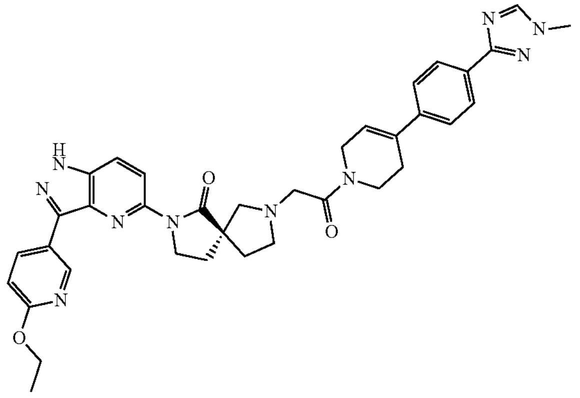

Example 81 was prepared following General Procedures A, B2, and C using Intermediate 4, 2-ethoxy-5-(4,4,5,5-tetramethyl-1,3,2-dioxaborolan-2-yl)pyridine and Intermediate 9. $^1H$ NMR (DMSO-$d_6$, 300 MHz) δ 13.35 (s, 1H), 9.27 (s, 1H), 8.60 (dd, 1H), 8.52-8.45 (m, 2H), 8.10 (d, 1H), 7.97 (d, 2H), 7.55 (d, 2H), 6.94 (d, 1H), 6.28 (br s, 1H), 4.41-4.30 (m, 3H), 4.13-4.09 (m, 3H), 3.92 (s, 3H), 3.81-3.67 (m, 2H), 3.52-3.46 (m, 1H), 3.97-3.37 (m, 2H), 2.92-2.80 (m, 2H), 2.77-2.69 (m, 1H), 2.63-2.56 (m, 2H), 2.28-2.13 (m, 3H), 1.89-1.85 (m, 1H), 1.35 (t, 3H). LCMS: 659.21 $[M+H]^+$.

Example 82

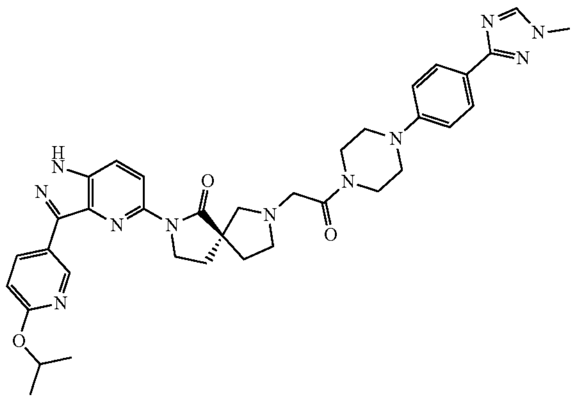

Example 82 was prepared following General Procedures A, B2, and C using Intermediate 4, 2-isopropoxy-5-(4,4,5,5-tetramethyl-1,3,2-dioxaborolan-2-yl)pyridine, and Intermediate 9. $^1$H NMR (400 MHz, DMSO-$d_6$) δ 13.39 (s, 1H), 9.24 (d, 1H), 8.57 (dd, 1H), 8.47 (d, 1H), 8.41 (s, 1H), 8.09 (d, 1H), 7.84 (d, 2H), 7.03 (d, 2H), 6.88 (d, 1H), 5.35-5.29 (m, 1H), 4.14-4.10 (m, 2H), 3.88 (s, 3H), 3.72-3.59 (m, 5H), 3.44-3.34 (m, 2H), 3.23-3.18 (m, 3H), 2.93-2.56 (m, 4H), 2.28-2.12 (m, 3H), 1.89-1.83 (m, 1H), 1.32 (d, 6H). LCMS: 676.20 [M+H]$^+$.

Example 83

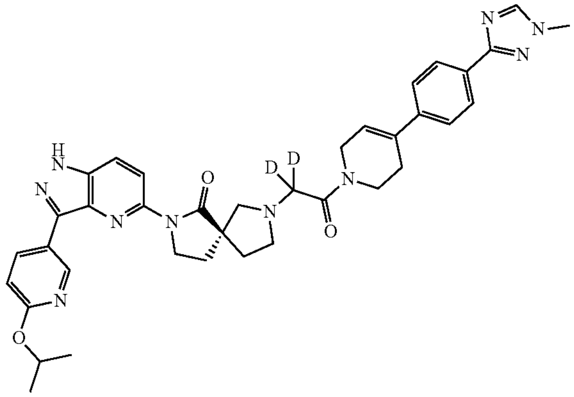

Example 83 was prepared following General Procedures A, B2, and C using Intermediate 4, 2-isopropoxy-5-(4,4,5,5-tetramethyl-1,3,2-dioxaborolan-2-yl)pyridine, and Intermediate 16. $^1$H NMR (400 MHz, DMSO-$d_6$) δ 13.40 (s, 1H), 9.25 (s, 1H), 8.57 (dd, 1H), 8.50 (s, 1H), 8.47 (d, 1H), 8.09 (d, 1H), 7.97 (d, 2H), 7.55 (d, 2H), 6.88 (d, 1H), 6.28 (s, 1H), 5.36-5.29 (m, 1H), 4.31-4.11 (m, 4H), 3.92 (s, 3H), 3.84-3.70 (m, 2H), 2.91-2.75 (m, 4H), 2.66-2.59 (m, 2H), 2.24-2.19 (m, 3H), 1.90-1.85 (m, 1H), 1.33 (d, 6H). LCMS: 675.16 [M+1]$^+$.

Example 84

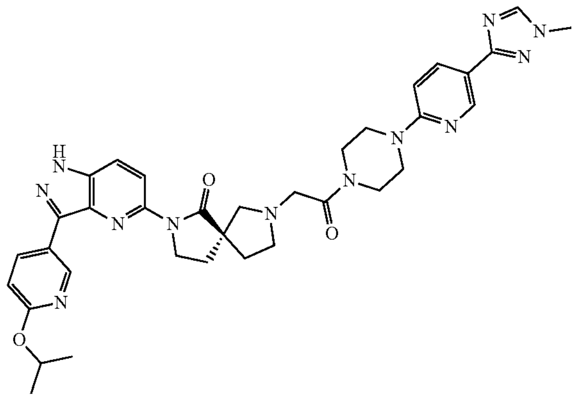

Example 84 was prepared following General Procedures A, B2, and C using Intermediate 4, 2-isopropoxy-5-(4,4,5,5-tetramethyl-1,3,2-dioxaborolan-2-yl)pyridine, and Intermediate 12. $^1$H NMR (400 MHz, DMSO-$d_6$) δ 13.60 (s, 1H), 9.26 (d, 1H), 8.72 (d, 1H), 8.58 (dd, 1H), 8.49-8.47 (m, 2H), 8.11-8.05 (m, 2H), 6.95 (d, 1H), 6.88 (d, 1H), 5.34-5.31 (m, 1H), 4.14-4.11 (m, 2H), 3.89 (s, 3H), 3.69-3.53 (m, 8H), 3.40-3.31 (m, 2H), 2.94-2.84 (m, 2H), 2.72-2.55 (m, 2H), 2.27-2.13 (m, 3H), 1.87-1.84 (m, 1H), 1.33 (d, 6H). LCMS: 677.49 [M+H]$^+$.

Example 85

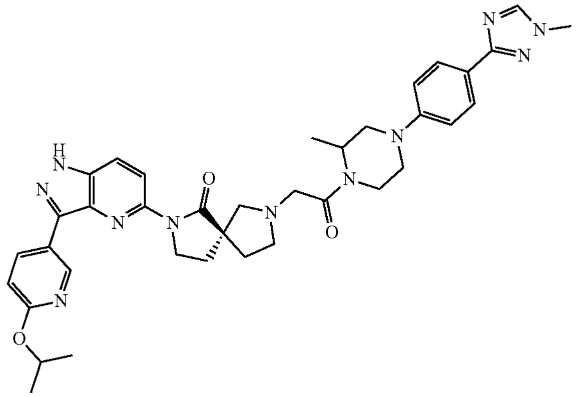

Example 85 was prepared following General Procedures A, B2, and C using Intermediate 4, 2-isopropoxy-5-(4,4,5,5-tetramethyl-1,3,2-dioxaborolan-2-yl)pyridine, and Intermediate 17. $^1$H NMR (DMSO-$d_6$, 400 MHz) δ 13.38 (s, 1H), 9.22 (s, 1H), 8.53 (d, 1H), 8.44 (d, 1H), 8.38 (s, 1H), 8.07

(d, 1H), 7.80 (d, 2H), 6.97 (d, 2H), 6.91 (d, 1H), 5.35-5.25 (m, 1H), 4.65-4.45 (m, 1H), 4.32-3.60 (m, 3H), 3.84 (s, 3H), 3.72-3.52 (m, 2H), 3.50-3.30 (m, 3H), 3.10-2.72 (m, 5H), 2.71-3.45 (m, 1H), 2.30-2.05 (m, 3H), 1.90-1.75 (m, 1H), 1.40-1.10 (m, 9H). LCMS: 690.46 [M+H]$^+$.

Example 86

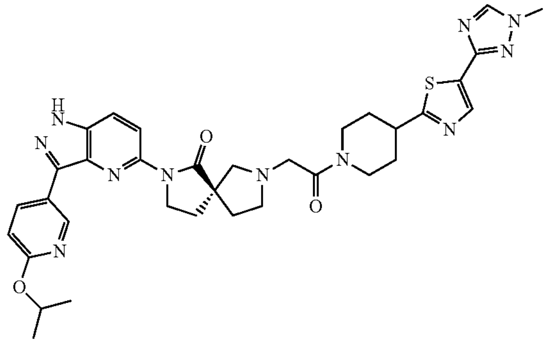

Example 86 was prepared following General Procedures A, B2, and C using Intermediate 4, 2-isopropoxy-5-(4,4,5,5-tetramethyl-1,3,2-dioxaborolan-2-yl)pyridine, and 2-chloro-1-(4-(5-(1-methyl-1H-1,2,4-triazol-3-yl)thiazol-2-yl)piperidin-1-yl)ethanone (prepared via $Pd(OH)_2$-mediated hydrogenation of Intermediate 13 in THF at rt). $^1$H NMR (400 MHz, DMSO-$d_6$) δ 13.40 (s, 1H), 9.25 (s, 1H), 8.58 (dd, 1H), 8.53 (s, 1H), 8.47 (d, 1H), 8.10-8.06 (m, 2H), 6.88 (d, 1H), 5.34-5.31 (m, 1H), 4.40-4.11 (m, 4H), 3.89 (s, 3H), 3.50-3.19 (m, 4H), 2.90-2.56 (m, 5H), 2.43-2.11 (m, 5H), 1.85-1.56 (m, 3H), 1.33 (d, 6H). LCMS: 682.54 [M+H]$^+$.

Example 87

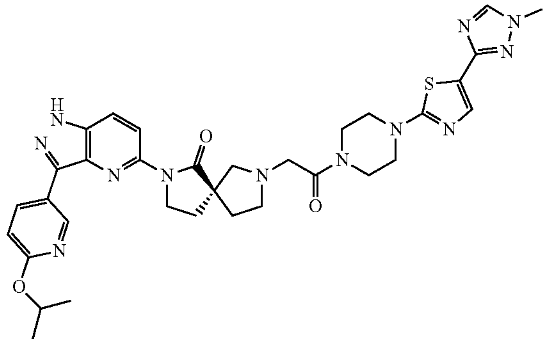

Example 87 was prepared following General Procedures A, B2, and C using Intermediate 4, 2-isopropoxy-5-(4,4,5,5-tetramethyl-1,3,2-dioxaborolan-2-yl)pyridine, and Intermediate 18. $^1$H NMR (400 MHz, DMSO-$d_6$) δ 13.40 (s, 1H), 9.26 (d, 1H), 8.57 (dd, 1H), 8.49-8.42 (m, 2H), 8.10 (d, 1H), 7.63 (s, 1H), 6.88 (d, 1H), 5.37-5.28 (m, 1H), 4.15-4.10 (m, 2H), 3.85 (s, 3H), 3.75-3.36 (m, 10H), 2.97-2.81 (m, 2H), 2.75-2.56 (m, 2H), 2.29-2.12 (m, 3H), 1.91-1.83 (m, 1H), 1.33 (d, 6H). LCMS: 683.42 [M+H]$^+$.

Example 88

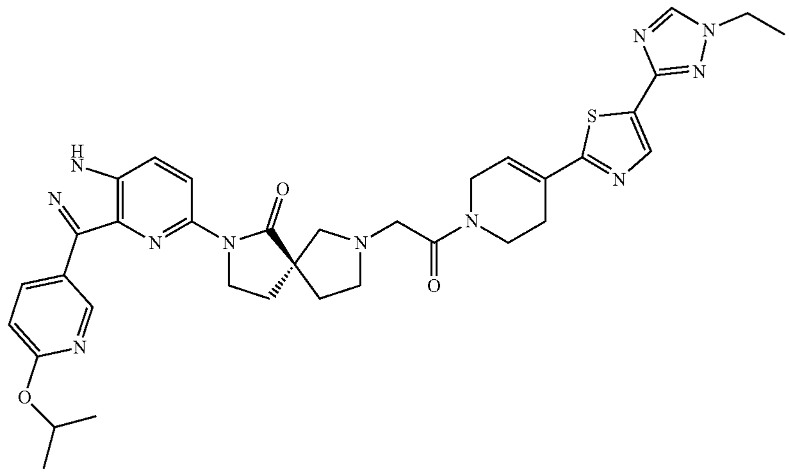

Example 88 was prepared following General Procedures A, B2, and C using Intermediate 4, 2-isopropoxy-5-(4,4,5,5-tetramethyl-1,3,2-dioxaborolan-2-yl)pyridine, and Intermediate 19. $^1$H NMR (DMSO-d$_6$, 400 MHz) δ 13.40 (s, 1H), 9.54 (d, 1H), 8.61 (s, 1H), 8.57 (dd, 1H), 8.47 (d, 1H), 8.19 (s, 1H), 8.08 (d, 1H), 6.87 (d, 1H), 6.73-6.70 (m, 1H), 5.40-5.28 (m, 1H), 4.39-4.36 (m, 1H), 4.29-4.09 (m, 5H), 3.88-3.58 (m, 2H), 3.51-3.38 (m, 2H), 2.93-2.80 (m, 2H), 2.78-2.66 (m, 2H), 2.62-2.51 (m, 2H), 2.27-2.13 (m, 3H), 1.90-1.80 (m, 1H), 1.42 (t, 3H), 1.32 (d, 6H). LCMS 694.32[M+H]$^+$.

Example 89

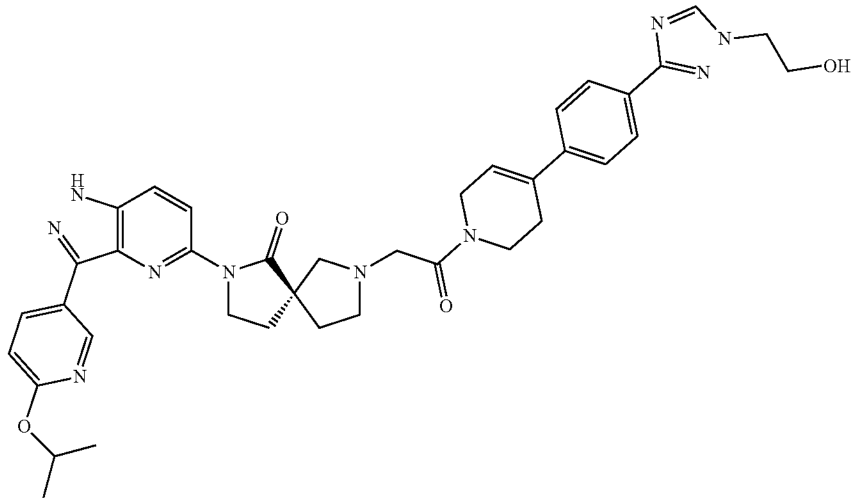

Example 89 was prepared following General Procedures A, B2, and C using Intermediate 4, 2-isopropoxy-5-(4,4,5,5-tetramethyl-1,3,2-dioxaborolan-2-yl)pyridine, and Intermediate 20. $^1$H NMR (400 MHz, DMSO-d$_6$) δ 13.4 (s, 1H), 9.26 (d, 1H), 8.58 (dd, 1H), 8.50-8.47 (m, 2H), 8.10 (d, 1H), 7.98 (d, 2H), 7.56 (d, 2H), 6.88 (d, 1H), 6.29 (s, 1H), 5.34-5.31 (m, 1H), 5.01-4.98 (m, 1H), 4.30-4.10 (m, 6H), 3.80-3.68 (m, 4H), 3.51-3.36 (m, 3H), 3.31-2.82 (m, 2H), 2.76-2.57 (m, 3H), 2.24-2.15 (m, 3H), 1.89-1.84 (m, 1H), 1.33 (d, 6H). LCMS: 703.47 [M+H]$^+$.

Example 90

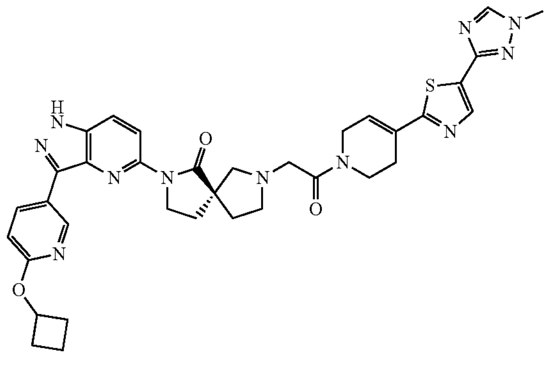

Example 90 was prepared following General Procedures A, B2, and C using Intermediate 4, 2-cyclobutoxy-5-(4,4,5,5-tetramethyl-1,3,2-dioxaborolan-2-yl)pyridine, and Intermediate 13. $^1$H NMR (400 MHz, DMSO-d$_6$) δ 13.41 (s, 1H), 9.23 (d, 1H), 8.61-8.57 (m, 2H), 8.47 (d 1H), 8.20 (s, 1H), 8.09 (d, 1H), 6.92 (d, 1H), 6.71 (s, 1H), 5.21 (qt, 1H), 4.39-4.37 (m, 1H), 4.21-4.05 (m, 3H), 3.91 (s, 3H), 3.83-3.62 (m, 2H), 3.52-3.37 (m, 2H), 2.96-2.81 (m, 2H), 2.74-2.69 (m, 2H), 2.62-2.53 (m, 2H), 2.45-2.37 (m, 2H), 2.29-2.02 (m, 5H), 1.90-1.62 (m, 3H). LCMS: 692.15 [M+H]$^+$.

Example 91

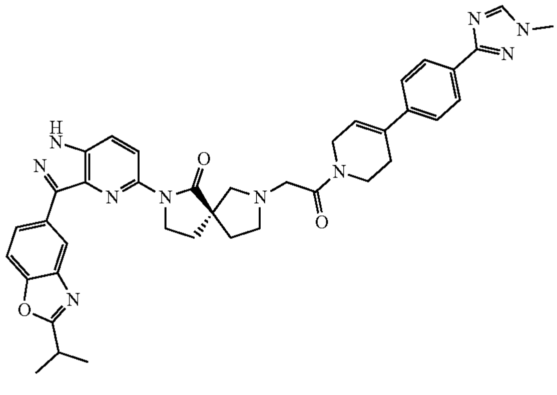

Example 91 was prepared following General Procedures A, B1, C and D using Intermediate 4, 2-isopropyl-5-(4,4,5,5-tetramethyl-1,3,2-dioxaborolan-2-yl)benzo[d]oxazole and Intermediate 9. $^1$H NMR (400 MHz, DMSO-d$_6$) δ 13.4 (s, 1H), 8.80 (s, 1H), 8.52-8.45 (m, 3H), 8.29 (s, 1H), 8.12 (d, 1H), 7.98 (d, 2H), 7.56 (d, 2H), 6.29 (s, 1H), 4.32 (br, 1H), 4.18-4.06 (m, 3H), 3.93 (s, 3H), 3.85-3.82 (m, 1H), 3.71-3.66 (m, 2H), 3.52-3.27 (m, 2H), 2.96-2.85 (m, 2H), 2.77-2.72 (m, 1H), 2.67-2.55 (m, 3H), 2.33-2.19 (m, 3H), 1.90-1.85 (m, 1H), 1.42 (d, 6H). LCMS: 697.20 [M+H]$^+$.

Example 92

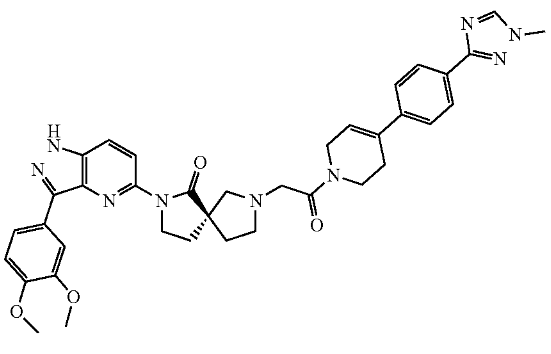

Example 92 was prepared following General Procedures A, B1, C and D using Intermediate 4, 2-(3,4-dimethoxyphenyl)-4,4,5,5-tetramethyl-1,3,2-dioxaborolane and Intermediate 9. $^{1}$H NMR (400 MHz, DMSO-$d_6$) δ 13.27 (s, 1H), 8.51-8.46 (m, 2H), 8.09-8.03 (m, 2H), 7.97 (d, 2H), 7.56 (d, 2H), 7.09 (d, 1H), 6.29 (s, 1H), 4.31 (br, 1H), 4.20-4.11 (m, 3H), 3.92 (s, 3H), 3.88 (s, 3H), 3.81 (s, 3H), 3.74-3.66 (m, 2H), 3.52-3.48 (m, 1H), 3.41-3.31 (m, 2H), 2.93-2.83 (m, 2H), 2.77-2.72 (m, 1H), 2.67-2.56 (m, 3H), 2.23-2.15 (m, 3H), 1.87-1.86 (m, 1H). LCMS: 674.20 $[M+H]^+$.

Example 93

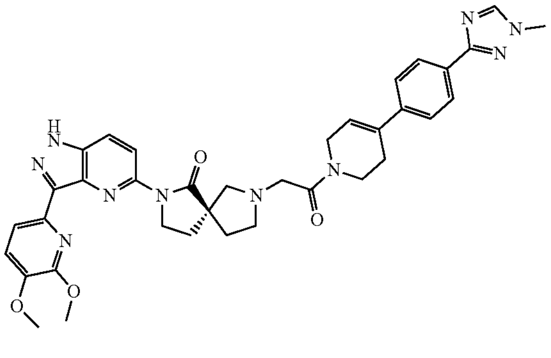

Example 93 was prepared following General Procedures A, B1, C and D using Intermediate 4, 2,3-dimethoxy-6-(4,4,5,5-tetramethyl-1,3,2-dioxaborolan-2-yl)pyridine and Intermediate 9. $^{1}$H NMR (400 MHz, DMSO-$d_6$) δ 13.16 (s, 1H), 8.77 (s, 1H), 8.51 (s, 1H), 8.19 (s, 1H), 7.96 (d, 2H), 7.87 (t, 1H), 7.71 (d, 1H), 7.55 (m, 3H), 7.41 (d, 1H), 6.29 (s, 1H), 4.32 (br, 1H), 4.20-4.10 (m, 4H), 3.92 (s, 3H), 3.84 (m, 6H), 3.50-3.35 (m, 4H), 3.02-2.91 (m, 2H), 2.69-2.62 (m, 2H), 2.23-2.14 (m, 3H), 1.86-1.79 (m, 1H). LCMS: 674.15 $[M+H]^+$.

Example 94

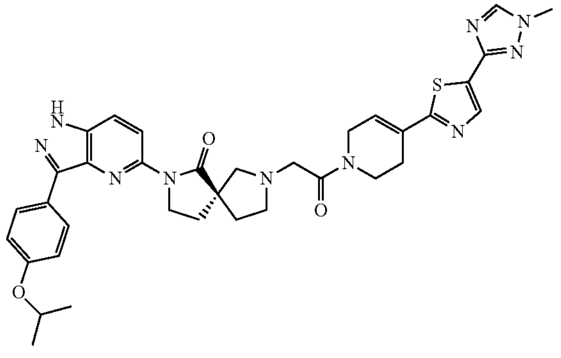

Example 94 was prepared following General Procedures A, B2, and C using Intermediate 4, 2-(4-isopropoxyphenyl)-4,4,5,5-tetramethyl-1,3,2-dioxaborolane and Intermediate 13. $^{1}$H NMR (400 MHz, DMSO-$d_6$) δ 13.20 (s, 1H), 8.56 (s, 1H), 8.44 (d, 1H), 8.37 (d, 2H), 8.19 (s, 1H), 8.05 (d, 1H) 7.03 (d, 2H), 6.71 (s, 1H), 4.72-4.62 (m, 1H), 4.37 (s, 1H), 4.25-4.05 (m, 3H), 3.91 (s, 3H), 3.85-3.65 (m, 3H), 3.51-3.30 (m, 2H), 2.95-2.82 (m, 2H), 2.78-2.65 (m, 2H), 2.61-2.50 (m, 2H), 2.30-2.10 (m, 2H), 1.90-1.80 (m, 1H), 1.30 (d, 6H). LCMS: 679.58 $[M+H]^+$.

Example 95

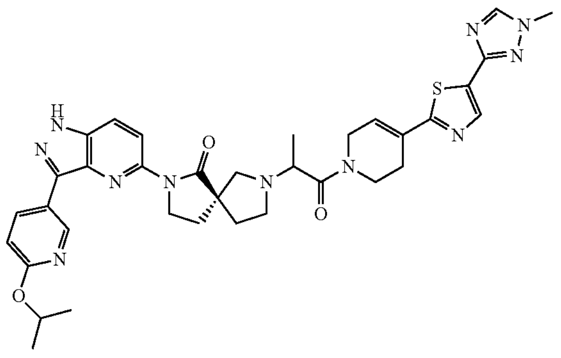

Example 95 was prepared following General Procedures A, B2, and C using Intermediate 4, 2-isopropoxy-5-(4,4,5,5-tetramethyl-1,3,2-dioxaborolan-2-yl)pyridine, and Intermediate 26. $^{1}$H NMR (400 MHz, DMSO-$d_6$) δ 13.4 (s, 1H), 9.28-9.22 (m, 1H), 8.59-8.53 (m, 2H), 8.49-8.43 (m, 2H), 8.20-8.16 (m, 1H), 8.11-8.05 (m, 1H), 6.89-6.86 (m, 1H), 6.73-6.69 (m, 1H), 5.35-5.30 (m, 1H), 4.56-4.52 (m, 1H), 4.31-3.98 (m, 4H), 3.91 (s, 3H), 3.85-3.68 (m, 2H), 2.83-2.53 (m, 6H), 2.30-2.09 (m, 3H), 1.85-1.80 (m, 1H), 1.34-1.31 (m, 6H), 1.24-1.15 (m, 3H). LCMS: 694.4 $[M+H]^+$.

Example 96

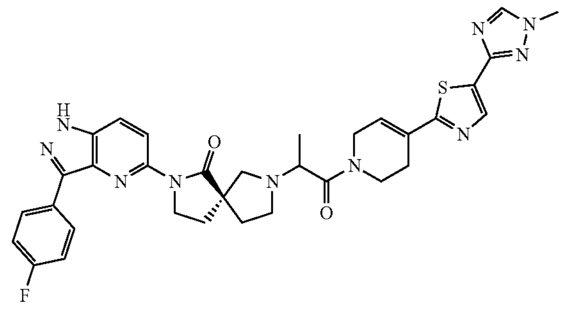

Example 96 was prepared following General Procedures A, B2, and C using Intermediate 4, 2-(4-fluorophenyl)-4,4,5,5-tetramethyl-1,3,2-dioxaborolane, and Intermediate 26. $^1$H NMR (400 MHz, DMSO-$d_6$) δ 13.40 (s, 1H), 8.58-8.44 (m, 4H), 8.20-8.16 (m, 1H), 8.12-8.04 (m, 1H), 7.38-7.26 (m, 2H), 6.76-6.69 (m, 1H), 4.60-4.50 (m, 1H), 4.40-4.00 (m, 4H), 3.91 (s, 3H), 3.80-3.60 (m, 2H), 2.90-2.52 (m, 6H), 2.30-2.05 (m, 3H), 1.88-1.76 (m, 1H), 1.24-1.15 (m, 3H). LCMS: 653.20 [M+H]$^+$.

Example 97

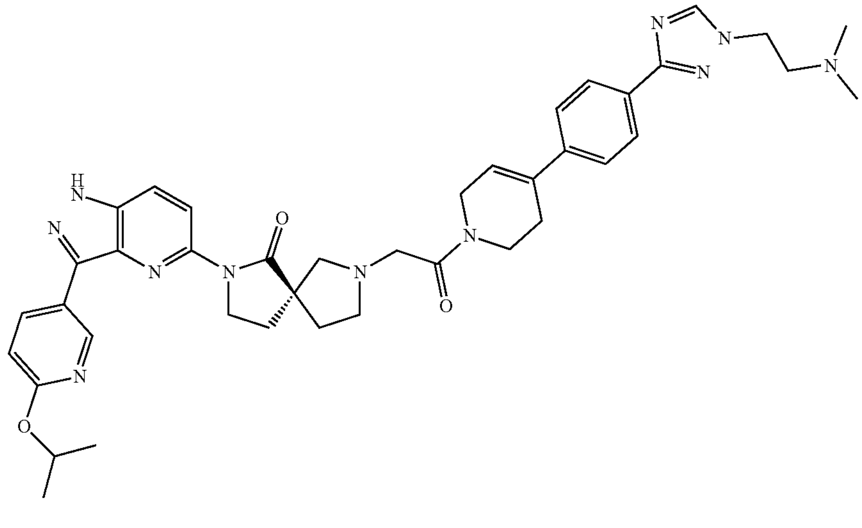

Example 97 was prepared following General Procedures A, B2, and C using Intermediate 4, 2-isopropoxy-5-(4,4,5,5-tetramethyl-1,3,2-dioxaborolan-2-yl)pyridine, and Intermediate 21. $^1$H NMR (400 MHz, DMSO-$d_6$) δ 13.40 (s, 1H), 9.25 (d, 1H), 8.59-8.52 (m, 2H), 8.47 (d, 1H), 8.09 (d, 1H), 7.97 (d, 2H), 7.55 (d, 2H), 6.88 (d, 1H), 6.30-6.26 (m, 1H), 5.35-5.29 (m, 1H), 4.35-4.29 (m, 3H), 4.15-4.10 (m, 3H), 3.83-3.68 (m, 2H), 3.58-3.40 (m, 2H), 3.01-2.80 (m, 4H), 2.73-2.62 (m, 4H), 2.30-2.13 (m, 9H), 1.96-1.73 (m, 1H), 1.33 (d, 6H). LCMS: 728.44 [M+H]$^+$.

Example 98

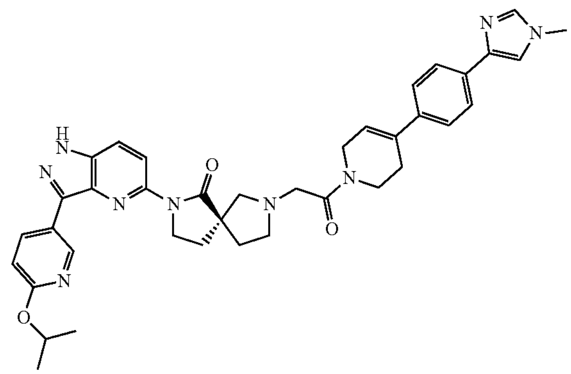

Example 98 was prepared following General Procedures A, B2, and C using Intermediate 4, 2-isopropoxy-5-(4,4,5,5-tetramethyl-1,3,2-dioxaborolan-2-yl)pyridine, and 2-chloro-1-(4-(4-(1-methyl-1H-imidazol-4-yl)phenyl)-5,6-dihydropyridin-1(2H)-yl)ethanone which was prepared as described in patent WO2016161160A1. $^1$H NMR (400 MHz, DMSO-$d_6$) δ 13.38 (s, 1H), 9.26 (d, 1H), 8.58 (dd, 1H), 8.47 (d, 1H), 8.09 (d, 1H), 7.71 (d, 2H), 7.60 (d, 2H), 7.44 (d, 2H), 6.88 (d, 1H), 6.20 (s, 1H), 5.36-5.29 (m, 1H), 4.31-4.26 (m, 1H), 4.18-4.07 (m, 3H), 3.83-3.68 (m, 5H), 3.54-3.41 (m, 2H), 2.95-2.76 (m, 3H), 2.66-2.60 (m, 3H), 2.26-2.16 (m, 3H), 1.91-2.85 (m, 1H), 1.33 (d, 6H). LCMS: 672.47 [M+H]$^+$.

Example 99

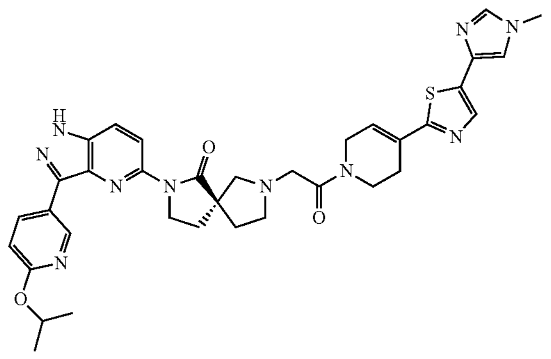

Example 99 was prepared following General Procedures A, B2, and C using Intermediate 4, 2-isopropoxy-5-(4,4,5,5-tetramethyl-1,3,2-dioxaborolan-2-yl)pyridine, and Intermediate 27. $^1$H NMR (400 MHz, DMSO-$d_6$) δ 13.41 (s, 1H), 9.25 (d, 1H), 8.57 (dd, 1H), 8.47 (d, 1H), 8.09 (d, 1H), 7.90 (s, 1H), 7.65 (s, 1H), 7.57 (s, 1H), 6.88 (d, 1H), 6.56 (s, 1H), 5.36-5.30 (m, 1H), 4.34-4.13 (m, 4H), 3.78-3.72 (m, 2H), 3.68 (s, 3H), 3.45-3.39 (m, 2H), 2.93-2.82 (m, 2H), 2.74-2.70 (m, 2H), 2.59-2.56 (m, 2H), 2.23-2.15 (m, 3H), 1.90-1.86 (m, 1H), 1.33 (d, 6H). LCMS: 679.14 $[M+H]^+$.

Example 100

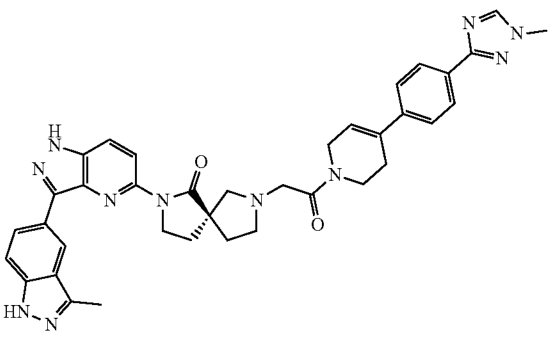

Example 100 was prepared following General Procedures A, B2, and C using Intermediate 4, 3-methyl-1-(tetrahydro-2H-pyran-2-yl)-5-(4,4,5,5-tetramethyl-1,3,2-dioxaborolan-2-yl)-1H-indazole and Intermediate 9. $^1$H NMR (400 MHz, DMSO-$d_6$) δ 13.25 (s, 1H), 12.70 (s, 1H), 8.92 (br s, 1H), 8.48 (d, 2H), 8.41 (d, 1H), 8.08 (d, 1H), 7.97 (d, 2H), 7.60-7.50 (m, 3H), 6.28 (br s, 1H), 4.40-4.30 (m, 1H), 4.25-4.0 (m, 3H), 3.92 (s, 3H), 3.90-3.60 (m, 2H), 3.55-3.20 (m, 2H), 3.00-2.80 (m, 3H), 2.79-2.70 (m, 1H), 2.65-2.50 (m, 5H), 2.40-2.15 (m, 3H), 2.00-1.80 (m, 1H). LCMS: 668.47 $[M+H]^+$.

Example 101

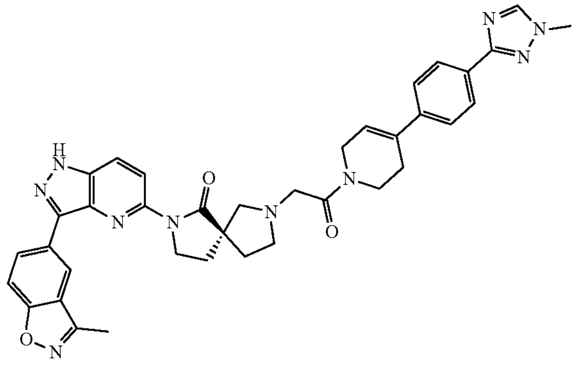 [SMILES: Cc1noc2ccc(-c3n[nH]c4ccc(N5CC[C@]6(CCN(CC(=O)N7CC=C(c8ccc(-c9ncn(C)n9)cc8)CC7)C6)C5=O)nc34)cc12]

Example 101 was prepared following General Procedures A, B2, and C using Intermediate 4, 3-methyl-5-(4,4,5,5-tetramethyl-1,3,2-dioxaborolan-2-yl)benzo[d]isoxazole and Intermediate 9. $^1$H NMR (300 MHz, DMSO-$d_6$) δ 13.05 (s, 1H), 8.93 (s, 1H), 8.75 (d, 1H), 8.51 (s, 2H), 8.13 (d, 1H), 7.97 (d, 2H), 7.83 (d, 1H), 7.55 (d, 2H), 6.28 (s, 1H), 4.40-4.10 (m, 4H), 3.92 (m, 3H), 3.85-3.60 (m, 3H), 3.10-2.80 (m, 3H), 2.72-2.55 (m, 7H), 2.30-2.10 (m, 3H), 2.0-1.80 (m, 1H). LCMS: 669.07 $[M+H]^+$.

Example 102

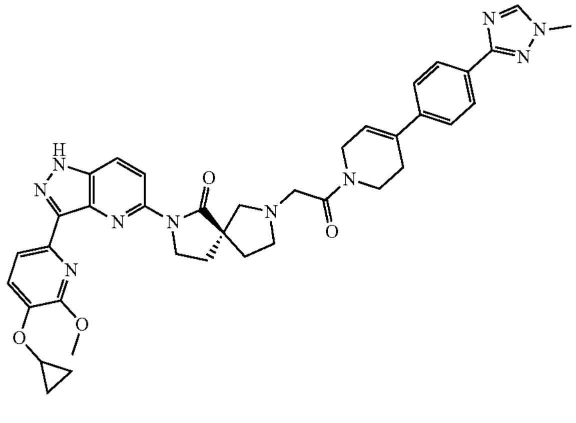 [SMILES: COc1nc(-c2n[nH]c3ccc(N4CC[C@]5(CCN(CC(=O)N6CC=C(c7ccc(-c8ncn(C)n8)cc7)CC6)C5)C4=O)nc23)ccc1OC1CC1]

Example 102 was prepared following General Procedures A, B2, and C using benzyl Intermediate 3, 3-cyclopropoxy-2-methoxy-6-(4,4,5,5-tetramethyl-1,3,2-dioxaborolan-2-yl) pyridine and Intermediate 9. $^1$H NMR (400 MHz, DMSO-$d_6$) δ 13.18 (s, 1H), 8.76 (s, 1H), 8.49 (s, 1H), 7.95 (d, 2H), 7.86 (t, 1H), 7.73 (d, 1H), 7.65 (d, 1H), 7.60-7.50 (m, 3H), 6.27 (s, 1H), 4.30-4.12 (m, 2H), 4.08 (s, 3H), 4.0-3.88 (m, 4H), 3.85-3.65 (m, 4H), 3.50-3.40 (m, 2H), 2.90-2.75 (m, 3H), 2.75-2.52 (m, 3H), 2.32-2.05 (m, 3H), 1.85-1.75 (m, 1H), 0.80-0.40 (m, 4H). LCMS: 700.46 $[M+H]^+$.

Example 103

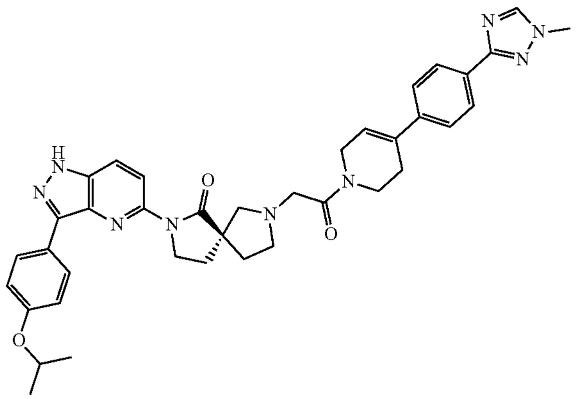 [SMILES: CC(C)Oc1ccc(-c2n[nH]c3ccc(N4CC[C@]5(CCN(CC(=O)N6CC=C(c7ccc(-c8ncn(C)n8)cc7)CC6)C5)C4=O)nc23)cc1]

Example 103 was prepared following General Procedures A, B2, and C using Intermediate 4, 2-(4-isopropoxyphenyl)-4,4,5,5-tetramethyl-1,3,2-dioxaborolane and Intermediate 9. $^1$H NMR (DMSO-$d_6$, 400 MHz) δ 13.33 (s, 1H), 8.50 (s, 1H), 8.44 (d, 1H), 8.37 (d, 2H), 8.05 (d, 1H), 7.97 (d, 2H), 7.55 (d, 2H), 7.03 (d, 2H), 6.32-6.25 (m, 1H), 4.80-4.60 (m, 1H), 4.40-4.00 (m, 4H), 3.92 (s, 3H), 3.90-3.60 (m, 2H), 3.60-3.20 (m, 2H), 3.0-2.68 (m, 4H), 2.67-2.40 (m, 2H), 2.40-2.10 (m, 3H), 1.90-1.80 (m, 1H), 1.30 (d, 6H). LCMS: 672.47 $[M+H]^+$.

Example 104

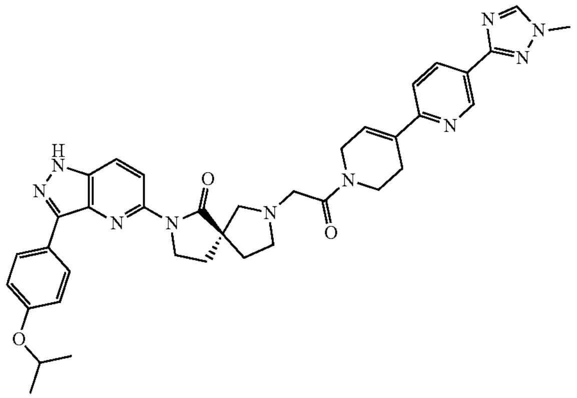 [SMILES: CC(C)Oc1ccc(-c2n[nH]c3ccc(N4CC[C@]5(CCN(CC(=O)N6CC=C(c7ccc(-c8ncn(C)n8)cn7)CC6)C5)C4=O)nc23)cc1]

Example 104 was prepared following General Procedures A, B2, and C using Intermediate 4, 2-(4-isopropoxyphenyl)-4,4,5,5-tetramethyl-1,3,2-dioxaborolane and Intermediate 22. $^1$H NMR (400 MHz, DMSO-$d_6$) δ 13.25 (s, 1H), 9.12 (d, 1H), 8.58 (s, 1H), 8.44 (d, 1H), 8.37 (d, 2H), 8.35-8.20 (m, 1H), 8.06 (d, 1H), 7.68 (d, 1H), 7.03 (d, 2H), 6.90-6.80 (m, 1H), 4.75-4.60 (m, 1H), 4.40-4.30 (m, 1H), 4.25-4.10 (m, 3H), 3.94 (s, 3H), 3.80-3.60 (m, 4H), 3.40-2.70 (m, 3H), 2.75-2.72 (m, 2H), 2.68-2.50 (m, 1H), 2.40-2.15 (m, 3H), 2.00-1.80 (m, 1H), 1.30 (d, 6H). LCMS: 673.4 $[M+H]^+$.

Example 105

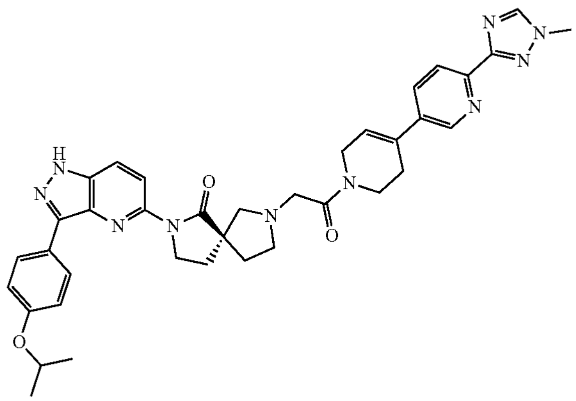 [SMILES: CC(C)Oc1ccc(-c2n[nH]c3ccc(N4CC[C@]5(CCN(CC(=O)N6CC=C(c7ccc(-c8ncn(C)n8)nc7)CC6)C5)C4=O)nc23)cc1]

Example 105 was prepared following General Procedures A, B2, and C using Intermediate 4, 2-(4-isopropoxyphenyl)-4,4,5,5-tetramethyl-1,3,2-dioxaborolane and Intermediate 23. $^1$H NMR (400 MHz, DMSO-$d_6$) δ 13.20 (s, 1H), 8.76 (s, 1H), 8.55 (s, 1H), 8.44 (d, 1H), 8.37 (d, 2H), 8.08-7.92 (m, 3H), 7.03 (d, 2H), 6.42-6.37 (m, 1H), 4.71-4.64 (m, 1H), 4.35-4.31 (m, 1H), 4.21-4.09 (m, 3H), 3.95 (s, 3H), 3.91-3.64 (m, 2H), 3.53-3.47 (m, 1H), 3.43-3.38 (m, 1H), 2.97-2.70 (m, 4H), 2.62-2.53 (m, 2H), 2.29-2.10 (m, 3H), 1.91-1.82 (m, 1H), 1.30 (d, 6H). LCMS: 673.11 $[M+H]^+$.

Example 106

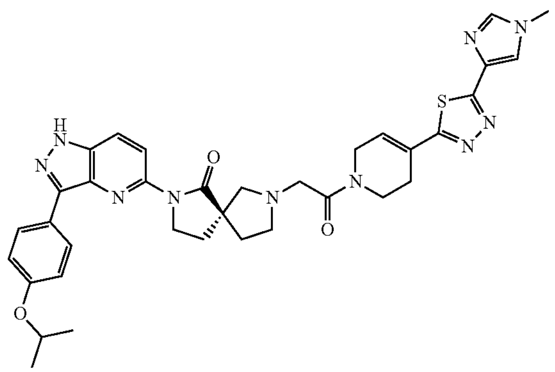 [SMILES: CC(C)Oc1ccc(-c2n[nH]c3ccc(N4CC[C@]5(CCN(CC(=O)N6CC=C(c7nnc(-c8cn(C)cn8)s7)CC6)C5)C4=O)nc23)cc1]

Example 106 was prepared following General Procedures A, B2, and C using Intermediate 4, 2-(4-isopropoxyphenyl)-4,4,5,5-tetramethyl-1,3,2-dioxaborolane and Intermediate 24. $^1$H NMR (400 MHz, DMSO-$d_6$) δ 13.25 (s, 1H), 8.72 (s, 1H), 8.45-8.37 (m, 3H), 8.07 (d, 1H), 7.04 (d, 2H), 6.81 (s, 1H), 4.69-4.66 (m, 1H), 4.35-4.15 (m, 4H), 3.99 (s, 3H), 3.81-3.72 (m, 3H), 3.39-3.34 (m, 1H), 3.10-2.82 (m, 5H), 2.75-2.67 (m, 1H), 2.34-1.95 (m, 4H), 1.31 (d, 6H). LCMS: 680.66 $[M+H]^+$.

Example 107

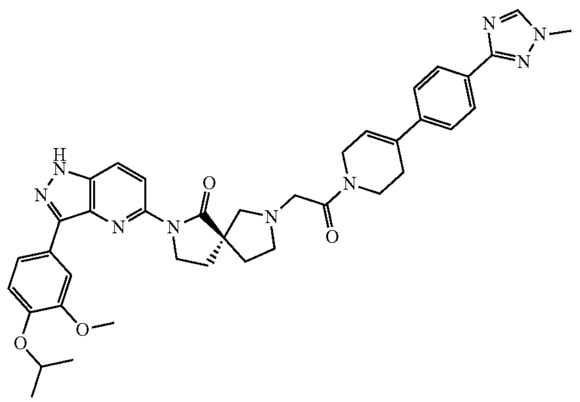 [SMILES: COc1cc(-c2n[nH]c3ccc(N4CC[C@]5(CCN(CC(=O)N6CC=C(c7ccc(-c8ncn(C)n8)cc7)CC6)C5)C4=O)nc23)ccc1OC(C)C]

Example 107 was prepared following General Procedures A, B2, and C using Intermediate 4, 2-(4-isopropoxy-3-methoxyphenyl)-4,4,5,5-tetramethyl-1,3,2-dioxaborolane and Intermediate 9. $^1$H NMR (400 MHz, DMSO-$d_6$) δ 13.23 (s, 1H), 8.53-8.43 (m, 2H), 8.17 (d, 1H), 8.10-7.93 (m, 4H), 7.55 (d, 2H), 7.07 (d, 1H), 6.30-6.26 (m, 1H), 4.66-4.54 (m, 1H), 4.32-4.28 (m, 1H), 4.18-4.06 (m, 3H), 3.92 (s, 3H), 3.87 (s, 3H), 3.82-3.65 (m, 2H), 3.54-3.37 (m, 2H), 2.95-2.70 (m, 3H), 2.69-2.55 (m, 3H), 2.28-2.15 (m, 3H), 1.91-1.82 (m, 1H), 1.28 (d, 6H). LCMS: 702.4 [M+H]$^+$.

Example 108

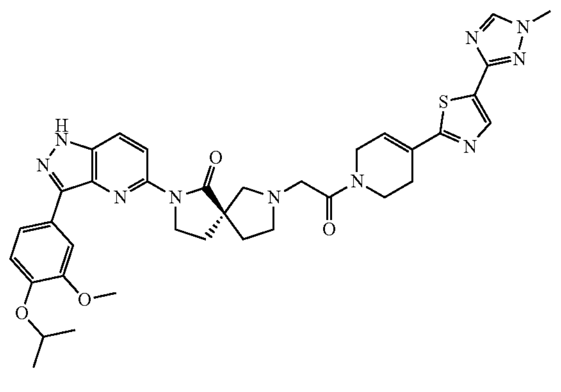 [SMILES: COc1cc(-c2n[nH]c3ccc(N4CC[C@]5(CCN(CC(=O)N6CC=C(c7ncc(-c8ncn(C)n8)s7)CC6)C5)C4=O)nc23)ccc1OC(C)C]

Example 108 was prepared following General Procedures A, B2, and C using Intermediate 4, 2-(4-isopropoxy-3-methoxyphenyl)-4,4,5,5-tetramethyl-1,3,2-dioxaborolane and Intermediate 13. $^1$H NMR (400 MHz, DMSO-$d_6$) δ 13.23 (s, 1H), 8.56 (s, 1H), 8.46 (d, 1H), 8.18 (dd, 2H), 8.06 (d, 1H), 7.99 (d, 1H), 7.07 (d, 1H), 6.75-6.69 (m, 1H), 4.65-4.55 (m, 1H), 4.39-4.35 (m, 1H), 4.23-4.03 (m, 3H), 3.91 (s, 3H), 3.87 (s, 3H), 3.84-3.62 (m, 2H), 3.52-3.36 (m, 2H), 2.95-2.81 (m, 2H), 2.75-2.72 (m, 2H), 2.62-2.57 (m, 2H), 2.29-2.12 (m, 3H), 1.91-1.82 (m, 1H), 1.28 (d, 6H). LCMS: 709.4 [M+H]$^+$.

Example 109

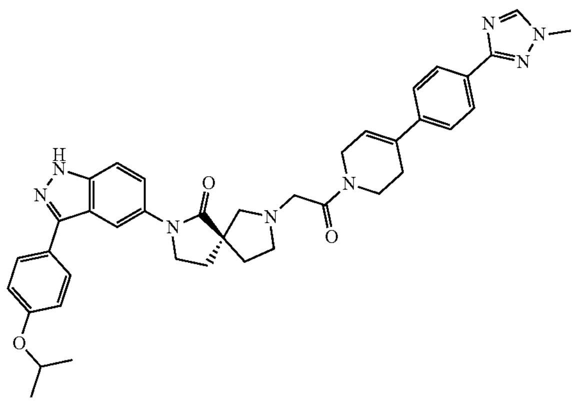 [SMILES: CC(C)Oc1ccc(-c2n[nH]c3ccc(N4CC[C@]5(CCN(CC(=O)N6CC=C(c7ccc(-c8ncn(C)n8)cc7)CC6)C5)C4=O)cc23)cc1]

Example 109 was prepared following General Procedures A, B2, and C using Intermediate 3, 4-isopropoxyphenylboronic acid and Intermediate 9. $^1$H NMR (400 MHz, DMSO-$d_6$) δ 13.01 (s, 1H), 8.49 (s, 1H), 8.15 (s, 1H), 7.96 (d, 2H), 7.85 (d, 2H), 7.70 (t, 1H), 7.60-7.50 (m, 3H), 7.05 (d, 2H), 6.28 (s, 1H), 4.75-4.65 (m, 1H), 4.40-4.22 (m, 1H), 4.20-4.05 (m, 1H), 3.91 (s, 3H), 3.90-3.80 (m, 2H), 3.80-3.60 (m, 2H), 3.48-3.38 (m, 2H), 2.98-2.80 (m, 2H), 2.75-2.50 (m, 4H), 2.30-2.05 (m, 3H), 1.90-1.70 (m, 1H), 1.38-1.25 (m, 6H). LCMS: 671.49 [M+H]$^+$.

Example 110

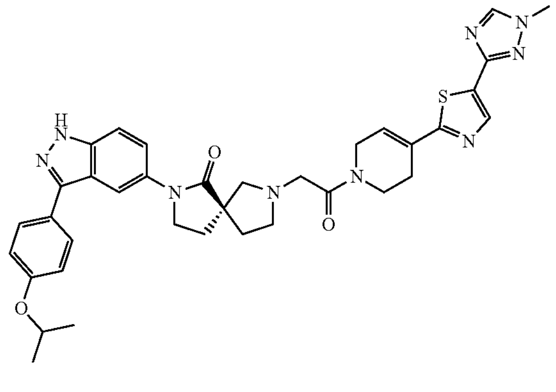 [SMILES: CC(C)Oc1ccc(-c2n[nH]c3ccc(N4CC[C@]5(CCN(CC(=O)N6CC=C(c7ncc(-c8ncn(C)n8)s7)CC6)C5)C4=O)cc23)cc1]

Example 110 was prepared following General Procedures A, B2, and C using Intermediate 3, 4-isopropoxyphenylboronic acid and Intermediate 13. H NMR (400 MHz, DMSO-$d_6$) δ 13.10 (s, 1H), 8.55 (s, 1H), 8.18 (s, 1H), 8.15 (s, 1H), 7.85 (d, 2H), 7.76-7.66 (m, 1H), 7.55 (d, 1H), 7.05 (d, 2H), 6.71 (s, 1H), 4.75-4.65 (m, 1H), 4.45-4.30 (m, 1H), 4.22-4.15 (m, 1H), 3.90 (s, 3H), 3.90-3.82 (m, 2H), 3.81-3.65 (m, 2H), 3.48-3.35 (m, 2H), 2.98-2.88 (m, 1H), 2.87-2.80 (m, 1H), 2.75-2.55 (m, 4H), 2.30-2.05 (m, 3H), 2.85-2.75 (m, 1H), 1.33 (d, 6H). LCMS: 678.45 [M+H]$^+$.

Example 111

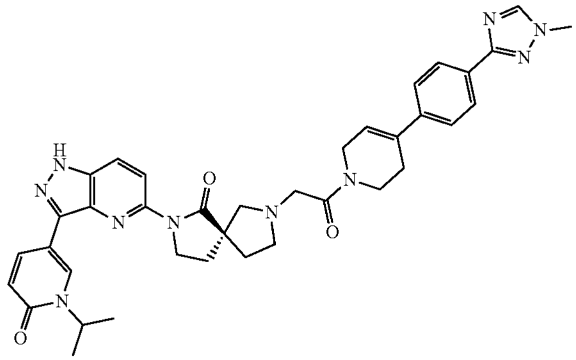 [SMILES: CC(C)n1cc(-c2n[nH]c3ccc(N4CC[C@]5(CCN(CC(=O)N6CC=C(c7ccc(-c8ncn(C)n8)cc7)CC6)C5)C4=O)nc23)ccc1=O]

Example 111 was prepared following General Procedures A, B2, and C using Intermediate 4, 1-isopropyl-5-(4,4,5,5-tetramethyl-1,3,2-dioxaborolan-2-yl)pyridin-2(1H)-one Intermediate 9. $^1$H NMR (400 MHz, DMSO-$d_6$) δ 13.25 (s, 1H), 8.89 (d, 1H), 8.48-8.46 (m, 2H), 8.15 (dd, 1H), 8.05 (d, 1H), 7.94 (d, 2H), 7.51 (d, 2H), 6.52 (d, 1H), 6.25 (s, 1H), 5.12-5.09 (m, 1H), 4.30-4.25 (m, 1H), 4.10-4.08 (m, 3H), 3.88 (s, 3H), 3.79-3.58 (m, 2H), 3.47-3.33 (m, 2H), 2.90-2.71 (m, 3H), 2.63-257 (m, 3H)),2.22-2.13 (m, 3H), 2.86-2.83 (m, 1H), 1.36 (d, 6H). LCMS: 673.44 [M+H]$^+$.

Example 112

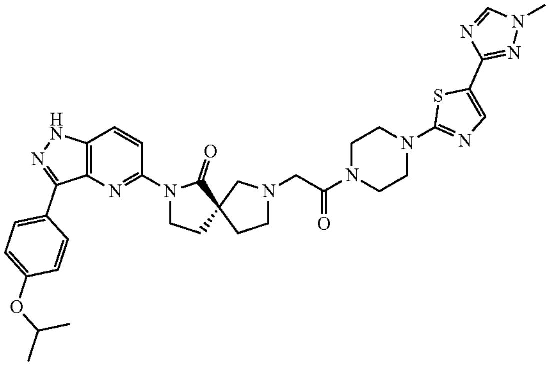 [SMILES: CC(C)Oc1ccc(-c2n[nH]c3ccc(N4CC[C@]5(CCN(CC(=O)N6CCN(c7ncc(-c8ncn(C)n8)s7)CC6)C5)C4=O)nc23)cc1]

Example 112 was prepared following General Procedures A, B2, and C using Intermediate 4, 4-isopropoxyphenylboronic acid and Intermediate 18. $^1$H NMR (DMSO-$d_6$, 400 MHz) δ 13.22 (s, 1H), 8.44 (d, 2H), 8.38 (d, 2H), 8.05 (d, 1H), 7.62 (s, 1H), 7.03 (d, 2H), 4.75-4.60 (m, 1H), 4.20-4.09 (m, 2H), 3.85 (s, 3H), 3.80-3.42 (m, 8H), 3.40-3.20 (m, 2H), 3.00-2.87 (m, 1H), 2.86-2.80 (m, 1H), 2.75-2.65 (m, 1H), 2.60-2.40 (m, 1H), 2.30-2.10 (m, 3H), 1.90-1.80 (m, 1H), 1.30 (d, 6H). LCMS: 682.41 [M+H]$^+$.

Example 113

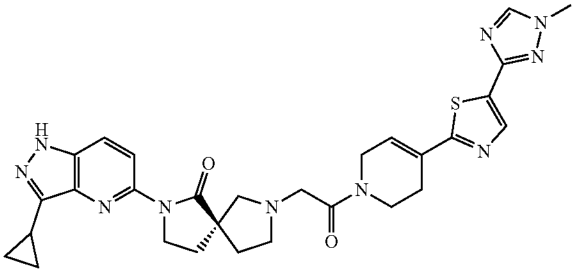 [SMILES: Cn1cnc(-c2cnc(C3=CCN(C(=O)CN4CC[C@]5(CCN(c6ccc7[nH]nc(C8CC8)c7n6)C5=O)C4)CC3)s2)n1]

Example 113 was prepared following General Procedures A, B2, and C using Intermediate 4, potassium cyclopropyltrifluoroborate and Intermediate 13. $^1$H NMR (400 MHz, DMSO-$d_6$) δ 12.79 (s, 1H), 8.56 (s, 1H), 8.33 (d, 1H), 8.19 (s, 1H), 7.92 (d, 1H), 6.74-6.68 (m, 1H), 4.39-4.35 (m, 1H), 4.20-4.10 (m, 1H), 4.05-3.95 (m, 2H), 3.91 (s, 3H), 3.80-3.60 (m, 2H), 3.52-3.35 (m, 2H), 2.95-2.82 (m, 2H), 2.79-2.70 (m, 2H), 2.62-2.57 (m, 2H), 2.29-2.10 (m, 4H), 1.90-1.80 (m, 1H), 1.29-1.16 (m, 2H), 1.00-0.94 (m, 2H). LCMS: 585.20 [M+H]$^+$.

Example 114

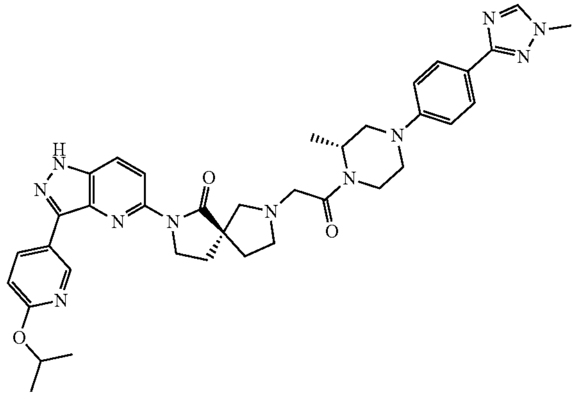 [SMILES: CC(C)Oc1ccc(-c2n[nH]c3ccc(N4CC[C@]5(CCN(CC(=O)N6CCN(c7ccc(-c8ncn(C)n8)cc7)C[C@H]6C)C5)C4=O)nc23)cn1]

Example 114 was prepared by chiral SFC separation of Example 85 using a chiral column (Chiralpak-IE (250x30) mm, 5u) eluted with 0.2% TFA in n-Hexane:Ethanol:Methanol (20:40:40) to afford Example 114 as the first eluted isomer. Stereochemisty is arbitrarily assigned. $^1$H NMR (DMSO-$d_6$, 400 MHz) δ 13.50 (s, 1H), 10.60-10.20 (m, 1H), 9.27 (d, 1H), 8.57 (d, 1H), 8.50-8.40 (m, 2H), 8.15 (d, 1H), 7.85 (d, 2H), 7.10-6.95 (m, 2H), 6.89 (d, 1H), 5.4-5.25 (m, 1H), 4.80-4.45 (m, 3H), 4.40-4.05 (m, 4H), 3.88 (s, 3H), 3.85-3.70 (m, 4H), 3.45-3.25 (m, 2H), 3.15-2.82 (m, 3H), 2.48-2.32 (m, 3H), 2.28-2.10 (m, 1H), 1.45-1.20 (m, 9H). LCMS: 688.46 [M−H]$^-$.

Example 115

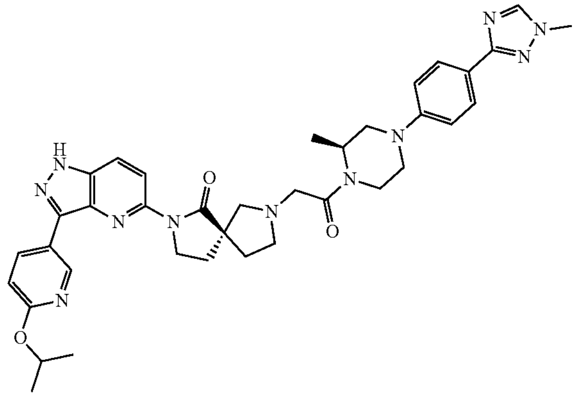 [SMILES: CC(C)Oc1ccc(-c2n[nH]c3ccc(N4CC[C@]5(CCN(CC(=O)N6CCN(c7ccc(-c8ncn(C)n8)cc7)C[C@@H]6C)C5)C4=O)nc23)cn1]

Example 115 was prepared by chiral SFC separation of Example 85 using a chiral column (Chiralpak-IE (250×30) mm, 5u) eluted with 0.2% TFA in n-Hexane:Ethanol:Methanol (20:40:40) to afford Example 115 as the second eluted isomer. Stereochemistry is arbitrarily assigned. 1H NMR (DMSO-$d_6$, 400 MHz) δ 13.50 (s, 1H), 10.60-10.20 (m, 1H), 9.27 (d, 1H), 8.57 (d, 1H), 8.50-8.40 (m, 2H), 8.15 (d, 1H), 7.85 (d, 2H), 7.10-6.95 (m, 2H), 6.89 (d, 1H), 5.40-5.25 (m, 1H), 4.80-4.40 (m, 3H), 4.40-4.0 (m, 4H), 3.88 (s, 3H), 3.85-3.70 (m, 4H), 3.45-3.25 (m, 2H), 3.25-2.95 (m, 3H), 2.48-2.32 (m, 3H), 2.28-2.10 (m, 1H), 1.45-1.20 (m, 9H). LCMS: 690.51 $[M+H]^+$.

Example 116

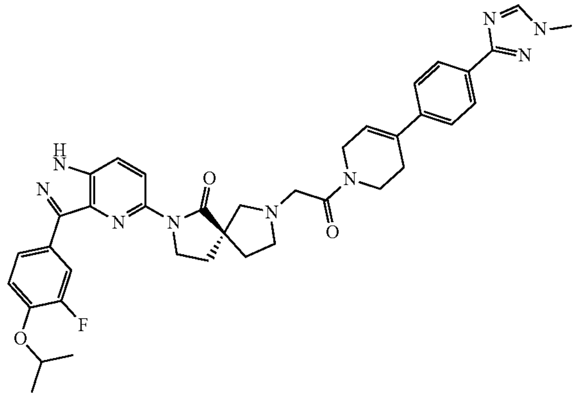

Example 116 was prepared following General Procedures A, B1, C, D and E using Intermediate 4, (3-fluoro-4-isopropoxyphenyl)boronic acid and Intermediate 9. Data for 1.0-HCl salt: 1H NMR (DMSO-$d_6$, 400 MHz) δ 13.60 (s, 1H), 10.50 (d, 1H), 8.56 (br, 1H), 8.48-8.44 (m, 1H), 8.26-8.23 (m, 2H), 8.17-8.14 (m, 1H), 8.00 (d, 2H), 6.31 (s, 1H), 4.74-4.70 (m, 1H), 4.66-4.64 (m, 1H), 4.41 (br, 7H), 4.21 (br, 1H), 4.16-4.11 (m, 3H), 3.93 (s, 3H), 3.88-3.77 (m, 2H), 3.63-3.59 (m, 1H), 3.39-3.34 (m, 1H), 2.51-2.49 (br, 1H), 2.38-2.33 (m, 2H), 2.24-2.19 (m, 1H), 1.34 (d, 6H). LCMS: 690.30 $[M+H]^+$.

Example 117

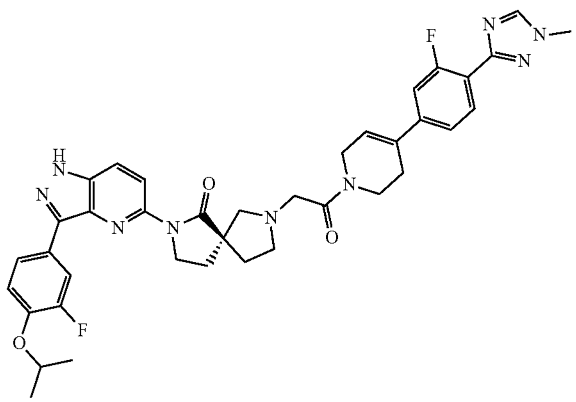

Example 117 was prepared following General Procedures A, B1, C, D and E using Intermediate 4, (3-fluoro-4-isopropoxyphenyl)boronic acid and Intermediate 25. Data for 1.0-HCl salt: 1H NMR (DMSO-$d_6$, 400 MHz) δ 13.49 (br, 1H), 10.40 (d, 1H), 8.58 (s, 1H), 8.48-8.44 (m, 1H), 8.28-8.23 (m, 2H), 8.17-8.14 (m, 1H), 7.99 (t, 1H), 7.48-7.41 (m, 2H), 7.35-7.30 (m, 1H), 6.43 (s, 1H), 4.74-4.68 (m, 1H), 4.61-4.55 (m, 2H), 4.29-4.10 (m, 5H), 3.94 (s, 3H), 3.83-3.78 (m, 3H), 3.51 (m, 2H), 2.68-2.66 (m, 2H), 2.40-2.33 (m, 3H), 1.34 (d, 6H). LCMS: 708.30 $[M+H]^+$.

Example 118

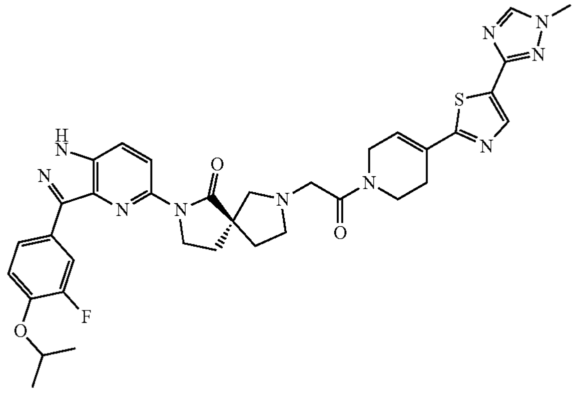

Example 118 was prepared following General Procedures A, B2, and C using Intermediate 4, (3-fluoro-4-isopropoxyphenyl)boronic acid and Intermediate 13. $^1H$ NMR (400 MHz, DMSO-$d_6$) δ 13.21 (s, 1H), 8.57 (s, 1H), 8.47 (d, 1H), 8.26-8.19 (m, 3H), 8.09 (d, 1H), 7.31 (t, 1H), 6.71 (s, 1H), 4.73-4.69 (m, 1H), 4.38-4.36 (m, 1H), 4.20-4.12 (m, 3H), 3.91 (s, 3H), 3.81-3.69 (m, 2H), 3.52-3.45 (m, 2H), 2.95-2.87 (m, 2H), 2.75-2.67 (m, 2H), 2.63-2.58 (m, 2H), 2.32-2.18 (m, 3H), 1.92-2.88 (m, 1H), 1.33 (d, 6H). LCMS: 697.43 $[M+H]^+$.

Example 119

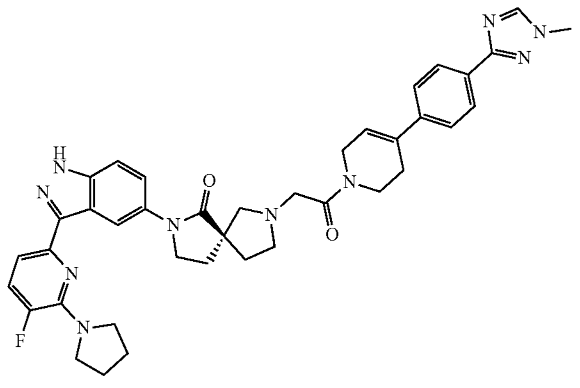

Example 119 was prepared following General Procedures A, B1, C and D using Intermediate 3, 3-fluoro-2-(pyrrolidin-1-yl)-6-(4,4,5,5-tetramethyl-1,3,2-dioxaborolan-2-yl)pyridine and Intermediate 9. $^1$H NMR (DMSO-$d_6$, 400 MHz) δ 13.27 (br, 1H), 10.35 (d, 1H), 8.77-8.76 (m, 1H), 8.53 (s, 1H), 8.00-797 (m, 2H), 7.87-7.85 (m, 1H), 7.61-7.54 (m, 3H), 7.51-7.45 (m, 1H), 7.39-7.36 (m, 1H), 6.32 (br, 1H), 4.64-4.58 (m, 2H), 4.22 (br, 1H), 4.13-4.08 (m, 2H), 3.93 (s, 3H), 3.82-3.74 (br, 3H), 3.61-3.60 (m, 2H), 3.46-3.35 (m, 3H), 2.68-2.67 (m, 1H), 2.56-2.53 (m, 2H), 2.39-2.29 (m, 4H), 2.22-2.17 (m, 1H), 1.99-1.97 (m, 4H). LCMS: 701.30 $[M+H]^+$.

Example 120

Compounds of Formula (I)

For some compounds, the foregoing syntheses are exemplary and can be used as a starting point to prepare additional compounds of Formula (I). Examples of additional compounds of Formula (I) are described below. These compounds can be prepared in various ways, including by those synthetic schemes shown and described herein. Those skilled in the art will be able to recognize modifications of the disclosed syntheses and to devise routes based on the disclosures herein; all such modifications and alternate routes are within the scope of the claims.

(S)-7-(2-(4-(5-(1-(2-hydroxyethyl)-1H-1,2,4-triazol-3-yl)thiazol-2-yl)-3,6-dihydropyridin-1(2H)-yl)-2-oxoethyl)-2-(3-(6-isopropoxypyridin-3-yl)-1H-pyrazolo[4,3-b]pyridin-5-yl)-2,7-diazaspiro[4.4]nonan-1-one, or a pharmaceutically acceptable salt thereof.

(S)-7-(2-(4-(5-(1-methyl-1H-1,2,4-triazol-3-yl)thiazol-2-yl)-3,6-dihydropyridin-1(2H)-yl)-2-oxoethyl)-2-(3-(2-methylbenzo[d]oxazol-5-yl)-1H-pyrazolo[4,3-b]pyridin-5-yl)-2,7-diazaspiro[4.4]nonan-1-one, or a pharmaceutically acceptable salt thereof.

(S)-2-(3-(6-isopropoxypyridin-3-yl)-1H-pyrazolo[4,3-b]pyridin-5-yl)-7-(2-(4-(5-(1-methyl-1H-1,2,4-triazol-3-yl)thiazol-2-yl)-3,6-dihydropyridin-1 (2H)-yl)-2-oxoethyl-1,1-d2)-2,7-diazaspiro[4.4]nonan-1-one, or a pharmaceutically acceptable salt thereof.

(S)-7-(2-(4-(5-(1-methyl-1H-1,2,4-triazol-3-yl)thiazol-2-yl)-3,6-dihydropyridin-1(2H)-yl)-2-oxoethyl)-2-(3-(2-methylpyridin-4-yl)-1H-pyrazolo[4,3-b]pyridin-5-yl)-2,7-diazaspiro[4.4]nonan-1-one, pharmaceutically acceptable salt thereof.

Example 121

Compounds of Formula (II)

For some compounds, the foregoing syntheses are exemplary and can be used as a starting point to prepare additional compounds of Formula (II). Examples of additional compounds of Formula (II) are described below. These compounds can be prepared in various ways, including by those synthetic schemes shown and described herein. Those skilled in the art will be able to recognize modifications of the disclosed syntheses and to devise routes based on the disclosures herein; all such modifications and alternate routes are within the scope of the claims.

(S)-2-(3-(5-fluoropyridin-2-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl-1,1-d2)-2,7-diazaspiro[4.4]nonan-1-one, or a pharmaceutically acceptable salt thereof.

(S)-7-(2-(4-(4-(1-Methyl-1H-1,2,4-triazol-3-yl)phenyl)-3,6-dihydropyridin-1(2H)-yl)-2-oxoethyl)-2-(3-(2-methyloxazolo[4,5-b]pyridin-5-yl)-1H-indazol-5-yl)-2,7-diazaspiro[4.4]nonan-1-one, or a pharmaceutically acceptable salt thereof.

Example 122

Compounds of Formula (III)

For some compounds, the foregoing syntheses are exemplary and can be used as a starting point to prepare additional compounds of Formula (III), such as (S)-7-(2-(4-(4-(1-methyl-1H-1,2,4-triazol-3-yl)phenyl)-3,6-dihydropyridin-1 (2H)-yl)-2-oxoethyl-1,1-d2)-2-(3-(tetrahydro-2H-pyran-4-yl)-1H-indazol-5-yl)-2,7-diazaspiro[4.4]nonan-1-one, or a pharmaceutically acceptable salt thereof. These compounds can be prepared in various ways, including by those synthetic schemes shown and described herein. Those skilled in the art will be able to recognize modifications of the disclosed syntheses and to devise routes based on the disclosures herein; all such modifications and alternate routes are within the scope of the claims.

Example 123

Active ERK1 and ERK2 Kinase Assay

Activated ERK1 and ERK2 activity was determined in a Mobility Shift Assay (MSA) format as follows: Compound and kinase solution were prepared with assay buffer (20 mM HEPES, 0.01% Triton X-100, 2 mM DTT, pH7.5) and mixed and incubated in for 30 mins at rt. ERK1 & ERK2 were then activated by the addition of F1-Substrate, ATP and metal solution and incubated for 1 h at rt. After 1 h, the reaction was terminated by the addition of 70 mL of Termination Buffer (QuickScout Screening Assist MSA; Carna Biosciences) to the well. The reaction mixture was applied to LabChip™ system (PerkinElmer), and the product and substrate peptide peaks were separated, analyzed and quantitated. The kinase reaction is evaluated by the product ratio calculated from peak heights of product (P) and substrate(S) peptides (P/(P+S)).

Compounds of Formulae (I), (II) and (III) are active in this assay as indicated in Table 1, where A=a single $IC_{50}\leq50$ nM; B=a single $IC_{50}\geq50$ nM and $\leq250$ nM; C=a single $IC_{50}\geq250$ nM.

TABLE 1

| Example # | ERK2 $IC_{50}$ (nM) |
|---|---|
| GDC-0994 | A |
| BVD-523 | A |
| SCH772984 | A |
| 1 | C |
| 2 | A |
| 3 | A |
| 4 | C |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | B |
| 40 | A |
| 41 | A |
| 42 | C |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |

TABLE 1-continued

| Example # | ERK2 $IC_{50}$ (nM) |
|---|---|
| 74 | A |
| 75 | — |
| 76 | A |
| 77 | A |
| 78 | — |
| 79 | A |
| 80 | A |
| 81 | A |
| 82 | A |
| 83 | — |
| 84 | A |
| 85 | — |
| 86 | — |
| 87 | — |
| 88 | — |
| 89 | A |
| 90 | — |
| 91 | A |
| 92 | A |
| 93 | A |
| 94 | — |
| 95 | — |
| 96 | — |
| 97 | — |
| 98 | — |
| 99 | — |
| 100 | — |
| 101 | — |
| 102 | — |
| 103 | — |
| 104 | — |
| 105 | — |
| 106 | — |
| 107 | — |
| 108 | — |
| 109 | — |
| 110 | — |
| 111 | — |
| 112 | — |
| 113 | — |
| 114 | — |
| 115 | — |
| 116 | — |
| 117 | — |
| 118 | — |
| 119 | — |

Example 124

ERK and RSK Target Engagement Biomarker (pERK and pRSK Western Blot) Protocols BRAF mutant melanoma cells A375 are plated at approximately 1×106 cells per 10 cm dish in growth media (RPMI 1640, 10% FBS, non-essential amino acids and glutamine). The next day the media is removed and replaced with serum free media (RPMI 1640, 0.1% FBS, non-essential amino acids and glutamine) and allowed to incubate overnight. The following day the serum free media is removed and replaced with fresh serum free media containing compound. Typical concentrations for drug treatments are 300 nM, 100 nM, 30 nM, 10 nM, 3 nM and 1 nM, with a final DMSO concentration of 0.1%. The controls include one plate with DMSO alone at 0.1% final concentration and another plate treated with a compound control at 10 nM final concentration. The cells are treated for 24 h. At the time of harvest, the cells are scraped directly into the media and spun down at 1800 rpm in order to capture the floating dead or dying cells as well. One wash with 5 mL of PBS is done, and the cell pellet are frozen or lysed immediately in lysis buffer. The protein concentrations of the lysates are determined using the Pierce BCA protein assay kit and 50 μg of total cell lysate is loaded per lane of a 15 well, 1.5 mm width Tris glycine gel. The gels are run at 125 Volts constant voltage until the dye just runs off the gel. They are transferred using the Invitrogen transfer apparatus onto nitrocellulose membranes at 25 Volts for 2 h. The nitrocellulose membrane is blocked in 5% (wt/vol) non-fat dried milk protein in TBS/Tween for 30 mins at rt. The blot is incubated with anti-RSK or with anti-ERK antibodies. The nitrocellulose membrane is washed 3 times for 10 minutes with vigorous rocking in 50 mL TBS/Tween then incubated 1 h with HRPx-labeled secondary antibody at room temperature. The secondary antibodies are diluted in 2% non-fat dried milk protein in TBS/Tween.

The nitrocellulose is washed as above then developed with freshly prepared ECL reagent. The nitrocellulose membranes are incubated for 1 minute with 5 mL ECL reagent. Excess reagent is removed by blotting on a clean paper towel, and the membrane is wrapped in cellophane before exposing to film. Several exposures of film are made for each blot. (The western blots may be developed and/or quantitated by other means if available.) Band densities are quantitated by densitometry, and the scanned densities are plotted using XLfit to give dose response curves.

Example 125

Proliferation Assay

A375 (melanoma), Colo-205 (colon cancer), Miapaca (pancreatic), HPAFII (pancreatic), sNF02.0 (neurofibromatosis type 1), sNF96.2 (neurofibromatosis type 1) and 8505 (Thyroid) cells were grown and maintained in RPMI-1640 medium containing 100 U/mL penicillin-streptomycin and 10% fetal bovine serum. Cells were in growth medium in 96-well opaque-walled clear bottom plates and incubated in the $CO_2$ incubator overnight before treatment. Cells were treated with compounds diluted in DMSO and a 10 point 3-fold serial dilutions were done. Plates were placed in 37° C., 5% $CO_2$ to incubate for 3 days. Before they were developed by adding 100 μL of CellTiter-Glo reagent (Promega) to the assay plate, plates were shaken briefly for 2 mins and allowed to incubate at room temperature for 10 mins. The bottom of the plates was pasted with white back seal and luminescence was recorded with Flexstation3 with setting of luminescence, integration time 500 ms.

Compounds of Formula (I), (II) and (III) are active in this assay as noted in Table 2. In Table 2: A=a single $IC_{50}$≤500 nM; B=a single $IC_{50}$≥500 nM and ≤1.0 μM; C=a single $IC_{50}$≥1.0 μM.

TABLE 2

| Example # | A375 $IC_{50}$ (nM) |
|---|---|
| GDC-0994 | B |
| BVD-523 | A |
| SCH772984 | A |
| 1 | C |
| 2 | A |
| 3 | B |
| 4 | C |
| 5 | A |
| 6 | A |
| 7 | C |
| 8 | C |

TABLE 2-continued

| Example # | A375 $IC_{50}$ (nM) |
|---|---|
| 9 | A |
| 10 | B |
| 11 | C |
| 12 | B |
| 13 | A |
| 14 | A |
| 15 | B |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | C |
| 40 | A |
| 41 | A |
| 42 | C |
| 43 | A |
| 44 | A |
| 45 | A |
| 46 | A |
| 47 | A |
| 48 | B |
| 49 | A |
| 50 | B |
| 51 | A |
| 52 | A |
| 53 | A |
| 54 | A |
| 55 | A |
| 56 | A |
| 57 | A |
| 58 | A |
| 59 | B |
| 60 | A |
| 61 | A |
| 62 | B |
| 63 | A |
| 64 | A |
| 65 | A |
| 66 | A |
| 67 | A |
| 68 | A |
| 69 | B |
| 70 | B |
| 71 | B |
| 72 | B |
| 73 | B |
| 74 | B |
| 75 | A |
| 76 | A |
| 77 | A |
| 78 | C |
| 79 | A |
| 80 | A |
| 81 | A |
| 82 | A |
| 83 | A |
| 84 | A |

TABLE 2-continued

| Example # | A375 $IC_{50}$ (nM) |
|---|---|
| 85 | A |
| 86 | A |
| 87 | A |
| 88 | A |
| 89 | A |
| 90 | A |
| 91 | B |
| 92 | A |
| 93 | A |
| 94 | A |
| 95 | C |
| 96 | C |
| 97 | A |
| 98 | C |
| 99 | A |
| 100 | A |
| 101 | A |
| 102 | A |
| 103 | A |
| 104 | A |
| 105 | B |
| 106 | A |
| 107 | A |
| 108 | A |
| 109 | A |
| 110 | A |
| 111 | A |
| 112 | A |
| 113 | A |
| 114 | C |
| 115 | A |
| 116 | A |
| 117 | A |
| 118 | A |
| 119 | B |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I):

(I)

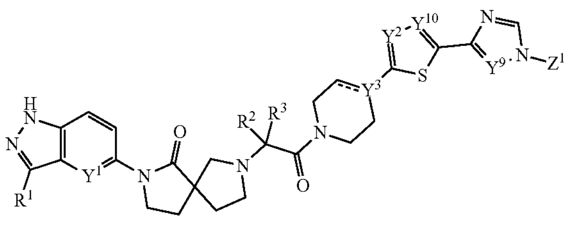

or a pharmaceutically acceptable salt thereof, wherein:

$R^1$ is selected from the group consisting of $C_{3-4}$ cycloalkyl, halophenyl, $C_{1-4}$ alkoxyphenyl, $C_{1-4}$ alkoxyhalophenyl, $C_{1-4}$ dialkoxyphenyl, halopyridinyl, $C_{1-4}$ alkoxypyridinyl, $C_{1-4}$ alkylpyridinyl, $C_{3-5}$ cycloalkoxypyridinyl, methylbenzoxazolyl and tetrahydropyranyl;

$R^2$ and $R^3$ are each independently methyl, hydrogen or deuterium;

$Y^1$ and $Y^2$ are each independently CH or N;

$Y^3$ is C, CH or N; and $Y^9$ and $Y^{10}$ are each independently CH or N;

$Z^1$ is $C_{1-3}$ alkyl optionally substituted with hydroxy;

wherein ------ is a single bond when $Y^3$ is N or CH and ------ is a double bond when $Y^3$ is C; and wherein the compound of Formula (I) is not

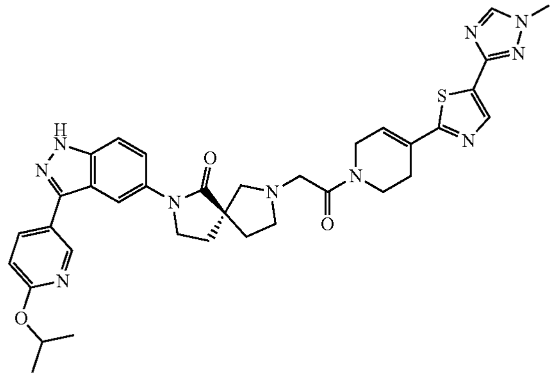

.

2. The compound of claim 1, or a pharmaceutically acceptable salt thereof, of the Formula (IA):

(IA)

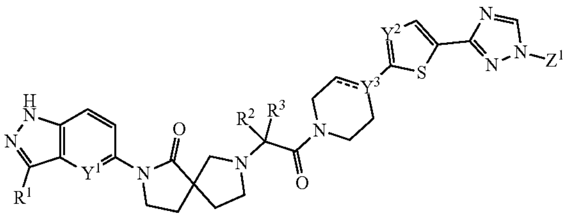

wherein:

$R^1$ is selected from the group consisting of halophenyl, halopyridinyl, $C_{1-4}$ alkoxypyridinyl, $C_{1-4}$ alkylpyridinyl, methylbenzoxazolyl and tetrahydropyranyl; and $R^2$ and $R^3$ are each independently hydrogen or deuterium.

3. The compound of claim 1, or a pharmaceutically acceptable salt thereof, wherein $R^1$ is halophenyl or halopyridinyl.

4. The compound of claim 3, or a pharmaceutically acceptable salt thereof, wherein $R^1$ is fluorophenyl or fluoropyridinyl.

5. The compound of claim 1, or a pharmaceutically acceptable salt thereof, wherein $R^1$ is $C_{1-4}$ alkoxypyridinyl or $C_{1-4}$ alkylpyridinyl.

6. The compound of claim 5, or a pharmaceutically acceptable salt thereof, wherein $R^1$ is isopropoxypyridinyl, methoxypyridinyl or methylpyridinyl.

7. The compound of claim 1, or a pharmaceutically acceptable salt thereof, wherein $R^1$ is methylbenzoxazolyl or tetrahydropyranyl.

8. The compound of claim 1, or a pharmaceutically acceptable salt thereof, wherein $R^1$ is selected from the group consisting of $C_{3-4}$ cycloalkyl, $C_{1-4}$ alkoxyphenyl, $C_{1-4}$ alkoxyhalophenyl, $C_{1-4}$ dialkoxyphenyl, and $C_{3-5}$ cycloalkoxypyridinyl.

9. The compound of claim 1, or a pharmaceutically acceptable salt thereof, wherein - - - - is a double bond.

10. The compound of claim 1, or a pharmaceutically acceptable salt thereof, wherein - - - - is a single bond.

11. The compound of claim 1, or a pharmaceutically acceptable salt thereof, wherein $Y^1$ is CH.

12. The compound of claim 1, or a pharmaceutically acceptable salt thereof, wherein $Y^1$ is N.

13. The compound of claim 1, or a pharmaceutically acceptable salt thereof, wherein $Y^2$ is CH.

14. The compound of claim 1, or a pharmaceutically acceptable salt thereof, wherein $Y^2$ is N.

15. The compound of claim 1, or a pharmaceutically acceptable salt thereof, wherein $Y^3$ is C.

16. The compound of claim 1, or a pharmaceutically acceptable salt thereof, wherein $Y^3$ is CH.

17. The compound of claim 1, or a pharmaceutically acceptable salt thereof, wherein $Y^3$ is N.

18. The compound of claim 1, or a pharmaceutically acceptable salt thereof, wherein $Y^9$ is N or CH.

19. The compound of claim 1, or a pharmaceutically acceptable salt thereof, wherein $Y^{10}$ is N or CH.

20. The compound of claim 1, selected from the group consisting of

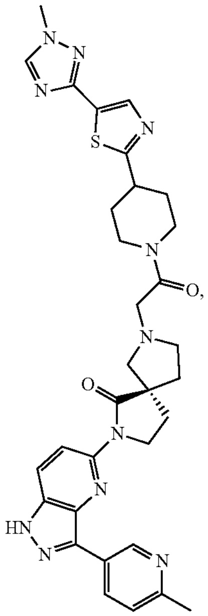

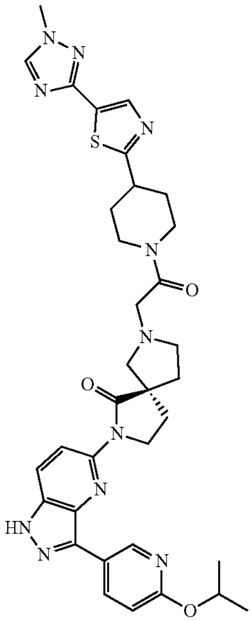

,

-continued

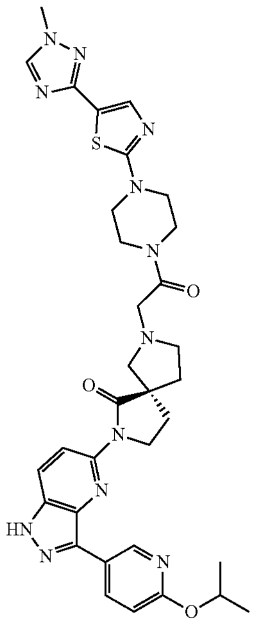

,

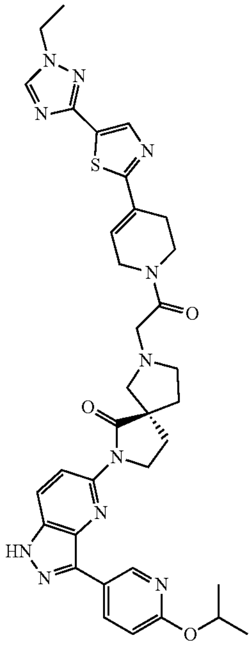

,

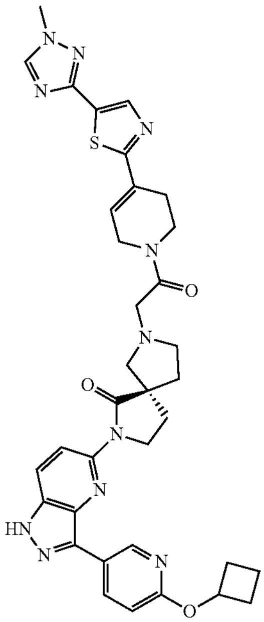

,

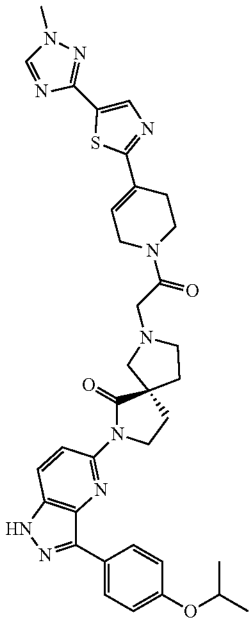

,

-continued
-continued
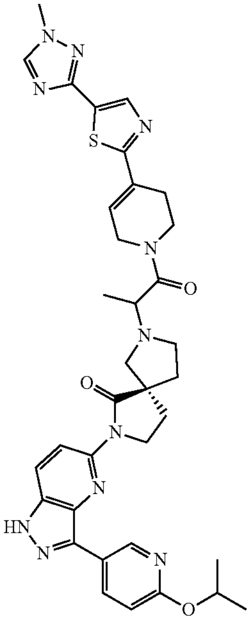
,
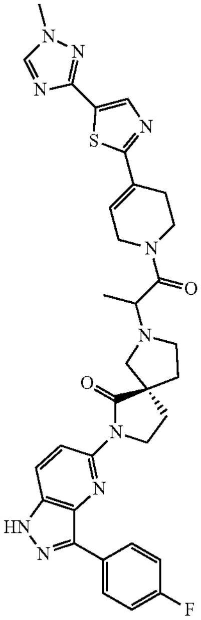
,
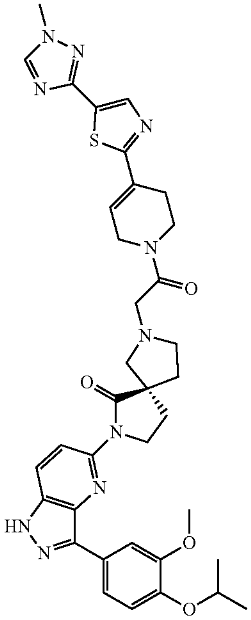
,
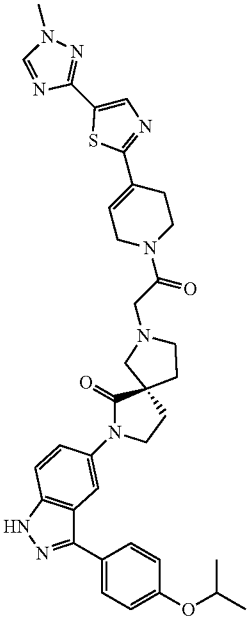
,
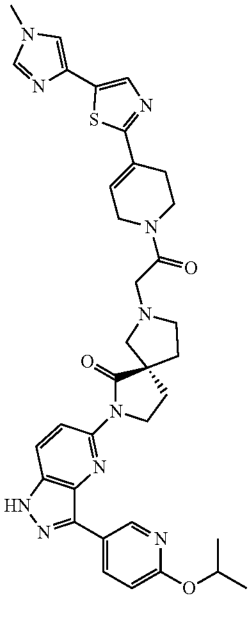
,
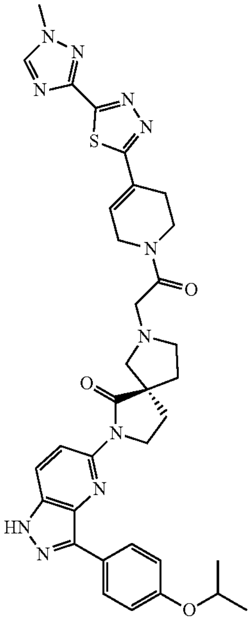
,
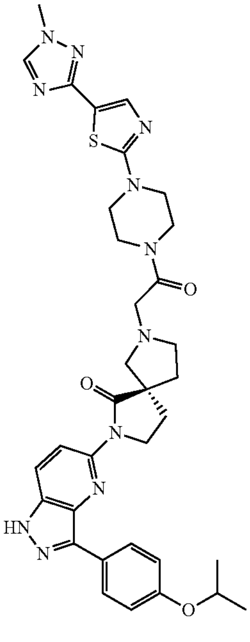
,
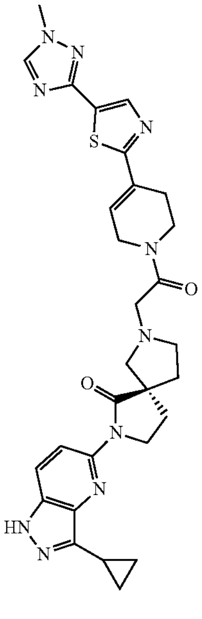
, and -continued
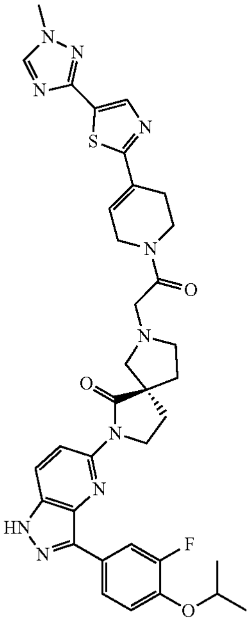,
or a pharmaceutically acceptable salt of the foregoing.
21. The compound of claim 2, selected from the group consisting of
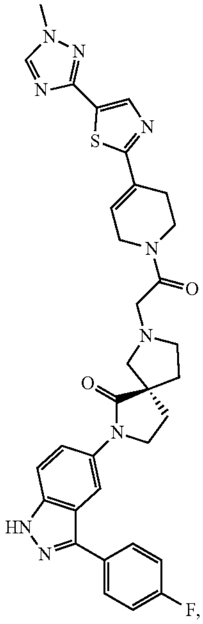,
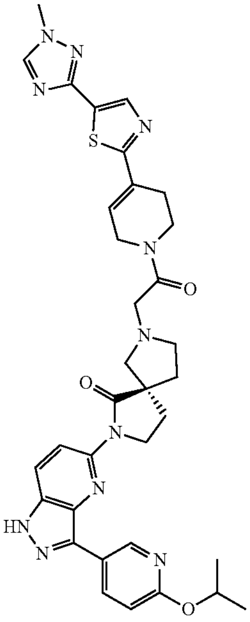,
-continued
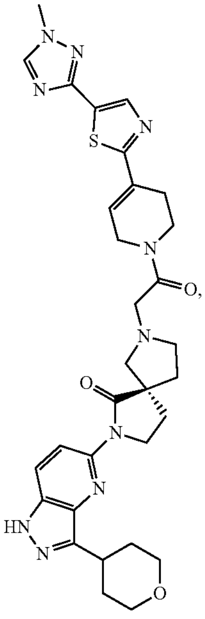,
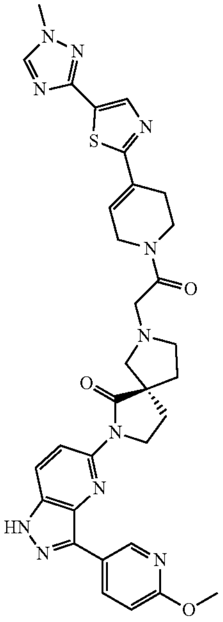,
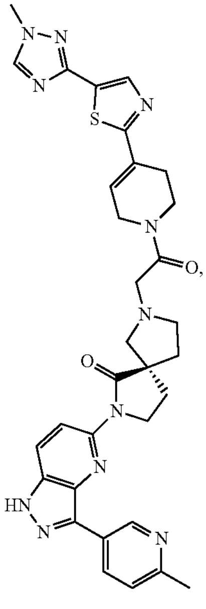,
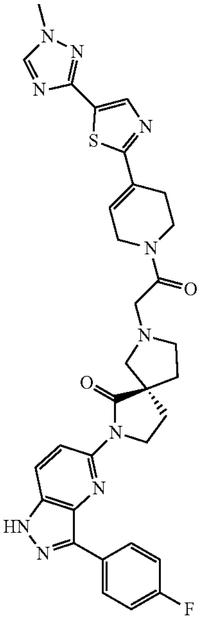

-continued

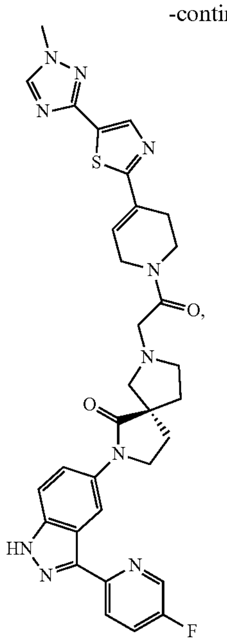

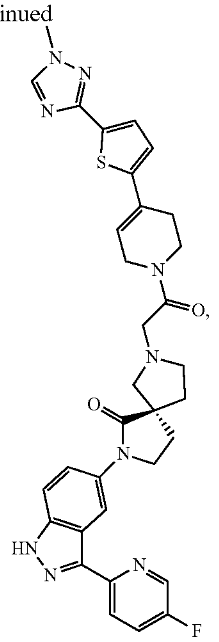

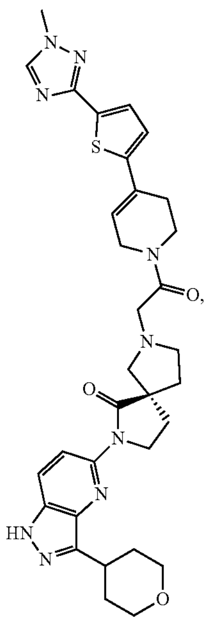

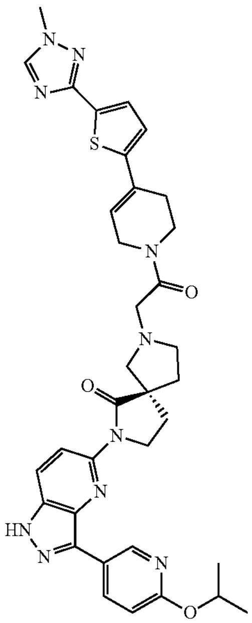

, and

-continued

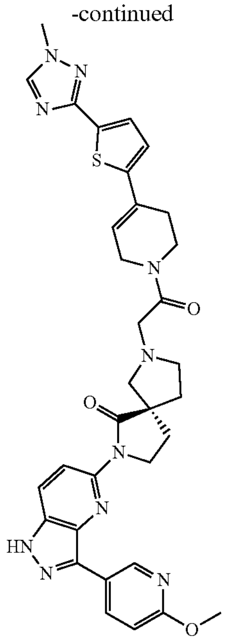

, or a pharmaceutically acceptable salt of the foregoing.

22. The compound of claim 1, selected from the group consisting of (S)-7-(2-(4-(5-(1-(2-hydroxyethyl)-1H-1,2,4-triazol-3-yl)thiazol-2-yl)-3,6-dihydropyridin-1(2H)-yl)-2-oxoethyl)-2-(3-(6-isopropoxypyridin-3-yl)-1H-pyrazolo[4,3-b]pyridin-5-yl)-2,7-diazaspiro[4.4]nonan-1-one;

(S)-7-(2-(4-(5-(1-methyl-1H-1,2,4-triazol-3-yl)thiazol-2-yl)-3,6-dihydropyridin-1(2H)-yl)-2-oxoethyl)-2-(3-(2-methylbenzo[d]oxazol-5-yl)-1H-pyrazolo[4,3-b]pyridin-5-yl)-2,7-diazaspiro[4.4]nonan-1-one;

(S)-2-(3-(6-isopropoxypyridin-3-yl)-1H-pyrazolo[4,3-b]pyridin-5-yl)-7-(2-(4-(5-(1-methyl-1H-1,2,4-triazol-3-yl)thiazol-2-yl)-3,6-dihydropyridin-1(2H)-yl)-2-oxoethyl-1,1-d2)-2,7-diazaspiro[4.4]nonan-1-one; and (S)-7-(2-(4-(5-(1-methyl-1H-1,2,4-triazol-3-yl)thiazol-2-yl)-3,6-dihydropyridin-1(2H)-yl)-2-oxoethyl)-2-(3-(2-methylpyridin-4-yl)-1H-pyrazolo[4,3-b]pyridin-5-yl)-2,7-diazaspiro[4.4]nonan-1-one;

or a pharmaceutically acceptable salt of the foregoing.

23. A pharmaceutical composition comprising an effective amount of a compound of claim 1, or a pharmaceutically acceptable salt thereof, and a pharmaceutically acceptable carrier, diluent, excipient, or combination thereof.

* * * * *